(12) United States Patent
Goodearl et al.

(10) Patent No.: US 6,232,286 B1
(45) Date of Patent: May 15, 2001

(54) METHODS OF STIMULATING MITOGENESIS IN GLIAL CELLS USING GLIAL MITOGENIC FACTORS

(75) Inventors: Andrew Goodearl, Chorleywood; Paul Stroobant, London, both of (GB); Luisa Minghetti, Bagnacavallo (IT); Michael Waterfield, Newbury (GB); Mark Marchioni; Mario Su Chen, both of Arlington, MA (US); Ian Hiles, London (GB)

(73) Assignees: Cambridge Neuroscience, Cambridge, MA (US); Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/470,339

(22) Filed: Jun. 6, 1995

Related U.S. Application Data

(60) Division of application No. 08/036,555, filed on Mar. 24, 1993, now Pat. No. 5,530,109, which is a continuation-in-part of application No. 07/863,703, filed on Apr. 3, 1992, now abandoned, which is a continuation-in-part of application No. 07/907,138, filed on Jun. 30, 1992, now abandoned, which is a continuation-in-part of application No. 07/940,389, filed on Sep. 3, 1992, now abandoned, which is a continuation-in-part of application No. 07/965,173, filed on Oct. 23, 1992, now abandoned.

(30) Foreign Application Priority Data

Apr. 10, 1991 (GB) .................................................. 9107566

(51) Int. Cl.$^7$ ........................... A61K 38/02; A61K 38/18

(52) U.S. Cl. .................................................. 514/2; 514/12

(58) Field of Search ........................ 514/2, 12; 435/69.1

(56) References Cited

U.S. PATENT DOCUMENTS

| | | |
|---|---|---|
| 4,935,341 | 6/1990 | Barbmann et al. . |
| 4,968,603 | 11/1990 | Slamon et al. . |

FOREIGN PATENT DOCUMENTS

| | | |
|---|---|---|
| WO8906692 | 7/1989 | (WO) . |
| WO9014357 | 11/1990 | (WO) . |
| WO9115230 | 10/1991 | (WO) . |
| WO9212174 | 1/1992 | (WO) . |
| WO9322339 | 11/1993 | (WO) . |
| WO932242 | 11/1993 | (WO) . |

OTHER PUBLICATIONS

Grierson et al. *Brain Res. Develop. Brain Res.*, vol. 55, pp. 11–19, 1990, (Abstract Only).*
Lupu et al., *Proc. Am. Assoc. Cancer Res.*, vol. 32, p. 50, 1991.*
Lemke et al., *Fed. Proceed.*, vol. 42, No. 9, 2627–2629, 1983.*
Benveniste, E.N. et al., P.N.A.S., "Purification and characterization of a human T–lymphocyte–derived glial growth promoting factor", 82: 3930–3934, Jun. 1985.
Kimura, H. et al., "Nature, Structure, expression and function of a Schwannoma derived growth factor", 348: 257–260, Nov. 15, 1990.
Falls et al., Cell, ARIA, a Protein that stimulates acetypcholine receptor synthesis, is a member of the Neu Ligand family, 72: 801–815 (1993).
Plowman et al., Nayure, Heregulin induces tyrosine phosphorylation of HER4/pl80bB4, 366: 473.
Brooks et al., "Purification and Preliminary Characterization of a Glial Growth Factor from the Bovine Pituitary", J. Biol. Chem. 255; 18, 8374–8377 (Sept. 1980).
Brookes et al., "The neuron as a source of mitogen: its influence on the proliferation of glial and non–neural cells", Garrod and Feldman eds, pp. 309–327 (1980).
Lemke et al., "An Immunochemical Approach to the Purification and Characterization of Glial Growth Factor", Monoclonal Antibodies to Neural Antigens, McKay, Raff and Reichardt, eds. pp. 133–140 (1981).
Lemke et al., "Identification and Purification of Glial Growth Factor", In Neuroscience, vol. 4, No. 1, pp. 75–83 (Jan. 1984).
Davis et al., "Platelet–derived Growth Factors and Fibroblasts Growth Factors Are Mitogens for Rat Schwann Cells", J. Cell Biology 110: 1353 (Apr. 1990).
Peles et al., "Isolation of the Neu/HER–2 Stimilatory Ligand: A 44 Kd Glyco–protein That Induces Differentiation of Mammary Tumor Cells", Cell 69: 205.
Lupu et al., "Direct Intera–tion of a Ligand for the erbB2 Oncogene Product with the EGF Receptor and p185$^{erbB2}$", Science 249: 1552 (Sept. 1990).
Yarden et al., "Biochemical Analysis of the Ligand for the neu Oncogenic Receptor", Biochemistry 30: 3543 (1991).
Dobanshi et al., "Characterization of a neu/c–erbB–2 protein–specific activating factor", P.N.A.S., USA. 88: 8582 (Oct. 1991).

(List continued on next page.)

*Primary Examiner*—Gary L. Kunz
*Assistant Examiner*—Stephen Gucker
(74) *Attorney, Agent, or Firm*—Clark & Elbing LLP; Kristina Bieker-Brady

(57) ABSTRACT

The invention features methods for stimulating glial cell mitogenesis by contacting the glial cells with p185$^{erbB2}$ ligand polypeptides, including glial growth factor (GGF), a GGF splice variant comprised of segments E, B, A, C, and C/D or C/D', a 35 kD polypeptide factor isolated from rat I-EJ transformed fibroblast cells, 75 kD polypeptide factor isolated from the LKBR-3 human breast cells, 44 kD polypeptide factor isolated from the rat I-EJ transformed fibroblast cells, 45 kD polypeptide factor isolated from MDA-MB 231 human breast cells, 7–14 kD polypeptide factor isolated from the ATL-2 human T-cells, 25 kD polypeptide factor isolated from activated mouse peritoneal macrophages, and 25 kD polypeptide factor isolated from bovine kidney.

8 Claims, 78 Drawing Sheets

OTHER PUBLICATIONS

Tarakhovsky et al., "A 25 kDa polypeptide in the ligand for p185neu and is secreted by activated macrophages", Oncogene 6: 2187 (1991).

Davis et al., "Isolation and characterization of a neu protein–specific activating factor from human ATL–2 cell conditioned medium", Biochem. Biophys. Research Communication 179: 1536 (Sept. 1991).

Huang et al., "Purification and Characterization of the neu/erb B2 Ligand–Growth Factor from Bovine Kidney", J. Biol. Chem. 257: 11508 (Jun. 1992).

Lupu et al., "Characterization of a growth factor that binds exclusively to the erbB–2 receptor and induces cellular responses", P.N.A.S., U.S.A. 89: 2287 (Mar. 1992).

Holmes et al., "Identification of Heregulin, a specific Activator of p185$^{erbB2}$", Science 256: 1205 (May 1992).

Wen et al., "Neu Differentiation Factor: A Transmembrane Glycoprotein Containing an EGF Domain and an Immunoglobulin Homology Unit", Cell 69: 559 (May 1992).

Yarden, "Growth Factor Receptor Tyrosine Kinases", Ann. Rev. Biochem. 57:443–478 (1998).

* cited by examiner

```
         N-terminus
GGF-I 01  F K G D A H T E                                    (SEQ ID NO: 1)

Trypsin peptides
GGF-I 02  K/R A S L A D E Y E Y M K K*                       (SEQ ID NO: 2)
GGF-I 03  K/R T E T S S S G L X L K*                         (SEQ ID NO: 3)
GGF-I 04  K/R K L G E M W A E                                (SEQ ID NO: 4)     HMG-1
GGF-I 05  K/R L G E K R A                                    (SEQ ID NO: 5)     HMG-1?
GGF-I 06  K/R I K S E H A G L S I G D T A K*                 (SEQ ID NO: 6)     HMG-2
GGF-I 07  K/R A S L A D E Y E Y M R K*                       (SEQ ID NO: 7)
GGF-I 08  K/R I K G E H P G L S I G D V A K*                 (SEQ ID NO: 8)     HMG-1
GGF-I 09  K/R M S E Y A F F V Q T X R*                       (SEQ ID NO: 9)     HMG-2
GGF-I 10  K/R S E H P G L S I G D T A K*                     (SEQ ID NO: 10)    HMG-1
GGF-I 11  K/R A G Y F A E X A R*                             (SEQ ID NO: 11)
GGF-I 12  K/R K L E F L X A K*                               (SEQ ID NO: 12)
GGF-I 13  K/R T T E M A S E Q G A                            (SEQ ID NO: 13)
GGF-I 14  K/R A K E A L A A L K*                             (SEQ ID NO: 14)
GGF-I 15  K/R F V L Q A K K*                                 (SEQ ID NO: 15)
GGF-I 16  K/R L G E M W                                      (SEQ II)NO: 16)    HMG-1

Protease V8 peptides
GGF-I 17  E T Q P D P G Q I L K K V P M V I G A Y T          (SEQ ID NO: 169)
GCF-I 18  E Y K C L K F K W F K K K A T V M                  (SEQ ID NO: 17)
GGF-I 19  E A K Y F S K X D A                                (SEQ ID NO: 18)    LH-alpha
GGF-I 20  E X K F Y V P                                      (SEQ ID NO: 19)
GGF-I 21  E L S F A S V R L P G C P P G V D P M V S F P V A L (SEQ ID NO: 20)   LH-beta
```

Fig. 9

GGF-I 01  F K G D A H T E                    (SEQ ID NO: 1)
GGF-I 02  A S L A D E Y E Y M X K            (SEQ ID NO: 22)
GGF-I 03  T E T S S G L X L K                (SEQ ID NO: 23)
GGF-I 07  A S L A D E Y E Y M R K            (SEQ ID NO: 24)
GGF-I 11  A G Y F A E X A R                  (SEQ ID NO: 25)
GGF-I 13  T T E M A S E Q G A                (SEQ ID NO: 26)
GGF-I 14  A K E A L A A L K                  (SEQ ID NO: 27)
GGF-I 15  F V L Q A K K                      (SEQ ID NO: 28)
GGF-I 17  E T Q P D P G Q I L K K V P M V I G A Y T  (SEQ ID NO: 29)
GGF-I 18  E Y K C L K F K W F K K K A T V M  (SEQ ID NO: 17)

Fig. 10A

GGF-I 20  E X K F Y V P                      (SEQ ID NO: 19)
GGF-I 12  K L E F L X A K                    (SEQ ID NO: 32)

Fig. 10B

```
Trypsin peptides
GGF-II 01    K/R  V H Q V W A A K *                        (SEQ ID NO: 33)
GGF-II 02    K/R  Y I F F M E P E A X S S G                (SEQ ID NO: 34)
GGF-II 03    K/R  L G A W G P P A F P V X Y                (SEQ ID NO: 35)
GGF-II 04    K/R  W F V V I E G K *                        (SEQ ID NO: 36)
GGF-II 05    K/R  A L A A A G Y D V E K *                  (SEQ ID NO: 164)
GGF-II 06    K/R  L V L R *                                (SEQ ID NO: 165)
GGF-II 07    K/R  X X Y P G Q I T S N            Histone H1 (SEQ ID NO: 166)
GGF-II 08    K/R  A S P V S V G S V Q E L V Q R * Trypsin   (SEQ ID NO: 37)
GGF-II 09    K/R  V C L L T V A A P P T                    (SEQ ID NO: 38)
GGF-II 10    K/R  D L L X V                                (SEQ ID NO: 39)

Lysyl Endopeptidase-C peptides
GGF-II 11    K V H Q V W A A K *                           (SEQ ID NO: 51)
GGF-II 12    K A S L A D S G E Y M X K*                    (SEQ ID NO: 52)
```

Fig. 11

```
GGF-II 01  V H Q V W A A K              (SEQ ID NO: 45)
GGF-II 02  Y I F F M E P E A X S S G    (SEQ ID NO: 46)
GGF-II 03  L G A W G P P A F P V X Y    (SEQ ID NO: 47)
GGF-II 04  W F V V I E G K              (SEQ ID NO: 48)
GGF-II 08  A S P V S V G S V Q E L V Q R (SEQ ID NO: 49)
GGF-II 09  V C L L T V A A P P T        (SEQ ID NO: 50)
GGF-II 11  K V H Q V W A A K            (SEQ ID NO: 51)
GGF-II 12  K A S L A D S G E Y M X K    (SEQ ID NO: 52)
```

Fig. 12A

```
       Novel Factor II Peptides - others

GGF-II 10  D L L L X V                  (SEQ ID NO: 53)
```

Fig. 12B

Degenerate Oligonucleotide Probes for Factor I & Factor II

| Oligo | Sequence | Peptide | | |
|---|---|---|---|---|
| 535 | TTYAARGGNGAYGCNCAYAC! | GGFI-1 | (SEQ ID NO: | 54) |
| 536 | CATRTAYTCRTAYTCRTCNGC! | GGFI-2 | (SEQ ID NO: | 55) |
| 537 | TGYTCNGANGCCATYTCNGT! | GGFI-13 | (SEQ ID NO: | 56) |
| 538 | TGYTCRCTNGCCATYTCNGT! | GGFI-13 | (SEQ ID NO: | 57) |
| 539 | CCDATNACCATNGGNACYTT! | GGFI-17 | (SEQ ID NO: | 58) |
| 540 | GCNGCCCANACYTGRTGNAC! | GGFII-1 | (SEQ ID NO: | 59) |
| 541 | GCYTCNGGYTCCATRAARAA! | GGFII-2 | (SEQ ID NO: | 60) |
| 542 | CCYTCDATNACNACRAACCA! | GGFII-4 | (SEQ ID NO: | 61) |
| 543 | TCNGCRAARTANCCNGC! | GGFI-11 | (SEQ ID NO: | 62) |
| 544 | GCNGCNAGNGCYTCYTTNGC! | GGFI-14 | (SEQ ID NO: | 63) |
| 545 | GCNGCYAANGCYTCYTTNGC! | GGFI-14 | (SEQ ID NO: | 64) |
| 546 | TTYTTNGCYTGNAGNACRAA! | GGFI-15 | (SEQ ID NO: | 65) |
| 551 | TTYTTNGCYTGYAANACRAA! | GGFI-15 | (SEQ ID NO: | 66) |
| 568 | TGNACNAGYTCYTGNAC! | GGFII-8 | (SEQ ID NO: | 67) |
| 569 | TGNACYAAYTCYTGNAC! | GGFII-8 | (SEQ ID NO: | 68) |
| 609 | CATRTAYTCNCCNGARTCNGC! | GGFII-12 | (SEQ ID NO: | 69) |
| 610 | CATRTAYTCNCCRCTRTCNGC! | GGFII-12 | (SEQ ID NO: | 70) |
| 649 | NGARTCNGCYAANGANGCYTT! | GGFII-12 | (SEQ ID NO: | 71) |
| 650 | NGARTCNGCNAGNGANGCYTT! | GGFII-12 | (SEQ ID NO: | 72) |
| 651 | RCTRTCNGCYAANGANGCYTT! | GGFII-12 | (SEQ ID NO: | 73) |
| 652 | RCTRTCNGCNAGNGANGCYTT! | GGFII-12 | (SEQ ID NO: | 74) |
| 653 | NGARTCNGCYAARCTNGCYTT! | GGFII-12 | (SEQ ID NO: | 75) |
| 654 | NGARTCNGCNAGRCTNGCYTT! | GGFII-12 | (SEQ ID NO: | 76) |
| 655 | RCTRTCNGCYAARCTNGCYTT! | GGFII-12 | (SEQ ID NO: | 78) |
| 656 | RCTRCTNGCNAGRCTNGCYTT! | GGFII-12 | (SEQ ID NO: | 79) |
| 659 | ACNACNGARATGGCTCNNGA! | GGFI-13 | (SEQ ID NO: | 80) |
| 660 | ACNACNGARATGGCAGYNGA! | GGFI-13 | (SEQ ID NO: | 81) |
| 661 | CAYCARGTNTGGGCNGCNAA! | GGFII-1 | (SEQ ID NO: | 82) |
| 662 | TTYGTNGTNATHGARGGNAA! | GGFII-4 | (SEQ ID NO: | 83) |
| 663 | AARGGNGAYGCNCAYACNGA! | GGFI-1 | (SEQ ID NO: | 84) |
| 664 | GARGCNYTNGCNGCNYTNAA! | GGDI-14 | (SEQ ID NO: | 85) |
| 665 | GTNGGNTCNGTNCARGARYT! | GGFII-8 | (SEQ ID NO: | 86) |
| 666 | GTNGGNAGYGTNCARGARYT! | GGFII-8 | (SEQ ID NO: | 87) |
| 694 | NACYTTYTTNARHATYTGNCC! | GGFI-17 | (SEQ ID NO: | 88) |

Fig. 21

Putative Bovine Factor II Gene Sequences

```
(SEQ ID NO: 89)  TCTAA AAC TAC AGA GAC TGT ATT TTC ATG ATC ATA GTT CTG TGA AAT ATA    53
(SEQ ID NO: 196)       Asn Tyr Arg Asp Cys Ile Phe Met Ile Ile Val Leu Xaa Asn Ile

CTT AAA CCG CTT TGG TCC TGA TCT TGT AGG AAG TCA GAA CTT CGC ATT     101
                 Leu Lys Pro Leu Trp Ser Xaa Ser Cys Arg Lys Ser Glu Leu Arg Ile

AGC AAA GCG TCA CTG GCT GAT TCT GGA GAA TAT ATG TGC AAA GTG ATC     149
                 Ser Lys Ala Ser Leu Ala Asp Ser Gly Glu Tyr Met Cys Lys Val Ile

AGC AAA CTA GGA AAT GAC AGT GCC TCT GCC AAC ATC ACC ATT GTG GAG     197
                 Ser Lys Leu Gly Asn Asp Ser Ala Ser Ala Asn Ile Arg Ile Val Glu

TCA AAC GGT AAG AGA TGC CTA CTG CGT GCT ATT TCT CAG TCT CTA AGA     245
                 Ser Asn Gly Lys Arg Cys Leu Leu Arg Ala Ile Ser Gln Ser Leu Arg

GGA GTG ATC AAG GTA TGT GGT CAC ACT TGA ATC ACG CAG GTG TGT GAA     293
                 Gly Val Ile Lys Val Cys Gly His Thr Xaa Ile Thr Gln Val Cys Glu

ATC TCA TTG TGA ACA AAT AAT CAT GAA AGG AAA ACT CTA TGT TTG         341
                 Ile Ser Cys Xaa Thr Asn Lys Asn His Glu Arg Lys Thr Leu Cys Leu

AAA TAT CTT ATG GGT CCT CCT GTA AAG CTC TTC ACT CCA TAA GGT GAA     389
                 Lys Tyr Leu Met Gly Pro Pro Val Lys Leu Phe Thr Pro Xaa Gly Glu

ATA GAC CTG AAA TAT ATA TAG ATT ATT T                              417
                 Ile Asp Leu Lys Tyr Ile Xaa Ile Ile
```

Fig. 22

PCR Primers for Factor I & Factor II

Degenerate PCR Primers

| Oligo | Sequence | Peptide | |
|---|---|---|---|
| 657 | CCGAATTCTGCAGGARACNCARCCNGAYCCNGG! | GGFI-17 | (SEQ ID NO: 90) |
| 658 | AAGGATCCTGCAGNGTRTANGCNCCHATNACCATNGG! | GGFI-17 | (SEQ ID NO: 91) |
| 667 | CCGAATTCTGCAGGCNGAYTCNGGNGARTAYATG! | GGFII-12 | (SEQ ID NO: 92) |
| 668 | CCGAATTCTGCAGGCNGAYATYGGNGARTAYAT! | GGFII-12 | (SEQ ID NO: 93) |
| 669 | AAGGATCCTGCAGNNNCATRTAYTCNCCNGARTC! | GGFII-12 | (SEQ ID NO: 94) |
| 670 | AAGGATCCTGCAGNNNCATRTAYTCNCCRRTRTC! | GGFII-12 | (SEQ ID NO: 95) |
| 671 | CCGAATTCTGCAGCAYCARGTNT'GGGCNGCNAA! | GGFII-1 | (SEQ ID NO: 96) |
| 672 | CCGAATTCTGCAGATRTTYTTYATGGARCCNGARG! | GGFII-2 | (SEQ ID NO: 97) |
| 673 | CCGAATTCTGCAGGGGGNCCNCCNGCNTTYCCNGT! | GGFII-3 | (SEQ ID NO: 98) |
| 674 | CCGAATTCTGCAGTGGTTYGTNGTNATHGARGG! | GGFII-4 | (SEQ ID NO: 99) |
| 677 | AAGGATCCTGCAGYTTNGCNGCCCANACYTGRTG! | GGFII-1 | (SEQ ID NO: 100) |
| 678 | AAGGATCCTGCAGGCYTCNGGYTCCATRAARAA! | GGFII-2 | (SEQ ID NO: 101) |
| 679 | AAGGATCCTGCAGACNGGRAANGCNGGNGGNCC! | GGFII-3 | (SEQ ID NO: 102) |
| 680 | AAGGATCCTGCAGYTTNCCYTCDATNACNACRAAC! | GGFII-4 | (SEQ ID NO: 103) |
| 681 | CATRTAYTCRTAYTCTCNGCAAGGATCCTGCAG! | GGFI-2 | (SEQ ID NO: 104) |
| 682 | CCGAATTCTGCAGAARGGNGAYGCNCAYACNGA! | GGFI-1 | (SEQ ID NO: 105) |
| 683 | GCNGCYAANGCYRCYTTNGCAAGGATCCTGCAG! | GGFI-14 | (SEQ ID NO: 106) |
| 684 | GCNCNAGNGCYTCYTTNGCAAGGATCCTGCAG! | GGFI-14 | (SEQ ID NO: 107) |
| 685 | TCNGCRAARTANCCNGCAAGGATCCTGCAG! | GGFI-1 | (SEQ ID NO: 108) |

Fig. 23A

PCR Primers for Factor I & Factor II

Unique PCR Primers for Factor II

| Oligo | Sequence | Comment | |
|---|---|---|---|
| 711 | CATCGATCTGCAGGCTGATTCTGGAGAATATATGTGCA! | 3' RACE | (SEQ ID NO: 109) |
| 712 | AAGGATCCTGCAGCCACATCTCGAGTCGACATCGATT! | 3' RACE | (SEQ ID NO: 110) |
| 713 | CCGAATTCTGCAGTGATCAGCAGAAACTAGGAAATGACA! | 3' RACE | (SEQ ID NO: 111) |
| 721 | CATCGATCTGCAGCCTAGTTTGCTGATCACTTTGCAC! | 5' RACE | (SEQ ID NO: 112) |
| 722 | AAGGATCCTGCAGTATATTCTCCAGAATCAGCCAGTG! | 5' RACE;ANCHORED | (SEQ ID NO: 113) |
| 725 | AAGGATCCTGCAGGCACGCAGTAGGCATCTCTTA! | EXON A | (SEQ ID NO: 114) |
| 726 | CCGAATTCTGCAGCAGAACTTCGCATTAGCAAAGC! | EXON A | (SEQ ID NO: 115) |
| 771 | CATCCCGGGATGAAGAGTCAGGAGTCTGTGGCA! | EXONS B+A | (SEQ ID NO: 116) |
| 772 | ATACCCGGGCTGCAGACAATGAGATTTCACACACCTGCG! | | (SEQ ID NO: 117) |
| 773 | AAGGATCCTGCAGTTTGGAACCTGCCACAGACTCCT! | ANCHORED | (SEQ ID NO: 118) |
| 776 | ATACCCGGGCTGCAGATGAGATTTCACACACCTGCGTGA! | EXONS B+A | (SEQ ID NO: 119) |

Fig. 23B

GGF-II Peptides Identified in Deduced Amino Acid
Sequences of Putative Bovine GGF-II Proteins

| Peptide | Pos. | Sequence match | ID Sequences |
|---|---|---|---|
| II-1 | | VHQVWAAK | (SEQ ID NO:45) |
| | 1: | HQVWAAK AAGLK | (SEQ ID NQ:120) |
| II-10 | | DLLLXV | (SEQ ID NO:53) |
| | 14: | GGLKK dslltv RLGAW | (SEQ IDNO:121) |
| II-03 | | LGAWGPPAFPVXY | (SEQ ID NO:122) |
| | 21: | LLTVR lgawghpafpscg RLKED | (SEQ ID NO:123) |
| II-02 | | YIFFMEPEAXSSG | (SEQ ID NO:124) |
| | 41: | KEDSR YIFFMEPEANSSG GPGRL | (SEQ ID NO:125) |
| II-6 | | LVLR | (SEQ ID NO:42) |
| | 103: | VAGSK LVLR CETSS | (SEQ ID NO:126) |
| I-18 | | EYKCLKFKWFKKATVM | (SEQ ID NO:127) |
| | 112: | CETSS eysslkfkwfkngsel SRKNK | (SEQ ID NO:128) |
| II-12 | | KASLADSGEYMXK | (SEQ ID NO:52) |
| | 151: | ELRIS KASLADSGEYMCK VISKL | (SEQ ID NO:130) |
| I-07 | | ASLADEYEYMRK | (SEQ ID NO:131) |
| | 152: | LRISK asladsgeymck VISKL | (SEQ ID NO:132) |

Fig. 27

```
                                                                                                                                    55
(SEQ ID NO: 133)CTC ACC GTG CGC CTG GGC GCC CCC CAC TTC ATG GAG CCC GAG        103
(SEQ ID NO: 190)Leu Thr Val Arg Leu Gly Ala Pro His Phe Met Glu Pro Glu

GGG CGC CTC AAG GAG GAC AGC AGG TAC ATC TTC TTC CCC GAG        151
                Gly Arg Leu Lys Glu Asp Ser Arg Tyr Ile Phe Phe Pro Glu

GCC AAC AGC AGC GGC GGG CCC CGC GGC CTC CTC CCC CCC            199
                Ala Asn Ser Ser Gly Gly Pro Arg Gly Leu Leu Pro Pro

TCT CGA GAC GGG CCG GAA CCT CAA GGA GGT CAG CCG GGT GCT GTG    247
                Ser Arg Asp Gly Pro Glu Pro Gln Gly Gly Gln Pro Gly Ala Val

CAA CGG TGC GCC TTG CCT CCC CGC TTG AAA GAG ATG AAG CAG GAG    295
                Gln Arg Cys Ala Leu Pro Pro Arg Leu Lys Glu Met Lys Gln Glu

TCT GTG GCA GGT TCC AAA CTA GTG CTT CGG TGC GAG ACC AGT GAA    343
                Ser Val Ala Gly Ser Lys Leu Val Leu Arg Cys Glu Thr Ser Glu

TAC TCC TCT CTC AAG TTC TGG TTC AAT GGG AGT GAA TTA AGC        391
                Tyr Ser Ser Leu Lys Phe Trp Phe Asn Gly Ser Glu Leu Ser

CGA AAG AAC CCA GAA AAC ATC AAG ATA CAG AAA AGG CCG GGG AAG    439
                Arg Lys Asn Pro Glu Asn Ile Lys Ile Gln Lys Arg Pro Gly Lys

TCA GAA CTT CGC ATT AGC AAA GCG TCA CTG GCT GAT TCT GGA GAA TAT 487
                Ser Glu Leu Arg Ile Ser Lys Ala Ser Leu Ala Asp Ser Gly Glu Tyr

ATG TGC AAA GTG GAG ATC AGC AAT CTA GGA AAT GGT AGC TCT GCC AAC 535
                Met Cys Lys Val Glu Ile Ser Asn Leu Gly Asn Asp Ser Ala Asn

ATC ACC ATT GTG GAG CTT CGC ATC AAC ACA TGC CTA CTG CGT GCT ATT 583
                Ile Thr Ile Val Glu Leu Arg Ile Asn Thr Cys Leu Leu Arg Ala Ile

TCT CAG TCT CTA AGA GGA GTG ATC AAG GTA TGT TGT CAC ACT        625
                Ser Gln Ser Leu Arg Gly Val Ile Lys Val Cys Cys His Thr

TGAATCACGC AGGTGTGTGA AATCTCATTG TGAACAAATA AAAATCATGA AAGGAAAAAA    685
                AAAAAAAAAA AATCGATGTC GACTCGAGAT GTGGCTGCAG GAGGATCCC                744
```

Fig. 28A

Nucleotide Sequences & Deduced Amino Acid Sequences of GGF2BPP2

```
(SEQ ID NO: 134) CCTGCAG CAT CAA GTG TGG GCG GCG AAA GCC GGG GGC TTG AAG GAC TCG CTG      55
(SEQ ID NO: 191)         His Gln Val Trp Ala Ala Lys Ala Gly Gly Leu Lys Asp Ser Leu

CTC ACC GTG CGC CTG CGC CTG GGC GCC TGG GGC CAC CCC GCC TTC CCC TGC     103
                 Leu Thr Val Arg Leu Arg Leu Gly Ala Trp Gly His Pro Ala Phe Pro Cys

GGG CGC CTC AAG GAG GAC AGC AGG TAC ATC TTC TTC ATG GAG CCC GAG         151
                 Gly Arg Leu Lys Glu Asp Ser Arg Tyr Ile Phe Phe Met Glu Pro Glu

GCC AAC AGC AGC GGT GGG CCC GGC CTT CCG AGC CTC CTT CCC CCC             199
                 Ala Asn Ser Ser Gly Gly Pro Gly Leu Pro Ser Leu Leu Pro Pro

TCT CGA GAC GGG CCG GAA CCT CAA GAA GGT GGG CAG CCG GGT GTG             247
                 Ser Arg Asp Gly Pro Glu Pro Gln Glu Gly Gly Gln Pro Gly Val

CAA CGG TGC GCC TTG CCT CCC CGC AAA GAG ATG AAG AGT CAG GAG             295
                 Gln Arg Cys Ala Leu Pro Pro Arg Leu Glu Met Lys Ser Gln Glu

TCT GTG GCA GGT TCC AAA CTA GTG CTT CGG TGC GAG ACC AGT TCT GAA         343
                 Ser Val Ala Gly Ser Lys Leu Val Leu Arg Cys Glu Thr Ser Ser Glu

TAC TCC TCT CTC AAG TTC AAG TGG TTC AAG AAT GGG AGT GAA TTA AGC         391
                 Tyr Ser Ser Leu Lys Phe Lys Trp Phe Lys Asn Gly Ser Glu Leu Ser

CGA AAG AAC AAA CCA GAA AAC ATC AAG ATA CAG AAA AGG CCG GGG AAG         439
                 Arg Lys Asn Lys Pro Glu Asn Ile Lys Ile Gln Lys Arg Pro Gly Lys

TCA GAA CTT CGC ATT AGC AAA GCG TCA CTG GCT GAT TCT GGA GAA TAT         487
                 Ser Glu Leu Arg Ile Ser Lys Ala Ser Leu Ala Asp Ser Gly Glu Tyr

ATG TGC AAA GTG ATC AGC AAA CTA GGA AAT GAC AGT TCT GCC AAC             535
                 Met Cys Lys Val Ile Ser Lys Leu Gly Asn Asp Ser Ala Asn
```

Fig. 28B

Nucleotide Sequences & Deduced Amino Acid Sequences of GGF2BPP2

```
ATC ACC ATT GTG GAG TCA AAC GCC ACA TCC ACA TCT ACA GCT GGG ACA    583
Ile Thr Ile Val Glu Ser Asn Ala Thr Ser Thr Thr Ala Gly Thr

AGC CAT GTC GTC AAG TGT GCA GAG AAG GAG AAA ACT TTC TGT GTG AAT    631
Ser His Val Val Lys Cys Ala Glu Lys Glu Lys Thr Phe Cys Val Asn

GGA GGC GAG TGC TTC ATG GTG AAA GAC CTT TCA AAT CCC TCA AGA TAC    679
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT    727
Leu Cys Lys Cys Gln Pro Gly Phe Thr Gly Ala Arg Cys Thr Glu Asn

GTG CCC ATG AAA GTC CAA ACC CAA GAA AGT GCC CAA ATG GCC AGT TTA CTG   775
Val Pro Met Lys Val Gln Thr Gln Glu Ser Ala Gln Met Ser Leu Leu

GTG ATC GCT GCC AAA ACT ACG TAATGGCCAG CTTCTACAGT ACGTCCACTC       826
Val Ile Ala Ala Lys Thr Thr

CCTTTCTGTC TCTGCCTGAA TAGCGCATCT CAGTCGGTGC CGCTTTCTTG TTGCCGCATC   886

TCCCCTCAGA TTCCTCCTAG AGCTAGATGC GTTTACCAG GTCTAACATT GACTGCCTCT    946

GCCTGTCGCA TGAGAACATT AACACAAGCG ATTGTATGAC TTCCTCTGTC CGTGACTAGT  1006

GGGCTCTGAG CTACTCGTAG GTGCGTAAGG CTCCAGTGTT TCTGAAATTG ATCTTGAATT  1066

ACTGTGATAC GACATGATAG TCCCCTCTCAC CCAGTGCAAT GACAATAAAG GCCTTGAAAA 1126

GTCAAAAAAA AAAAAAAAAA AAAAAATCGA TGTCGACTCG AGATGTGGCT GCAGGTCGAC  1186

TCTAGAG                                                            1193
```

Fig. 28C

Nucleotide Sequences & Deduced Amino Acid Sequences of GGF2BPP3

(SEQ ID NO: 135)
(SEQ ID NO: 193)

```
CCTGCAG CAT CAA GTG TGG GCG GCG AAA GCC GGG GGC TTG AAG AAG GAC TCG CTG      55
        His Gln Val Trp Ala Ala Lys Ala Gly Gly Leu Lys Lys Asp Ser Leu

CTC ACC GTG CGC CTG GGC GCC TGG GGC CAC CCC GCC TTC CCC TCC TGC              103
Leu Thr Val Arg Leu Gly Ala Trp Gly His Pro Ala Phe Pro Ser Cys

GGG CGC CTC AAG GAG GAC AGC AGG TAC ATC TTC TTC ATG GAG CCC GAG              151
Gly Arg Leu Lys Glu Asp Ser Arg Tyr Ile Phe Phe Met Glu Pro Glu

GCC AAC AGC AGC GGG CCC CGC CTT CCG AGC CTC CTT CCC CCC                      199
Ala Asn Ser Ser Gly Pro Gly Arg Leu Pro Ser Leu Leu Pro Pro

TCT CGA GAC GGG CCG GAA CCT CAA GGA GGT CAG CCG GGT GCT GTG                  247
Ser Arg Asp Gly Pro Glu Pro Gln Glu Gly Gln Pro Gly Ala Val

CAA CGG TGC GCC TTG CCT CCC CGC TTG AAA GAG ATG AAG AGT CAG GAG              295
Gln Arg Cys Ala Leu Pro Pro Arg Leu Lys Glu Met Lys Ser Gln Glu

TCT GTG GCA GGT TCC AAA CTA GTG CTT GTG CTT GAG ACC AGT TCT GAA              343
Ser Val Ala Gly Ser Lys Leu Val Leu Val Arg Cys Glu Thr Ser Glu

TAC TCC TCT CTC AAG TTC AAG TGG TTC AAG AAT GGG AGT GAA TTA AGC              391
Tyr Ser Ser Leu Lys Phe Lys Trp Phe Lys Asn Gly Ser Glu Leu Ser

CGA AAG AAC AAA CCA GAA AAC ATC AAG ATA CAG AAA AGG CCG GGG AAG              439
Arg Lys Asn Lys Pro Glu Asn Ile Lys Ile Gln Lys Arg Pro Gly Lys

TCA GAA CTT CGC ATT AGC AAA GCG TCA CTG GCT GAT TCT GGA GAA TAT              487
Ser Glu Leu Arg Ile Ser Lys Ala Ser Leu Ala Asp Ser Gly Glu Tyr
```

Fig. 28D

Nucleotide Sequences & Deduced Amino Acid Sequences of GGF2BPP3

```
ATG TGC AAA GTG ATC AGC AAA CTA GGA AAT GAC AGT GCC TCT GCC AAC      535
Met Cys Lys Val Ile Ser Lys Leu Gly Asn Asp Ser Ala Ser Ala Asn

ATC ACC ATT GTG GAG TCA AAC GCC ACA TCC ACA TCT ACA GCT GGG ACA      583
Ile Arg Ile Val Glu Ser Asn Ala Thr Ser Thr Ser Thr Ala Gly Thr

AGC CAT CTT GTC AAG TGT GCA GAG AAA GAC CTT TCA ACT TGT TGT AAT      631
Ser His Leu Val Lys Cys Ala Glu Lys Asp Leu Ser Thr Phe Cys Asn

GGA GGC GAG TGC TTC ATG GTG AAA GAC CTT TCA AAT CCC TCA AGA TAC      679
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC      727
Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTT CCT      775
Val Met Ala Ser Phe Tyr Ser Thr Ser Thr Pro Phe Leu Ser Leu Pro

GAA TAGCGCATCT CAGTCGGTGC CGCTTTCTTG TTGCCGCCATC TCCCCCTCAGA TTCCGCCTAG   838
Glu

AGCTAGATGC GTTTTACCAG GTCTAACATT GACTGCCTCT GCCTGTCGCA TGAGAACATT         898

AACACAAGCG ATTGTATGAC TTCCCTCTGTC CGTGACTAGT GGGCTCTGAG CTACTCGTAG        958

GTGCGTAAGG CTCCAGTGTT TCTGAAATTG ATCTTGAATT ACTGTGATAC GACATGATAG         1018

TCCCTCTCAC CCAGTGCAAT GACAATAAAG GCCTTGAAAA GTCAAAAAAA AAAAAAAAAA         1078

AAAAATCGAT GTCGACTCGA GATGTGGCTG                                          1108
```

Fig. 28E

CODING SEGMENT F: (bovine,top;human,bottom)

```
AGTTTCCCCC CCCAACTTGT CGGAACTCTG GGCTCGCGCG CAGGGCAGGA GCGGAGCGGC      60
GGCGGCTGCC CAGGCGATGC GAGCGCGGGC CGGACGGTAA TCGCCTCTCC CTCCTCGGGC     120
TGCGAGCGCG CCGGACCGAG GCAGCGACAG GAGCGGACCG CGGCGGGAAC CGAGGACTCC     180
CCAGCGGCGC GCCAGCAGGA GCCACCCCGC GAGNCGTGCG ACCGGGACGG AGCGCCCGCC     240
AGTCCCAGGT GGCCCGGACC GCACGTTGCG TCCCCGCGCT CCCCGCCGGC GACAGGAGAC     300
GCTCCCCCCC ACGCCGCGCG CGCCTCGCGG CGGTCGCTGG CCCGCCTCCA CTCCGGGGAC     360
          |||||||||| ||||||||||          ||||||||||  |||
          CGCCTCAGCG CGCCCTCAGC          CGGCCGCTCG CTCTC..CCC CTCGAGGGAC
AAACTTTTCC CGAAGCCGAT CCCAGCCCTC GGACCCAAAC TTGTCGCGCG TCGCCTTCGC     420
|||||||||| |||||||||| ||||||||||  |||||||||                ||||||||||
AAACTTTTCC CAAACCCGAT CCGAGCCCTT GGACCAAA                   TCGCCTGCGC

Met Ser Glu Arg Arg
CGGGAGCCGT CCGGCAGAG CGTGCACTTC TCGGGCGAG ATG TCG GAG CGC AGA         474
|||||||||| ||||||||| ||||| |||| |||||||||| ||| ||| ||| ||| |||
CGAGAGCCGT CCGCGTAGAG CGCTC.CGTC TCCGGCGAG ATG TCC GAG CGC AAA
                                                             K

Glu Gly Lys Gly Lys Gly Lys Gly Lys Lys Asp Arg Gly Ser Gly
GAA GGC AAA GGC AAG GGG AAG GGG AAG AAG GAC CGA GGC TCC GGG          522
||| ||| ||| ||| ||| ||  ||| ||  ||| ||| ||| ||  ||| ||| |||
GAA AGA GGC AAA GGC AAG GGC AAG AAG AAG GAG CGA GGC TCC GGC
 R                                        E

Lys Lys Pro Val Pro Ala Ala Gly Gly Pro Ser Pro Ala
AAG AAG CCC GTG CCC GCG GCT GGC GGC CCG AGC CCA                      559
||| ||| ||| ||  |||  || |||  || ||| ||| ||| |||
AAG AAG CCG GAG TCC GCG GCG GGC AGC CAG AGC CCA
 E          S
```

Coding Segments of Glial Growth Factor/Heregulin Gene 1. (SEQ ID NO: 136)
2. (SEQ ID NO: 197)
3. (SEQ ID NO: 173)
4. (SEQ ID NO: 208)

Fig. 31A

CODING SEGMENT E:

(SEQ ID NO: 137)CC CAT CAN GTG TGG GCG AAA GCC GGG GGC TTG AAG AAG GAC TCG 47
(SEQ ID NO: 198)     His Gln Val Trp Ala Lys Ala Gly Gly Leu Lys Lys Asp Ser

CTG CTC ACC GTG CGC CTG GGC GCC TGG GGC CAC CCC GCC TTC CCC TCC 95
Leu Leu Thr Val Arg Leu Gly Ala Trp Gly His Pro Ala Phe Pro Ser

TGC GGG CGC CTC AAG GAG GAC AGC AGG TAC ATC TTC TTC ATG GAG CCC 143
Cys Gly Arg Leu Lys Glu Asp Ser Arg Tyr Ile Phe Phe Met Glu Pro

GAG GCC AAC AGC AGC GGC GGG CCC CGC CTT CCG AGC CTC CTT CCC 191
Glu Ala Asn Ser Ser Gly Gly Pro Gly Arg Leu Pro Ser Leu Leu Pro

CCC TCT CGA GAC GAC CCG GAA CCT CAA GAA GGA GGT CAG CCG GGT GCT 239
Pro Ser Arg Asp Asp Gly Pro Glu Pro Gln Glu Gly Gly Gln Pro Gly Ala

GTG CAA CGG TGC G 252
Val Gln Arg Cys

Fig. 31B

CODING SEGMENT B: (bovine,top;human,bottom)

```
      Leu Pro Pro Arg Leu Lys Glu Met Lys Ser Gln Glu Ser Val Ala                  (SEQ ID NO: 138)
   CC TTG CCT CCC CGC TTG AAA GAG ATG AAG AGT CAG GAG TCT GTG GCA               47 (SEQ ID NO: 199)
      ||| ||| ||| ——— ||| ||| ||| ||| ||| ||| ||| ||| ——— ||| ———
   CC TTG CCT CCC CGA TTG AAA GAG ATG AAG AGC CAG GAA TCG GCT GCA                  (SEQ ID NO: 174)
                     A                                                             (SEQ ID NO: 210)

Gly Ser Lys Leu Val Leu Arg Cys Glu Thr Ser Ser Glu Tyr Ser Ser                 95
   GGT TCC AAA CTA GTG CTT CGG TGC GAG ACC AGT TCT GAA TAC TCC TCT
   ——— ——— ||| ||| ||| ||| ||| ||| ||| ||| ||| ||| ||| ||| ||| |||
   GGT TCC AAA CTA GTC CTT CGG TGT GAA ACC AGT TCT GAA TAC TCC TCT
           R

Leu Lys Phe Lys Trp Lys Asn Gly Ser Glu Leu Ser Arg Lys Asn                    143
   CTC AAG TTC AAG TGG AAG AAT GGG AGT GAA TTA AGC CGA AAG AAC
   ——— ||| ——— ||| ||| ||| ——— ||| ——— ||| ——— ——— ——— ||| |||
   CTC AGA TTC AAG TGG AAG AAT GGG AAT GAA TTG AAT CGA AAA AAC
                                       N                N

Lys Pro Gln Asn Ile Lys Ile Gln Lys Arg Pro Gly                                 178
   AAA CCA CAA AAC ATC AAG ATA CAG AAA AGG CCG GG
   ——— ||| ||| ||| ——— ||| ——— ||| ||| ——— ——— ———
   AAA CCA CAA AAT ATC AAG ATA CAA AAA AAG CCA GG
                                       K
```

Fig. 31C

CODING SEGMENT A:(bovine,top;human,bottom)

```
(SEQ ID NO: 139)  Lys Ser Glu Leu Arg Ile Ser Lys Ala Ser Leu Ala Asp Ser Gly
(SEQ ID NO: 200)G AAG TCA GAA CTT CGC ATT AGC AAA GCG TCA CTG GCT GAT TCT GGA
                 ||| ||| ||| ||| ||| ||| ||  ||| ||  ||| ||| ||| ||| ||| |||
(SEQ ID NO: 175)G AAG TCA GAA CTT CGC ATT AAC AAA GCA TCA CTG GCT GAT TCT GGA
(SEQ ID NO: 211)                          N
                                                                           46

Glu Tyr Met Cys Lys Val Ile Ser Lys Leu Gly Asn Asp Ser Ala Ser
                  GAA TAT ATG TGC AAA GTG ATC AGC AAA CTA GGA AAT GAC AGT GCC TCT
                  ||| ||| ||| ||| ||| ||| ||| ||| ||| ||  ||| ||  ||| ||| ||| |||
                  GAG TAT ATG TGC AAA GTG ATC AGC AAA TTA GGA AAT GAC AGT GCC TCT
                                                                                94

Ala Asn Ile Thr Ile Val Glu Ser Asn Ala
                  GCC AAC ATC ACC ATT GTG GAG TCA AAC G
                  ||  ||| ||| ||| ||| ||| ||| ||| ||| |
                  GCC AAT ATC ACC ATC GTG GAA TCA AAC G
                                                                    122
```

Fig. 31D

CODING SEGMENT A'

(SEQ ID NO: 140) TCTAAAACTA CAGAGACTGT ATTTTCATGA TCATCATAGT TCTGTGAAAT ATACTTAAAC    60

CGCTTTGGTC CTGATCTTGT AGG AAG TCA GAA CTT CGC ATT AGC AAA GCG    110
(SEQ ID NO: 206)                Lys Ser Glu Leu Arg Ile Ser Lys Ala

TCA CTG GCT GAT TCT GGA GAA TAT ATG TGC AAA GTG ATC AGC AAA CTA    158
Ser Leu Ala Asp Ser Gly Glu Tyr Met Cys Lys Val Ile Ser Lys Leu

GGA AAT GAC AGT GCC TCT GCC AAC ATC ACC ATT GAG TCA AAC GGT    206
Gly Asn Asp Ser Ala Ser Ala Asn Ile Thr Ile Val Glu Ser Asn Gly

AAG AGA TGC CTA CTG CGT GCT ATT TCT CAG TCT CTA AGA GGA GTG ATC    254
Lys Arg Cys Leu Leu Arg Ala Ile Ser Gln Ser Leu Arg Gly Val Ile

AAG GTA TGT GGT CAC ACT TGAATCACGC AGGTGTGTGA AATCTCATTG    302
Lys Val Cys Gly His Thr

TGAACAAATA AAAATCATGA AAGGAAAACT CTATGTTTGA AATATCTTAT GGGTCCTCCT    362

GTAAAGCTCT TCACTCCATA AGTGAAATA GACCTGAAAT ATATATAGAT TATTT    417

Fig. 31E

CODING SEGMENT G: (bovine, top; human, bottom)

```
                                                                                              47
(SEQ ID NO: 201)Glu Ile Thr Thr Gly Met Pro Ala Ser Thr Glu Thr Ala Tyr Val Ser
(SEQ ID NO: 141)AG  ATC ACC ACT GGC ATG CCA GCC TCA ACT GAG ACA GCG TAT GTG TCT
                    ||| ||| ||| ||| ||| ||| ||| ||| ||| ||| ||| ||| ||| ||| |||
(SEQ ID NO: 213)AG  ATC ACT GGT ATG CCA GCC TCA ACT GAA GGA GCA TAT GTG TCT
(SEQ ID NO: 176)        I                                      G

95
                Ser Glu Ser Pro Ile Arg Ile Ser Val Ser Thr Glu Gly Thr Asn Thr
                TCA GAG TCT CCC ATT AGA ATA TCA GTA TCA ACA GAA GGA ACA AAT ACT
                ||| ||| ||| ||| ||| ||| ||| ||| ||| ||| ||| ||| ||| ||| ||| |||
                TCA GAG TCT CCC ATT AGA ATA TCA GTA TCA ACA GAA GGA GCA AAT ACT
                                                                        A

102
                Ser Ser Ser
                TCT TCA T
                ||| ||| —
                TCT TCA T
```

Fig. 31F

CODING SEGMENT C: (bovine,top; human,bottom)

```
                    Thr Ser Thr Ser Ala Gly Thr Ser His Leu Val Lys Cys Ala
(SEQ ID NO: 202)    ACA TCC ACA TCT GCT GGG ACA AGC CAT CTT GTC AAG TGT GCA    47
(SEQ ID NO: 160) CC  ||| ||| ||| ||  |   ||| ||| ||| ||| ||| ||| ||| ||| ||
(SEQ ID NO: 177) CT ACA TCT ACA TCC ACT GGG ACA AGC CAT CTT GTA AAA TGT GCG
(SEQ ID NO: 214)                        T

Glu Lys Thr Phe Cys Val Asn Gly Gly Glu Cys Phe Met Val
                    GAG AAA ACT TTC TGT GTG AAT GGA GGC GAG TGC TTC ATG GTG    95
                    ||| ||| ||| ||| ||| ||| ||| ||| ||| ||| ||| ||| ||| |||
                    GAG AAA ACT TTC TGT GTG AAT GGA GGG GAG TGC TTC ATG GTG

Lys Asp Leu Ser Asn Pro Ser Arg Tyr Leu Cys
                    AAA GAC CTT TCA AAT CCC TCA AGA TAC TTG TGC                128
                    ||| ||| ||| ||| ||| ||| |   ||| ||| ||| |||
                    AAA GAC CTT TCA AAC CCC TCG AGA TAC TTG TGC
```

Fig. 31G

CODING SEGMENT C/D: (bovine,top;human,bottom)

```
1  Lys Cys Gln Pro Gly Phe Thr Gly Ala Arg Cys Thr Glu Asn Val Pro                48
2  AAG TGC CAA CCT GGA TTC ACT GGA GCG AGA TGT ACT GAG AAT GTG CCC
    ||| ||| ||| ||| ||| ||| ||| ||| ||  ||| ||| ||| ||| ||| ||| |||
3  AAG TGC CAA CCT GGA TTC ACT GGA GCA AGA TGT ACT GAG AAT GTG CCC

Met Lys Val Gln Thr Gln Glu                                                    69
4  ATG AAA GTC CAA ACC CAA GAA
    ||| ||| ||| ||| ||  ||| |||
   ATG AAA GTC CAA AAC CAA GAA
                    N
```

1. (SEQ ID NO: 203)
2. (SEQ ID NO: 142)
3. (SEQ ID NO: 178)
4. (SEQ ID NO: 215)

Fig. 31H

CODING SEGMENT C/D' (bovine,top;human,bottom)

(SEQ ID NO: 207) Lys Cys Pro Asn Glu Phe Thr Gly Asp Arg Cys Gln Asn Tyr Val Met
(SEQ ID NO: 143) AAG TGC CCA AAT GAG TTT ACT GGT GAT CGC TGC CAA AAC TAC GTA ATG    48
                 ||| ||| ||| ||| ||| ||| ||| ||| ||| ||| ||| ||| ||| ||| ||| |||
                 AAG TGC CCA AAT GAG TTT ACT GGT GAT CGC TGC CAA AAC TAC GTA ATG

Ala Ser Phe Tyr
                 GCC AGC TTC TAC                                                    60
                 ||| ||| ||| |||
                 GCC AGC TTC TAC

Fig. 31I

CODING SEGMENT D: (SEQ ID NO: 144 bovine,top;human,bottom)

(SEQ ID NO: 208) Ser Thr Ser Thr Pro Phe Leu Ser Leu Pro Glu *
(SEQ ID NO: 144) AGT ACG TCC ACT CCC TTT CTG TCT CTG CCT GAA TAG    36
                 ||| ||| ||| ||| ||| ||| ||| ||| ||| ||| ||| |||
                 AGT ACG TCC ACT CCC TTT CTG TCT CTG CCT GAA TAG

Fig. 31J

CODING SEGMENT D': (human)

(SEQ ID NO: 216) Lys His Leu Gly Ile Glu Phe Met Glu
(SEQ ID NO: 145) AAG CAT CTT GGG ATT GAA TTT ATG GAG    27

Fig. 31K

CODING SEGMENT H: (bovine,top;human,bottom)

```
(SEQ ID NO: 204) Lys Ala Glu Leu Tyr Gln Lys Arg Val Leu Thr Ile Thr Gly Ile
(SEQ ID NO: 146) AAA GCG GAG CTC TAC CAG AAG AGA GTG CTC ACC ATT ACC GGC ATT    48
                 ||| ||| ||| ||| ||| ||| ||| ||| ||| ||| ||| ||| ||| ||| |||
(SEQ ID NO:  44) AAG GCG GAG CTG TAC CAG AAG AGA GTG CTG ACC ATA ACC GGC ATC
(SEQ ID NO: 217)

Cys Ile Ala Leu Leu Val Val Gly Ile Met Cys Val Val Tyr Cys
                 TGC ATC GCG CTG CTC GTT GGC ATC ATG TGT GTG GTC TAC TGC        96
                 ||| ||| ||| ||| ||| ||| ||| ||| ||| ||| ||| ||| ||| |||
                 TGC ATC GCC CTC CTT GTG GGC ATC ATG TGT GTG GTG GCC TAC TGC
                                                                 A

Lys Thr Lys Lys Gln Arg Lys Lys Leu His Asp Arg Leu Arg Gln Ser
                 AAA ACC AAG AAA CAA CGG AAA AAG CTT CAT GAC CGG CTT CGG CAG AGC   144
                 ||| ||| ||| ||| ||| ||| ||| ||| ||| ||| ||| ||| ||| ||| |||
                 AAA ACC AAG CAG CAG AAA AAG CTG CAT GAC CGT CGT CGG CAG AGC

Leu Arg Ser Glu Arg Asn Thr Met Met Asn Val Ala Asn Gly Pro His
                 CTT GAA AGA AAC ACC ATG ATG AAC GTA GCC AAC GGG CCC CAC           192
                 ||| ||| ||| ||| ||| ||| ||| ||| ||| ||| ||| ||| ||| |||
                 CTT CGG TCT GAA CGA AAC ATG ATG AAC GCC ATT GCC AAT GGG CCT CAC
                                 N                        T

His Pro Asn Pro Pro Glu Asn Val Gln Leu Val Asn Gln Tyr Val
                 CAC CCC AAT CCG CCC GAG AAC GTG CAG CTG GTG AAT CAA TAC GTA       240
                 ||| ||| ||| ||| ||| ||| ||| ||| ||| ||| ||| ||| ||| ||| |||
                 CAT CCT AAC CCA CCA GAG AAT GTC CAG CTG GTG AAT CAA TAC GTA

Ser Lys Asn Val Ile Ser Glu His Ile Val Glu Arg Glu Ala Glu
                 TCT AAA AAT GTC ATC TCT AGC GAG CAT ATT GTT GAG AGA GCG GAG       288
                 ||| ||| ||| ||| ||| ||| ||| ||| ||| ||| ||| ||| ||| ||| |||
                 TCT AAA AAC GTC AGT TCC GAG CAT ATT GTT GAG AGA GCA GAA GAG
```

CODING SEGMENT K: (HUMAN)

```
(SEQ ID NO: 161) A CAT AAC CTT ATA GCT GAG CTA AGG AGA AAC AAG GCC CAC AGA TCC    46
(SEQ ID NO: 218)    His Asn Leu Ile Ala Glu Leu Arg Arg Asn Lys Ala His Arg Ser

AAA TGC ATG CAG ATC CAG CTT TCC GCA ACT CAT CTT AGA GCT TCT TCC    94
                 Lys Cys Met Gln Ile Gln Leu Ser Ala Thr His Leu Arg Ala Ser Ser

ATT CCC CAT TGG GCT TCA TTC TCT AAG ACC CCT TGG CCT TTA GGA AG    141
                 Ile Pro His Trp Ala Ser Phe Ser Lys Thr Pro Trp Pro Leu Gly Arg
```

Fig. 31N

CODING SEGMENT L: (bovine,top;human,bottom)

```
       Tyr Val Ser Ala Met Thr Thr Pro Ala Arg Met Ser Pro Val Asp
1    G TAT GTA TCA GCA ATG ACC ACC CCG GCT CGT ATG TCA CCT GTA GAT ===   46
2    ===|===|===|===|===|===|===|===|===|===|===|===|===|===|===|
3    G TAT GTG TCA GCC ATG ACC ACC CCG GCT CGT ATG TCA CCT GTA GAT ===
4

Phe His Thr Pro Ser Ser Pro Lys Ser Pro Pro Ser Glu Met Ser Pro
1      TTC CAC ACG CCA AGC TCC CCC AAG TCA CCC CCT TCG GAA ATG TCC CCG   94
2      ===|===|===|===|===|===|===|===|===|===|===|===|===|===|===|===|
3      TTC CAC ACG CCA AGC TCC CCC AAA TCG CCC CCT TCG GAA ATG TCT CCA
4

Pro Val Ser Ser Thr Thr Val Ser Met Pro Ser Met Ala Val Ser Pro
1      CCC GTG TCC AGC ACG ACG GTC TCC ATG CCC ATG GCG GTC AGT CCC       142
2      ===|===|===|===|===|===|===|===|===|===|===|===|===|===|===|===|
3      CCC GTG TCC AGC ACG ACG GTG TCC ATG CCT ATG GCG GTC AGC CCC
4         M

Phe Val Glu Glu Arg Pro Leu Leu Val Thr Pro Pro Arg Leu
1      TTC GTG GAA GAG AGA CCC CTC CTT GTG ACG CCA CCA CGG CTG            190
2      ===|===|===|===|===|===|===|===|===|===|===|===|===|===|
3      TCC ATG GAA GAG AGA CCT CTA CTT GTG ACA CCA CCA AGG CTG
4       N

Arg Glu Lys  -  Tyr Asp His His Ala Gln Gln Phe Asn Ser Phe His
1      CGG GAG AAG ... TAT GAC CAC CAC GCC CAG CAA TTC AAC TCG TTC CAC   238
2      ===|===|===|===|===|===|===|===|===|===|===|===|===|===|===|===|
3      CGG GAG AAG AAG TTT GAC CAT CAC CCT CAG CAG TTC AGC TCC TTC CAC
4       K              F                  P

Cys Asn Pro Ala His Glu Ser Asn Ser Leu Pro Pro Ser Pro Leu Arg
1      TGC AAC CCC GCG CAT GAG AGC AAC AGC CTG CCC CCC AGC CCC TTG AGG   286
2      ===|===|===|===|===|===|===|===|===|===|===|===|===|===|===|===|
3      CAC AAC CCC GCG CAT GAC AGT GAC AAC AGC CTC CCT GCT AGC CCC TTG AGG
4                          D                           A
```

1. (SEQ ID NO: 205)
2. (SEQ ID NO: 147)
3. (SEQ ID NO: 77)
4. (SEQ ID NO: 219)

Fig. 31O

```
Ile Val Glu Asp Glu Glu Tyr Glu Thr Gln Glu Tyr Glu Pro Ala
ATA GTG GAG GAT GAG GAA TAT GAA ACG CAG GAG TAC GAA CCA GCT    334
||| ||| ||| ||| ||| ||  ||| ||| ||| ||  ||| ||| ||| ||| ||
ATA GTG GAG GAT GAG GAG TAT GAA ACG CAA GAG TAC GAG CCA GCC

Gln Glu Pro Val Lys Lys Leu Thr Asn Ser Ser Arg Arg Ala Lys Arg
CAA GAG CCG GTT AAA CTC ACC AAC AGC AGC CGG CGG GCC AAA AGA    382
||| ||| ||  ||  ||| ||| ||| ||  ||| ||| ||| ||| ||| ||| |||
CAA GAG CCT GTT AAG CTC AAA CTC GCC AA. ..T AGC CGG GCC AAA AGA
                            A

Thr Lys Pro Asn Gly His Ile Ala His Arg Leu Glu Met Asp Asn Asn
ACC AAG CCC AAT GGT CAC ATT GCC CAC AGG TTG GAA ATG GAC AAC AAC    430
||| ||| ||| ||  ||| ||| ||| ||  ||| ||| ||| ||| ||| ||| ||| |||
ACC AAG CCC AAT GGC CAC ATT GCT AAC AGA TTG GAA GTG GAC AGC AAC
                            N               V           S

Thr Gly Ala Asp Ser Ser Asn Ser Glu Ser Glu Thr Glu Asp Glu Arg
ACA GGC GCT GAC AGC AGT AAC TCA GAG AGC GAA ACA GAG GAT GAA AGA    478
||| ||  ||  --- ||| ||| ||  ||| ||| ||| ||| ||| ||| ||| ||| |||
ACA AGC TCC CAG --- AGT AAC TCA GAG AGT GAA ACA GAA GAT GAA AGA
    S   S   Q

Fig. 31P
```

```
Val Gly Asp Thr Pro Phe Leu Ala Ile Glu Asn Pro Leu Ala Ala
GTA GGA GAT ACG CCT TTC CTG GCC ATA CAG AAC CCC CTG GCA GCC      526
=== === === === === === === === === === === === === === ===
GTA GAA GAT ACG CCT TTC CTG GGC ATA CAG AAC CCC CTG GCA GCC
                            G

Ser Leu Glu Ala Ala Pro Ala Phe Arg Leu Val Asp Ser Arg Thr Asn
AGT CTC GAG GCG GCC CCT GCC TTC CGC CTG GTC GAC AGC AGG ACT AAC  574
=== === === === === === === === === === === === === === === ===
AGT CTT GAG GCA ACA CCT GCC TTC CGC CTG GCT GAC AGC AGG ACT AAC
                T                       A

Pro Thr Gly Gly Phe Ser Pro Gln Glu Glu Leu Gln Ala Arg Leu Ser
CCA ACA GGC CGC TCT CCG CAG GAA GAA TTG CAG GCC AGG CTC TCC      622
=== === === === === === === === === === === === === === === ===
CCA GCA GGC CGC TTC TCG ACA CAG GAA GAA ATC CAG GCC AGG CTG TCT
    A           R       T                I

Gly Val Ile Ala Asn Gln Asp Pro Ile Ala Val *
GGT GTA ATC GCT AAC CAA GAC CCT ATC GCT GTC TAA AAC CGA AAT ACA  672
=== === === === === === === === === === === === === === === ===
AGT GTA ATT GCT AAC CAA GAC CCT ATT GCT GTA TAA AAC CTA AAT AAA
S

CCC ATA GAT TCA CCT GTA AAA CTT TAT TTT ATA TAA TAA AGT ATT CCA  718
=== === === === === === === === === === === === === === === ===
CAC ATA GAT TCA CCT GTA AAA CTT TAT TTT ATA TAA TAA AGT ATT CCA

CCT TAA ATT AAA CAA                                              733
=== === === === ===
CCT TAA ATT AAA CAA
```

Fig. 31Q (SEQ ID NO: 163)
(SEQ ID NO: 210)

HUMAN CODING SEGMENT E:

```
ATG AGA TGG CGA CGC GCC CCG CGC GCC CCC GGC CCC CGG                             48
Met Arg Trp Arg Arg Ala Pro Arg Ala Pro Gly Pro Arg

GCC CAG CGC CCC GGC TCC GGG CGT CCC GGC CTG CCC CTG                             96
Ala Gln Arg Pro Gly Ser Gly Arg Pro Gly Leu Pro Leu

CTG CCA CTA CTG CTG CTG CTG CTG TCG CCG CCG CCG CCG                            144
Leu Pro Leu Leu Leu Leu Leu Leu Ser Pro Pro Pro Pro

GCG GGC AAC GAG GTG GCT GCG GCG ACC GCC GCG GGG GCG                            192
Ala Gly Asn Glu Val Ala Ala Ala Thr Ala Ala Gly Ala

TCC CCG CCC AGC GAG GTG GGA TCG AGC GCG TCG GCC TGC                            240
Ser Pro Pro Ser Glu Val Gly Ser Ser Ala Ser Ala Cys

GTG GTG ATC GAG AAG GTG CAG AAG CTA CAG GCT CAG CGC                            288
Val Val Ile Glu Lys Val Gln Lys Leu Gln Ala Gln Arg

CTC GAC AGG AAG GCG GCG CCA CAC GGC CAC CGG CAG GCA                            336
Leu Asp Arg Lys Ala Ala Pro His Gly His Arg Gln Ala

GGC GAT CGC GAG GAG CCA GCC AAC GGC GAG CGG GCG GCG                            384
Gly Asp Arg Glu Glu Pro Ala Asn Gly Glu Arg Ala Ala

GCC GAG GAG CCG CTG CTC CCC GCC GCC GCC ACC GTG CTG                            432
Ala Glu Glu Pro Leu Leu Pro Ala Ala Ala Thr Val Leu

ACC CCG GTG CCC AGC GCC GCG GGG GAG GAG CCC CCC TCT                            480
Thr Pro Val Pro Ser Ala Ala Gly Glu Glu Pro Pro Ser

CTG GTG AAG GTG CAC CAG GTG TGG GCG GTG AAA GCC GGC                            528
Leu Val Lys Val His Gln Val Trp Ala Val Lys Ala Gly

AAG GAC TCG CTC ACC CGC GTG CTG GGG ACC TGG CAC GGC                            576
Lys Asp Ser Leu Thr Arg Val Leu Gly Thr Trp Gly Gly

TTC CCC TGC TGG CCC AGG CTC AAG GAG GAG GAC TAC ATC                            624
Phe Pro Cys Trp Pro Arg Leu Lys Glu Glu Asp Tyr Ile

ATG GAG CCC GAC GCC AAC AGC ACC AGC GCC CGC GCC AAG                            672
Met Glu Pro Asp Ala Asn Ser Thr Ser Ala Arg Ala Lys

GCC TCT TTC CCC CCT CTG GAG ACG CGG AAC CTC AAG GAG                            720
Ala Ser Phe Pro Pro Leu Glu Thr Arg Asn Leu Lys Glu

AGC CGG GTG CTG TGC AAG CGG TGC G                                              745
Ser Arg Val Leu Cys Lys Arg Cys
```

Fig. 31R

GGF2BPP5 Nucleotide Sequence & Deduced Protein Sequence (SEQ ID NO 148)

```
AGTTCCCCCC CCCAACTTGT CGGAACTCTG GGCTCGCGCG CAGGGCAGGA GCGGAGCGGC        60
GGCGGCTGCC CAGGCGATGC GAGGCGCGGGC CGGACGGTAA TCGCCTCTCC CTCCTCGGGC       120
TGCGAGCGCG CCGGACCGAG GCAGCGACAG GAGCGGACCG CGGCGGGAAC CGAGGACTCC       180
CCAGCGGCGC GCCAGCAGGA GCCACCCCGC GAGCGTGCGA CCGGACGGA GCGCCCGCCA       240
GTCCCAGGTG GCCCGGACCG CACGTTGCGT CCCCGCGCTC CCCGCCGGCG ACAGGAGACG       300
CTCCCCCCCA CGCCGCGCGC GCCTCGGCCC GGTCGCTGGC CCGCCTCCAC TCCGGGACA       360
AACTTTCCC GAAGCCGATC CCAGCCCTCG GACCCAAACT TGTCGCGCGT CGCCTTCGCC       420
GGGAGCCGTC CGCGCAGAGC GTGCACTTCT CGGGGCGAG ATG TCG GAG CGC AGA         475
                                         Met Ser Glu Arg Arg
```

(SEQ ID NO 195)

```
GAA GGC AAA GGC AAG GGG AAG GGC GGG AAG GAC CGA GGC TCC GGG            523
Glu Gly Lys Gly Lys Gly Lys Gly Gly Lys Asp Arg Gly Ser Gly

AAG AAG CCC GTG CCC GCG GCT GGC ATG AGC CCG AGC CCA GCC TTG CCT CCC    571
Lys Lys Pro Val Pro Ala Ala Gly Met Ser Pro Ser Pro Ala Leu Pro Pro

CGC TTG AAA GAG ATG AAG CAG GAG TCT GTG GCA GGT TCC AAA CTA            619
Arg Leu Lys Glu Met Lys Gln Glu Ser Val Ala Gly Ser Lys Leu

GTG CTT CGG TGC GAG ACC AGT TCT GAA TAC TCC AAG TTC CTC AAG TTC AAG    667
Val Leu Arg Cys Glu Thr Ser Ser Glu Tyr Ser Lys Leu Lys Phe Lys

TGG TTC AAG AAT GGG AGT GAA TTA AGG CGA AAG AAC CCA CAA AAC            715
Trp Phe Lys Asn Gly Ser Glu Leu Ser Arg Lys Asn Pro Gln Asn

ATC AAG ATA CAG CAG AAA AGG CCG GGG TCA GAA CTT CGC ATT AGC AAA        763
Ile Lys Ile Gln Gln Lys Arg Pro Gly Ser Glu Leu Arg Ile Ser Lys

GCG TCA CTG GCT GAT TCT GGA GAA TAT ATG TGC AAA GTG ATC AGC AAA        811
Ala Ser Leu Ala Asp Ser Gly Glu Tyr Met Cys Lys Val Ile Ser Lys
```

Fig. 32A

GGF2BPP5 Nucleotide Sequence & Deduced Protein Sequence

```
CTA GGA AAT GAC AGT GCC TCT GCC AAC ATC ACC ATT GTG GAG TCA AAC      859
Leu Gly Asn Asp Ser Ala Ser Ala Asn Ile Thr Ile Val Glu Ser Asn

GAG ATC ACC ACT GGC ATG CCA GCC TCA ACT GAG ACA GCG TAT GTG TCT      907
Glu Ile Thr Thr Gly Met Pro Ala Ser Thr Glu Thr Ala Tyr Val Ser

TCA GAG TCT CCC ATT AGA ATA TCA GTA TCA ACA GAA GGA ACA AAT ACT      955
Ser Glu Ser Pro Ile Arg Ile Ser Val Ser Thr Glu Gly Thr Asn Thr

TCT TCA TCC ACA TCC ACA TCT ACA GCT GGG ACA AGC CAT CTT GTC AAG     1003
Ser Ser Ser Thr Ser Thr Ser Thr Ala Gly Thr Ser His Leu Val Lys

TGT GCA GAG AAG AAA ACT TTC TGT GTG AAT GGA GGC GAG TGC TTC         1051
Cys Ala Glu Lys Lys Thr Phe Cys Val Asn Gly Gly Glu Cys Phe

ATG GTG AAA GAC CTT CTT TCA AAT CCC TCA AGA TAC TTG TGC AAG TGC CCA 1099
Met Val Lys Asp Leu Leu Ser Asn Pro Ser Arg Tyr Leu Cys Lys Cys Pro

AAT GAG TTT ACT GGT GAT CGC TTT CTG TAC CAA AAC TAC GTA ATG GCC TTC 1147
Asn Glu Phe Thr Gly Asp Arg Phe Leu Tyr Gln Asn Tyr Val Met Ala Ser Phe

TAC AGT TCC ACG TCC ACT CCC TTT CTG TCT CCT GAA TAGGCGCATG         1193
Tyr Ser Thr Ser Thr Pro Phe Leu Ser Pro Glu

CTCAGTCGGT GCCGCTTTCT TGTTGCCGCA TCTCCCCTCA GATTCAACCT AGAGCTAGAT  1253

GCGTTTTACC AGTCTAACA TTGACTGCCT CTGCCTGTCG CATGAGAACA TTAACACAAG   1313

CGATTGTATG ACTTCCTCTG TCCGTGACTA GTGGGCTCTG AGCTACTCGT AGGTGCGTAA  1373

GGCTCCAGTG TTTCTGAAAT TGATCTTGAA TTACTGTGAT ACGACATGAT AGTCCCTCTC  1433

ACCCAGTGCA ATGACAATAA AGGCCTTGAA AAGTCTCACT TTTATTGAGA AAATAAAAAT  1493

CGTTCCACGG GACAGTCCCT CTTCTTTATA AATGACCCT ATCCTTGAAA AGGAGGTGTG   1553

TTAAGTTGTA ACCAGTACAC ACTTGAAATG ATGGTAAGTT CGCTTCGGTT CAGAATGTGT  1613

TCTTTCTGAC AAATAAACAG AATAAAAAAA AAAAAAAAA A                       1654
```

Fig. 32B

GGF2BPP2 Nucleotide Sequence & Deduced Protein Sequence

```
(SEQ ID NO: 149) CAT CAN GTG TGG GCG AAA GCC GGG GGC TTG AAG GAC TCG CTG        48
(SEQ ID NO: 192) His Gln Val Trp Ala Lys Ala Gly Gly Leu Lys Asp Ser Leu

CTC ACC GTG CGC CTG GGC GCC TGG GGC CAC CCC GCC TTC CCC TGC    96
                 Leu Thr Val Arg Leu Gly Ala Trp Gly His Pro Ala Phe Pro Cys

GGG CGC CTC AAG GAG GAC AGC TAC ATC TTC TTC ATG GAG CCC GAG   144
                 Gly Arg Leu Lys Glu Asp Ser Tyr Ile Phe Phe Met Glu Pro Glu

GCC AAC AGC AGC GGG CCC CGC GGC CTT CCG AGC CTC CTT CCC CCC   192
                 Ala Asn Ser Ser Gly Pro Arg Gly Leu Pro Ser Leu Leu Pro Pro

TCT CGA GAC CCG GAA CCT CAA GGT GGA CCG CAG GGT GCT GTG       240
                 Ser Arg Asp Pro Glu Pro Gln Gly Gly Pro Gln Gly Ala Val

CAA CGG TGC GCC TTG CCT CCC CGC AAA CTA GTG CTT CTT CGG CTT   288
                 Gln Arg Cys Ala Leu Pro Pro Arg Lys Leu Val Leu Leu Arg Leu

TCT GTG GCA GGT TCC AAA CTA GTG CTT TTC AAG TGG TTC AAG AAT   336
                 Ser Val Ala Gly Ser Lys Leu Val Leu Phe Lys Trp Phe Lys Asn

TAC TCC TCT CTC AAG TTC AAG TGG TTC AAG AAT GGG AGT GAA TTA AGC  384
                 Tyr Ser Ser Leu Lys Phe Lys Trp Phe Lys Asn Gly Ser Glu Leu Ser

CGA AAG AAC CCA GAA AAC ATC AAG ATA ATA CAG AAG AGG CCG GGG AAG  432
                 Arg Lys Asn Pro Glu Asn Ile Lys Ile Ile Gln Lys Arg Pro Gly Lys

TCA GAA CTT CGC ATT AGC AAA GCG TCA CTG GCT GAT TCT GGA GAA TAT  480
                 Ser Glu Leu Arg Ile Ser Lys Ala Ser Leu Ala Asp Ser Gly Glu Tyr

ATG TGC AAA GTG ATC AGC AAG AAA CTA GGA AAT GAC AGT GCC TCT AAC  528
                 Met Cys Lys Val Ile Ser Lys Lys Leu Gly Asn Asp Ser Ala Ser Asn
```

Fig. 33A

GGF2BPP2 Nucleotide Sequence & Deduced Protein Sequence

```
ATC ACC ATT GTG GAG TCA AAC GCC ACA TCC ACA TCT ACA GCT GGG ACA    576
Ile Thr Ile Val Glu Ser Asn Ala Thr Ser Thr Ser Thr Ala Gly Thr

AGC CAT GTC AAG CTT GTC AAG TGT GCA GAG AAG GAG AAA ACT TTC TGT GTG AAT    624
Ser His Val Lys Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    672
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT    720
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT    768
Val Pro Met Lys Val Gln Thr Gln Glu Lys Cys Pro Asn Glu Phe Thr

GGT GAT CGC TGC CAA TAC GTA ATG TAC TTC TAC AGT ACG TCC    816
Gly Asp Arg Cys Gln Tyr Val Met Tyr Phe Tyr Ser Thr Ser

ACT CCC TTT CTG TCT CCT CTG GAA TAGCGCATCT CAGTCGGTGC CGCTTTCTTG    870
Thr Pro Phe Leu Ser Pro Leu Glu

TTGCCGCATC TCCCCCTCAGA TTCCNCCTAG AGCTAGATGC GTTTTACCAG GTCTAACATT    930

GACTGCCTCT GCCTGTCGCA TGAGAACATT AACACAAGCG ATTGTATGAC TTCCTCTGTC    990

CGTGACTAGT GGGCTCTGAG CTACTCGTAG GTGCGTAAGG CTCCAGTGTT TCTGAAATTG    1050

ATCTTGAATT ACTGTGATAC GACATGATAG TCCCCTCTCAC CCAGTGCAAT GACAATAAAG    1110

GCCTTGAAAA GTCAAAAAAA AAAAAAAAAA    1140
```

Fig. 33B

GGF2BPP4 Nucleotide Sequence & Deduced Protein Sequence (SEQ ID NO: 150) G AAG TCA GAA CTT CGC ATT AGC AAA GCG TCA CTG GCT GAT TCT GGA GAA    49
(SEQ ID NO: 194)   Lys Ser Glu Leu Arg Ile Ser Lys Ala Ser Leu Ala Asp Ser Gly Glu TAT ATG TGC AAA GTG ATC AGC AAA CTA GGA AAT GAC AGT GCC TCT GCC    97
Tyr Met Cys Lys Val Ile Ser Lys Leu Gly Asn Asp Ser Ala Ser Ala AAC ATC ACC ATT GTG GAG ATT GTG TCA AAC GCC ACA TCC ACA TCT GCT GGG   145
Asn Ile Thr Ile Val Glu Ile Val Ser Asn Ala Thr Ser Thr Ala Gly ACA AGC CAT CTT GTC AAG GAG TGT GCA GAG AAG GAG AAA ACT TTC TGT GTG   193
Thr Ser His Leu Val Lys Glu Cys Ala Glu Lys Glu Lys Thr Phe Cys Val AAT GGA GGC GAC TGC TTC ATG GTG AAA GAC CTT TCA AAT CCC TCA AGA       241
Asn Gly Gly Asp Cys Phe Met Val Lys Asp Leu Ser Asn Pro Ser Arg TAC TTG TGC AAG TGC CAA CCT GGA TTC ACT GGA GCG AGA TGT ACT GAG       289
Tyr Leu Cys Lys Cys Gln Pro Gly Phe Thr Gly Ala Arg Cys Thr Glu AAT GTG CCC ATG AAA GTC CAA ACC CAA GAA GCG AAA GCG GAG GAG CTC TAC   337
Asn Val Pro Met Lys Val Gln Thr Gln Glu Ala Lys Ala Glu Glu Leu Tyr CAG AAG AGA GTG CTC ACC ATT ACC GGC ATT ACC TGC ATC GCG CTG CTC GTG   385
Gln Lys Arg Val Leu Thr Ile Thr Gly Ile Thr Cys Ile Ala Leu Leu Val GTT GGC ATC ATG ATG TGT GTG GTC TAC CAG CTT CGG AGC TCT GAA AGA AAC   433
Val Gly Ile Met Met Cys Val Val Tyr Gln Leu Arg Ser Ser Glu Arg Asn AAA AAG CTT CAT GAC CGG CTT CGG CAG AGC CCC AAC CAC CCC AAT CCG CCC CCC   481
Lys Lys Leu His Asp Arg Leu Arg Gln Ser Pro Asn His Pro Asn Pro Pro ACC ATG ATC AAC GTA GCC AAC GGG CCC CAC CAC CCC AAT CCG CCC CCC       529
Thr Met Met Asn Val Ala Asn Gly Pro His His Pro Asn Pro Pro Pro GAG AAC GTG CAG CTG GTG AAT CAA TAC GTA TCT AAA AAT GTC ATC TCT       577
Glu Asn Val Gln Leu Val Asn Gln Tyr Val Ser Lys Asn Val Ile Ser

Fig. 34A

GGF2BPP4 Nucleotide Sequence & Deduced Protein Sequence

```
AGC GAG CAT ATT GTT GAG AGA GAG GCG GAG AGC TCT TTT TCC ACC AGT      625
Ser Glu His Ile Val Glu Arg Glu Ala Glu Ser Phe Ser Thr Ser

CAC TAC ACT TCG ACA GCT CAT CAT CAT AGC ACT ACT GTC ACT CAG ACT CCC  673
His Tyr Thr Ser Thr Ala His His His Ser Thr Thr Val Thr Gln Thr Pro

AGT CAC AGC TGG AGC AAT GGA CAC CAC ACT GAA AGC ATC ATT TCG GAA AGC  721
Ser His Ser Trp Ser Asn Gly His His Thr Glu Ser Ile Ile Ser Glu Ser

CAC TCT GTC ATC GTG ATG TCA TCC GTA GAA AAC AGT AGG CAC AGC AGC      769
His Ser Val Ile Val Met Ser Ser Val Glu Asn Ser Arg His Ser Ser

CCG ACT GGG GGC CCG AGA CGT CTC AAT GGC TTG GGA GGC CCT CGT          817
Pro Thr Gly Gly Pro Arg Arg Leu Asn Gly Leu Gly Gly Pro Arg

GAA TGT TCT CCT CAT CAG AGA GAA CAT AAC GCC AGA GAA CTT ATA GCT TCC TAC  865
Glu Cys Ser Pro His Arg Glu His Asn Ala Arg Glu Leu Ile Ala Ser Tyr

CGA GAC TCT CAT AGT GAA AGA AAC TGC ATG CAG ATC CAG CTT TCC GAG CTA AGG 913
Arg Asp Ser His Ser Glu Arg Asn Cys Met Gln Ile Gln Leu Ala Glu Leu Arg

AGA AAC GCC AAG TCC AGA TCC ATT CCC CAT TGG GCT TCA TTC TCT TCC GCA  961
Arg Asn Ala Lys Ser Arg Ser Ile Pro His Trp Ala Ser Phe Ser Ala

ACT CAT CTT AGA GCT TCT CCT CCT ATT CCC ATT GTA GCA ATG ACC ACC CCG GCT 1009
Thr His Leu Arg Ala Ser Pro Pro Ile Pro Ile Val Ala Met Thr Thr Pro Ala

ACC CCT TGG CCT TTA GGA AGG TAT GTA TCA AGC CCA ACC TCC AAG          1057
Thr Pro Trp Pro Leu Gly Arg Tyr Val Ser Ala Met Thr Thr Pro Lys

CGT ATG TCA CCT GTA GAT TTC CAC ACG CCA AGC TCC CCC AAG TCA CCC      1105
Arg Met Ser Pro Val Asp Phe His Thr Pro Ser Ser Pro Lys Ser Pro

CCT TCG GAA ATG TCC CCG CCC GTG TCC AGC ACG GTC TCC ATG CCC          1153
Pro Ser Glu Met Ser Pro Pro Val Ser Ser Thr Val Ser Met Pro
```

```
          GGF2BPP4 Nucleotide Sequence & Deduced Protein Sequence

TCC ATG GCG GTC AGT CCC TTC GTG GAA GAG AGA CCC CTG CTC CTT          1201
Ser Met Ala Val Ser Pro Phe Val Glu Glu Arg Pro Leu Leu Leu

GTG ACG CCA CGG CTG CGG GAG AAG TAT GAC CAC CAC GCC CAG CAA          1249
Val Thr Pro Arg Leu Arg Glu Lys Tyr Asp His His Ala Gln Gln

TTC AAC TCG TTC CAC TGC AAC CCC GCG CAT GAG AGC AAC AGC CCC          1297
Phe Asn Ser Phe His Cys Asn Pro Ala His Glu Ser Asn Ser Pro

CCC AGC CCC TTG AGG ATA GTG GAG GAT GAG GAA TAT GAA ACG CAC          1345
Pro Ser Pro Leu Arg Ile Val Glu Asp Glu Glu Tyr Glu Thr His

GAG TAC GAA CCA GCT CAA GAG CCG GTT AAG AAA CTC ACC AAC AGC AGC      1393
Glu Tyr Glu Pro Ala Gln Glu Pro Val Lys Lys Leu Thr Asn Ser Ser

CGG CGG GCC AAA AGA ACC AAG CCC AAT GGT CAC ATT GCC CAC AGG TTG      1441
Arg Arg Ala Lys Arg Thr Lys Pro Asn Gly His Ile Ala His Arg Leu

GAA ATG GAC AAC ACA GCT GGC AGC AGT GAC AAC TCA GAG AGC GAA          1489
Glu Met Asp Asn Thr Ala Gly Ser Ser Asp Asn Ser Glu Ser Glu

ACA GAG GAT GAA AGA GTA GGA GAA GAT CTC GAG GCG CCT GCC TTC CTG GTC  1537
Thr Glu Asp Glu Arg Val Gly Glu Asp Leu Glu Ala Pro Phe Leu Val

AAC CCC CTG GCA GCC AGT CTC AAC CCA ACA GGC GGC TTC TCT CCG GAA TTG  1585
Asn Pro Leu Ala Ala Ser Leu Asn Pro Thr Gly Gly Phe Ser Pro Glu Leu

GAC AGC AGG ACT AAC CCA ACA GCT GTA ATC GAC CAA AAC GCT ATC GCT GTC  1633
Asp Ser Arg Thr Asn Pro Thr Gly Val Ile Asp Gln Asn Ala Ile Ala Val

CAG GCC AGG CTC TCC GGT GTA ATC GAC CCT ATC GCT GTC                  1681
Gln Ala Arg Leu Ser Gly Val Ile Ala Asn Gln Asp Pro Ile Ala Val

TAAAACCGAA ATACACCCAT AGATTCACCT GTAAAACTTT ATTTATATA ATAAAGTATT     1741

CCACCTTAAA TTAAACAAAA AAA                                            1764
```

```
GGF2bpp5  (SEQ ID NO: 151)   KCAEKEKTFCVNGGECFMVKDLSNPSRYLCKCPNEFTGDRCQNYVMASFY
GGF2bpp4  (SEQ ID NO: 152)   KCAEKEKTFCVNGGDCFMVKDLSNPSRYLCKCQPGFTGARCTENVPMKVQ
hEGF      (SEQ ID NO: 153)   ECLRKYKDFCIH-GECKYVKELRAPS---CKCQQEYFGERCGEKSNKTHS
```

Fig. 35

GGF/Heregulin Splicing Variants

GGF/Hergulin       E-B-A-C-C/D-D
    Splicing Variants  E-B-A-C-C/D-H
                       E-B-A-C-C/D-H-L
                       E-B-A-C-C/D-H-K-L
                       E-B-A-C-C/D-D'-H
                       E-B-A-C-C/D-D'-H-L
                       E-B-A-C-C/D-D'-H-K-L
                       E-B-A-C-C/D'-D
                       E-B-A-C-C/D'-H
                       E-B-A-C-C/D'-H-L
                       E-B-A-C-C/D'-H-K-L
                       E-B-A-C-C/D'-D'-H
                       E-B-A-C-C/D'-D'-H-L
                       E-B-A-C-C/D'-D'-H-K-L
                       E-B-A-C-C/D-C/D'-D
                       E-B-A-C-C/D-C/D'-H
                       E-B-A-C-C/D-C/D'-H-L
                       E-B-A-C-C/D-C/D'-H-K-L
                       E-B-A-C-C/D-C/D'-D'-H
                       E-B-A-C-C/D-C/D'-D'-H-L
                       E-B-A-C-C/D-C/D'-D'-H-K-L E-B-A-G-C-C/D-D
                       E-B-A-G-C-C/D-H-L
                       E-B-A-G-C-C/D-H-K-L
                       E-B-A-G-C-C/D-D'-H
                       E-B-A-G-C-C/D-D'-H-L
                       E-B-A-G-C-C/D-D'-H-K-L
                       E-B-A-G-C-C/D'-D
                       E-B-A-G-C-C/D'-H
                       E-B-A-G-C-C/D'-H-L
                       E-B-A-G-C-C/D'-H-K-L
                       E-B-A-G-C-C/D'-D'-H
                       E-B-A-G-C-C/D'-D'-H-L
                       E-B-A-G-C-C/D'-D'-H-K-L
                       E-B-A-G-C-C/D-C/D'-D
                       E-B-A-G-C-C/D-C/D'-H
                       E-B-A-G-C-C/D-C/D'-H-L
                       E-B-A-G-C-C/D-C/D'-H-K-L
                       E-B-A-G-C-C/D-C/D'-D'-H
                       E-B-A-G-C-C/D-C/D'-D'-H-L
                       E-B-A-G-C-C/D-C/D'-D'-H-K-L
```

Fig. 37B

EGFL1

```
(SEQ ID NO: 154) AGC CAT CTT GTC AAG TGT GCA GAG AAG GAG AAA ACT TTC TGT GTG AAT    48
(SEQ ID NO: 220) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
                 Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
                 Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT   192
                 Val Met Ala Ser Phe Tyr Ser Thr Ser Thr Pro Phe Leu Ser Leu Pro

GAA TAG                                                            198
                 Glu
```

Fig. 38

EGFL2

```
(SEQ ID NO: 155) AGC CAT CTT GTC AAG TGT GCA GAG AAG GAG AAA ACT TTC TGT GTG AAT    48
(SEQ ID NO: 221) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
                 Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
                 Leu Cys Lys Cys Gln Pro Gly Phe Thr Gly Ala Arg Cys Thr Glu Asn

GTG CCC ATG AAA GTC CAA ACC CAA GAA AAA GCG GAG GAG CTC TAC TAA   192
                 Val Pro Met Lys Val Gln Thr Gln Glu Lys Ala Glu Glu Leu Tyr
```

Fig. 39

EGFL3

(SEQ ID NO: 156) AGC CAT CTT GTC AAG TGT GCA GAG AAG GAG AAA ACT TTC TGT GTG AAT  48
(SEQ ID NO: 222) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC  96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC  144
Leu Cys Lys Cys Pro Asn Glu Phe Thr Gly Asp Arg Cys Gln Asn Tyr

GTA ATG GCC AGC TTC TAC AAA GCG GAG CTC TAC TAA  183
Val Met Ala Ser Phe Tyr Lys Ala Glu Leu Tyr

Fig. 40

EGFL4

```
(SEQ ID NO: 157) AGC CAT CTT GTC AAG TGT GCA GAG AAG GAG AAA ACT TTC TGT GTG AAT    48
(SEQ ID NO: 223) Ser His Leu Val Lys Cys Ala Glu Lys Glu Lys Thr Phe Cys Val Asn

GGA GGC GAG TGC TTC ATG GTG AAR GAC CTT TCA AAT CCC TCA AGA TAC    96
                 Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
                 Leu Cys Lys Cys Pro Asn Glu Phe Thr Gly Asp Arg Cys Gln Asn Tyr

GTA ATG GCC AGC TTC TAC AAG CAT CTT GGG ATT GAA TTT ATG GAG AAA   192
                 Val Met Ala Ser Phe Tyr Lys His Leu Gly Ile Glu Phe Met Glu Lys

GCG GAG GAG CTC TAC TAA                                           210
                 Ala Glu Glu Leu Tyr
```

Fig. 41

EGFL5

```
(SEQ ID NO: 158) AGC CAT CTT GTC AAG TGT GCA GAG AAG GAG AAA ACT TTC TGT GTG AAT    48
(SEQ ID NO: 224) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
                 Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
                 Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
                 Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC   240
                 Gly Asp Arg Cys Gln Asn Tyr Val Met Ala Ser Phe Tyr Ser Thr Ser

ACT CCC TTT CTG TCT CTG CCT GAA TAG                               267
                 Thr Pro Phe Leu Ser Leu Pro Glu
```

Fig. 42

EGFL6

```
(SEQ ID NO: 159) AGC CAT CTT GTC AAG TGT GCA GAG AAG GAG AAA ACT TTC TGT GTG AAT      48
(SEQ ID NO: 225) Ser His Leu Val Lys Cys Ala Glu Lys Glu Lys Thr Phe Cys Val Asn

GGA GGC GAG TGC ATG TTC CCC AAA GAC CTT TCA AAT CCC TCA AGA TAC       96
                 Gly Gly Glu Cys Met Phe Pro Lys Asp Leu Ser Asn Pro Ser Arg Tyr

TTG TGC AAG TGC CAA CCT GGA TTC ACT GGA AGA GCG AGA TGT ACT GAG AAT  144
                 Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT       192
                 Val Pro Met Lys Val Gln Thr Gln Glu Lys Cys Pro Asn Glu Phe Thr

GGT GAT CGC TGC CAA AAC TAC GTA ATG GCC AGC TTC TAC AAA GCG GAG       240
                 Gly Asp Arg Cys Gln Asn Tyr Val Met Ala Ser Phe Tyr Lys Ala Glu

GAG CTC TAC TAA                                                       252
                 Glu Leu Tyr
```

Fig. 43

Nucleotide Sequence & Deduced Acid Sequence of GGF2HBS5

```
(SEQ ID NO: 21)GGAATTCCTT TTTTTTTTTT TTTTTTTCTT NNTTTTTTTT TGCCCTTATA CCTCTTCGCC     60
               TTTCTGTGGT TCCATCCACT TCTCCCCCT  CCTCCTCCCA TAAACAACTC TCCTACCCCT    120
               GCACCCCCAA TAAATAAATA AAAGGAGGAG GGCAAGGGGG GAGGAGGAGG AGTGGTGCTG    180
               CGAGGGGAAG GAAAAGGGAG GCAGCGCGAG AAGAGCCGGG CAGAGTCCGA ACCGACAGCC    240
               AGAAGCCCGC ACGCACCTCG CACC ATG AGA TGG CGA CGC GCC CCG CGC CGC        291
(SEQ ID NO: 170)                         Met Arg Trp Arg Arg Ala Pro Arg Arg

TCC GGG CGT CCC GGC GGG GCC CAG CGC CCC GGC TCC GCC GCC CGC         339
               Ser Gly Arg Pro Gly Gly Ala Gln Arg Pro Gly Ser Ala Ala Arg

TCG CCG CCG CTG CTG CCA CTG CTA CTG CCA CTG CTG CTG CTG GGG ACC     387
               Ser Pro Pro Leu Leu Pro Leu Leu Pro Leu Leu Leu Leu Gly Thr
                                                             Val Cys Leu Thr Val
                                                                (SEQ ID NO: 50)GGF-II 09

GCG GCC CTG GCG GCG CCG GGG GCG GCC AAC GAG GCG GCT CCC GCG         435
               Ala Ala Leu Ala Pro Gly Ala Ala Gly Asn Glu Ala Ala Pro Ala
               Ala Ala Leu Pro Pro

GGG GCC TCG GTG TGC TAC TCG TCC CCG CCC AGC GTG TGC GGA TCG GTG CAG  483
               Gly Ala Ser Val Cys Tyr Ser Ser Pro Pro Ser Val Cys Gly Ser Val Gln
               Ala Ser Pro Val Ser Val Gly Ser Val Gln
                            (SEQ ID NO: 49)GGF-II 08

GAG CTA GCT CAG CGC|GCC GCG GTG GTG ATC GAG GGA AAG GTG CAC CCG     531
               Glu Leu Ala Gln Arg|Ala Ala Val Val Ile Glu Gly Lys Val His Pro
               Glu Leu Val Gln Arg|Trp Phe Val Ile Glu Gly Lys
                            (SEQ ID NO: 48)GGF-II 04
```

Fig. 45A

Nucleotide Sequence & Deduced Acid Sequence of GGF2HBS5

```
CAG CGG CAG CAG GGG GCA CTC GAC AGG AAG GCG GCG GCG GCG           579
Gln Arg Gln Gln Gly Ala Leu Asp Arg Lys Ala Ala Ala Ala

GGC GAG GCA GGG GCG TGG GGC GAT CGC GAG CCA GCC GCG GGC           627
Gly Glu Ala Gly Ala Trp Gly Gly Asp Arg Glu Pro Ala Gly

CCA CGG GCG CTG GGG CCG GCC GAG CTG CTC GCC GCC AAC               675
Pro Arg Ala Leu Gly Pro Ala Glu Leu Leu Ala Ala Asn

GGG ACC GTC CCC TCT TGG CCC ACC GCC CCG GTG CCC GGC GAG           723
Gly Thr Val Pro Ser Trp Pro Thr Ala Pro Val Pro Ser Ala Gly Glu

CCC GGG GAG GAG GCG CCC TAT CTG GTG GTG AAG GTG CAC CAG GTG TGG GCG   771
Pro Gly Glu Glu Ala Pro Tyr Leu Val Val Lys Val His Gln Val Trp Ala
                                Lys Val His Glu Val Trp Ala
(SEQ ID NO 45&NO: 51) GGF-II 01 & GGF-II 11

GTG AAA GCC GGG GGC TTG GGC AAG GAC TCG CTG CTC ACC GTG CGC CTG   819
Val Lys Ala Gly Gly Leu Gly Lys Asp Ser Leu Leu Thr Val Arg Leu
                             Asp Leu Leu Leu Xaa Val Leu
Ala Lys
(SEQ ID NO: 53) GGF-II 10

GGG ACC TGG GGC CAC CCC GCC TTC TCC TGC GGG AGG CTC AAG GAG       867
Gly Thr Trp Gly His Pro Ala Phe Ser Cys Gly Arg Leu Lys Glu
Gly Ala Trp Gly Pro Pro Ala Phe Pro Val Xaa Tyr
(SEQ ID NO: 47)GGF-II 03

GAC AGC AGG TAC ATC TTC TTC ATG GAG CCC GAC GCC AAC AGC ACC AGC    915
Asp Ser Arg Tyr Ile Phe Phe Met Glu Pro Asp Ala Asn Ser Thr Ser
Tyr Ile Phe Phe Met Glu Pro Gla Ala Xaa Ser Ser Gly
(SEQ ID NO: 46) GGF-II 02
```

Fig. 45B

Nucleotide Sequence & Deduced Acid Sequence of GGF2HBS5

```
CGC GCG CCG GCC GCC TTC CGA GCC TCT TTC CCC CCT CTG GAG ACG GGC    963
Arg Ala Pro Ala Ala Phe Arg Ala Ser Phe Pro Pro Leu Glu Thr Gly

CGG AAC CTC AAG GAG GTC AGC GTC CTG TGC AAG CGG TGC GCC           1011
Arg Asn Leu Lys Glu Val Ser Val Leu Cys Lys Arg Cys Ala

TTG CCT CCC CAA TTG AAA GAG ATG AAA AGC CAG GAA TCG GCT GCA GGT   1059
Leu Pro Pro Gln Leu Lys Glu Met Lys Ser Gln Glu Ser Ala Ala Gly

TCC AAA CTA GTC CTT CGG TGT GAA ACC AGT TCT GAA TAC TCC TCT CTC   1107
Ser Lys Leu Val Leu Arg Cys Glu Thr Ser Ser Glu Tyr Ser Ser Leu
Leu Val Arg
(SEQ ID NO: 129)GGF-II 06

AGA TTC AAG TGG TTC AAG AAT GGG AAT GAA TTG AAT CGA AAA AAC AAA   1155
Arg Phe Lys Trp Phe Lys Asn Gly Asn Glu Leu Asn Arg Lys Asn Lys

CCA CAA AAT ATC AAG CAA ATA CAA AAG AAG CCA GGG TCA GAA CTT CGC   1203
Pro Gln Asn Ile Lys Gln Ile Gln Lys Lys Pro Gly Ser Glu Leu Arg

ATT AAC GCA TCA CTG GAT TCT GGA GAG GGT TAT ATG TGC AAA GTG       1251
Ile Asn Ala Ser Leu Asp Ser Gly Glu Gly Tyr Met Cys Lys Val
Lys Ala Ser Leu Asp Ser Gly
(SEQ ID NO: 52)GGF-II 12

ATC AGC AAA TTA GGA AAT GAC AGT TCT GCC TCT GCC AAT ATC ACC ATC GTG   1299
Ile Ser Lys Leu Gly Asn Asp Ser Ser Ala Ser Ala Asn Ile Thr Ile Val

GAA TCA AAC GCT ACA TCT ACA TCC ACC ACT GGG ACA AGC CAT CTT GTA   1347
Glu Ser Asn Ala Thr Ser Thr Ser Thr Thr Gly Thr Ser His Leu Val
```

Fig. 45C

Nucleotide Sequence & Deduced Acid Sequence of GGF2HBS5

```
AAA TGT GCG GAG AAG GAG AAA ACT TTC TGT GTG AAT GGA GGG GAG TGC       1395
Lys Cys Ala Glu Lys Glu Lys Thr Phe Cys Val Asn Gly Gly Glu Cys

TTC ATG GTG AAA GAC CTT TCA AAC CCC TCG AGA TAC TTG TGC AAG TGC       1443
Phe Met Val Lys Asp Leu Ser Asn Pro Ser Arg Tyr Leu Cys Lys Cys

CCA AAT GAG TTT ACT GGT GAT CGC TGC CAA AAC TAC GTA ATG GCC AGC       1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                   1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCTCA GATTCCACCT     1590

AGAGCTAGAT GTGTCTTACC AGATCTAATA TTGACTGCCT CTGCCTGTCG CATGAGAACA     1650

TTAACAAAAG CAATTGTATT ACTTCCTCTG TTCGCGACTA GTTGGCTCTG AGATACTAAT     1710

AGTGTGTGTGA GGCTCCGGAT GTTCTGGAA TTGATATATTGA ATGATGTGAT ACAAATTGAT   1770

AGTCAATATC AAGCAGTGAA ATATGATAAT AAAGGCATTT CAAAGTCTCA CTTTTATTGA     1830

TAAAATAAAA ATCATTCTAC TGAACAGTCC ATCTTCTTTA TACAATGACC ACATCCTGAA     1890

AAGGGTGTTG CTAAGCTGTA ACCGATATGC ACTTGAAATG ATGGTAAGTT AATTTGATT      1950

CAGAATGTGT TATTTGTCAC AAATAAACAT AATAAAAGGA AAAAAAAAA AAA             2003
```

Fig. 45D

Deduced Sequences of Human & Bovine Glial Growth Factors

```
                                                           1
SEQ ID NO: 170 GGFHBS5   1 MRMRRAPRRSGRPGPRAQRPGSAARSPPPLPLLPLLLLLGTAALAPGAAAGNEAAPAGAS
                                      II-8           II-4
                      61 VCYSSPPSVGSVQELAQRAAVIEGKVHPQRRQQGALDRKAAAAGEAGAWGGDREPPAA
                                                         II-1            II-10
                     121 GPRALGPPAEEPLLAANGTVPSWPTAPVPSAGEPGEEAPYLVKVHQVWAVKAGGLKKDSL
                                    II-3                  II-2
                     181 LTVRLGTWGHPAFPSCGRLKEDSRYIFFMEPDANSTSRAPAAFRASFPPLETGRNLKKEV
                                        0                                    3
SEQ ID NO: 171 GGFHBS5 241 SRVLCKRC............OMSERKEGRGKGKKERGSGKKPESAAGSQSP......ALPPQLKEMKSQESAAGSK
SEQ ID NO: 171 GGFHFB1   1                                              R                   R
SEQ ID NO: 172 GGFBPP5   1                       O                      R  K  G  D          VP  GP    R      V
                                   II-14                                         II-11    I-7, II-12,
                     268 II-6        II-18                                                        III-13
                      53 LVLRCETSSEYSSLRFKNFKNGNELNRKNKPQNIKIQKKPGKSELRINKASLADSGEYMC............ATSTS
                      53                        *                                          *
                                 II-12                                 K    S   S          R   S
                     328 KVISKLGNDSASANITTVESN.............EIITGMPASTEGAYVSSESPIRISVSTEGANTSSS
                     113                                                                   T         T
                     113                                                                                   ▼      ▼
                     354 TTGTSHLVKCAEKEKTFCVNGGECFMVKDLSNPSRYLCKCPNEFTGDRCQNYVMASFYST
                     173                                          II-15
                     173 A                              *       *          *  *                * *
                     413 STPFLSLPE*
                     232
                     232
```

Fig. 53

METHODS OF STIMULATING MITOGENESIS IN GLIAL CELLS USING GLIAL MITOGENIC FACTORS

CROSS REFERENCE TO RELATED APPLICATION

This application is a divisional of application Ser. No. 08/036,555 filed Mar. 24, 1993, now U.S. Pat. No. 5,530,109, which is a continuation-in-part of Ser. No. 07/863,703 filed Apr. 3, 1992 (abandoned), which in turn is a continuation-in-part of Ser. No. 07/907,138 filed Jun. 30, 1992 (abandoned), which is a continuation-in-part of Ser. No. 07/940,389 filed Sep. 3, 1992 (abandoned), which is a continuation-in-part of Ser. No. 07/965,173 filed Oct. 23, 1992 (abandoned).

BACKGROUND OF THE INVENTION

This invention relates to polypeptides found in vertebrate species, which polypeptides are mitogenic growth factors for glial cells, including Schwann cells. The invention is also concerned with processes capable of producing such factors, and the therapeutic application of such factors.

The glial cells of vertebrates constitute the specialized connective tissue of the central and peripheral nervous systems. Important glial cells include Schwann cells which provide metabolic support for neurons and which provide myelin sheathing around the axons of certain peripheral neurons, thereby forming individual nerve fibers. Schwann cells support neurons and provide a sheath effect by forming concentric layers of membrane around adjacent neural axons, twisting as they develop around the axons. These myelin sheaths are a susceptible element of many nerve fibers, and damage to Schwann cells, or failure in growth and development, can be associated with significant demyelination or nerve degeneration characteristic of a number of peripheral nervous system diseases and disorders. In the development of the nervous system, it has become apparent that cells require various factors to regulate their division and growth, and various such factors have been identified in recent years, including some found to have an effect on Schwann cell division or development.

Thus, Brockes et al., inter alia, in J. Neuroscience, 4 (1984) 75–83 describe a protein growth factor present in extracts from bovine brain and pituitary tissue, which was named Glial Growth Factor (GGF). This factor stimulated cultured rat Schwann cells to divide against a background medium containing ten percent fetal calf serum. The factor was also described as having a molecular weight of 31,000 Daltons and as readily dimerizing. In Meth. Enz., 147 (1987), 217–225, Brockes describes a Schwann cell-based assay for GGF.

Brockes et al., supra, also describes a method of purification of GGF to apparent homogeneity. In brief, one large-scale purification method described involves extraction of the lyophilized bovine anterior lobes and chromatography of material obtained thereby using NaCl gradient elution from CM cellulose. Gel filtration is then carried out with an Ultrogel column, followed by elution from a phosphocellulose column, and finally, small-scale SDS gel electrophoresis. Alternatively, the CM-cellulose material was applied directly to a phosphocellulose column, fractions from the column were pooled and purified by preparative native gel electrophoresis, followed by a final SDS gel electrophoresis.

Brockes et al. observe that in previously reported gel filtration experiments (Brockes et al., J. Biol. Chem. 255 (1980) 8374–8377), the major peak of growth factor activity was observed to migrate with a molecular weight of 56,000 Daltons, whereas in the first of the above-described procedures activity was predominantly observed at molecular weight 31,000. It is reported that the GGF dimer is largely removed as a result of the gradient elution from CM-cellulose in this procedure.

Benveniste et al. (PNAS, 82 (1985), 3930–3934) describe a T lymphocyte-derived glial growth promoting factor. This factor, under reducing conditions, exhibits a change in apparent molecular weight on SDS gels.

Kimura et al. (Nature, 348 (1990), 257–260) describe a factor they term Schwannoma-derived growth factor (SDGF) which is obtained from a sciatic nerve sheath tumor. The authors state that SDGF does not stimulate the incorporation of tritium-labelled TdR into cultured Schwann cells under conditions where, in contrast, partially purified pituitary fraction containing GGF is active. SDGF has an apparent molecular weight of between 31,000 and 35,000.

Davis and Stroobant (J. Cell. Biol., 110 (1990), 1353–1360) describe the screening of a number of candidate mitogens. Rat Schwann cells were used, the chosen candidate substances being examined for their ability to stimulate DNA synthesis in the Schwann cells in the presence of 10% FCS (fetal calf serum), with and without forskolin. One of the factors tested was GGF-carboxymethyl cellulose fraction (GGF-CM), which was mitogenic in the presence of FCS, with and without forskolin. The work revealed that in the presence of forskolin, inter alia, platelet derived growth factor (PDGF) was a potent mitogen for Schwann cells, PDGF having previously been thought to have no effect on Schwann cells.

Holmes et al. Science (1992) 256: 1205 and Wen et al. Cell (1992) 69: 559 demonstrate that DNA sequences which encode proteins binding to a receptor ($p185^{erbB2}$) are associated with several human tumors.

The $p185^{erbB2}$ protein is a 185 kilodalton membrane spanning protein with tyrosine kinase activity. The protein is encoded by the erbB2 proto-oncogene (Yarden and Ullrich Ann. Rev. Biochem. 57: 443 (1988)). The erbB2 gene, also referred to as HER-2 (in human cells) and neu (in rat cells), is closely related to the receptor for epidermal growth factor (EGF). Recent evidence indicates that proteins which interact with (and activate the kinase of) $p185^{erbB2}$ induce proliferation in the cells bearing $p185^{erbB2}$ (Holmes et al. Science 256: 1205 (1992); Dobashi et al. Proc. Natl. Acad. Sci. 88: 8582 (1991); Lupu et al. Proc. Natl. Acad. Sci. 89: 2287 (1992)). Furthermore, it is evident that the gene encoding $p185^{erbB2}$ binding proteins produces a number of variably-sized, differentially-spliced RNA transcripts that give rise to a series of proteins, which are of different lengths and contain some common peptide sequences and some unique peptide sequences. This is supported by the differentially-spliced RNA transcripts recoverable from human breast cancer (MDA-MB-231) (Holmes et al. Science 256: 1205 (1992) ). Further support derives from the wide size range of proteins which act as (as disclosed herein) ligands for the $p185^{erbB2}$ receptor (see below).

SUMMARY OF THE INVENTION

In general the invention provides methods for stimulating glial cell (in particular, Schwann cell and glia of the central nervous system) mitogenesis, as well as new proteins exhibiting such glial cell mitogenic activity. In addition, DNA encoding these proteins and antibodies which bind these and related proteins are provided.

The novel proteins of the invention include alternative splicing products of sequences encoding known polypeptides. Generally, these known proteins are members of the GGF/p185$^{erbB2}$ family of proteins.

Specifically, the invention provides polypeptides of a specified formula, and DNA sequences encoding those polypeptides. The polypeptides have the formula

WYBAZCX wherein WYBAZCX is composed of the amino acid sequences shown in FIGS. 31A–31D, 31F–31Q (SEQ ID Nos. 197–200, 201–205, 207, 208, 216, 218); wherein W comprises the polypeptide segment F, or is absent; wherein Y comprises the polypeptide segment E, or is absent; wherein Z comprises the polypeptide segment G or is absent; and wherein X comprises the polypeptide segments C/D HKL, C/D H, C/D HL, C/D D, C/D' HL, C/D' HKL, C/D' H, C/D' D, C/D C/D' HKL, C/D C/D' H, C/D C/D' HL, C/D C/D' D, C/D D' H, C/D D' HL, C/D D' HKL, C/D' D' H, C/D' D' HL, C/D' D' HKL, C/D C/D' D' H, C/D C/D' D' HL, or C/D C/D' D' HKL; provided that, either a) at least one of F, Y, B, A, Z, C, or X is of bovine origin; or b) Y comprises the polypeptide segment E; or c) X comprises the polypeptide segments C/D HKL, C/D D, C/D' HKL, C/D C/D' HKL, C/D C/D' D, C/D D' H, C/D D' HL, C/D D' HKL, C/D' D' H, C/D' D' HKL, C/D C/D' D' H, C/D C/D' D' HL, C/D C/D' D' HKL, C/D'H, C/D C/D'H, or C/D C/D' HL.

In addition, the invention includes the DNA sequence comprising coding segments 5'FBA3' as well as the with corresponding polypeptide segments having the amino acid sequences shown in FIGS. 31A, 31C, 31D (SEQ ID Nos.197, 199, 200);

the DNA sequence comprising the coding segments 5'FBA'3' as well as the corresponding polypeptide segments having the amino acid sequences shown in FIGS. 31A, 31C, 31E (SEQ ID Nos.136, 138, 140);

the DNA sequence comprising the coding segments 5'FEBA3' as well as the corresponding polypeptide segments having the amino acid sequences shown in FIGS. 31A–31D (SEQ ID Nos. 197–200);

the DNA sequence comprising the coding segments 5'FEBA'3' as well as the corresponding polypeptide segments having the amino acid sequences shown in FIG. 31 (SEQ ID Nos. 136–138, 140); and the DNA sequence comprising the polypeptide coding segments of the GGF2HBS5 cDNA clone (ATCC Deposit No. 75298, deposited Sep. 2, 1992).

The invention further includes peptides of the formula FBA, FEBA, FBA' FEBA' and DNA sequences encoding these peptides wherein the polypeptide segments correspond to amino acid sequences shown in FIGS. 31A–31E (SEQ ID Nos. 197,199 and 200), (197–200) and (197, 199 and 206) and (197–199 and 206) respectively. The purified GGF-II polypeptide (SEQ ID No. 170) is also included as a part of the invention.

Further included as an aspect of the invention are peptides and DNA encoding such peptides which are useful for the treatment of glia and in particular oligodendrocytes, microglia and astrocytes, of the central nervous system and methods for the administration of these peptides.

The invention further includes vectors including DNA sequences which encode the amino acid sequences, as defined above. Also included are a host cell containing the isolated DNA encoding the amino acid sequences, as defined above. The invention further includes those compounds which bind the p185$^{erbB2}$ receptor and stimulate glial cell mitogenesis in vivo and/or in vitro.

Also a part of the invention are antibodies to the novel peptides described herein. In addition, antibodies to any of the peptides described herein may be used for the purification of polypeptides described herein. The antibodies to the polypeptides may also be used for the therapeutic inhibition of glial cell sitogenesis.

The invention further provides a method for stimulating glial cell sitogenesis comprising contacting glial cells with a polypeptide defined by the formula

WYBAZCX wherein WYBAZCX is composed of the polypeptide segments shown in FIGS. 31A–31D, 31F–31Q (SEQ ID Nos.197–200, 201–205, 207, 208, 216, 218); wherein W comprises the polypeptide segment F, or is absent wherein Y comprises the polypeptide segment E, or is absent; wherein Z comprises the polypeptide segment G or is absent; and wherein X comprises the polypeptide segment C/D HKL, C/D H, C/D HL, C/D D, C/D' HL, C/D' HKL, C/D' H, C/D' D, C/D C/D' HKL, C/D C/D' H, C/D C/D' HL, C/D C/D' D, C/D D' H, C/D D' HL, C/D D' HKL, C/D' D' H, C/D' D' HL, C/D' D' HKL, C/D C/D' D' H, C/D C/D' D' HL, or C/D C/D' D' HKL.

The invention also includes a method for the preparation of a glial cell mitogenic factor which consist of culturing modified host cells as defined above under conditions permitting expression of the DNA sequences of the invention.

The peptides of the invention can be used to make a pharmaceutical or veterinary formulation for pharmaceutical or veterinary use. Optionally, the formulation may be used together with an acceptable diluent, carrier or excipient and/or in unit dosage form.

A method for stimulating mitogenesis of a glial cell by contacting the glial cell with a polypeptide defined above as a glial cell mitogen in vivo or in vitro is also an aspect of the invention. A method for producing a glial cell mitogenic effect in a vertebrate (preferably a mammal, more preferably a human) by administering an effective amount of a polypeptide as defined is also a component of the invention.

Methods for treatment of diseases and disorders using the polypeptides described are also a part of the invention. For instance, a method of treatment or prophylaxis for a nervous disease or disorder can be effected with the polypeptides described. Also included are a method for the prophylaxis or treatment of a pathophysiological condition of the nervous system in which a cell type is involved which is sensitive or responsive to a polypeptide as defined are a part of the invention.

Included in the invention as well, are methods for treatment when the condition involves peripheral nerve damage; nerve damage in the central nervous system; neurodegenerative disorders; demyelination in peripheral or central nervous system; or damage or loss of Schwann cells oligodendrocytes, microglia, or astrocytes. For example a neuropathy of sensory or motor nerve fibers; or the treatment of a neurodegenerative disorder are included. In any of these cases, treatment consists of administering an effective amount of the polypeptide.

The invention also includes a method for inducing neural regeneration and/or repair by administering an effective amount of a polypeptide as defined above. Such a medicament is made by administering the polypeptide with a pharmaceutically effective carrier.

The invention includes the use of a polypeptide as defined above in the manufacture of a medicament.

The invention further includes the use of a polypeptide as defined above
- to immunize a mammal for producing antibodies, which can optionally be used for therapeutic or diagnostic purposes
- in a competitive assay to identify or quantify molecules having receptor binding characteristics corresponding to those of the polypeptide; and/or
- for contacting a sample with a polypeptide, as mentioned above, along with a receptor capable of binding specifically to the polypeptide for the purpose of detecting competitive inhibition of binding to the polypeptide.
- in an affinity isolation process, optionally affinity chromatography, for the separation of a corresponding receptor.

The invention also includes a method for the prophylaxis or treatment of a glial tumor. This method consists of administering an effective amount of a substance which inhibits the binding of a factor as defined by the peptides above.

Furthermore, the invention includes a method of stimulating glial cell mitogenic activity by the application to the glial cell of a
- 30 kD polypeptide factor isolated from the MDA-MB 231 human breast cell line; or
- 35 kD polypeptide factor isolated from the rat I-EJ transformed fibroblast cell line to the glial cell or
- 75 kD polypeptide factor isolated from the SKBR-3 human breast cell line; or
- 44 kD polypeptide factor isolated from the rat I-EJ transformed fibroblast cell line; or
- 25 kD polypeptide factor isolated from activated mouse peritoneal macrophages; or
- 45 kD polypeptide factor isolated from the MDA-MB 231 human breast cell; or
- 7 to 14 kD polypeptide factor isolated from the ATL-2 human T-cell line to the glial cell; or
- 25 kD polypeptide factor isolated from the bovine kidney cells; or
- 42 kD polypeptide factor (ARIA) isolated from brains.

The invention further includes a method for the use of the EGFL1, EGFL2, EGFL3, EGFL4, EGFL5, and EGFL6 polypeptides, FIGS. 38 to 43 and SEQ ID Nos. 220–225, respectively, for the stimulation of glial cell mitogenesis in vivo and in vitro.

Also included in the invention is the administration of the GGF-II polypeptide whose sequence is shown in FIG. 45 for the stimulation of glial cell mitogenesis.

An additional aspect of the invention includes the use of the above-referenced peptides for the purpose of stimulating Schwann cells to produce growth factors which may, in turn, be harvested for scientific or therapeutic use.

Furthermore, the peptides described herein may be used to induce central glial proliferation and remyelination for treatment of diseases, e.g., MS, where re-myelination is desired.

In an additional aspect of the invention, the novel polypeptides described herein may be used to stimulate the synthesis of acetylcholine receptors.

As mentioned above, the invention provides new glial growth factors from mammalian sources, including bovine and human, which are distinguished from known factors. These factors are mitogenic for Schwann cells against a background of fetal calf plasma (FCP). The invention also provides processes for the preparation of these factors, and an improved method for defining activity of these and other factors. Therapeutic application of the factors is a further significant aspect of the invention.

Thus, important aspects of the invention are:
(a) a basic polypeptide factor having glial cell mitogenic activity, more specifically, Schwann cell mitogenic activity in the presence of fetal calf plasma, a molecular weight of from about 30 kD to about 36 kD, and including within its amino acid sequence any one or more of the following peptide sequences:
FKGDAHTE (SEQ ID NO: 1)
ASLADEYEYMXK (SEQ ID NO: 22)
TETSSSGLXLK (SEQ ID NO: 23)
ASLADEYEYMRK (SEQ ID NO: 24)
AGYFAEXAR (SEQ ID NO: 25)
TTEMASEQGA (SEQ ID NO: 26)
AKEALAALK (SEQ ID NO: 27)
FVLQAKK (SEQ ID NO: 28)
ETQPDPGQILKKVPMVIGAYT (SEQ ID NO: 29)
EYKCLKFKWFKKATVM (SEQ ID NO: 17)
EXKFYVP (SEQ ID NO: 19)
KLEFLXAK; and (SEQ ID NO: 32)
(b) a basic polypeptide factor which stimulates glial cell mitogenesis, particularly the division of Schwann cells, in the presence of fetal calf plasma, has a molecular weight of from about 55 kD to about 63 kD, and including within its amino acid sequence any one or more of the following peptide sequences:
VHQVWAAK (SEQ ID NO: 45)
YIFFMEPEAXSSG (SEQ ID NO: 46)
LGAWGPPAFPVXY (SEQ ID NO: 47)
WFVVIEGK (SEQ ID NO: 48)
ASPVSVGSVQELQR (SEQ ID NO: 49)
VCLLTVAALPPT (SEQ ID NO: 50)
KVHQVWAAK (SEQ ID NO: 51)
KASLADSGEYMXK (SEQ ID NO: 52)
DLLLXV (SEQ ID NO: 53)
EGKVHPQRRGALDRK (SEQ ID NO: 185)
PSCGRLKEDSRYIFFME (SEQ ID NO: 186)
ELNRKNKPQNIKIQKK (SEQ ID NO: 187)

The novel peptide sequences set out above, derived from the smaller molecular weight polypeptide factor, and from the larger molecular weight polypeptide factor, are also aspects of this invention in their own right. These sequences are useful as probe sources for polypeptide factors of the invention, for investigating, isolating or preparing such factors (or corresponding gene sequences) from a range of different species, or preparing such factors by recombinant technology, and in the generation of corresponding antibodies, by conventional technologies, preferably monoclonal antibodies, which are themselves useful investigative tools and are possible therapeutics. The invention also includes an isolated glial cell mitogenic activity encoding gene sequence, or fragment thereof, obtainable by the methods set out above for the novel peptide sequences of the invention.

The availability of short peptides from the highly purified factors of the invention has enabled additional sequences to be determined (see Examples to follow).

Thus, the invention further embraces a polypeptide factor having glial cell mitogenic activity and including an amino acid sequence encoded by:
(a) a DNA sequence shown in any one of FIGS. 28A, 28B, 28C, 28D or 28E, SEQ ID Nos. 133–135, respectively;
(b) a DNA sequence shown in FIG. 22, SEQ ID No. 89;
(c) the DNA sequence represented by nucleotides 281–557 of the sequence shown in FIG. 28a, SEQ ID. No. 133; or (d) a DNA sequence hybridizable to any one of the DNA sequences according to (a), (b) or (c).

The invention further includes sequences which have greater than 60%, preferably 80%, sequence identity of homology to the sequences indicated above.

While the present invention is not limited to a particular set of hybridization conditions, the following protocol gives general guidance which may, if desired, be followed:

DNA probes may be labelled to high specific activity (approximately $10^8$ to $10^9$ $^{32}$Pdmp/µg) by nick-translation or by PCR reactions according to Schowalter and Sommer (Anal. Biochem., 177:90–94, 1989) and purified by desalting on G-150 Sephadex columns. Probes may be denatured (10 minutes in boiling water followed by immersion into ice water), then added to hybridization solutions of 80% buffer B (2 g polyvinylpyrolidine, 2 g Ficoll-400, 2 g bovine serum albumin, 50 ml 1 M Tris HCL (pH 7.5), 58 g NaCl, 1 g sodium pyrophosphate, 10 g sodium dodecyl sulfate, 950 ml $H_2O$) containing 10% dextran sulfate at $10^6$ dpm $^{32}$P per ml and incubated overnight (approximately 16 hours) at 60° C. The filters may then be washed at 60° C., first in buffer B for 15 minutes followed by three 20-minute washes in 2× SSC, 0.1% SDS then one for 20 minutes in 1× SSC, 0.1% SDS.

In other respects, the invention provides:

(a) a basic polypeptide factor which has, if obtained from bovine pituitary material, an observed molecular weight, whether in reducing conditions or not, of from about 30 kD to about 36 kD on SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phoshorylase B (rabbit muscle) | 97,400; | which factor has glial cell mitogenic activity including stimulating the division of rat Schwann cells in the presence of fetal calf plasma, and when isolated using reversed-phase HPLC retains at least 50% of said activity after 10 weeks incubation in 0.1% trifluoroacetic acid at 4° C.; and (b) a basic polypeptide factor which has, if obtained from bovine pituitary material, an observed molecular weight, under non-reducing conditions, of from about 55 kD to about 63 kD on SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | which factor the human equivalent of which is encoded by DNA clone GGF2HBS5 described herein and which factor has glial cell mitogenic activity including stimulating the division of rat Schwann cells in the presence of fetal calf plasma, and when isolated using reversed-phase HPLC retains at least 50% of the activity after 4 days incubation in 0.1% trifluoroacetic acid at 4° C.

For convenience of description only, the lower molecular weight and higher molecular weight factors of this invention are referred to hereafter as "GGF-I" and "GGF-II", respectively. The "GGF2" designation is used for all clones isolated with peptide sequence data derived from GGF-II protein (i.e., GGF2HBS5, GGF2BPP3).

It will be appreciated that the molecular weight range limits quoted are not exact, but are subject to slight variations depending upon the source of the particular polypeptide factor. A variation of, say, about 10% would not, for example, be impossible for material from another source.

Another important aspect of the invention is a DNA sequence encoding a polypeptide having glial cell mitogenic activity and comprising:

(a) a DNA sequence shown in any one of FIGS. 28a, 28b or 28c, SEQ ID Nos. 133–135:

(b) a DNA sequence shown in FIG. 22, SEQ ID No. 89;

(c) the DNA sequence represented by nucleotides 281–557 of the sequence shown in FIG. 28a, SEQ ID No. 133; or (d) a DNA sequence hybridizable to any one of the DNA sequences according to (a), (b) or (c).

Another aspect of the present invention uses the fact that the Glial Growth Factors and $p185^{erbB2}$ ligand proteins are encoded by the same gene. A variety of messenger RNA splicing variants (and their resultant proteins) are derived from this gene and many of these products show $p185^{erbB2}$ binding and activation. Several of the (GGF-II) gene products have been used to show Schwann cell mitogenic activity. This invention provides a use for all of the known products of the GGF/$p185^{erbB2}$ ligand gene (described in the references listed above) as Schwann cell mitogens.

This invention also relates to other, not yet naturally isolated splicing variants of the Glial Growth Factor gene. FIG. 30, shows the known patterns of splicing derived from polymerase chain reaction experiments (on reverse transcribed RNA) and analysis of cDNA clones (as presented within) and derived from what has been published as sequences encoding $p185^{erbB2}$ ligands (Peles et al., Cell 69:205 (1992) and Wen et al., Cell 69:559 (1992)). These patterns, as well as additional ones disclosed herein, represent probable splicing variants which exist. Thus another aspect of the present invention relates to the nucleotide sequences encoding novel protein factors derived from this gene. The invention also provides processes for the preparation of these factors. Therapeutic application of these new factors is a further aspect of the invention.

Thus other important aspects of the invention are:

(a) A series of human and bovine polypeptide factors having glial cell mitogenic activity including stimulating the division of Schwann cells. These peptide sequences are shown in FIGS. 31, 32, 33 and 34, SEQ ID Nos. 192, 194, 197–219, respectively.

(b) A series of polypeptide factors having glial cell mitogenic activity including stimulating the division of Schwann cells and purified and characterized according to the procedures outlined by Lupu et al. Science 249: 1552 (1990); Lupu et al. Proc. Natl. Aced. Sci 89: 2287 (1992); Holmes at al. Science 256: 1205 (1992); Pales et al. 69: 205 (1992); Yarden and Peles Biochemistry 30: 3543 (1991); Dobashi et al. Proc. Natl. Acad. Sci. 88: 8582 (1991); Davis et al. Biochem. Biophys. Res. Commun. 179: 1536 (1991); Beaumont et al., patent application PCT/US91/03443 (1990); Greene at al. patent application PCT/US91/02331 (1990); Usdin and Fischbach, J. Cell. Biol. 103:493–507 (1986); Falls et al., Cold Spring Harbor Symp. Quant. Biol. 55:397–406 (1990); Harris et al., Proc. Natl. Acad. Sci. USA 88:7664–7668 (1991); and Falls et al., Cell 72:801–815 (1993).

(c) A polypeptide factor (GGFBPP5) having glial cell mitogenic activity including stimulating the division of Schwann cells. The amino acid sequence is shown in FIG. 32, SEQ ID No. 195, and is encoded by the bovine DNA sequence shown in FIG. 32, SEQ ID No. 148.

The novel human peptide sequences described above and presented in FIGS 31A–31Q (SEQ ID No. 206–219), respectively, represent a series of splicing variants which can be isolated as full length complementary DNAs (cDNAs) from natural sources (cDNA libraries prepared from the appropriate tissues) or can be assembled as DNA constructs with individual exons (e.g., derived as separate exons) by someone skilled in the art.

Other compounds in particular, peptides, which bind specifically to the $p185^{erbB2}$ receptor can also be used according to the invention as a glial cell mitogen. A candidate compound can be routinely screened for $p185^{erbB2}$ binding, and, if it binds, can then be screened for glial cell mitogenic activity using the methods described herein.

The invention includes any modifications or equivalents of the above polypeptide factors which do not exhibit a significantly reduced activity. For example, modifications in which amino acid content or sequence is altered without substantially adversely affecting activity are included. By way of illustration, in EP-A 109748 mutations of native proteins are disclosed in which the possibility of unwanted disulfide bonding is avoided by replacing any cysteine in the native sequence which is not necessary for biological activity with a neutral amino acid. The statements of effect and use contained herein are therefore to be construed accordingly, with such uses and effects employing modified or equivalent factors being part of the invention.

The new sequences of the invention open up the benefits of recombinant technology. The invention thus also includes the following aspects:

(a) DNA constructs comprising DNA sequences as defined above in operable reading frame position within vectors (positioned relative to control sequences so as to permit expression of the sequences) in chosen host cells after transformation thereof by the constructs (preferably the control sequence includes regulatable promoters, e.g. Trp). It will be appreciated that the selection of a promoter and regulatory sequences (if any) are matters of choice for those of skill in the art;

(b) host cells modified by incorporating constructs as defined in (a) immediately above so that said DNA sequences may be expressed in said host cells—the choice of host is not critical, and chosen cells may be prokaryotic or eukaryotic and may be genetically modified to incorporate said constructs by methods known in the art; and, (c) a process for the preparation of factors as defined above comprising cultivating the modified host cells under conditions permitting expression of the DNA sequences. These conditions can be readily determined, for any particular embodiment, by those of skill in the art of recombinant DNA technology. Glial cell mitogens prepared by this means are included in the present invention.

None of the factors described in the art has the combination of characteristics possessed by the present new polypeptide factors.

As indicated, the Schwann cell assay used to characterize the present factors employs a background of fetal calf plasma. In all other respects, the assay can be the same as that described by Brockes et al. in Meth. Enz., supra, but with 10% FCP replacing 10% FCS. This difference in assay techniques is significant, since the absence of platelet-derived factors in fetal calf plasma (as opposed to serum) enables a more rigorous definition of activity on Schwann cells by eliminating potentially spurious effects from some other factors.

The invention also includes a process for the preparation of a polypeptide as defined above, extracting vertebrate brain material to obtain protein, subjecting the resulting extract to chromatographic purification by hydroxylapatite HPLC and then subjecting these fractions to SDS-polyacrylamide gel electrophoresis. The fraction which has an observed molecular weight of about 30 kD to 36 kD and/or the fraction which has an observed molecular weight of about 55 kD to 63 kD is collected. In either case, the fraction is subjected to SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; |

In the case of the smaller molecular weight fraction, the SDS-polyacrylamide gel is run in non-reducing conditions in reducing conditions or, and in the case of the larger molecular weight fraction the gel is run under non-reducing conditions. The fractions are then tested for activity stimulating the division of rat Schwann cells against a background of fetal calf plasma.

Preferably, the above process starts by isolating a relevant fraction obtained by carboxymethyl cellulose chromatography, e.g. from bovine pituitary material. It is also preferred that hydroxylapatite HPLC, cation exchange chromatography, gel filtration, and/or reversed-phase HPLC be employed prior to the SDS-Polyacrylamide gel electrophoresis. At each stage in the process, activity may be determined using Schwann cell incorporation of radioactive iododeoxyuridine as a measure in an assay generally as described by Brockes in Meth. Enz., supra, but modified by substituting 10% FCP for 10% FCS. As already noted, such as assay is an aspect of the invention in its own substance for CNS or PNS cell, e.g. Schwann cell, mitogenic effects.

Thus, the invention also includes an assay for glial cell mitogenic activity in which a background of fetal calf plasma is employed against which to assess DNA synthesis in glial cells stimulated (if at all) by a substance under assay.

Another aspect of the invention is a pharmaceutical or veterinary formulation comprising any factor as defined above formulated for pharmaceutical or veterinary use, respectively, optionally together with an acceptable diluent, carrier or excipient and/or in unit dosage form. In using the factors of the invention, conventional pharmaceutical or veterinary practice may be employed to provide suitable formulations or compositions.

Thus, the formulations of this invention can be applied to parenteral administration, for example, intravenous, subcutaneous, intramuscular, intraorbital, opthalmic, intraventricular, intracranial, intracapsular, intraspinal, intracisternal, intraperitoneal, topical, intranasal, aerosol, scarification, and also oral, buccal, rectal or vaginal administration.

The formulations of this invention may also be administered by the transplantation into the patient of host cells expressing the DNA of the instant invention or by the use of surgical implants which release the formulations of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The present factors can be used as the sole active agents, or can be used in combination with other active ingredients, e.g., other growth factors which could facilitate neuronal survival in neurological diseases, or peptidase or protease inhibitors.

The concentration of the present factors in the formulations of the invention will vary depending upon a number of issues, including the dosage to be administered, and the route of administration.

In general terms, the factors of this invention may be provided in an aqueous physiological buffer solution containing about 0.1 to 10% w/v compound for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the pathophysiological condition being addressed, the overall health of the patient, the make up of the formulation, and the route of administration.

As indicated above, Schwann cells (the glial cells of the peripheral nervous system) are stimulated to divide in the presence of the factors of the invention. Schwann cells of the peripheral nervous system are involved in supporting neurons and in creating the myelin sheath around individual nerve fibers. This sheath is important for proper conduction of electrical impulses to muscles and from sensory receptors.

There are a variety of peripheral neuropathies in which Schwann cells and nerve fibers are damaged, either primarily or secondarily. There are many neuropathies of both sensory and motor fibers (Adams and Victor, Principles of Neurology). The most important of those neuropathies are probably the neuropathies associates with diabetes, multiple sclerosis, Landry-Guillain-Barr syndrome, neuropathies caused by carcinomas, and neuropathies caused by toxic agents (some of which are used to treat carcinomas).

The invention, however, envisages treatment or prophylaxis of conditions where nervous system damage has been brought about by any basic cause, e.g. infection or injury. Thus, in addition to use of the present factors in the treatment of disorders or diseases of the nervous system where demyelination or loss of Schwann cells is present, such glial growth factors can be valuable in the treatment of disorders of the nervous system that have been caused by damage to the peripheral nerves. Following damage to peripheral nerves, the regeneration process is led by the growth or the re-establishment of Schwann cells, followed by the advancement of the nerve fibre back to its target. By speeding up the division of Schwann cells one could promote the regenerative process following damage.

Similar approaches could be used to treat injuries or neurodegenerative disease of the central nervous system (brain and spinal cord).

Furthermore, there are a variety of tumors of glial cells the most common of which is probably neurofibromatosis, which is a patchy small tumor created by overgrowth of glial cells. Also, it has been found that an activity very such like GGF can be found in some Schwann cell tumors, and therefore inhibitors of the action of the present factors on their receptors provides a therapy of a glial tumor, which comprises administering an effective amount of a substance which inhibits the binding of a factor, as defined above, to a receptor.

In general, the invention includes the use of present polypeptide factors in the prophylaxis or treatment of any pathophysiological condition of the nervous system in which a factor-sensitive or factor-responsive cell type is involved.

The polypeptide factors of the invention can also be used as immunogens for making antibodies, such as monoclonal antibodies, following standard techniques. Such antibodies are included within the present invention. These antibodies can, in turn, be used for therapeutic or diagnostic purposes. Thus, conditions perhaps associated with abnormal levels of the factor may be tracked by using such antibodies. In vitro techniques can be used, employing assays on isolated samples using standard methods. Imaging methods in which the antibodies are, for example, tagged with radioactive isotopes which can be imaged outside the body using techniques for the art of tumour imaging may also be employed.

The invention also includes the general use of the present factors as glial cell mitogens in vivo or in vitro, and the factors for such use. One specific embodiment is thus a method for producing a glial cell mitogenic effect in a vertebrate by administering an effective amount of a factor of the invention. A preferred embodiment is such a method in the treatment or prophylaxis of a nervous system disease or disorder.

A further general aspect of the invention is the use of a factor of the invention in the manufacture of a medicament, preferably for the treatment of a nervous disease or disorder, or for neural regeneration or repair.

Also included in the invention are the use of the factors of the invention in competitive assays to identify or quantify molecules having receptor binding characteristics corresponding to those of said polypeptides. The polypeptides may be labelled, optionally with a radioisotope. A competitive assay can identify both antagonists and agonists of the relevant receptor.

In another aspect, the invention provides the use of each one of the factors of the invention in an affinity isolation process, optionally affinity chromatography, for the separation of a respective corresponding receptor. Such processes for the isolation of receptors corresponding to particular proteins are known in the art, and a number of techniques are available and can be applied to the factors of the present invention. For example, in relation to IL-6 and IFNγ the reader is referred to Novick, D.; et al., J. Chromatogr. (1990) 510: 331–7. With respect to gonadotropin releasing hormone reference is made to Hazum, E., J. (1990) Chromatogr. 510: 233–8. In relation to G-CSF reference is made to Fukunaga, R., et al., J. Biol. Chem., 265: 13386–90. In relation to IL-2 reference is made to Smart, J. E., et al., (1990) J. Invest. Dermatol., 94:158S–163S, and in relation to human IFN-gamma reference is made to Stefanos, S, et al., (1989) J. Interferon Res., 9:719–30.

BRIEF DESCRIPTION OF THE DRAWINGS

The drawings will first be described.
Drawings
FIGS. 1 to 8 relate to Example 1, and are briefly described below:

FIGS. 9 to 12 depict the peptide sequences derived from GGF-I and GGF-II, SEQ ID Nos. 1–20, 22–29, 32–53 and 169, (see Example 2 hereinafter), FIGS. 10 and 12 specifically depict novel sequences:

FIG. 9 shows the 21 peptide sequences (SEQ ID Nos 1–20, and 169) obtained from lysyl endopeptidase and protease V8 digestion of purified bovine pituitary GGF-I.

In FIGS. 10A and 10B, the sequences of GGF-I peptides used to design degenerate oligonucleotide probes and degenerate PCR primers are listed (SEQ ID Nos. 1, 22–29, and 17). Some of the sequences in FIG. 10A were also used to design synthetic peptides. FIG. 10B is a listing of the sequences of novel peptides that were too short (less than 9 amino acids) for the design of degenerate probes or degenerate PCR primers (SEQ ID Nos. 19 and 32);

FIG. 11 shows various trypsin and lysyl endopeptidase C are peptide sequences derived from GGF-II, SEQ ID Nos. 33–39, 164–166, 51–52.

In FIGS. 12A and 12B, Panel A, is a listing of the sequences of GGF-II peptides used to design degenerate oligonucleotide probes and degenerate PCR primers (SEQ ID Nos. 45–52). Some of the sequences in Panel A were used to design synthetic peptides. Panel B is a listing of the novel peptide that was too short (less than 6 amino acids) for the design of degenerate probes or degenerate PCR primers (SEQ ID No. 53);

FIGS. 13 to 20 relate to Example 3, below and depict the mitogenic activity of factors of the invention;

FIGS. 21 to 28 (a, b and c) relate to Example 4, below and are briefly described below:

FIG. 13 shows a graph comparing BrUdR-ELISA and [$^{125}$I]UdR counting methods for the DNA synthesis assay in Schwann cell cultures.

FIG. 15 shows the mitogenic response of rat sciatic nerve Schwann cells to GGFs.

FIG. 16 shows a graph quantifying DNA synthesis in rat sciatic nerve Schwann cells and 3T3 fibroblasts in the presence of GGFs.

FIG. 17 shows a graph of the mitogenic response of BHK 21 C13 cells to FCS and GGFs.

FIG. 18 shows a graph of survival and proliferation of BH 21 C13 cell micro cultures after 48 hours in the presence of GGFs.

FIG. 19 shows a graph of the mitogenic response of C6 cells to FCS.

FIG. 21 is a listing of the degenerate oligonucleotide probes (SEQ ID Nos. 54–76, 78–88) designed from the novel peptide sequences in FIG. 10, Panel A and FIG. 12, Panel A;

FIG. 22 depicts a stretch of the putative bovine GGF-II gene sequence from the recombinant bovine genomic phage GGF2BG1, containing the binding site of degenerate oligonucleotide probes 609 and 650 (see FIG. 21, SEQ ID Nos. 69 and 72, respectively). The figure is the coding strand of the DNA sequence (SEQ ID No. 89) and the deduced amino acid sequence (SEQ. ID No. 196) in the third reading frame. The sequence of peptide 12 from factor 2 (bold) is part of a 66 amino acid open reading frame (nucleotides 75272);

FIGS. 23A and 23B is the degenerate PCR primers (SEQ ID Nos. 90–108) and FIG. 22B shows the unique PCR primers (SEQ ID Nos. 109–119) used in experiments to isolate segments of the bovine GGF-II coding sequences present in RNA from posterior pituitary;

FIG. 24 depicts of the nine distinct contiguous bovine GGF-II cDNA structures and sequences that were obtained in PCR amplification experiments using the list of primers in FIG. 12, Panels A and B, and RNA from posterior pituitary. The top line of the Figure is a schematic of the coding sequences which contribute to the cDNA structures that were characterized;

FIG. 25 is a physical map of bovine recombinant phage of GGF2BG1. The bovine fragment is roughly 20 kb in length and contains two axons (bold) of the bovine GGF-II gene. Restriction sites for the enzymes Xbal, SpeI, NdeI, EcoRI, Kpnl, and SstI have been placed on this physical map. Shaded portions correspond to fragments which were subcloned for sequencing;

FIG. 26 is a schematic of the structure of three alternative gene products of the putative bovine GGF-II gene. Exons are listed A through E in the order of their discovery. The alternative splicing patterns 1, 2 and 3 generate three overlapping deduced protein structures (GGF2BPP1, 2, and 3), which are displayed in the various FIGS. 28a, b, c (described below);

FIG. 27 (SEQ ID Nos. 120–132, 45, 52, and 53) is a comparison of the GGF-I and GGF-II sequences identified in the deduced protein sequences shown in FIGS. 28A–28E (described below) with the novel peptide sequences listed in FIGS. 10 and 12. The Figure shows that six of the nine novel GGF-II peptide sequences are accounted for in these deduced protein sequences. Two peptide sequences similar to GGF-I sequences are also found;

FIG. 28A is a listing of the coding strand DNA sequence (SEQ ID NO: 133) and deduced amino acid sequence (SEQ ID NO: 190) of the cDNA obtained from splicing pattern number 1 in FIG. 26. This partial cDNA of the putative bovine GGF-II gene encodes a protein of 206 amino acids in length. Peptides in bold were those identified from the lists presented in FIGS. 10 and 12. Potential glycosylation sites are underlined (along with polyadenylation signal AATAAA) (SEQ ID NO: 226);

FIGS. 28(B–C) is a listing of the coding strand DNA sequence (SEQ ID NO: 134) and deduced amino acid sequence (SEQ ID NO: 191) of the cDNA obtained from splicing pattern number 2 in FIG. 26. This partial cDNA of the putative bovine GGF-II gene encodes a protein of 281 amino acids in length. Peptides in bold are those identified from the lists presented in FIGS. 10 and 12. Potential glycosylation sites are underlined (along with polyadenylation signal AATAAA) (SEQ ID NO: 226);

FIGS. 28(D–E) is a listing of the coding strand DNA sequence (SEQ ID NO: 135) and deduced amino acid sequence (SEQ ID NO: 193) of the cDNA obtained from splicing pattern number 3 in FIG. 26. This partial cDNA of the putative bovine GGF-II gene encodes a protein of 257 amino acids in length. Peptides in bold are those identified from the lists in FIGS. 10 and 12. Potential glycosylation sites are underlined (along with polyadenylation signal AATAAA) (SEQ ID NO: 226).

FIGS. 31(A–R) is a listing of the DNA sequences (SEQ ID Nos. 44, 77, 136–147, 160–163, 173–178) and predicted peptide sequences (SEQ ID Nos. 196–218) of the coding segments of GGF. Line 1 is a listing of the predicted amino acid sequences of bovine GGF, line 2 is a listing of the nucleotide sequences of bovine GGF, line 3 is a listing of the nucleotide sequences of human GGF (heregulin) (nucleotide base matches are indicated with a vertical line) and line 4 is a listing of the predicted amino acid sequences of human GGF/heregulin where it differs from the predicted bovine sequence. Coding segments E, A' and K represent only the bovine sequences. Coding segment D' represents only the human (heregulin) sequence.

FIGS. 32(A–B) is the predicted GGF2 amino acid sequence and nucleotide sequence of BPP5 (SEQ ID NO: 195 and SEQ ID NO: 148 respectively). The upper line is the nucleotide sequence and the lower line is the predicted amino acid sequence.

FIGS. 33(A–B) is the predicted amino acid sequence and nucleotide sequence of GGF2BPP2 (SEQ ID NO: 149 and SEQ ID NO: 192 respectively). The upper line is the nucleotide sequence and the lower line is the predicted amino acid sequence.

FIGS. 34(A–C) is the predicted amino acid sequence and nucleotide sequence of GGF2BPP4 (SEQ ID NO: 194 and SEQ ID NO: 150 respectively). The upper line is the nucleotide sequence and the lower line is the predicted amino acid sequence.

FIG. 35 (SEQ ID Nos. 151–152) depicts the alignment of two GGF peptide sequences (GGF2bpp4 and GGF2bpp5) with the human EGF (hEGF). Asterisks indicate positions of conserved cysteines.

FIGS. 37(A–B) is a list of splicing variants derived from the sequences shown in FIGS. 31(A–R).

FIG. 38 is the predicted amino acid sequence, bottom (SEQ ID NO: 220), and nucleic sequence, top, of EGFL1 (SEQ ID No. 154).

FIG. 39 is the predicted amino acid sequence, bottom (SEQ ID NO: 221), and nucleic sequence, top, of EGFL2 (SEQ ID No. 155).

FIG. 40 is the predicted amino acid sequence, bottom (SEQ ID NO: 222), and nucleic sequence, top, of EGFL3 (SEQ ID No. 156).

FIG. 41 is the predicted amino acid sequence, bottom (SEQ ID NO: 223), and nucleic sequence, top, of EGFL4 (SEQ ID No. 157).

FIG. 42 is the predicted amino acid sequence, bottom (SEQ ID NO: 224), and nucleic sequence, top, of EGFL5 (SEQ ID No. 158).

FIG. 43 is the predicted amino acid sequence, bottom (SEQ ID NO: 225), and nucleic sequence, top, of EGFL6 (SEQ ID No. 159).

FIGS. 45(A–D) is the predicted amino acid sequence (SEQ ID No. 170) (middle) (SEQ ID NO: 170) and nucleic acid sequence (SEQ ID No. 21) (top) of GGF2HBS5. The bottom (intermittent) sequence represents peptide sequences derived from GGF-II preparations (see FIGS. 11, 12).

FIG. 53 is the sequences of GGFHBS5, GGFHFB1 and GGFBPP5 polypeptides (SEQ ID NOS: 170, 171, and 172 respectively).

DETAILED DESCRIPTION

Figure 1:
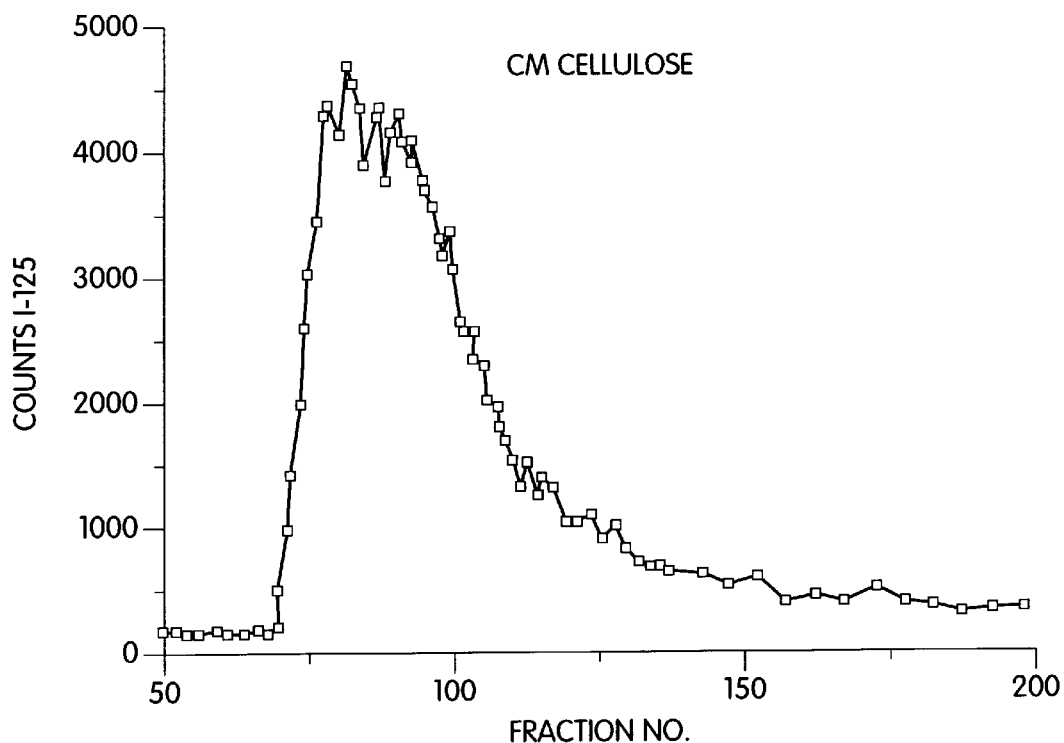
FIG. 1 is the profile for product from carboxymethyl cellulose chromatography.
Figure 2:
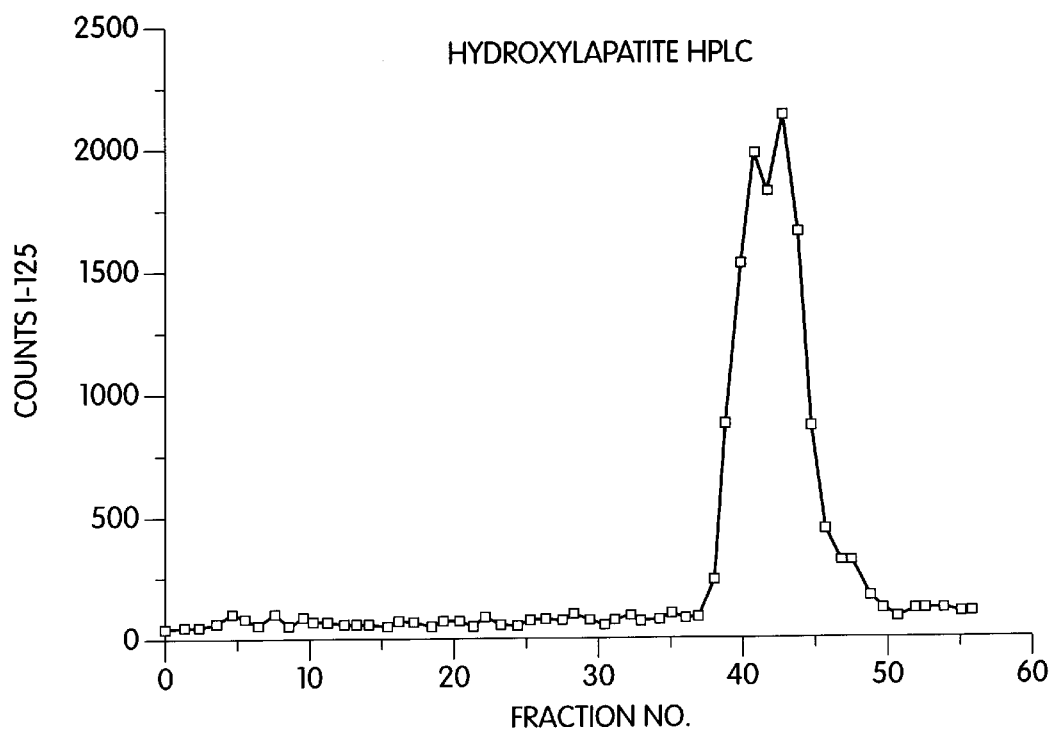
FIG. 2 is the profile for product from hydroxylapatite HPLC.
Figure 3:
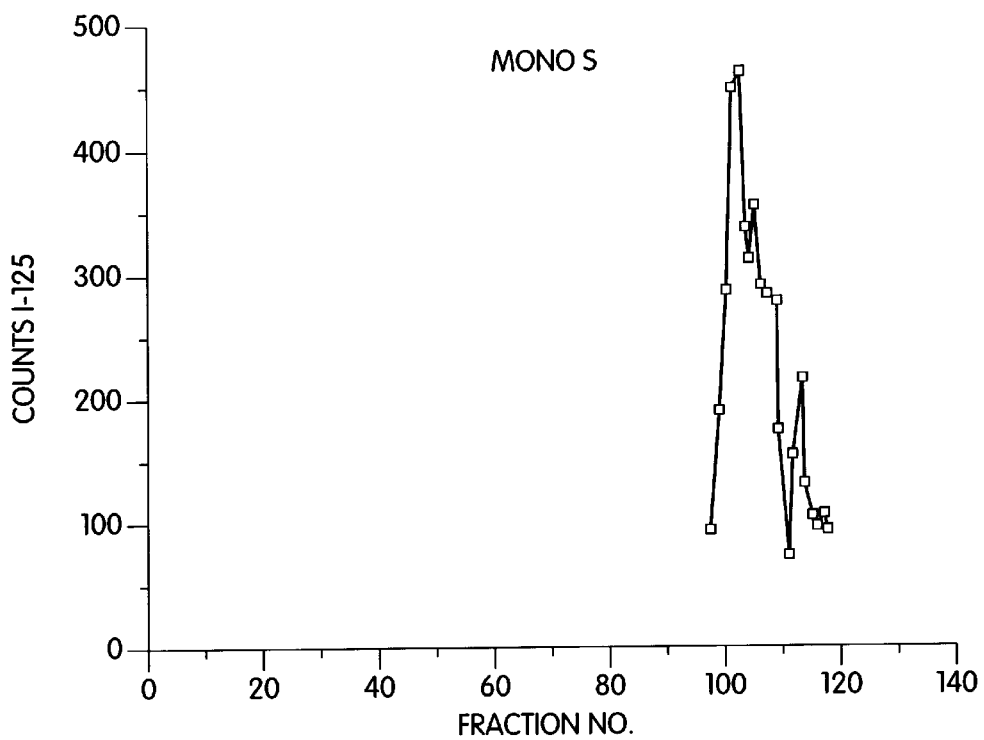
FIG. 3 is the profile for product from Mono S FPLC.
Figure 4:
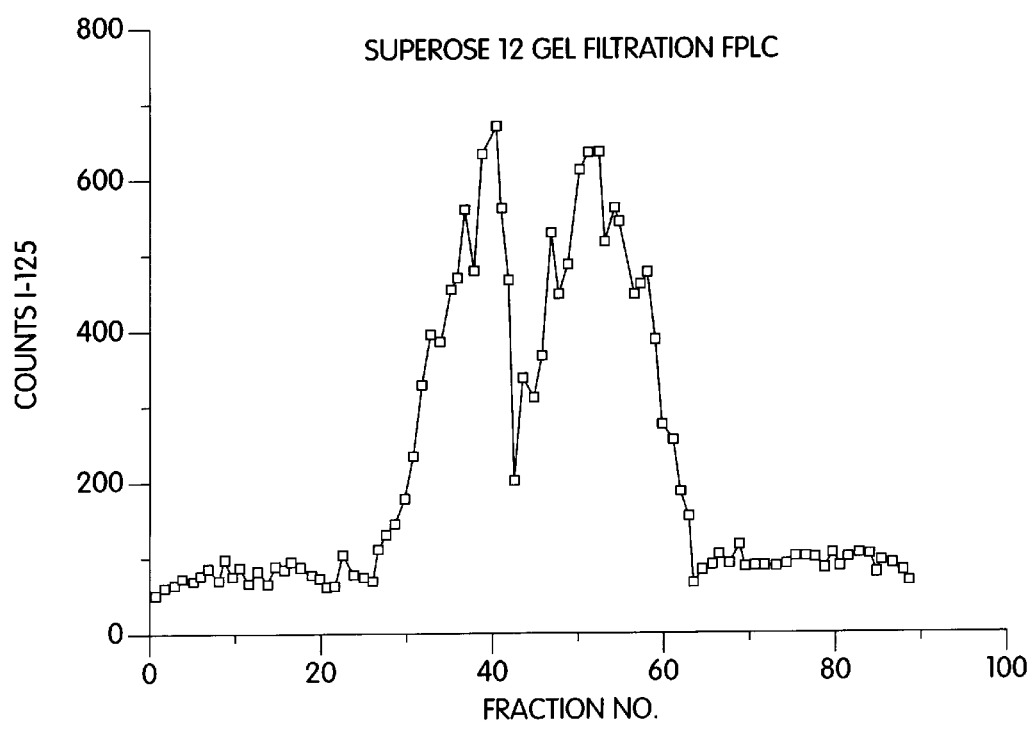
FIG. 4 is the profile for product from Gel filtration FPLC.
Figure 5:
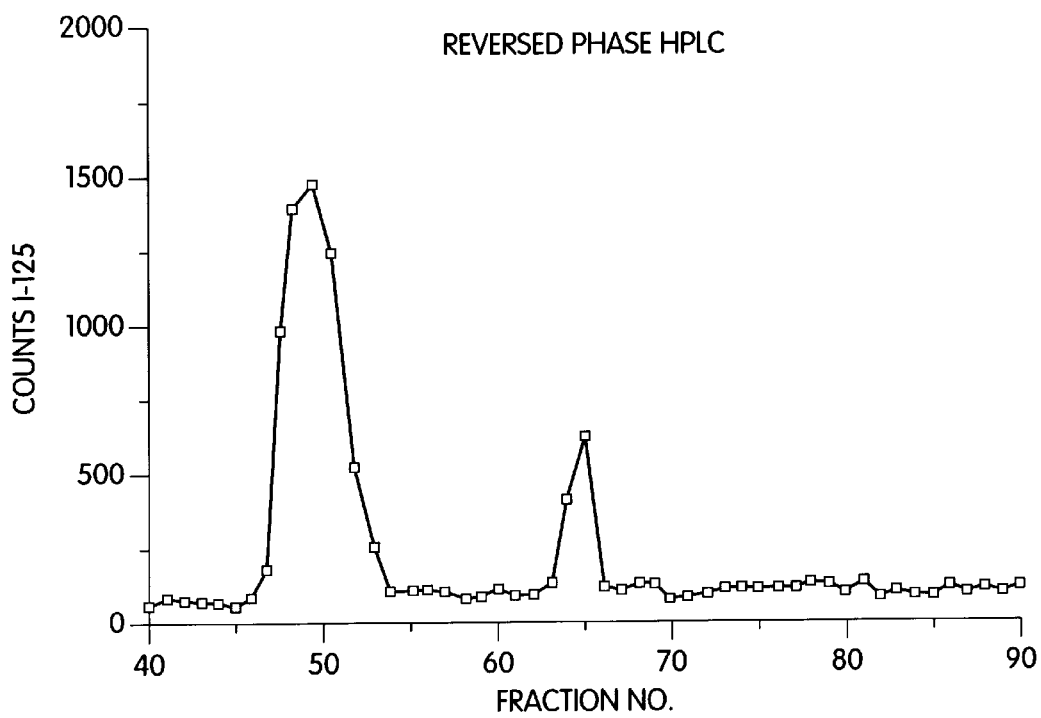
FIGS. 5 and 6 depict the profiles for the two partially purified polypeptide products from reversed-phase HPLC.
Figure 6:
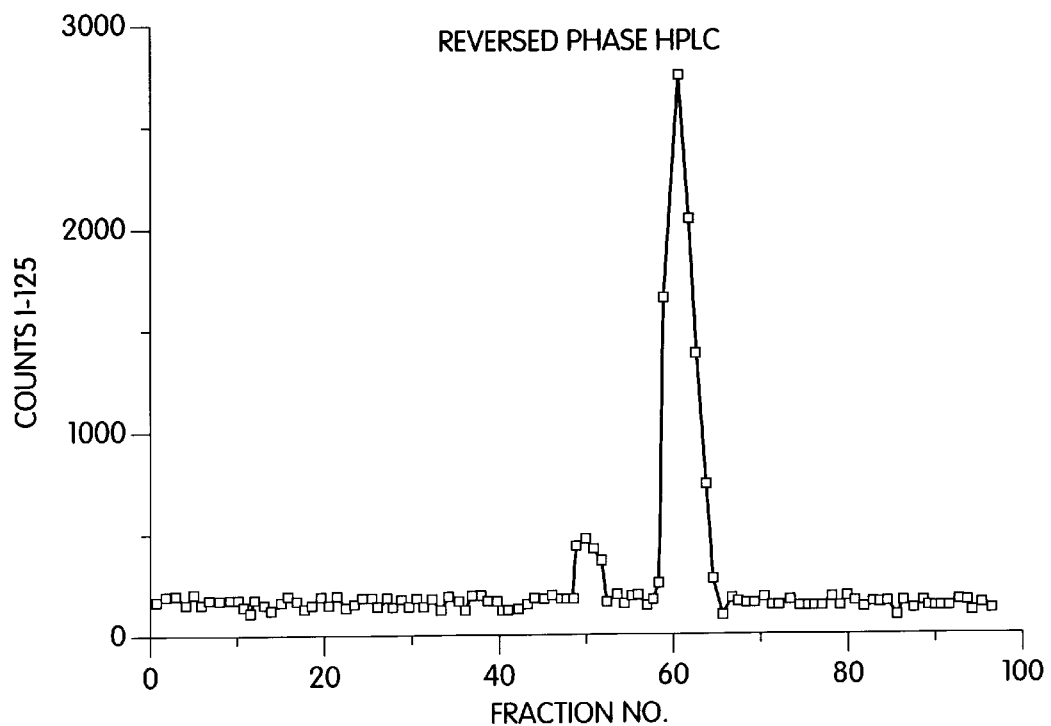

The invention pertains to the isolation and purification of novel Glial Growth factors and the cloning of DNA sequences encoding these factors. Other components of the invention are several gene splicing variants which potentially encode a series of glial growth factors, in particular the GGF2HBS5 in particular a variant which encodes the human equivalent of bovine GGF-II. It is evident that the gene encoding GGF's and p185$^{erbB2}$ binding proteins produces a number of variably-sized, differentially-spliced RNA transcripts that give rise to a series of proteins, which are of different lengths and contain some common peptide sequences and some unique peptide sequences. This is supported by the differentially-spliced sequences which are recoverable from bovine posterior pituitary RNA (as presented herein), human breast cancer (MDA-MB-231) (Holmes et al. Science 256: 1205 (1992) and chicken brain RNA (Falls et al. Cell 72:1–20 (1993)). Further support derives from the wide size range of proteins which act as both mitogens for Schwann cells (as disclosed herein) and as ligands for the p185$^{erbB2}$ receptor (see below).

Further evidence to support the fact that the genes encoding GGF and p185$^{erbB2}$ are homologous comes from nucleotide sequence comparison. Science, 256 (1992), 1205–1210) Holmes et al. demonstrate the purification of a 45-kilodalton human protein (Heregulin-α) which specifically interacts with the receptor protein p185$^{erbB2}$, which is associated with several human malignancies. Several complementary DNA clones encoding Heregulin-α were isolated. Peles et al. (Cell 69:205 (1992)) and Wen et al (Cell 69:559 (1992)) describe a complementary DNA isolated from rat cells encoding a protein called "neu differentiation factor" (NDF). The translation product of the NDF cDNA has p185$^{erbB2}$ binding activity. Usdin and Fischbach, J. Cell. Biol. 103:493–507 (1986); Falls et al., Cold Spring Harbor Symp. Quant. Biol. 55:397–406 (1990); Harris et al., Proc. Natl. Acad. Sci. USA 88:7664–7668 (1991); and Falls et al., Cell 72:801–815 (1993) demonstrate the purification of a 42 kd glycoprotein which interacts with a receptor protein p185$^{erbB2}$ and several complementary cDNA clones were isolated (Falls et al. Cell 72:801–815 (1993). Several other groups have reported the purification of proteins of various molecular weights with p185$^{erbB2}$ binding activity. These groups include Lupu et al. (1992) Proc. Natl. Acad. Sci. USA 89:2287; Yarden and Peles (1991) Biochemistry 30:3543; Lupu et al. (1990) Science 249:1552); Dobashi et al. (1991) Biochem. Biophys. Res. Comm. 179:1536; and Huang et al. (1992) J. Biol. Chem. 257:11508–11512.

Other Embodiments

The invention includes any protein which is substantially homologous to the coding segments in FIGS. 31(A–R) (SEQ ID Nos. 136–147, 160, and 161) as well as other naturally occurring GGF polypeptides. Also included are: allelic variations; natural mutants; induced mutants; proteins encoded by DNA that hybridizes under high or low stringency conditions to a nucleic acid naturally occurring (for definitions of high and low stringency see Current Protocols in Molecular Biology, John Wiley & Sons, New York, 1989, 6.3.1–6.3.6, hereby incorporated by reference); and polypeptides or proteins specifically bound by antisera to GGF polypeptide. The term also includes chimeric polypeptides that include the GGF polypeptides comprising sequences from FIGS. 31(A–R).

The following examples are not intended to limit the invention, but are provided to usefully illustrate the same, and provide specific guidance for effective preparative techniques.

As will be seen from Example 3, below, the present factors exhibit mitogenic activity on a range of cell types. The activity in relation to fibroblasts indicates a wound repair ability, and the invention encompasses this use. The general statements of invention above in relation to formulations and/or medicaments and their manufacture should clearly be construed to include appropriate products and uses. This in clearly a reasonable expectation for the present invention, given reports of similar activities for fibroblast growth factors (FGFs). Reference can be made, for example, to Sporn et al., "Peptide Growth Factors and their Receptors I", page 396 (Baird and Bohlen) in the section headed "FGFs in Wound Healing and Tissue Repair".

EXAMPLE 1

Purification of GGF-I and GGF-II from Bovine Pituitaries

I. Preparation of Factor-CM Fraction 4,000 frozen whole bovine pituitaries (c.a. 12 kg) were thawed overnight, washed briefly with water and then homogenized in an equal volume of 0.15 M ammonium sulphate in batches in a Waring Slender. The homogenate was taken to pH 4.5 with 1.0 M HCl and centrifuged at 4,900 g for 80 minutes. Any fatty material in the supernatant was removed by passing it through glass wool. After taking the pH of the supernatant to 6.5 using 1.0 M NaOH, solid ammonium sulphate was added to give a 36% saturated solution. After several hours stirring, the suspension was centrifuged at 4,900 g for 80 minutes and the precipitate discarded. After filtration through glass wool, further solid ammonium sulphate was added to the supernatant to give a 75% saturated solution which was once again centrifuged at 4,900 g for 80 minutes after several hours stirring. The pellet was resuspended in c.a. 2 L of 0.1 M sodium phosphate pH 6.0 and dialyzed against 3×40 L of the same buffer. After confirming that the conductivity of the dialysate was below 20.0 μSiemens, it was loaded onto a Bioprocess column (120×113 mm, Pharmacia) packed with carboxymethyl cellulose (CM-52, Whatman) at a flow rate of 2 ml min$^{-1}$. The column was washed with 2 volumes of 0.1 M sodium phosphate pH 6.0, followed by 2 volumes of 50 mM NaCl, and finally 2 volumes of 0.2 M NaCl both in the same buffer. During the final step, 10 mL (5 minute) fractions were collected. Fractions 73 to 118 inclusive were pooled, dialyzed against 10 volumes of 10 mM sodium phosphate pH 6.0 twice and clarified by centrifugation at 100,000 g for 60 minutes.

II. Hydroxylapatite HPLC

Hydroxylapatite HPLC is not a technique hitherto used in isolating glial growth factors, but proved particularly efficacious in this invention. The material obtained from the above CM-cellulose chromatography was filtered through a 0.22 μm filter (Nalgene), loaded at room temperature on to a high performance hydroxylapatite column (50×50 mm, Biorad) equipped with a guard column (15×25 mm, Biorad) and equilibrated with 10 mM potassium phosphate pH 6.0. Elution at room temperature was carried out at a flow rate of 2 ml.minute$^{-1}$ using the following programmed linear gradient:

| time (min) | % B | Solvent A: 10 mM potassium phosphate pH 6.0 |
|---|---|---|
| 0.0 | 0 | Solvent B: 1.0 M potassium phosphate pH 6.0 |
| 5.0 | 0 | |
| 7.0 | 20 | |
| 70.0 | 20 | |
| 150.0 | 100 | |
| 180.0 | 100 | |
| 185.0 | 0 | |

6.0 mL (3 minutes) fractions were collected during the gradient elution. Fractions 39–45 were pooled and dialyzed against 10 volumes of 50 mM sodium phosphate pH 6.0.

III. Mono S FPLC

Mono S FPLC enabled a more concentrated material to be prepared for subsequent gel filtration.

Any particulate material in the pooled material from the hydroxylapatite column was removed by a clarifying spin at 100,000 g for 60 minutes prior to loading on to a preparative HR10/10 Mono S cation exchange column (100×10 mm, Pharmacia) which was then re-equilibrated to 50 mM sodium phosphate pH 6.0 at room temperature with a flow rate of 1.0 ml/minute$^{-1}$. Under these conditions, bound protein was eluted using the following programmed linear gradient:

| time (min) | % B | Solvent A: 50 mM potassium phosphate pH 6.0 |
|---|---|---|
| 0.0 | 0 | Solvent B: 1.2 M sodium chloride, 50 mm |
| 70.0 | 30 | sodium phosphate pH 6.0 |
| 240.0 | 100 | |
| 250.0 | 100 | |
| 260.0 | 0 | |

1 mL (1 minute) fractions were collected throughout this gradient program. Fractions 99 to 115 inclusive were pooled.

IV. Gel Filtration FPLC

This step commenced the separation of the two factors of the invention prior to final purification, producing enriched fractions.

For the purposes of this step, a preparative Superose 12 FPLC column (510×20 mm, Pharmacia) was packed according to the manufacturers' instructions. In order to standardize this column, a theoretical plates measurement was made according to the manufacturers' instructions, giving a value of 9,700 theoretical plates.

The pool of Mono S eluted material was applied at room temperature in 2.5 Ml aliquots to this column in 50 mM sodium phosphate, 0.75 NaCl pH 6.0 (previously passed through a C18 reversed phase column (Sep-pak, Millipore) at a flow rate of 1.0 mL/minute$^{-1}$. 1 mL (0.5 minute) fractions were collected from 35 minutes after each sample was applied to the column. Fractions 27 to 41 (GGF-II) and 42 to 57 (GGF-I) inclusive from each run were pooled.

V. Reversed-Phase HPLC

The GGF-I and GGF-II pools from the above Superose 12 runs were each divided into three equal aliquots. Each aliquot was loaded on to a C8 reversed-phase column (Aquapore RP-300 7μ C8 220×4.6 mm, Applied Biosystems) protected by a guard cartridge (RP-8, 15×3.2 mm, Applied Biosystems) and equilibrated to 40° C. at 0.5 mL.minute. Protein was eluted under these conditions using the following programmed linear gradient:

| time (min) | % B | Solvent A: 0.1% trifluoroacetic acid (TFA) |
|---|---|---|
| 0 | 0 | Solvent B: 90% acetonitrile, 0.1% TFA |
| 60 | 66.6 | |
| 62.0 | 100 | |
| 72.0 | 100 | |
| 75.0 | 0 | |

200 μL (0.4 minute) fractions were collected in siliconized tubes (Multilube tubes, Bioquote) from 15.2 minutes after the beginning of the programmed gradient.

VI. SDS-Polyacrylamide Gel Electrophoresis

In this step, protein molecular weight standards, low range, catalogue no. 161-0304, from Bio-Rad Laboratories Limited, Watford, England were employed. The actual proteins used, and their molecular weight standards, have been listed herein previously.

Fractions 47 to 53 (GGF-I) and fractions 61 to 67 (GGFII) inclusive from the reversed-phase runs were individually pooled. 7 μL of the pooled material was boiled in an equal volume of 0.0125 M Tris-Cl, 4% SDS, 20% glycerol, and 10% β-mercaptoethanol for GGF-I, for 5 minutes and loaded on to an 11% polyacrylamide Laemmli gel with a 4% stacking gel and run at a constant voltage of 50 V for 16 hours. This gel was then fixed and stained using a silver staining kit (Amersham). Under these conditions, the factors are each seen as a somewhat diffuse band at relative molecular weights 30,000 to 36,000 Daltons (GGF-I) and 55,000 to 63,000 Daltons (GGFII) as defined by molecular weight markers. From the gel staining, it is apparent that there are a small number of other protein species present at equivalent levels to the GGF-I and GGF-II species in the material pooled from the reversed-phase runs.

VII. Stability in Trifluoroacetic Acid

Stability data were obtained for the present Factors in the presence of trifluoroacetic acid, as follows:

GGF-I: Material from the reversed-phase HPLC, in the presence of 0.1% TFA and acetonitrile, was assayed within 12 hours of the completion of the column run and then after 10 weeks incubation at 40° C. Following incubation, the GGF-I had at least 50% of the activity of that material assayed directly off the column.

GGF-II: Material from the reversed-phase HPLC, in the presence of 0.1% TFA and acetonitrile, and stored at −20° C., was assayed after thawing and then after 4 days incubation at 40° C. Following incubation, the GGF-II had at least 50% of the activity of that material freshly thawed.

It will be appreciated that the trifluoroacetic acid concentration used in the above studies is that most commonly used for reversed-phase chromatography.

VIII. Activity Assay Conditions

Unless otherwise indicated, all operations were conducted at 37° C., and, with reference to FIGS. 1 to 6, activity at each stage was determined using the Brockes (Meth. Enz., supra) techniques with the following modifications. Thus, in preparing Schwann cells, 5 μM forskolin was added in addition to DMEM (Dulbecco's modified Eagle's medium), FCS and GGF. Cells used in the assay were fibroblast-free Schwann cells at passage number less than 10, and these cells were removed from flasks with trypsin and plated into flat-bottomed 96-well plates at 3.3 thousand cells per microwell. [$^{125}$I]IUdR was added for the final 24 hours after the test solution addition. The background (unstimulated) incorporation to each assay was less than 100 cpm, and maximal incorporation was 20 to 200 fold over background depending on Schwann cell batch and passage number.

Figure 7:
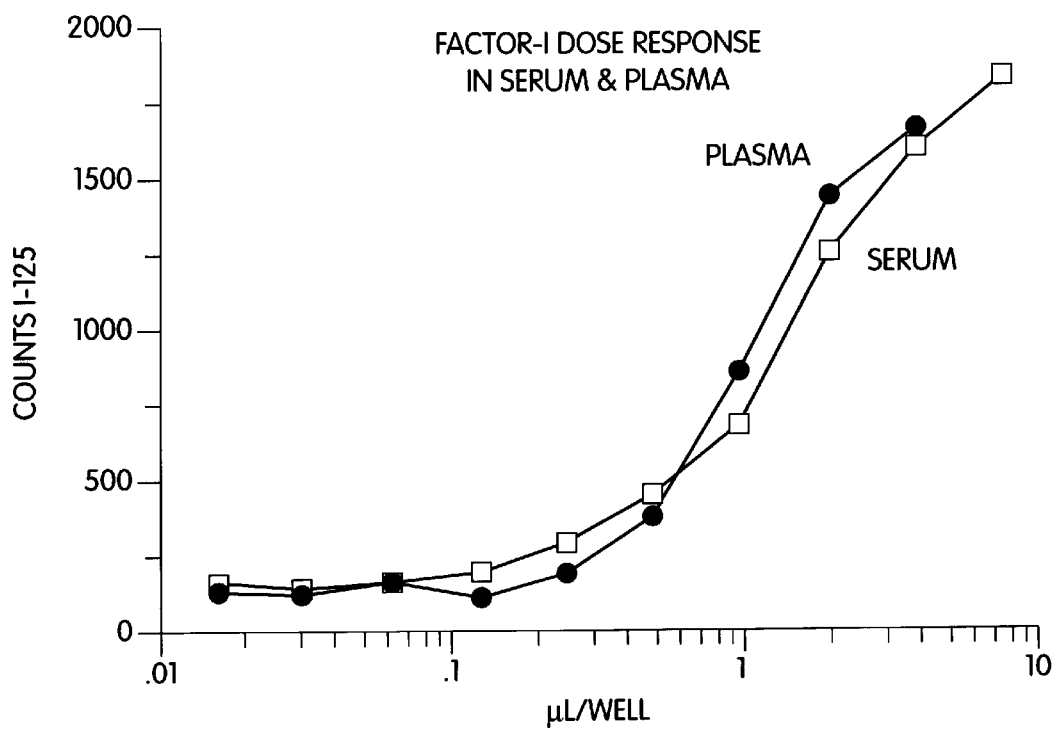
FIGS. 7 and 8 depict dose-response curves for the GGF-I and GGF-II fractions from reversed-phase HPLC using either a fetal calf serum or a fetal calf plasma background.
Figure 8:
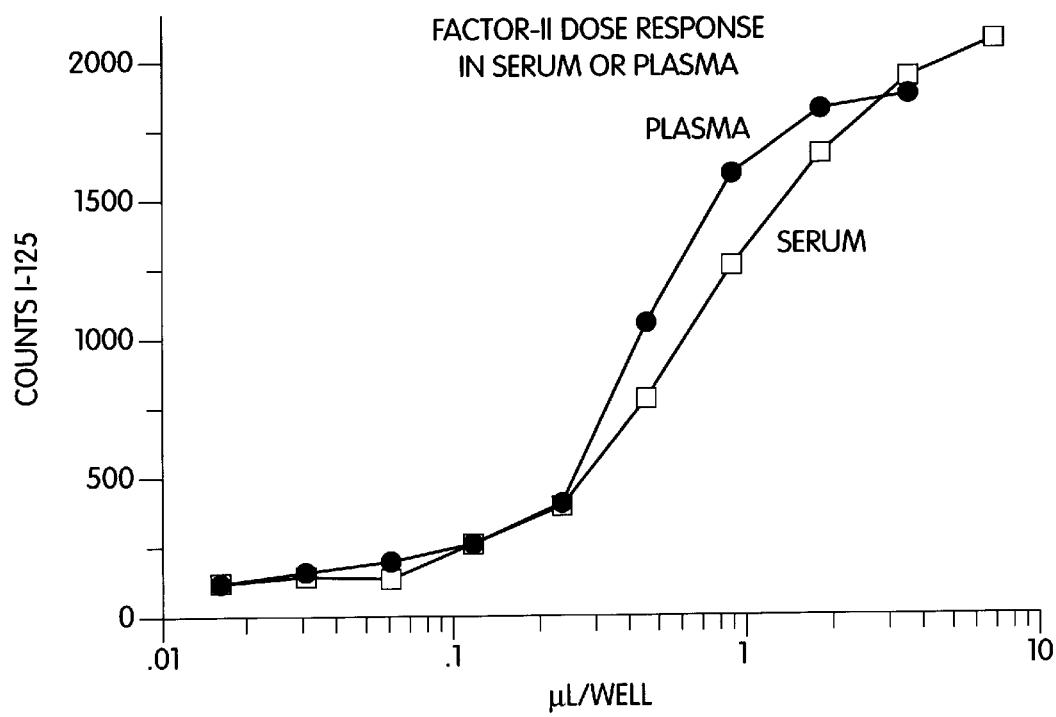

In the case of the GGF-I and GGF-II fractions from reversed-phase HPLC as described above, two dose response curves were also produced for each factor, using exactly the above method for one of the curves for each factor, and the above method modified in the assay procedure only by substituting foetal calf plasma for fetal calf serum to obtain the other curve for each factor. The results are in FIGS. 7 and 8.

EXAMPLE 2

Amino Acid Sequences of Purified GGF-I and GGF-II

Amino acid sequence analysis studies were performed using highly purified bovine pituitary GGF-I and GGF-II. The conventional single letter code was used to describe the sequences. Peptides were obtained by lysyl endopeptidase and protease V8 digests, carried out on reduced and carboxymethylated samples, with the lysyl endopeptidase digest of GGF-II carried out on material eluted from the 55–65 RD region of a 11% SDS-PAGE (MW relative to the above-quoted markers).

A total of 21 peptide sequences (see FIG. 9, SEQ ID Nos. 1–20, 169) were obtained for GGF-I, of which 12 peptides (see FIG. 10, SEQ ID Nos. 1, 22–29, 17, 19, and 32) are not present in current protein databases and therefore represent unique sequences. A total of 12 peptide sequences (see FIG. 11, SEQ ID Nos. 33–39, 164–166, 51, 52) were obtained for GGF-II, of which 10 peptides (see FIG. 12, SEQ ID Nos. 45–53) are not present in current protein databases and therefore represent unique sequences (an exception is peptide GGF-II 06 which shows identical sequences in many proteins which are probably of no significance given the small number of residues). These novel sequences are extremely likely to correspond to portions of the true amino acid sequences of GGFs I and II.

Particular attention can be drawn to the sequences of GGF-I 07 and GGF-II 12, which are clearly highly related. The similarities indicate that the sequences of these peptides are almost certainly those of the assigned GGF species, and are most unlikely to be derived from contaminant proteins.

In addition, in peptide GGF-II 02, the sequence X S S is consistent with the presence of an N linked carbohydrate moiety on an asparagine at the position denoted by X.

In general, in FIGS. 9 and 11, X represents an unknown residue denoting a sequencing cycle where a single position could not be called with certainty either because there was more than one signal of equal size in the cycle or because no signal was present. As asterisk denotes those peptides where the last amino acid called corresponds to the last amino acid present in that peptide. In the remaining peptides, the signal strength after the last amino acid called was insufficient to continue sequence calling to the end of that peptide. The right hand column indicates the results of a computer database search using the GCG package FASTA and TFASTA programs to analyze the NBRF and EMBL sequence databases. The name of a protein in this column denotes identity of a portion of its sequence with the peptide amino acid sequence called allowing a maximum of two mismatches. A question mark denotes three mismatches allowed. The abbreviations used are as follows:

| HMG-1 | High Mobility Group protein-1 |
| HMG-2 | High Mobility Group protein-2 |
| LH-alpha | Luteinizing hormone alpha subunit |
| LH-beta | Luteinizing hormone beta subunit |

EXAMPLE 3

Mitogenic Activity of Purified GGF-I and GGF-II

The mitogenic activity of a highly purified sample containing both GGFs I and II was studied using a quantitative method, which allows a single microculture to be examined for DNA synthesis, cell morphology, cell number and expression of cell antigens. This technique has been modified from a method previously reported by Muir at al., Analytical Biochemistry 185, 377–382, 1990. The main modifications are: 1) the use of uncoated microtiter plates, 2) the cell number per well, 3) the use of 5% Foetal Bovine Plasma (FBP) instead of 10% Foetal Calf Serum (FCS), and 4) the time of incubation in presence of mitogens and bromodeoxyuridine (BrdU), added simultaneously to the cultures. In addition the cell monolayer was not washed before fixation to avoid loss of cells, and the incubation time of monoclonal mouse anti-BrdU antibody and peroxidase conjugated goat anti-mouse immunoglobulin (IgG) antibody were doubled to increase the sensitivity of the assay. The assay, optimized for rat sciatic nerve Schwann cells, has also been used for several cell lines, after appropriate modifications to the cell culture conditions.

I. Methods of Mitogenesis Testing

On day 1, purified Schwann cells were plated onto uncoated 96 well plates in 5% FBP/Dulbecco's Modified Eagle Medium (DMEM) (5,000 cells/well). On day 2, GGFs or other test factors were added to the cultures, as well as BrdU at a final concentration of 10 $\mu$m. After 48 hours (day 4) BrdU incorporation was terminated by aspirating the medium and cells were fixed with 200 $\mu$l/well of 70% ethanol for 20 min at room temperature. Next, the cells were washed with water and the DNA denatured by incubation with 100 $\mu$l 2N HCl for 10 min at 37° C. Following aspiration, residual acid was neutralized by filling the wells with 0.1 M borate buffer, pH 9.0, and the calls were washed with phosphate buffered saline (PBS). Cells were then treated with 50 $\mu$l of blocking buffer (PBS containing 0.1% Triton X 100 and 2% normal goat serum) for 15 min at 37° C. After aspiration, monoclonal mouse anti-BrdU antibody (Dako Corp., Santa Barbara, Calif.) (50 $\mu$l/well, 1.4 $\mu$g/ml diluted in blocking buffer) was added and incubated for two hours at 37° C. Unbound antibodies were removed by three washes in PBS containing 0.1% Triton X-100 and peroxidase-conjugated goat ant-mouse IgG antibody (Dako Corp., Santa Barbara, Calif.) (50 $\mu$l/well, 2 $\mu$g/ml diluted in blocking buffer) was added and incubated for one hour at 37° C. After three washes in PBS/Triton and a final rinse in PBS, wells received 100 $\mu$l/well of 50 mM phosphate/citrate buffer, pH 5.0, containing 0.05% of the soluble chromogen o-phenylenediamine (OPD) and 0.02% $H_2O_2$. The reaction was terminated after 5–20 min at room temperature, by pipetting 80 $\mu$l from each well to a clean plate containing 40 $\mu$l/well of 2N sulfuric acid. The absorbance was recorded at 490 nm using a plate reader (Dynatech Labs). The assay plates containing the cell monolayers were washed twice with PBS and immunocytochemically stained for BrdU-DNA by adding 100 $\mu$l/well of the substrate diaminobenzidine (DAB) and 0.02% $H_2O_2$ to generate an insoluble product. After 10–20 min the staining reaction was stopped by washing with water, and BrdU-positive nuclei observed and counted using an inverted microscope occasionally, negative nuclei were counterstained with 0.001% Toluidine blue and counted as before.

II. Cell Lines Used for Mitogenesis Assays

Swiss 3T3 Fibroblasts: Cells, from Flow Labs, were maintained in DMEM supplemented with 10% FCS, penicillin and streptomycin, at 37° C. in a humidified atmosphere of 10% $CO_2$ in air. Cells were fed or subcultured every two days. For mitogenic assay, cells were plated at a density of 5,000 cells/well in complete medium and incubated for a week until cells were confluent and quiescent. The serum containing medium was removed and the cell monolayer washed twice with serum free-medium. 100 $\mu$l of serum free medium containing mitogens and 10 $\mu$M of BrdU were added to each well and incubated for 48 hours. Dose responses to GGFs and serum or PDGF (as a positive control) were performed.

BHK (Baby Hamster Kidney) 21 C13 Fibroblasts: Cells from European Collection of Animal Cell Cultures (ECACC), were maintained in Glasgow Modified Eagle Medium (GMEM) supplemented with 5% tryptose phosphate broth, 5% FCS, penicillin and streptomycin, at 37° C. in a humidified atmosphere of 5% $CO_2$ in air. Cells were fed or subcultured every two to three days. For mitogenic assay, cells were plated at a density of 2,000 cell/well in complete medium for 24 hours. The serum containing medium was then removed and after washing with serum free medium, replaced with 100 $\mu$l of 0.1% FCS containing GMEM or GMEM alone. GGFs and FCS or bFGF as positive controls were added, coincident with 10 $\mu$M BrdU, and incubated for 48 hours. Cell cultures were then processed as described for Schwann cells.

C6 Rat Glioma Cell Line: Cells, obtained at passage 39, were maintained in DMEM containing 5% FCS, 5% Horse serum (HS), penicillin and streptomycin, at 37° C. in a humidified atmosphere of 10% $CO_2$ in air. Cells were fed or subcultured every three days. For mitogenic assay, cells were plated at a density of 2,000 cells/well in complete medium and incubated for 24 hours. Then medium was replaced with a mixture of 1:1 DMEM and F12 medium containing 0.1% FCS, after washing in serum free medium. Dose responses to GGFs, FCS and $\alpha$FGF were then performed and cells were processed through the ELISA as previously described for the other cell types.

PC12 (Rat Adrenal Pheochromocytoma Cells): Cells from ECACC, were maintained in RPMI 1640 supplemented with 10% HS, 5% FCS, penicillin and streptomycin, in collagen coated flasks, at 37° C. in a humidified atmosphere of 5% $CO_2$ in air. Cells were fed every three days by replacing 80% of the medium. For mitogenic assay, cells were plated at a density of 3,000 cells/well in complete medium, on collagen coated plates (50 $\mu$l/well collagen, Vitrogen Collagen Corp., diluted 1:50, 30 min at 37° C.) and incubated for 24 hours. The medium was then placed with fresh RPMI either alone or containing 1 mM insulin or 1% FCS. Dose responses to FCS/HS (1:2) as positive control and to GGFs were performed as before. After 48 hours cells were fixed and the ELISA performed as previously described.

III. Results of Mitogenesis Assays:

All the experiments presented in this Example were performed using a highly purified sample from a Sepharose 12 chromatography purification step (see Example 1, section D) containing a mixture of GGF-I and GGF-II (GGFs).

First, the results obtained with the BrdU incorporation assay were compared with the classical mitogenic assay for Schwann cells based on [125]I-UdR incorporation into DNA of dividing cells, described by J. P. Brockes (Methods Enzymol. 147:217, 1987).

Figure 13:
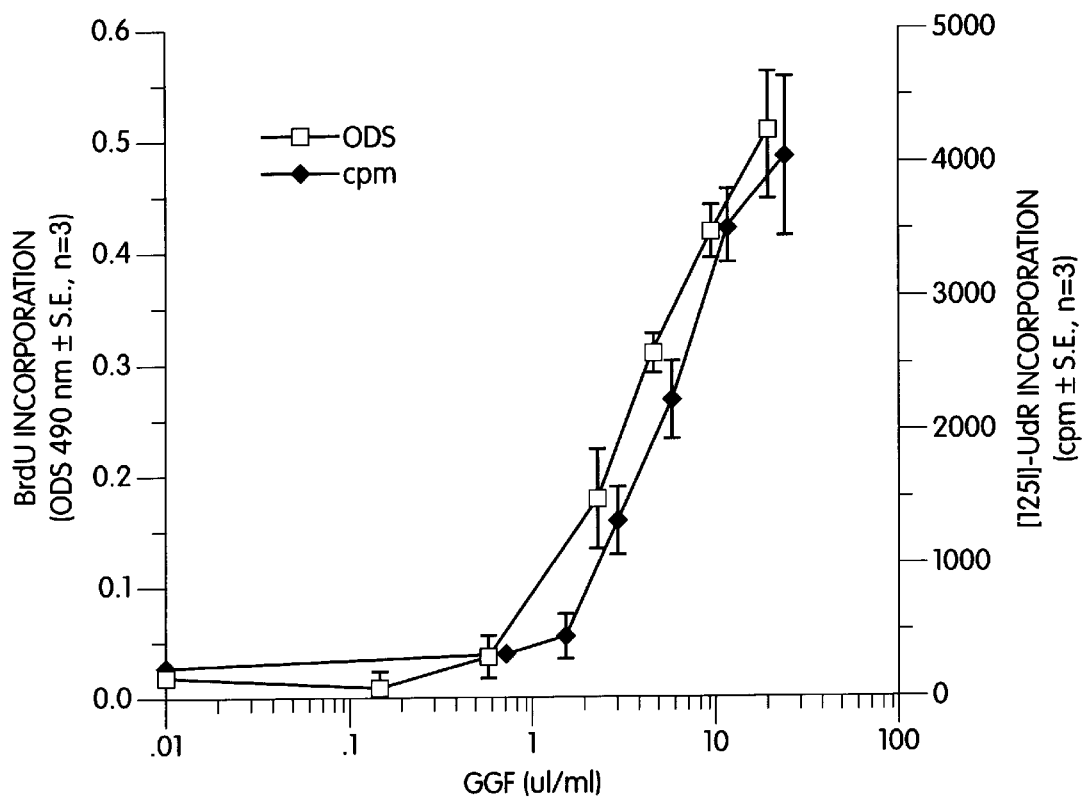

FIG. 13 shows the comparison of data obtained with the two assays, performed in the same cell culture conditions (5,000 cells/well, in 5% FBP/DMEM, incubated in presence of GGFs for 48 hrs). As clearly shown, the results are comparable, but BrdU incorporation assay appears to be slightly more sensitive, as suggested by the shift of the curve to the left of the graph, i.e. to lower concentrations of GGFS.

As described under the section "Methods of Mitogenesis Testing", after the immunoreactive BrdU-DNA has been quantitated by reading the intensity of the soluble product of the OPD peroxidase reaction, the original assay plates containing cell monolayers can undergo the second reaction resulting in the insoluble DAB product, which stains the BrdU positive nuclei. The microcultures can then be examined under an inverted microscope, and cell morphology and the numbers of BrdU-positive and negative nuclei can be observed.

Figure 14A:
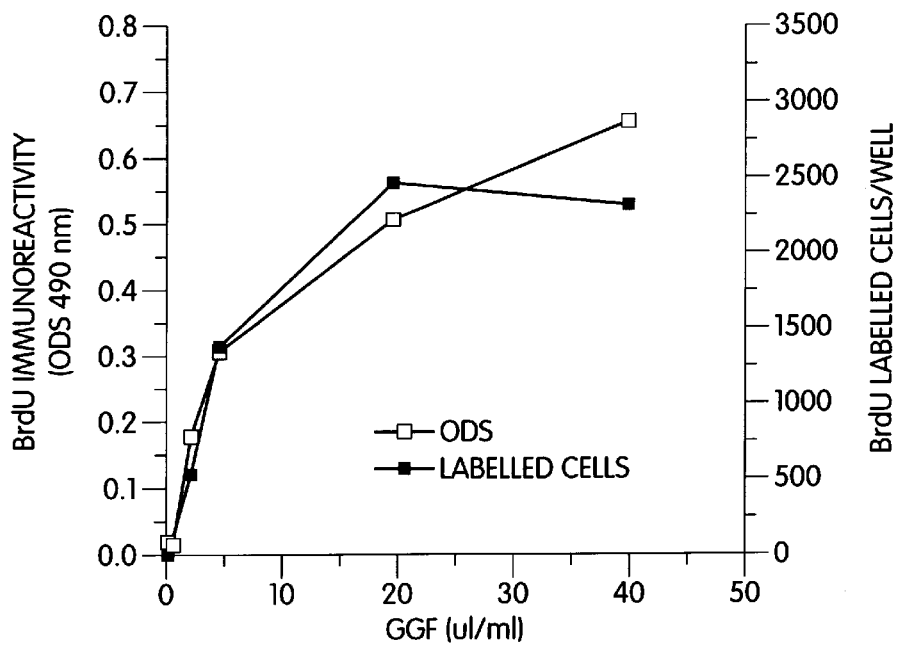
FIGS. 14A and 14B show graphs comparing Br-UdR immunoreactivity with the number of Br-UdR labeled cells.
Figure 14B:
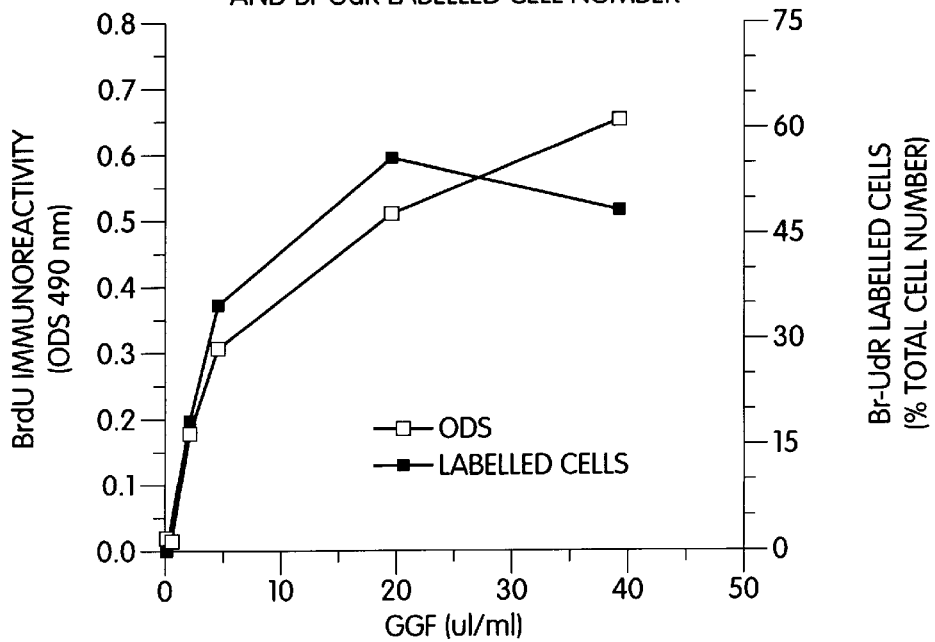

In FIG. 14a and FIG. 14b the BrdU-DNA immunoreactivity, evaluated by reading absorbance at 490 nm, is compared to the number of BrdU-positive nuclei and to the percentage of BrdU-positive nuclei on the total number of cells per well, counted in the same cultures. Standard deviations were less than 10%. The two evaluation methods show a very good correlation and the discrepancy between the values at the highest dose of GGFs can be explained by the different extent of DNA synthesis in cells detected as BrdU-positive.

Figure 15:
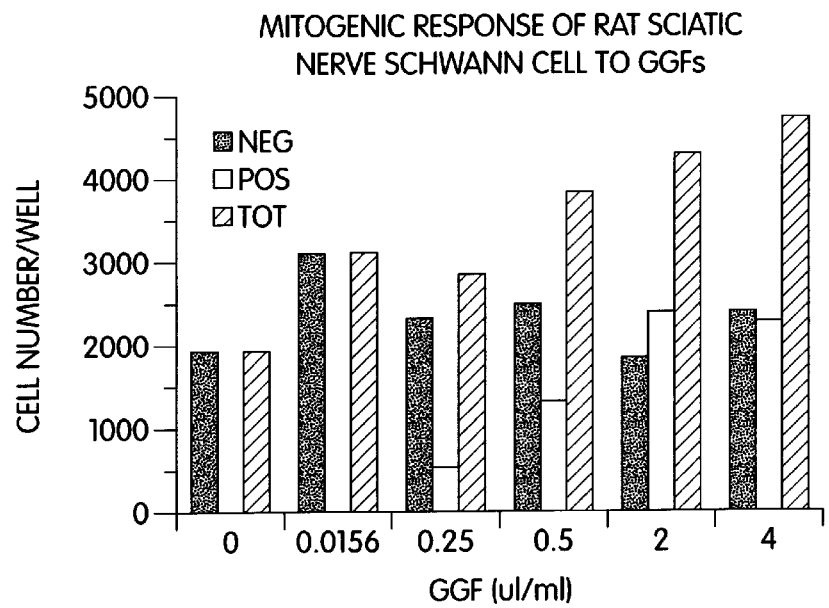

The BrdU incorporation assay can therefore provide additional useful information about the biological activity of polypeptides on Schwann cells when compared to the (125) I-UdR incorporation assay. For example, the data reported in FIG. 15 show that GGFs can act on Schwann cells to induce DNA synthesis, but at lower doses to increase the number of negative cells present in the microculture after 48 hours.

Figure 16:
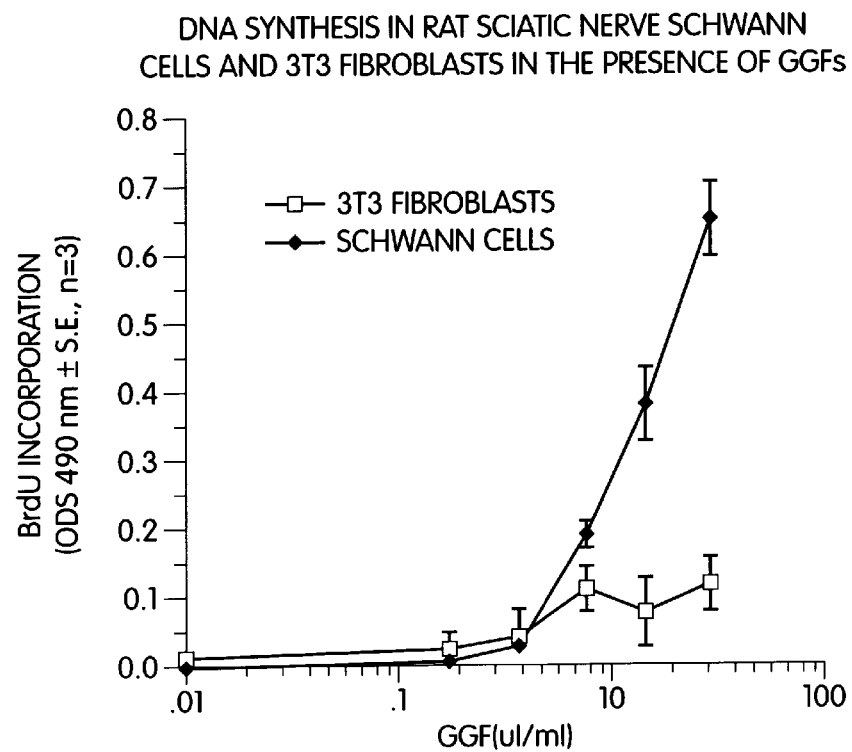

The assay has then been used on several cell lines of different origin. In FIG. 16 the mitogenic responses of Schwann cells and Swiss 3T3 fibroblasts to GGFs are compared; despite the weak response obtained in 3T3 fibroblasts, some clearly BrdU-positive nuclei were detected in these cultures. Control cultures were run in parallel in presence of several doses of FCS or human recombinant PDGF, showing that the cells could respond to appropriate stimuli (not shown).

Figure 17:
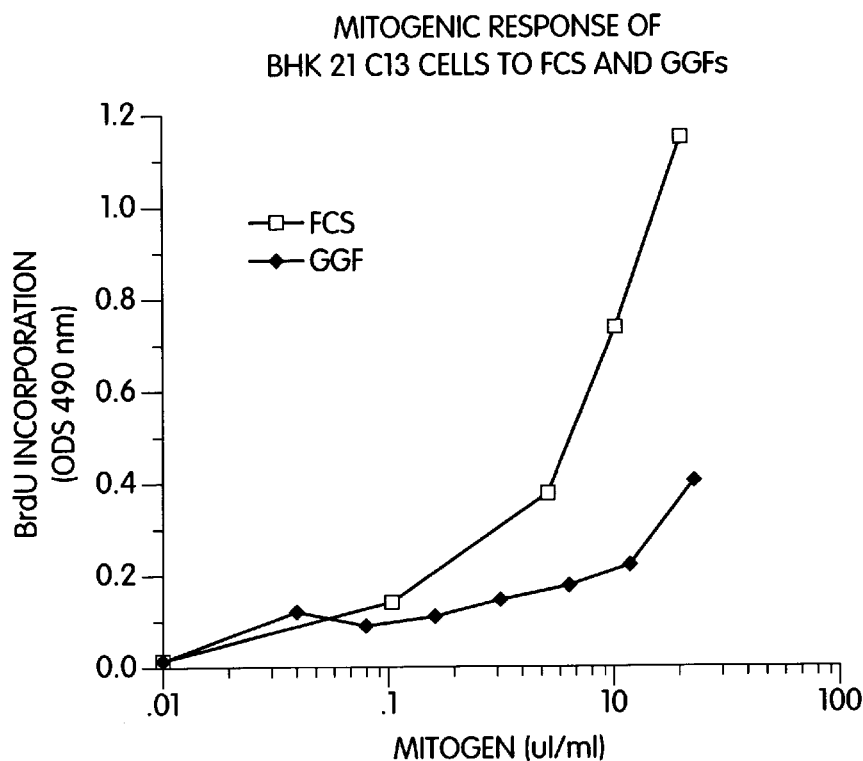
Figure 18:
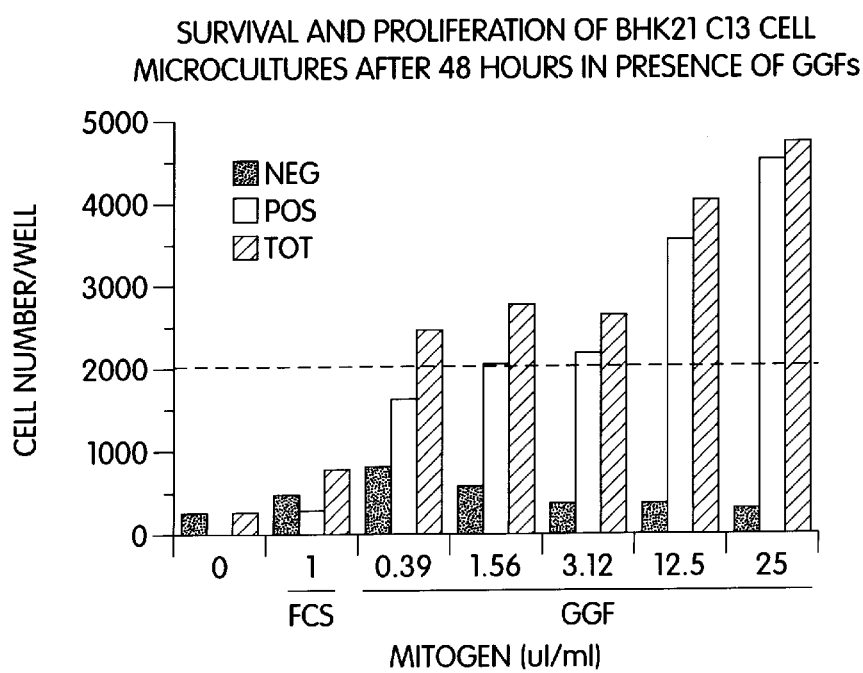

The ability of fibroblasts to respond to GGFs was further investigated using the BHK 21 C13 cell line. These fibroblasts, derived from kidney, do not exhibit contact inhibition or reach a quiescent state when confluent. Therefore the experimental conditions were designed to have a very low background proliferation without compromising the cell viability. GGFs have a significant mitogenic activity on BHK21 C13 cells as shown by FIG. 17 and FIG. 18. FIG. 17 shows the Brdu incorporation into DNA by BHK 21 C13 cells stimulated by GGFS in the presence of 0.1% FCS. The good mitogenic response to FCS indicates that cell culture conditions were not limiting. In FIG. 18 the mitogenic effect of GGFs is expressed as the number of BrdU-positive and BrdU-negative cells and as the total number of cells counted per well. Data are representative of two experiments run in duplicates; at least three fields per well were counted. As observed for Schwann cells in addition to a proliferative effect at low doses, GGFs also increase the numbers of nonresponding cells surviving. The percentage of BrdU positive cells is proportional to the increasing amounts of GGFs added to the cultures. The total number of cells after 48 hours in presence of higher doses of GGFs is at least doubled, confirming that GGFs induce DNA synthesis and proliferation in BHK21 C13 cells. Under the same conditions, cells maintained for 48 hours in the presence of 2% FCS showed an increase of about six fold (not shown).

Figure 19:
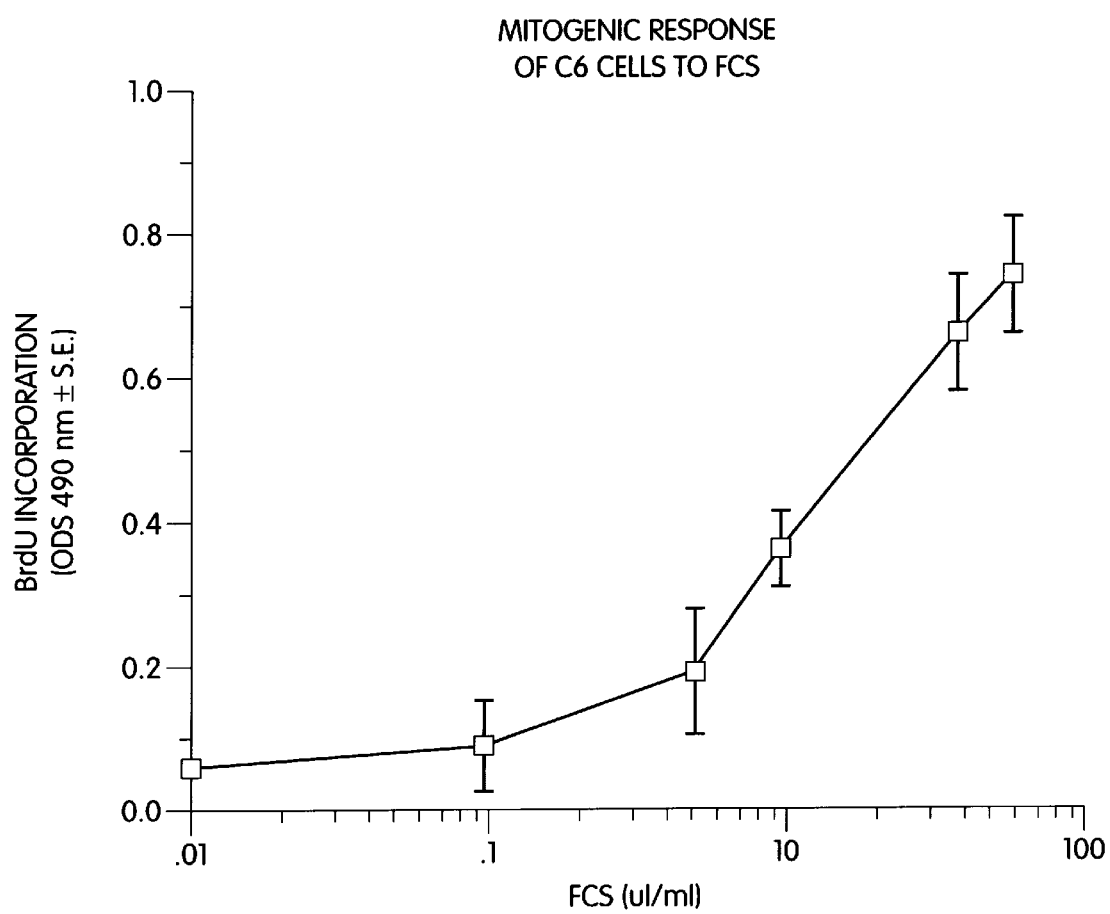

C6 glioma cells have provided a useful model to study glial cell properties. The phenotype expressed seems to be dependent on the cell passage, the cells more closely resembling an astrocyte phenotype at an early stage, and an oligodendrocyte phenotype at later stages (beyond passage 70). C6 cells used in these experiments were from passage 39 to passage 52. C6 cells are a highly proliferating population, therefore the experimental conditions were optimized to have a very low background of brdU incorporation. The presence of 0.1% serum was necessary to maintain cell viability without significantly affecting the mitogenic responses, as shown by the dose response to FCS (FIG. 19).

Figure 20A:
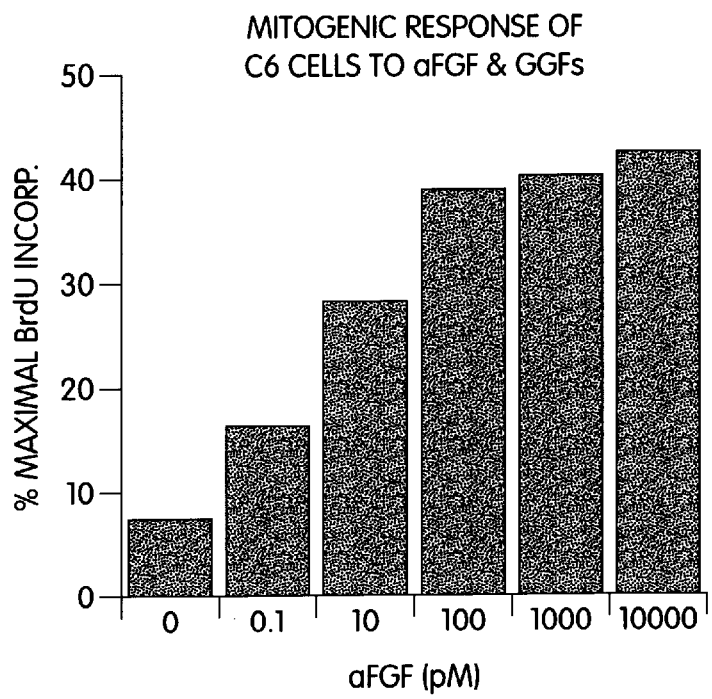
FIGS. 20A and 20B are graphs showing the mitogenic response of C6 cells to aFGF and GGFs.
Figure 20B:
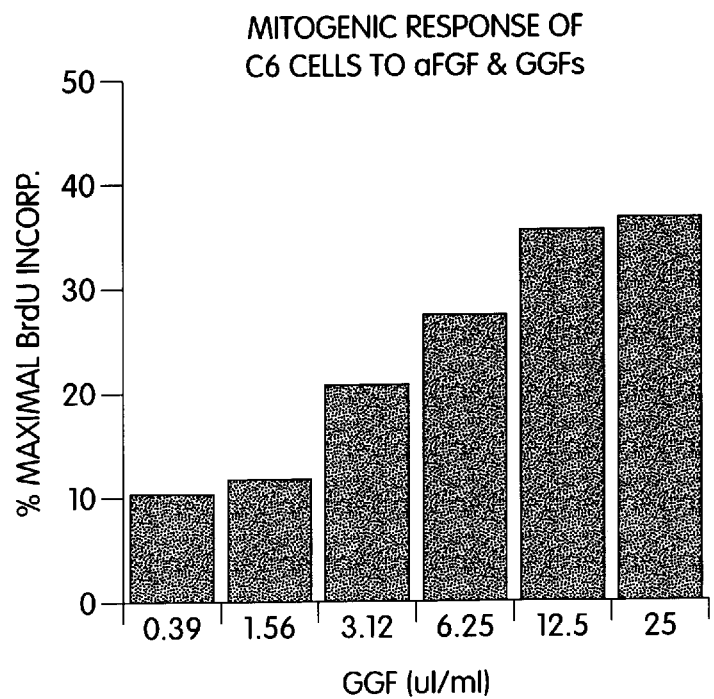

In FIG. 20 the mitogenic responses to aFGF (acidic Fibroblast growth factor) and GGFs are expressed as the percentages of maximal BrdU incorporation obtained in the presence of FCS (8%). Values are averages of two experiments, run in duplicates. The effect of GGFs was comparable to that of a pure preparation of aFGF. aFGF has been described as a specific growth factor for C6 cells (Lim R. et al., Cell Regulation 1:741–746, 1990) and for that reason it was used as a positive control. The direct counting of BrdU positive and negative cells was not possible because of the high cell density in the microcultures. In contrast to the cell lines so far reported, PC12 cells did not show any evident responsiveness to GGFS, when treated under culture conditions in which PC12 could respond to sera (Mixture of FCS and HS as used routinely for cell maintenance). Nevertheless the number of cells plated per well seems to affect the behavior of PC12 cells, and therefore further experiments are required.

EXAMPLE 4

Isolating and Cloning of Nucleotide Sequences Encoding Proteins Containing GGF-I and GGF-II Peptides Isolation and cloning of the GGF-II nucleotide sequences was performed as outlined herein, using peptide sequence information and library screening, and was performed as set out below. It will be appreciated that the peptides of FIGS. 4 and 5 can be used as the starting point for isolation and cloning of GGF-I sequences by following the techniques described herein. Indeed, FIG. 21, SEQ ID Nos. 54–88) shows possible degenerate oligonucleotide probes for this purpose, and FIGS. 23(A–B), SEQ ID Nos. 90–119, lists possible PCR primers. DNA sequence and polypeptide sequence should be obtainable by this means as with GGF-II, and also DNA constructs and expression vectors incorporating such DNA sequence, host cells genetically altered by incorporating such constructs/vectors, and protein obtainable by cultivating such host cells. The invention envisages such subject matter.

I. Design and Synthesis of Oligonucleotide Probes and Primers

Degenerate DNA oligomer probes were designed by backtranslating the amino acid sequences (derived from the peptides generated from purified GGF protein) into nucleotide sequences. Oligomers represented either the coding strand or the non-coding strand of the DNA sequence. When serine, arginine or leucine were included in the oligomer design, than two separate syntheses were prepared to avoid ambiguities. For example, serine was encoded by either TCN or AGY as in 537 and 538 or 609 and 610. Similar codon splitting was done for arginine or leucine (e.g. 544, 545). DNA oligomers were synthesized on a Biosearch 8750 4-column DNA synthesizer using β-cyanoethyl chemistry operated at 0.2 micromole scale synthesis. Oligomers were cleaved off the column (500 angstrom CpG resins) and deprotected in concentrated ammonium hydroxide for 6–24 hours at 55–60° C. Deprotected oligomers were dried under vacuum (Speedvac) and purified by electrophoresis in gels of 15% acrylamide (20 mono:1 bis), 50 mM Tris-borate-EDTA buffer containing 7M urea. Full length oligomers were detected in the gels by UV shadowing, then the bands were excised and DNA oligomers eluted into 1.5 mls H20 for 4–16 hours with shaking. The eluate was dried, redissolved in 0.1 ml H$_2$O and absorbance measurements were taken at 260 nm.

Concentrations were determined according to the following formula:

(A 260×units/ml) (60.6/length=x$\mu$M)

All oligomers were adjusted to 50 $\mu$M concentration by addition of H$_2$O.

Degenerate probes designed as above are shown in FIG. 21, SEQ ID Nos. 54–88.

PCR primers were prepared by essentially the same procedures that were used for probes with the following modifications. Linkers of thirteen nucleotides containing restriction sites were included at the 5' ends of the degenerate oligomers for use in cloning into vectors. DNA synthesis was performed at 1 micromole scale using 1,000 angstrom CpG resins and inosine was used at positions where all four nucleotides were incorporated normally into degenerate probes. Purifications of PCR primers included an ethanol precipitation following the gel electrophoresis purification.

II. Library Construction and Screening

A bovine genomic DNA library was purchased from Stratagene (Catalogue Number: 945701). The library contained 2×10$^6$ 15–20 kb Sau3Al partial bovine DNA fragments cloned into the vector lambda DashII. A bovine total brain cDNA library was purchased from Clonetech (Catalogue Number: BL 10139). Complementary DNA libraries were constructed (In Vitrogen; Stratagene) from mRNA prepared from bovine total brain, from bovine pituitary and from bovine posterior pituitary. In Vitrogen prepared two cDNA libraries: one library was in the vector lambda g10, the other in vector pcDNAI (a plasmid library). The Stratagene libraries were prepared in the vector lambda unizap. Collectively, the cDNA libraries contained 14 million primary recombinant phage.

The bovine genomic library was plated on E. coli K12 host strain LE392 on 23×23 cm plates (Nunc) at 150,000 to 200,000 phage plaques per plate. Each plate represented approximately one bovine genome equivalent. Following an overnight incubation at 37° C., the plates were chilled and replicate filters were prepared according to procedures of Maniatis et al. (2:60–81). Four plague lifts were prepared from each plate onto uncharged nylon membranes (Pall Biodyne A or MSI Nitropure). The DNA was immobilized onto the membranes by cross-linking under UV light for 5 minutes or, by baking at 80° C. under vacuum for two hours. DNA probes were labelled using T4 polynucleotide kinase (New England Biolabs) with gamma 32P ATP (New England Nuclear; 6500 Ci/mmol) according to the specifications of the suppliers. Briefly, 50 pmols of degenerate DNA oligomer were incubated in the presence of 600 $\mu$Ci gamma $^{32}$P-ATP and 5 units T4 polynucleotide kinase for 30 minutes at 37° C. Reactions were terminated, gel electrophoresis loading buffer was added and then radiolabelled probes were purified by electrophoresis. 32P labelled probes were excised from gel slices and eluted into water. Alternatively, DNA probes were labelled via PCR amplification by incorporation of α-32P-dATP or α-32P dCTP according to the protocol of Schowalter and Sommer, Anal. Biochem 177:90–94 (1989). Probes labelled in PCR reactions were purified by desalting on Sephadex G-150 columns.

Prehybridization and hybridization were performed in GMC buffer (0.52 M NaPi, 7% SDS, 1% BSA, 1.5 mM EDTA, 0.1 M NaCl 10 mg/ml tRNA). Washing was performed in oligowash (160 ml 1 M $Na_2HPO_4$, 200 ml 20% SDS, 8.0 ml 0.5 M EDTA, 100 ml 5M NaCl, 3632 ml H20). Typically, 20 filters (400 sq. centimeters each) representing replicate copies of ten bovine genome equivalents were incubated in 200 ml hybridization solution with 100 pmols of degenerate oligonucleotide probe (128–512 fold degenerate). Hybridization was allowed to occur overnight at 5° C. below the minimum melting temperature calculated for the degenerate probe. The calculation of minimum melting temperature assumes 2° C. for an AT pair and 4° C. for a GC pair.

Filters were washed in repeated changes of oligowash at the hybridization temperatures four to five hours and finally, in 3.2M tetramethylammonium chloride, 1% SDS twice for 30 min at a temperature dependent on the DNA probe length. For 20 mers, the final wash temperature was 60° C. Filters were mounted, then exposed to X-ray, film (Kodak XAR5) using intensifying screens (Dupont Cronex Lightening Plus). Usually, a three to five day film exposure at minus 80° C. was sufficient to detect duplicate signals in these library screens. Following analysis of the results, filters could be stripped and reprobed. Filters were stripped by incubating through two successive cycles of fifteen minutes in a microwave oven at full power in a solution of 1% SDS containing 10 mM EDTA pH8. Filters were taken through at least three to four cycles of stripping and reprobing with various probes.

III. Recombinant Phage Isolation, Growth and DNA Preparation

These procedures followed standard protocol as described in *Recombinant DNA* (Maniatis et al 2:60–2:81).

IV. Analysis of Isolated Clones Using DNA Digestion and Southern Blots

Recombinant Phage DNA samples (2 micrograms) were digested according to conditions recommended by the restriction endonuclease supplier (New England Biolabs). Following a four hour incubation at 37° C., the reactions products were precipitated in the presence of 0.1M sodium acetate and three volumes of ethanol. Precipitated DNA was collected by centrifugation, rinsed in 75% ethanol and dried. All resuspended samples were loaded onto agarose gels (typically 1% in TAE buffer; 0.04M Tris acetate, 0.002M EDTA). Gel runs were at 1 volt per centimeter from 4 to 20 hours. Markers included lambda Hind III DNA fragments and/or ØX174HaeIII DNA fragments (New England Biolabs). The gels were stained with 0.5 micrograms/ml of ethidium bromide and photographed. For southern blotting, DNA was first depurinated in the gel by treatment with 0.125 N HCl, denatured in 0.5 N NaOH and transferred in 20× SSC (3M sodium chloride, 0.03 M sodium citrate) to uncharged nylon membranes. Blotting was done for 6 hours up to 24 hours, then the filters were neutralized in 0.5 Tris HCl pH 7.5, 0.15 M sodium chloride, then rinsed briefly in 50 mM Tris-borate EDTA.

For cross-linking, the filters were wrapped first in transparent plastic wrap, then the DNA side exposed for five minutes to an ultraviolet light. Hybridization and washing was performed am described for library screening (see section 2 of this Example). For hybridization analysis to determine whether similar genes exist in other species slight modifications were made. The DNA filter was purchased from Clonetech (Catalogue Number 7753-1) and contains 5 micrograms of EcoRI digested DNA from various species per lane. The probe was labelled by PCR amplification reactions as described in section 2 above, and hybridizations were done in 80% buffer B(2 g polyvinylpyrrolidine, 2 g Ficoll-400, 2 g bovine serum albumin, 50 ml 1M Tris-HCl (pH 7.5) 58 g NaCl, 1 g sodium pyrophosphate, 10 g sodium dodecyl sulfate, 950 ml $H_2O$) containing 10% dextran sulfate. The probes were denatured by boiling for ten minutes then rapidly cooling in ice water. The probe was added to the hybridization buffer at $10^6$ dpm $^{32}P$ per ml and incubated overnight at 60° C. The filters were washed at 60° C. first in buffer B followed by 2× SSC, 0.1% SDS then in 1× SSC, 0.1% SDS. For high stringency, experiments, final washes were done in 0.1× SSC, 1% SDS and the temperature raised to 65° C.

Southern blot data were used to prepare a restriction map of the genomic clone and to indicate which subfragments hybridized to the GGF probes (candidates for subcloning).

V. Subcloning of Segments of DNA Homologous to Hybridization Probes

DNA digests (e g. 5 micrograms) were loaded onto 1% agarose gels then appropriate fragments excised from the gels following staining. The DNA was purified by adsorption onto glass beads followed by elution using the protocol described by the supplier (Bio 101). Recovered DNA fragments (100–200 ng) were ligated into linearized dephosphorylated vectors, e.g. pT3T7 (Ambion), which is a derivative of pUC18, using T4 ligase (New England Biolabs). This vector carries the *E. coli* β lactamase gene, hence, transformants can be selected on plates containing ampicillin. The vector also supplies β-galactosidase complementation to the host cell, therefore non-recombinants (blue) can be detected using isopropylthiogalactoside and Bluogal (Bethesda Research Labs). A portion of the ligation reactions was used to transform *E. coli* K12 XL1 blue competent cells (Stratagene Catalogue Number: 200236) and then the transformants were selected on LB plates containing 50 micrograms per ml ampicillin. White colonies were selected and plasmid mini preps were prepared for DNA digestion and for DNA sequence analysis. Selected clones were retested to determine if their insert DNA hybridized with the GGF probes.

VI. DNA Sequencing

Double stranded plasmid DNA templates were prepared from 5 ml cultures according to standard protocols. sequencing was by the dideoxy chain termination method using Seguenase 2.0 and a dideoxynucleotide sequencing kit (US Biochemical) according to the manufacturers protocol (a modification of Sanger et al. PNAS; USA 74:5463 (1977)]. Alternatively, sequencing was done in a DNA thermal cycler (Perkin Elmer, model 4800) using a cycle sequencing kit (New England Biolabs; Bethesda Research Laboratories) and was performed according to manufacturers instructions using a 5'-end labelled primer. Sequence primers were either those supplied with the sequencing kits or were synthesized according to sequence determined from the clones. Sequencing reactions were loaded on and resolved on 0.4 mm thick sequencing gels of 6% polyacrylamide. Gels were dried and exposed to X-Ray film. Typically, 35S was incorporated when standard sequencing kits were used and a 32P end labelled primer was used for cycle sequencing reactions. Sequences were read into a DNA sequence editor from the bottom of the gel to the top (5' direction to 3') and data were analyzed using programs supplied by Genetics Computer Group (GCG, University of Wisconsin).

VII. RNA Preparation and PCR Amplification

Open reading frames detected in the genomic DNA and which contained sequence encoding GGF peptides were extended via PCR amplification of pituitary RNA. RNA was prepared from frozen bovine tissue (Pelfreeze) according to the guanidine neutral-CsCl procedure (Chirgwin et. al. Biochemistry 18:5294(1979).) Polyadenylated RNA was selected by oligo-dT cellulose column chromatography (Aviv and Leder PNAS (USA) 69:1408 (1972)).

Specific DNA target sequences were amplified beginning with either total RNA or polyadenylated RNA samples that had been converted to cDNA using the Perkin Elmer PCR/ RNA Kit Number: N808-0017. First strand reverse transcription reactions used 1 $\mu$g template RNA and either primers of oligo dT with restriction enzyme recognition site linkers attached or specific antisense primers determined from cloned sequences with restriction sites attached. To produce the second strand, the primers either were plus strand unique sequences as used in 3' RACE reactions (Frohman at. al., PNAS (USA) 85:8998 (1988)) or were oligo dT primers with restriction sites attached if the second target site had been added by terminal transferase tailing first strand reaction products with dATP (e. g. 5' race reactions, Frohman et. al., ibid). Alternatively, as in anchored PCR reactions the second strand primers were degenerate, hence, representing particular peptide sequences.

The amplification profiles followed the following general scheme: 1) five minutes soak file at 95° C.; 2) thermal cycle file of 1 minute, 95° C.; 1 minute ramped down to an annealing temperature of 45° C., 50° C. or 55° C.; maintain the annealing temperature for one minute; ramp up to 72° C. over one minute; extend at 72° C. for one minute or for one minute plus a 10 second auto extension; 3) extension cycle at 72° C., five minutes, and; 4) soak file 4° C. for infinite time. Thermal cycle files (#2) usually were run for 30 cycles. A sixteen $\mu$l sample of each 100 $\mu$l amplification reaction was analyzed by electrophoresis in 2% Nusieve 1% agarose gels run in TAE buffer at 4 volts per centimeter for three hours. The gels were stained, then blotted to uncharged nylon membranes which were probed with labelled DNA probes that were internal to the primers.

Specific sets of DNA amplification products could be identified in the blotting experiments and their positions used as a guide to purification and reamplification. When appropriate, the remaining portions of selected samples were loaded onto preparative gels, then following electrophoresis four to five slices of 0.5 mm thickness (bracketing the expected position of the specific product) were taken from the gel. The agarose was crushed, then soaked in 0.5 ml of electrophoresis buffer from 2–16 hours at 40° C. The crushed agarose was centrifuged for two minutes and the aqueous phase was transferred to fresh tubes.

Reamplification was done on five microliters (roughly 1% of the product) of the eluted material using the same sets of primers and the reaction profiles as in the original reactions. When the reamplification reactions were completed, samples were extracted with chloroform and transferred to fresh tubes. Concentrated restriction enzyme buffers and enzymes were added to the reactions in order to cleave at the restriction sites present in the linkers. The digested PCR products were purified by gel electrophoresis, then sub- cloned into vectors as described in the subcloning section above. DNA sequencing was done described as above.

VIII. DNA Sequence Analysis

DNA sequences were assembled using a fragment assembly program and the amino acid sequences deduced by the GCG programs GelAssemble, Map and Translate. The deduced protein sequences were used as a query sequence to search protein sequence databases using WordSearch. Analysis was done on a VAX Station 3100 workstation operating under VMS 5.1. The database search was done on SwissProt release number 21 using GCG Version 7.0.

IX. Results of Cloning and Sequencing of Genes Encoding GGF-I and GGF-II

As indicated above, to identify the DNA sequence encoding bovine GGF-II degenerate oligonucleotide probes were designed from GGF-II peptide sequences. GGF-II 12 (SEQ ID No. 44), a peptide generated via lysyl endopeptidase digestion of a purified GGF-II preparation (see FIGS. 11 and 12) showed strong amino acid sequence homology with GGF-I 07 (SEQ ID No. 39), a tryptic peptide generated from a purified GGF-I preparation. GGF-II 12 was thus used to create ten degenerate oligonucleotide probes (see oligos 609, 610 and 649 to 656 in FIG. 21, SEQ ID Nos. 69, 70, 71 and 79, respectively). A duplicate set of filters were probed with two sets (set 1=609, 610; set 2=649–5656) of probes encoding two overlapping portions of GGF-II 12. Hybridization signals were observed, but, only one clone hybridized to both probe sets. The clone (designated GGF2BG1) was purified.

Southern blot analysis of DNA from the phage clone GGF2BG1 confirmed that both sets of probes hybridized with that bovine DNA sequence, and showed further that both probes reacted with the same set of DNA fragments within the clone. Based on those experiments a 4 kb Eco RI sub-fragment of the original clone was identified, subcloned and partially sequenced. FIG. 22 shows the nucleotide sequence, SEQ ID No. 89) and the deduced amino acid sequence (SEQ ID NO: 196) of the initial DNA sequence readings that included the hybridization sites of probes 609 and 650, and confirmed that a portion of this bovine genomic DNA encoded peptide 12 (KASLADSGEYM) SEQ ID NO: 129.

Further sequence analysis demonstrated that GGF-II 12 resided on a 66 amino acid open reading frame (see below) which has become the starting point for the isolation of overlapping sequences representing a putative bovine GGF-II gene and a cDNA.

Figure 24:
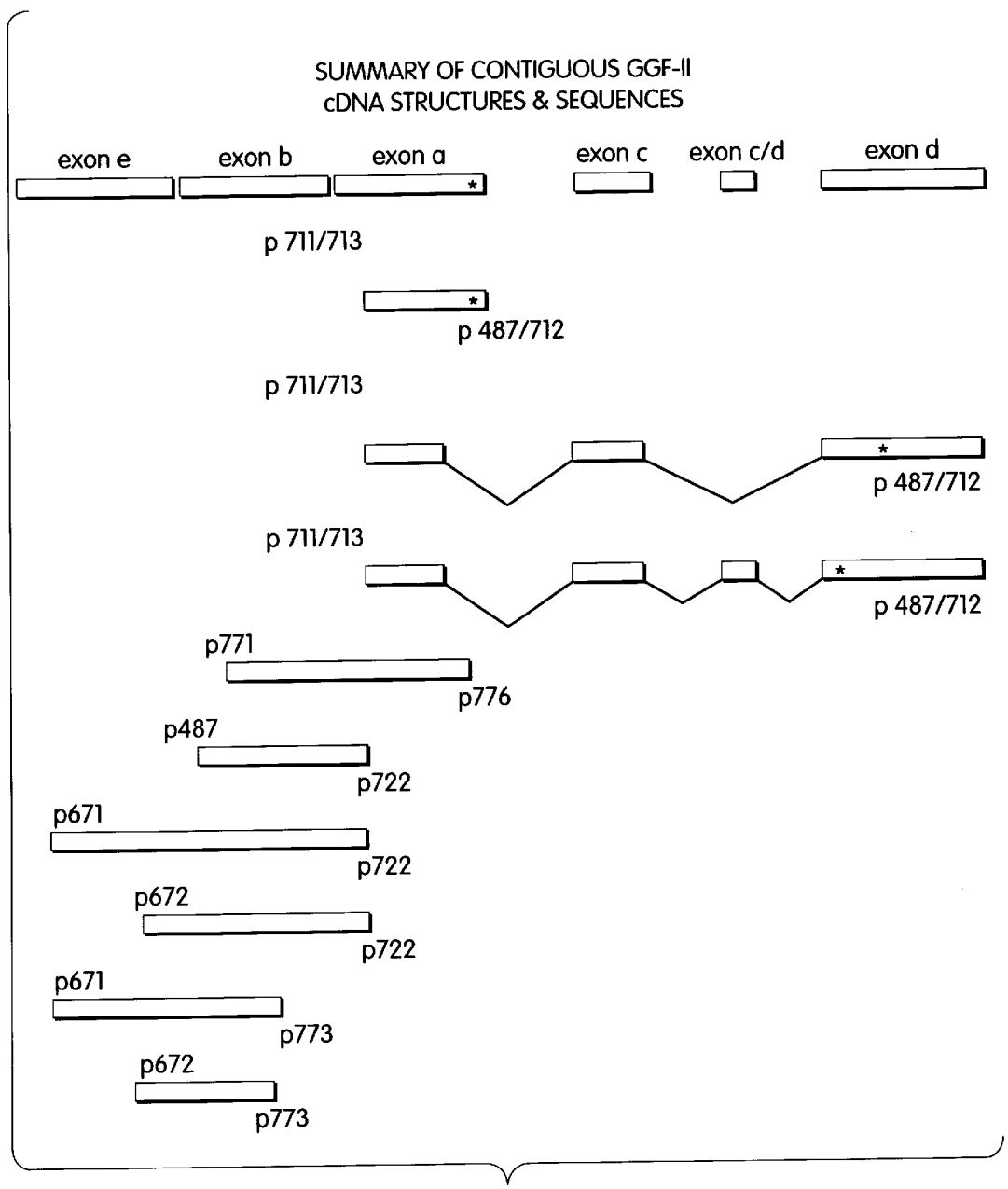

Several PCR procedures were used to obtain additional coding sequences for the putative bovine GGF-II gene. Total RNA and oligo dT-selected (poly A containing) RNA samples were prepared from bovine total pituitary, anterior pituitary, posterior pituitary, and hypothalamus. Using primers from the list shown in FIG. 23, SEQ ID Nos. 109–119, one-sided PCR reactions (RACE) were used to amplify cDNA ends in both the 3' and 5' directions, and anchored PCR reactions were performed with degenerate oligonucleotide primers representing additional GGF-II peptides. FIG. 24 summarizes the contiguous DNA structures and sequences obtained in those experiments. From the 3' RACE reactions, three alternatively spliced cDNA sequences were produced, which have been cloned and sequenced. A 5' RACE reaction led to the discovery of an additional axon containing coding sequence for at least 52 amino acids. Analysis of that deduced amino acid sequence revealed peptides GGF-II-6 and a sequence similar to GGF-I-18 (see below). The anchored PCR reactions led to the identification of (cDNA) coding sequences of peptides GGF-II-1, 2, 3 and 10 contained within an additional cDNA segment of 300 bp. The 5' limit of this segment (i.e., segment E, see FIG. 31) is defined by the oligonucleotide which encodes paptide GGF-II-1 and which was used in the PCR reaction (additional 5' sequence data exists as described for the human clone in Example 6). Thus this clone contains nucleotide sequences encoding six out of the existing total of nine novel GGF-II peptide sequences.

Figure 25:
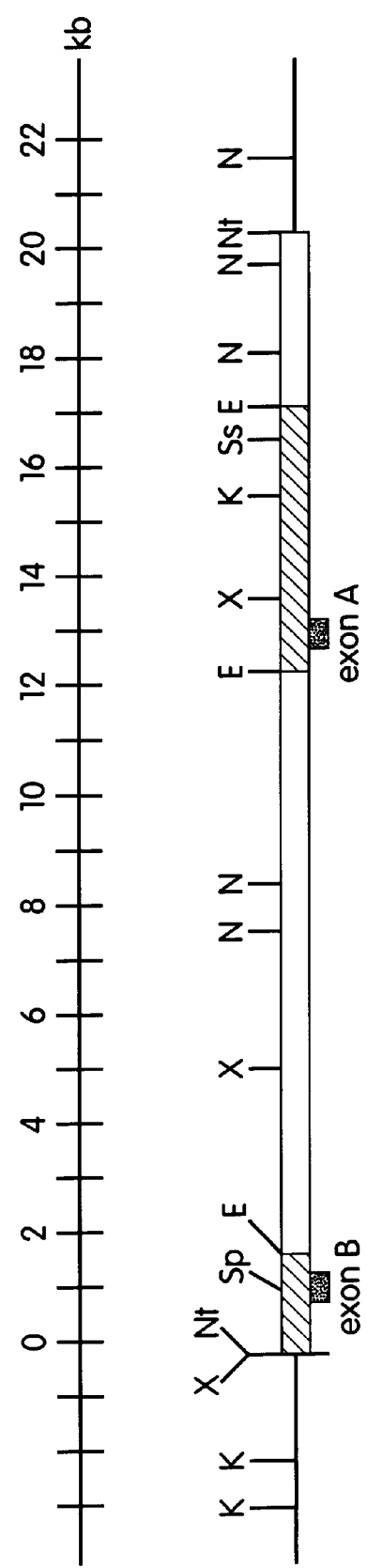
Figure 26:
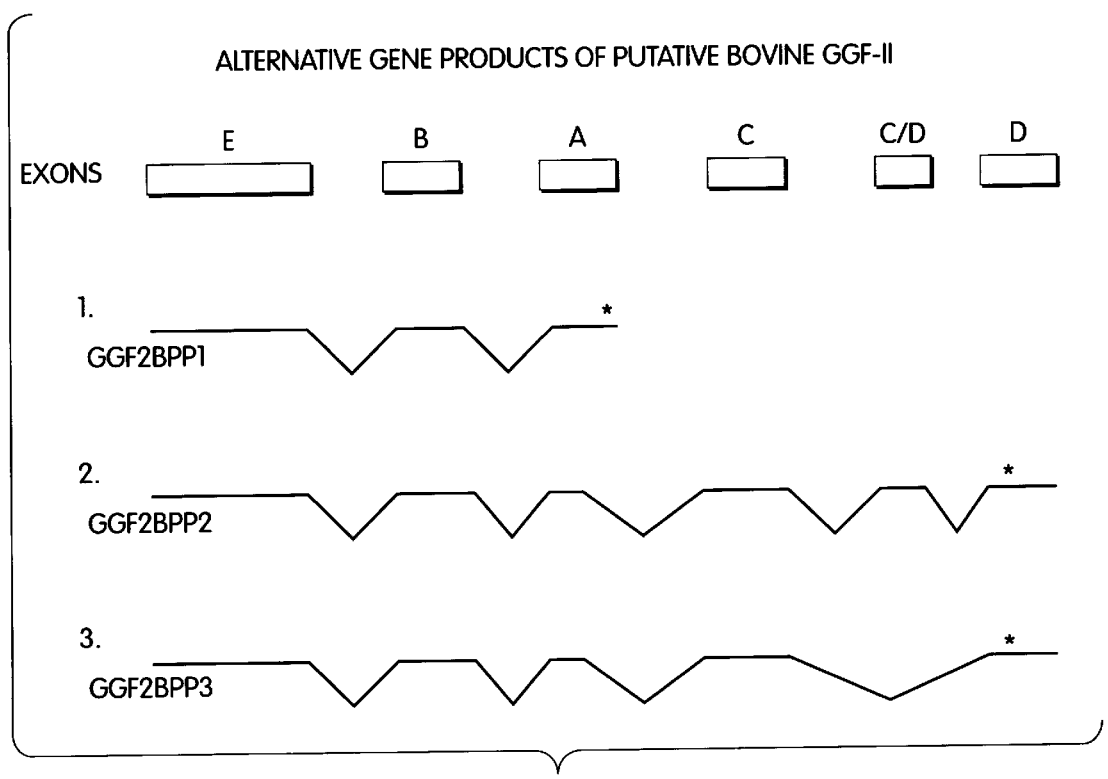

The cloned gene was characterized first by constructing a physical map of GGF2BG1 that allowed us to position the coding sequences as they were found (see below, FIG. 25). DNA probes from the coding sequences described above have been used to identify further DNA fragments containing the axons on this phage clone and to identify clones that overlap in both directions. The putative bovine GGF-II gene is divided into at least 5 coding segments. Coding segments are defined as discrete lengths of DNA sequence which can be translated into polypeptide sequences using the universal genetic code. The coding segments described in FIG. 31 and referred to in the present application are: 1) particular exons present within the GGF gene (e.g. coding segment a), or 2) derived from sets of two or more exons that appear in specific sub-groups of mRNAs, where each set can be translated into the specific polypeptide segments as in the gene products shown. The polypeptide segments referred to in the claims are the translation products of the analogous DNA coding segments. Only coding segments A and B have been defined as exons and sequenced and mapped thus far. The summary of the contiguous coding sequences identified is shown in FIG. 26. The exons are listed (alphabetically) in the order of their discovery. It is apparent from the intron/exon boundaries that axon B may be included in cDNAs that connect coding segment E and coding segment A. That is, exon B cannot be spliced out without compromising the reading frame. Therefore, we suggest that three alternative splicing patterns can produce putative bovine GGF-II cDNA sequences 1, 2 and 3. The coding sequences of these, designated GGF2BPP1.CDS, GGF2BPP2.CDS and GGF2BPP3.CDS, respectively, are given in FIGS. 28A (SEQ ID No. 133), 28(B–C) (SEQ ID No. 134), and 28(D–E) (SEQ ID No. 135), respectively. The deduced amino acid sequence of the three cDNAs is also given in FIGS. 28A (SEQ ID NO: 190), 28(B–C) (SEQ ID NO: 191), and 28(D–F) (SEQ ID No. 193).

The three deduced structures encode proteins of lengths 206, 281 and 257 amino acids. The first 183 residues of the deduced protein sequence are identical in all three gene products. At position 184 the clones differ significantly. A codon for glycine GGT in GGF2BPP1 also serves as a splice donor for GGF2BPP2 and GGF2BPP3, which alternatively add on exons C, C/D, C/D' and D or C, C/D and D, respectively, and shown in FIG. 33, SEQ ID No. 149). GGFIIBPP1 is a truncated gene product which is generated by reading past the coding segment A splice junction into the following intervening sequence (intron). This represents coding segment A' in FIG. 31 (SEQ ID No. 140). The transcript ends adjacent to a canonical AATAAA polyadenylation sequence, and we suggest that this truncated gene product represents a bona fide mature transcript. The other two longer gene products share the same 3' untranslated sequence and polyadenylation site.

All three of these molecules contain six of the nine novel GGF-II peptide sequences (see FIG. 12) and another peptide is highly homologous to GGF-I-18 (see FIG. 27). This finding gives a high probability that this recombinant molecule encodes at least a portion of bovine GGF-II. Furthermore, the calculated isoelectric points for the three peptides are consistent with the physical properties of GGF-I and II. Since the molecular size of GGF-II is roughly 60 kD, the longest of the three cDNAs should encode a protein with nearly one-half of the predicted number of amino acids.

Figure 30:
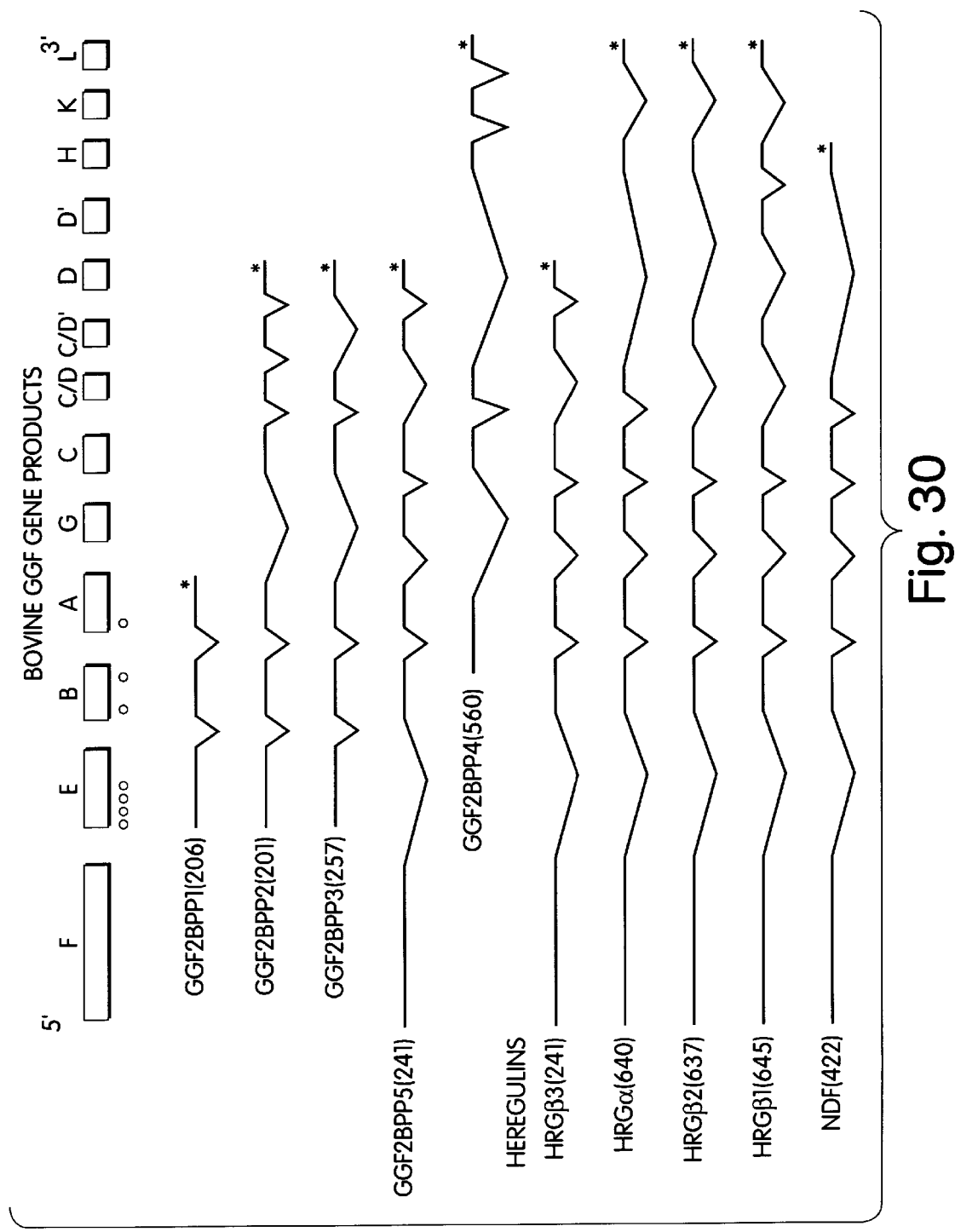
FIG. 30 is a diagram of representative splicing variants. The coding segments are represented by F, E, B, A, G, C, C/D, C/D', D, D', H, K and L. The location of the peptide sequences derived from purified protein are indicated by "o".

A probe encompassing the B and A exons was labelled via PCR amplification and used to screen a cDNA library made from RNA isolated from bovine posterior pituitary. One clone (GGF2BPP5) showed the pattern indicated in FIG. 30 and contained an additional DNA coding segment (G) between coding segments A and C. The entire nucleic acid sequence is shown in FIG. 32 (SEQ ID No. 148). The predicted translation product from the longest open reading frame is 241 amino acids. A portion of a second cDNA (GGF2BPP4) was also isolated from the bovine posterior pituitary library using the probe described above. This clone showed the pattern indicated in FIG. 30. This clone is incomplete at the 5' end, but is a splicing variant in the sense that it lacks coding segments G and D. BPP4 also displays a novel 3' end with regions H, K and L beyond region C/D. The sequence of BPP4 is shown in FIGS. 34(A–C) (SEQ ID No. 150).

EXAMPLE 5

GGF Sequences in Various Species

Figure 29:
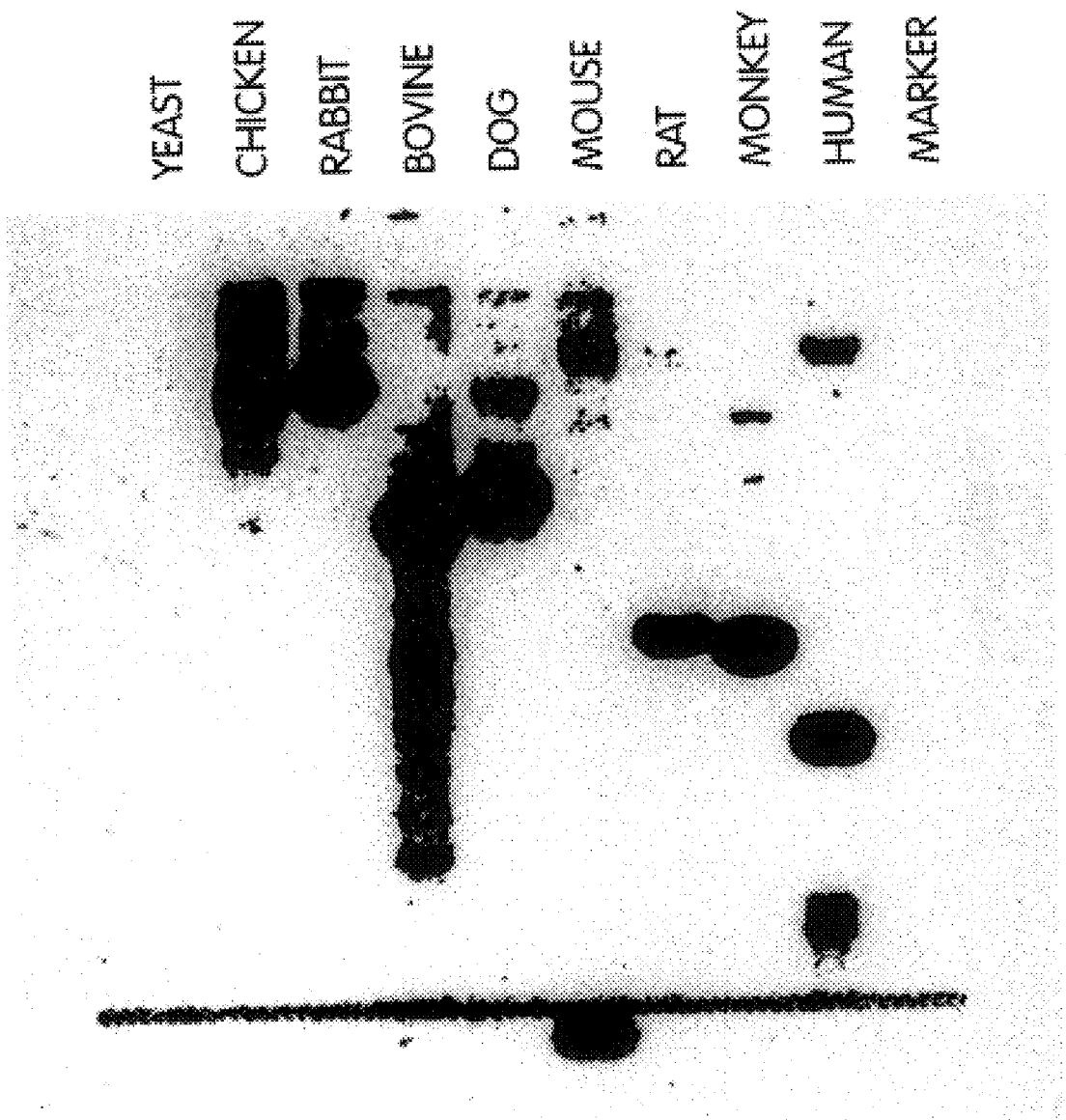
FIG. 29, which relates to Example 6 hereinafter, is an autoradiogram of a cross hybridization analysis of putative bovine GGF-II gene sequences to a variety of mammalian DNAs on a southern blot. The filter contains lanes of EcoRI-digested DNA (5 μg per lane) from the species listed in the Figure. The probe detects a single strong band in each DNA sample, including a four kilobase fragment in the bovine DNA as anticipated by the physical map in FIG. 25. Bands of relatively minor intensity are observed as well, which could represent related DNA sequences. The strong hybridizing band from each of the other mammalian DNA samples presumably represents the GGF-II homologue of those species.

Database searching has not revealed any meaningful similarities between any predicted GGF translation products and known protein sequences. This suggests that GGF-II is the first member of a new family or superfamily of proteins. In high stringency cross hybridization studies (DNA blotting experiments) with other mammalian DNAs we have shown, clearly, that DNA probes from this bovine recombinant molecule can readily detect specific sequences in a variety of samples tested. A highly homologous sequence is also detected in human genomic DNA. The autoradiogram is shown in FIG. 29. The signals in the lanes containing rat and human DNA represent the rat and human equivalents of the GGF gene, the sequences of several cDNA's encoded by this gene have been recently reported by Holmes et al. (Science 256: 1205 (1992)) and Wen et al. (Cell 69:559 (1992)).

EXAMPLE 6

Isolation of a Human Sequence Encoding Human GGF2

Several human clones containing sequences from the bovine GGFII coding segment E were isolated by screening a human cDNA library prepared from brain stem (Stratagene catalog #935206). This strategy was pursued based on the strong link between most of the GGF2 peptides (unique to GGF2) and the predicted peptide sequence from clones containing the bovine E segment. This library was screened as described in Example 4, Section II using the oligonucleotide probes 914–919 listed below.

914TCGGGCTCCATGAAGAAGATGTA (SEQ ID NO: 179)

915TCCATGAAGAAGATGTACCTGCT (SEQ ID NO: 180)

916ATGTACCTGCTGTCCTCCTTGA (SEQ ID NO: 181)

917TTGAAGAAGGACTCGCTGCTCA (SEQ ID NO: 182)

918AAAGCCGGGGGCTTGAAGAA (SEQ ID NO: 183)

919ATGARGTGTGGGCGGCGAAA (SEQ ID NO: 184)

Figure 44:
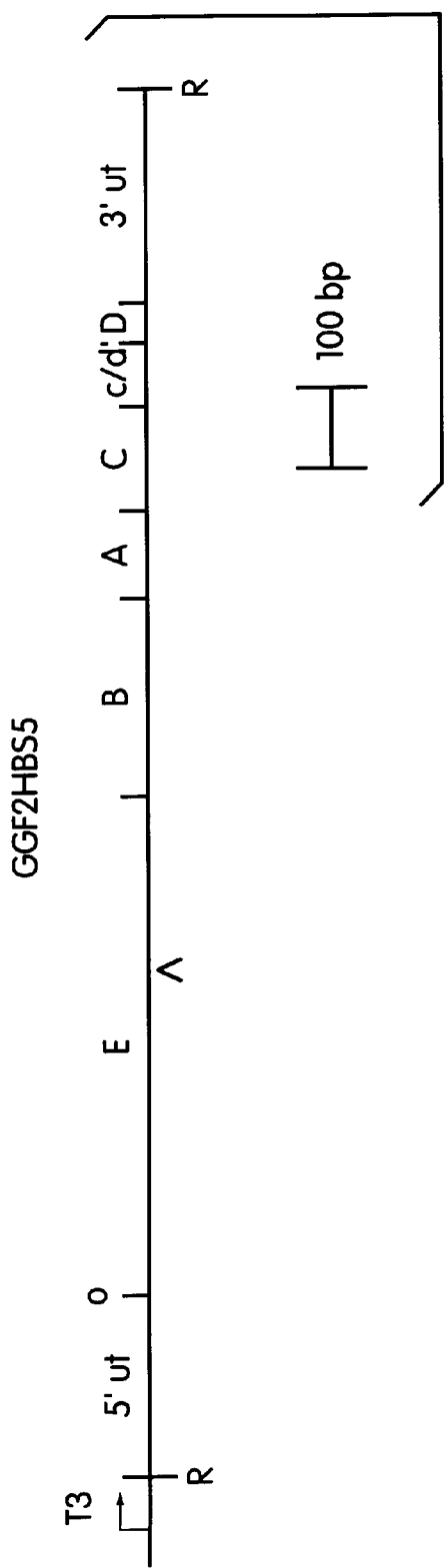
FIG. 44 is a scale coding segment map of the clone. T3 refers to the bacteriophage promoter used to produce mRNA from the clone. R=flanking EcoRI restriction enzyme sites. 5' UT refers to the 5' untranslated region. E, B, A, C, C/D', and D refer to the coding segments. O=the translation start site. Λ=the 5' limit of the region homologous to the bovine E segment (see example 6) and 3' UT refers to the 3' untranslated region.

Clones detected with these probes were further analyzed by hybridization. A probe derived from coding segment A (see FIG. 21), which was produced by labeling a polymerase chain reaction (PCR) product from segment A, was also used to screen the primary library. Several clones that hybridized with both A and E derived probes were selected and one particular clone, GGF2HBS5, was selected for further analysis. This clone is represented by the pattern of coding segments (EBACC/D'D as shown in FIG. 31). The E segment in this clone is the human equivalent of the truncated bovine version of E shown in FIG. 37. GGF2HBS5 is the most likely candidate to encode GGF-II of all the "putative" GGF-II candidates described. The length of coding sequence segment E is 786 nucleotides plus 264 bases of untranslated sequence. The predicted size of the protein encoded by GGF2HBS5 is approximately 423 amino acids (approximately 45 kilodaltons, see FIGS. 45(A–D), SEQ ID NO: 170), which is similar to the size of the deglycosylated form of GGF-II (see Example 16). Additionally, seven of the GGF-II peptides listed in FIG. 27 have equivalent sequences which fall within the protein sequence predicted from region E. Peptides II-6 and II-12 are exceptions, which fall in coding segment B and coding segment A, respectively. RNA encoding the GGF2HBS5 protein was produced in an in vitro transcription system driven by the bacteriophage T7 promoter resident in the vector (Bluescript SK [Stratagene Inc.] see FIG. 44) containing the GGF2HBS5 insert. This RNA was translated in a cell free (rabbit reticulocyte) translation system and the size of the protein product was 45 Kd. Additionally, the cell-free product has been assayed in a Schwann cell mitogenic assay to confirm biological activity. Schwann cells treated with conditioned medium show both increased proliferation as measured by incorporation of $^{125}$I-Uridine and phosphorylation on tyrosine of a protein in the 185 kilodalton range. Thus the size of the product encoded by GGF2HBS5 and the presence of DNA sequences which encode human peptides highly homologous to the bovine peptides shown in FIG. 12 confirm that GGF2HBS5 encodes the human equivalent of bovine GGF2. The fact that conditioned media prepared from cells transformed with this clone elicits Schwann cell mitogenic activity confirms that the GGFIIHBS5 gene produce (unlike the BPP5 gene product) is secreted. Additionally the GGFI-IBPP5 gene product seems to mediate the Schwann cell proliferation response via a receptor tyrosine kinase such as p185$^{erbB2}$ or a closely related receptor (see Example 14).

EXAMPLE 7

Expression of Human Recombinant GGF2 in Mammalian and Insect Cells

The GGF2HBS5 cDNA clone encoding human GGF2 (as described in Example 6 and also referred to herein as HBS5) was cloned into vector pcDL-SRα296 (Takebe et al. Mol. Cell. Biol. 8:466–472 (1988) and COS-7 cells were transfected in 100 mm dishes by the DEAE-dextran method (Sambrook et al. Molecular Cloning: A Laboratory Manual 2nd ed. CSH Laboratory NY (1989). Cell lysates or conditioned media from transiently expressing COS cells were harvested at 3 or 4 days post-transfection. To prepare lysates, cell monolayers were washed with PBS, scraped from the dishes, lysed by three freeze/thaw cycles in 150 μl of 0.25 M Tris-HCl, pH 8. Cell debris was pelleted and the supernatant recovered. Conditioned media samples (7 ml.) were collected, then concentrated and buffer exchanged with 10 mM Tris, pH 7.4 using Centiprep-10 and Centricon-10 units as described by the manufacturer (Amicon, Beverly, Mass.).

Figure 46:
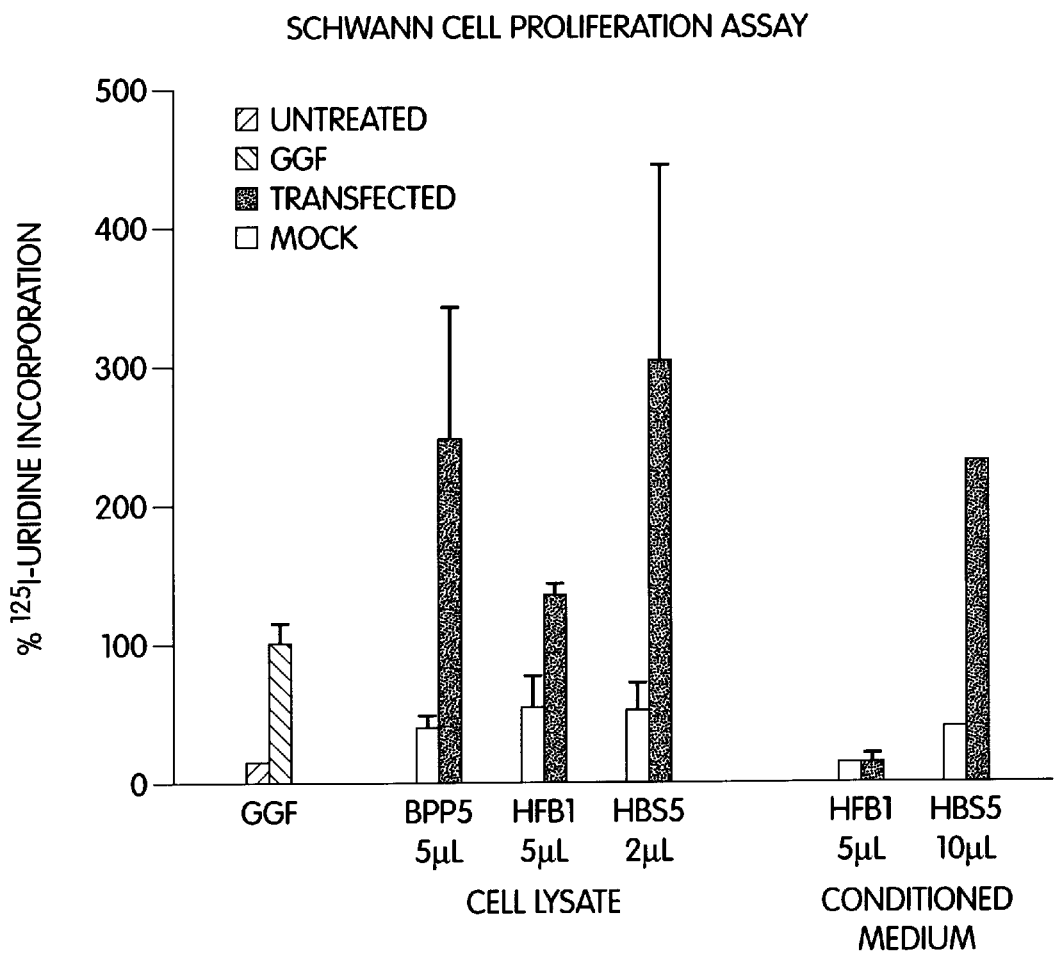
FIG. 46 is a graph depicting the Schwann cell mitogenic activity of recombinant human and bovine glial growth factors.

Rat nerve Schwann cells were assayed for incorporation of DNA synthesis precursors, as described (see Example 3). Conditioned media or cell lysate samples were tested in the Schwann cell proliferation assay as described in Example 3. The mitogenic activity data are shown in FIG. 46. The cDNA, GGF2HBS5, encoding GGF2 directed the secretion of the protein product to the medium. A small proportion of total activity was detectable inside the cells as determined by assays using cell lysates. GGF2HFB1 and GGFBPP5 cDNA's failed to direct the secretion of the product to the extracellular medium. GGF activity from these clones was detectable only in cell lysates (FIG. 46).

Figure 47:
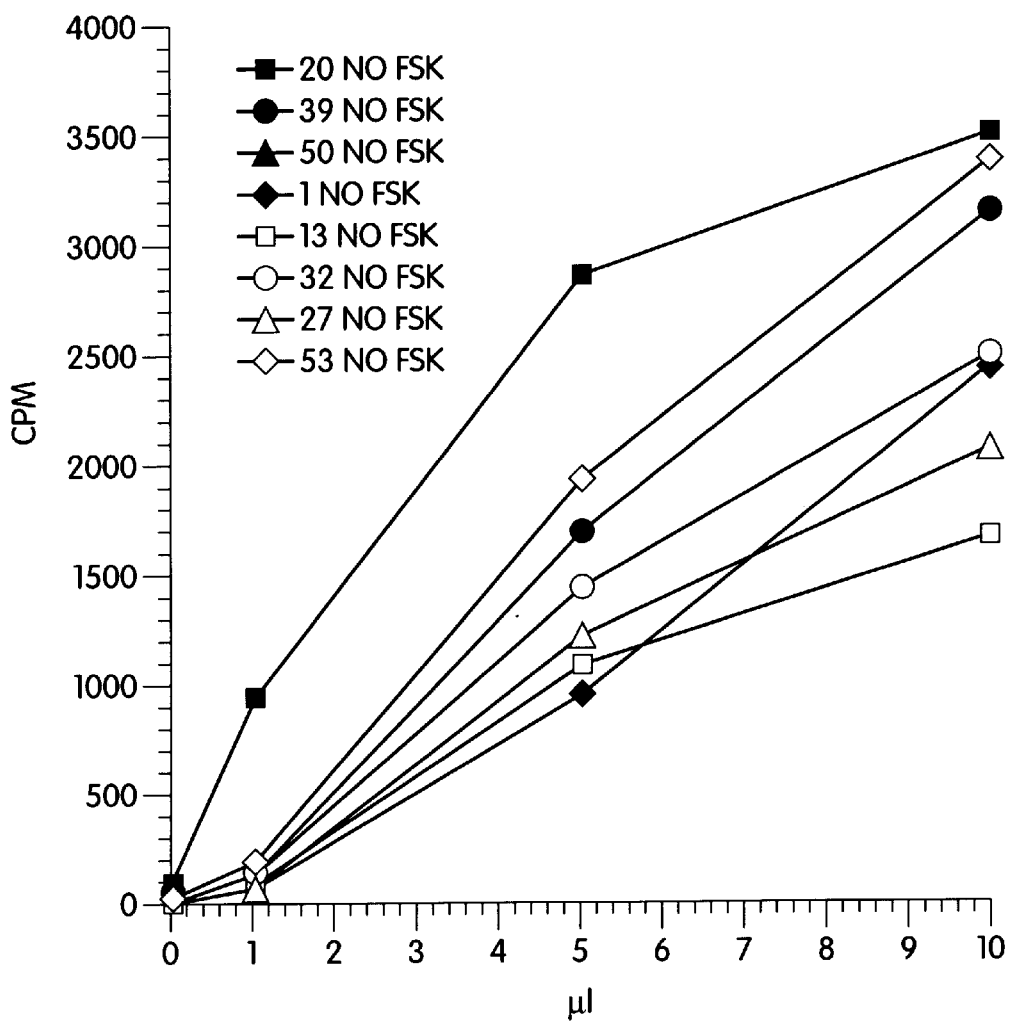
FIG. 47 is a dose-response curve depicting Schwann cell proliferation activity data resulting from administration of different size aliquots of CHO cell conditioned medium.
Figure 49:
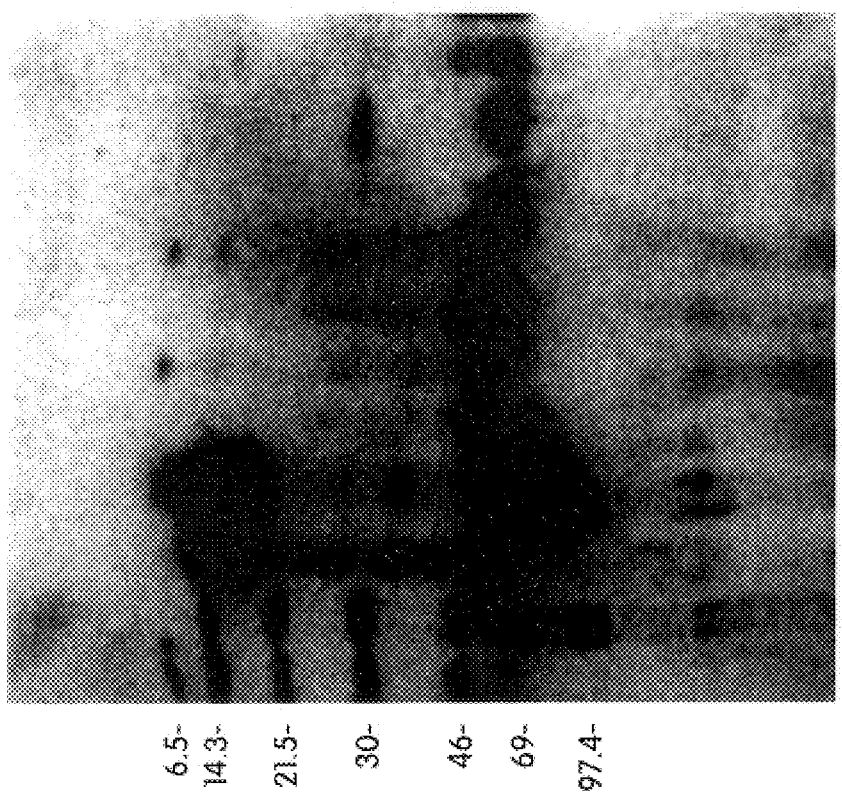
FIG. 49 is a Western blot of recombinant CHO cell conditioned medium using a GGF peptide antibody.
Figure 54:
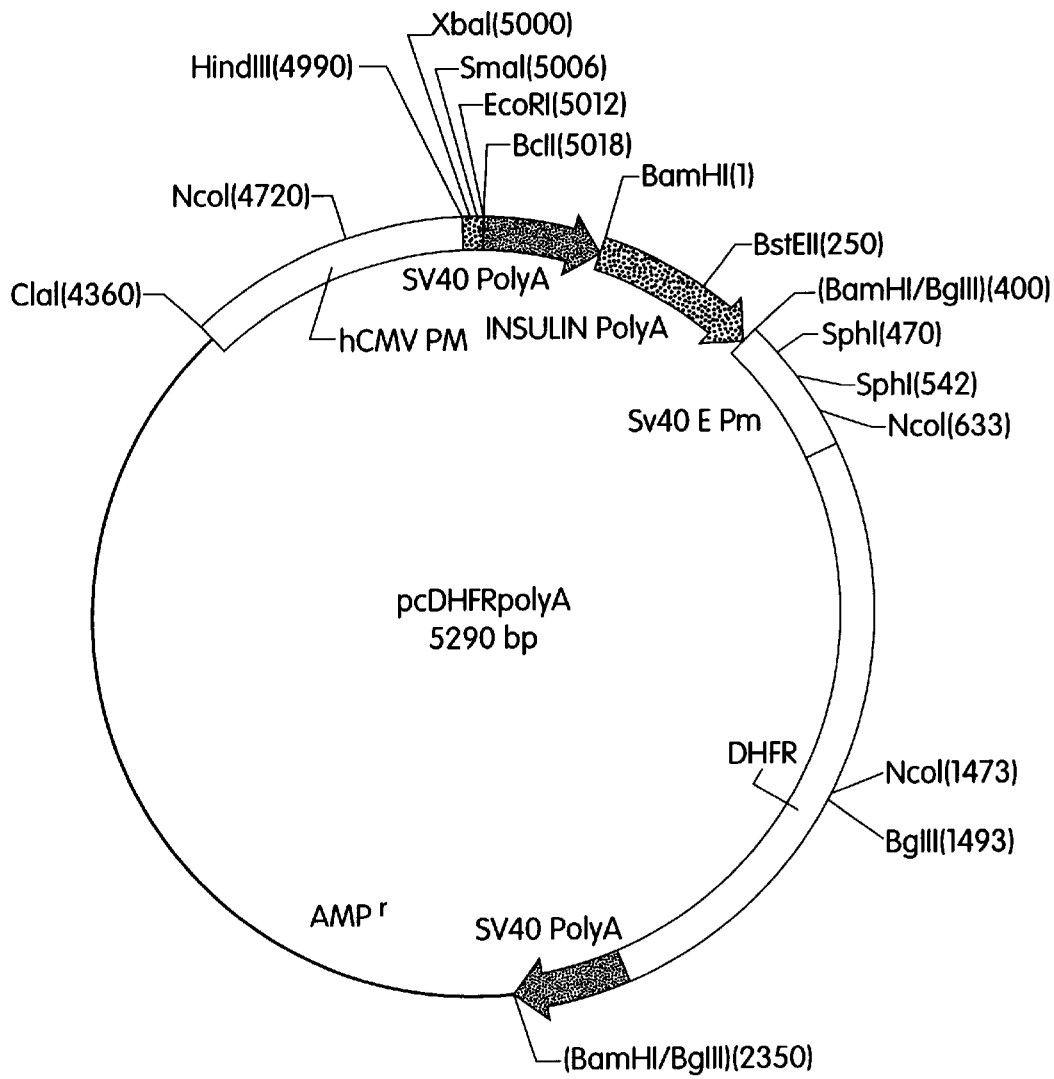
FIG. 54 is a map of the CHO cell-expression vector pcDHFRpolyA.

Recombinant GGF2 was also expressed in CHO cells. The GGF2HBS5 cDNA encoding GGF2 was cloned into the EcoRI site of vector pcdhfrpolyA (FIG. 54) and transfected into the DHFR negative CHO cell line (DG44) by the calcium phosphate coprecipitation method (Graham and Van Dar Eb, Virology 52:456–467 (1973). Clones were selected in nucleotide and nucleoside free α medium (Gibco) in 96-well plates. After 3 weeks, conditioned media samples from individual clones were screened for expression of GGF by the Schwann cell proliferation assay as described in Example 3. Stable clones which secreted significant levels of GGF activity into the medium were identified. Schwann cell proliferation activity data from different volume aliquots of CHO cell conditioned medium were used to produce the dose response curve shown in FIG. 47 (ref., Graham and Van Der Eb, Virology 52:456, 1973). This material was analyzed on a Western blot probed with polyclonal antisera raised against a GGF2 specific peptide. A broad band of approximately 69–90 Kd (the expected size of GGF2 extracted from pituitary and higher molecular weight glycoforms) is specifically labeled (FIG. 49, lane 12).

Figure 48:
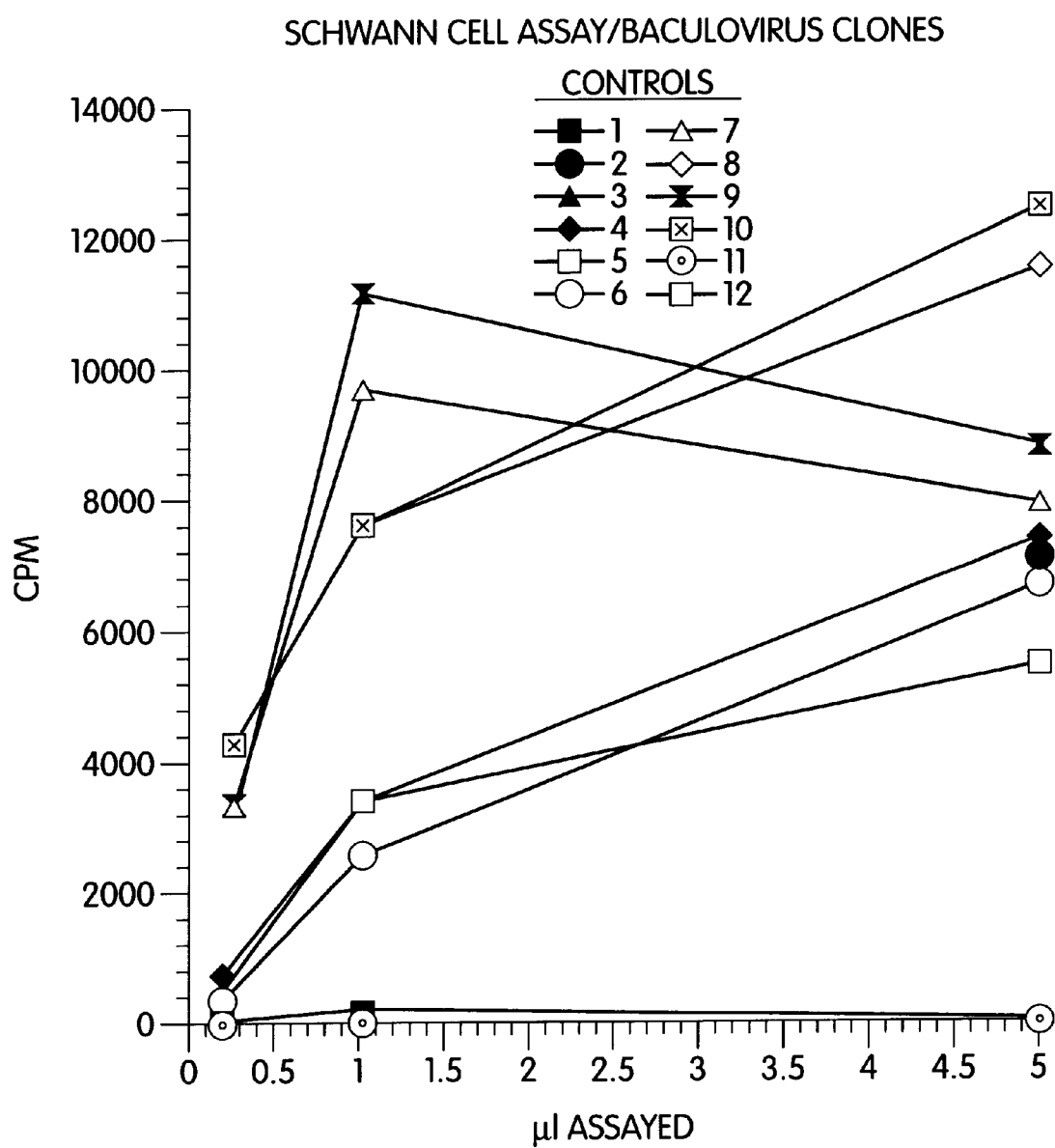
FIG. 48 is a dose-response curve depicting Schwann cell mitogenic activity secreted into the extracellular medium by SF9 insect cells infected with baculovirus containing the GGF2HBS5 cDNA clone.

Recombinant GGF2 was also expressed in insect cells using Baculovirus expression. Sf9 insect cells were infected with baculovirus containing the GGF2HBS5 cDNA clone at a multiplicity of 3–5 (10$^6$ cells/ml) and cultured in Sf900-II medium (Gibco). Schwann cell mitogenic activity was secreted into the extracellular medium (FIG. 48). Different volumes of insect cell conditioned medium were tested in the Schwann cell proliferation assay in the absence of forskolin and the data used to produce the dose response curve shown in FIG. 48.

This material was also analyzed on a Western blot (FIG. 47) probed with the GGF II specific antibody described above. A band of 45 Kd, the size of deglycosylated GGF-II (see Example 16) was seen.

The methods used in this example were as follows:

Schwann call mitogenic activity of recombinant human and bovine glial growth factors was determined as follows: Mitogenic responses of cultured Schwann cells were measured in the presence of 5 μM forskolin using crude recombinant GGF preparations obtained from transient mammalian expression experiments. Incorporation of [$^{125}$I]-Uridine was determined following an 18–24 hour exposure to materials obtained from transfected or mock transfected COS cells as described in the Methods. The mean and standard deviation of four sets of data are shown. The mitogenic response to partially purified native bovine pituitary GGF (carboxymethyl cellulose fraction; Goodearl et al., submitted) is shown (GGF) as a standard of one hundred percent activity.

cDNAs (FIG. 53) were cloned into pcDL-SRα296 (Takebe et al., Mol. Cell Biol. 8:466–472 (1988)), and COS-7 cells were transfected in 100 mm dishes by the DEAE-dextran method (Sambrook et al., *In Molecular*

*Cloning. A Laboratory Manual,* 2nd. ed. (Cold Spring Harbor Laboratory Press, Cold Spring Harbor, N.Y., 1989)). Cell lysates or conditioned media were harvested at 3 or 4 days post-transfection. To prepare lysates, cell monolayers were washed with PBS, scraped from the dishes, and lysed by three freeze/thaw cycles in 150 μl of 0.25 M Tris-HCl, pH 8. Cell debris was pelleted and the supernate recovered. Conditioned media samples (7 mls) were collected, then concentrated and buffer exchanged with 10 mM Tris, pH 7.4 using Centriprep-10 and Centricon-10 units as described by the manufacturer (Amicon, Beverly, Mass.). Rat sciatic nerve Schwann cells were assayed for incorporation of DNA synthesis precursors, as described (Davis and Stroobant, J. Cell Biol. 110:1353–1360 (1990); Brockes et al., Brain Res. 165:105–118 (1979)).

Western blots of recombitant CHO cell conditioned medium were performed as follows: A recombinant CHO clone was cultured in 7 ml. of MCDB302 protein-free medium for 3 days. 2 ml of conditioned medium was concentrated, buffer exchanged against 10 mM Tris-HCl, pH 7.4 and lyophilized to dryness. The pellet was resuspended in SDS-PAGE sample buffer, subjected to reducing SDS gel electrophoresis and analyzed by Western blotting with a GGF peptide antibody. A CHO control was done by using conditioned medium from untransfected CHO-DG44 host and the CHO HBS5 levels were assayed using conditioned medium from a recombinant clone.

EXAMPLE 8

Isolation of Other Human Sequences Related to Bovine GGF

The result in Examples 5 and 6 indicate that GGF related sequences from human sources can also be easily isolated by using DNA probes derived from bovine GGF sequences. Alternatively the procedure described by Holmes et al. (Science 256: 1205 (1992)) can be used. In this example a human protein (heregulin α), which binds to and activates the p185$^{erbB2}$ receptor (and is related to GGF), is purified from a tumor cell line and the derived peptide sequence is used to produce oligonucleotide probes which were utilized to clone the cDNA's encoding heregulin. The biochemical assay for p185$^{erbB2}$ receptor activation is distinguished from Schwann cell proliferation. This is a similar approach to that used in examples 1–4 for the cloning of GGF sequences from pituitary cDNAs. The heregulin protein and complementary DNAs were isolated from tumor cell lines according to the following procedures. Heregulin was purified from medium conditioned by MDA-MB-231 breast cancer cells (ATCC #HTB 26) grown on Percell Biolytica microcarrier beads (Hyclone Labs). The medium (10 liters) was concentrated ~25-fold by filtration through a membrane (10-kD cutoff) (Millipore) and clarified by centrifugation and filtration through a filter (0.22 μm). The filtrate was applied to a heparin Sepharose column (Pharmacia) and the proteins were eluted with steps of 0.3, 0.6, and 0.9 M NaCl in phosphate-buffered saline. Activity in the various chromatographic fractions was measured by quantifying the increase in tyrosine phosphorylation of p185$^{erbB2}$ in MCF-7 breast tumor calls (ATCC #HTB 22). MCF-7 cells were plated in 24-well Costar plates in F12 (50%) Dulbecco's minimum essential medium (50%) containing serum (10%) ($10^5$ cells per well), and allowed to attach for at least 24 hours. Prior to assay, cells were transferred into medium without serum for a minimum of 1 hour. Column fractions (10 to 100 μl) were incubated for 30 min. at 37°. Supernatants were then aspirated and the reaction was stopped by the addition of SDS-PAGE sample buffer 100 μl). Samples were beated for 5 min. at 100° C., and portions (10 to 15 μl) were applied to a tris-glycine gel (4 to 20%) (Novex). After electrophoresis, proteins were electroblotted onto a polyvinylidenedifluoride (PVDF) membrane and then blocked with bovine serum albumin (5%) in tris-buffered saline containing Tween-20 (0.05%) (TBST). Slots were probed with a monoclonal antibody (1:1000 dilution) to phosphotyrosine (Upstate Biotechnology) for a minimum of 1 hour at room temperature. Blots were washed with TBST, probed with an antibody to mouse immunoglobulin G conjugated to alkaline phosphatase (Promega) (diluted 1:7500) for a minimum of 30 min. at room temperature. Reactive bands were visualized with 5-brono-4-chloro-3-indoyl-1-phosphate and nitro-blue tetrazolium. Immunoblots were scanned with a Scan Jet Plus (Hewlett-Packard) densitometer. Signal intensities for unstimulated MCF-7 cells were 20 to 30 units. Fully stimulated p185$^{erbB2}$ yielded signals of 180 to 200 units. The 0.6 M NaCl pool, which contained most of the activity, was applied to a polyaspartic acid (PolyLC) column equilibrated in 17 mM sodium phosphate (pH 6.8) containing ethanol (30%). A linear gradient from 0.3 M to 0.6 M NaCl in the equilibration buffer was used to elute bound proteins. A peak of activity (at ~0.45 M NaCl) was further fractionated on a C4 reversed-phase column (SynChropak RP-4) equilibrated in buffer containing TFA (0.1%) and acetonitrile (15%). Proteins were eluted from this column with an acetonitrile gradient from 25 to 40% over 60 min. Fractions (1 ml) were collected, assayed for activity, and analyzed by SDS-PAGE on tris-glycine gels (4–20%, Novex). HPLC-purified HRG-α was digested with lysine C in SDS (0.1%), 10 mM dithiothreitol, 0.1 M NH$_4$HCO$_3$ (pH 8.0) for 20 hours at 37° C. and the resultant fragments were resolved on a Synchrom C4 column (4000 Å°, 0.2 by 10 cm). The column was equilibrated in 0.1% TFA and eluted with a 1-propanol gradient in 0.1% TFA (W. J. Henzel, J. T. Stults, C. Hsu, D. W. Aswad, *J. Biol. Chem.* 264, 15905 (1989)). Peaks from the chromatographic run were dried under vacuum and sequenced. One of the peptides (eluting at ~24% 1-propanol) gave the sequence [A]AEKEKTF[C] VNGGEXFVKDLXNP (SEQ ID No. 162). Residues in brackets were uncertain and an X represents a cycle in which it was not possible to identify the amino acid. The initial yield was 8.5 pmol and the sequence did not correspond to any known protein. Residues 1, 9, 15, and 22 were later identified in the cDNA sequence as cysteine. Direct sequencing of the ~45-kD band from a gel that had been overloaded and blotted onto a PVDF membrane revealed a low abundance sequence XEXKE[G][R]GK[G]K[G] KKKEXGXG[K] (SEQ ID No. 30) with a very low initial yield (0.2 pmol). This corresponded to amino acid residues 2 to 22 of heregulin-α (FIG. 31), suggesting that serine 2 is the NH$_2$-terminus of proHRG-α. Although the NH$_2$ terminus was blocked, it was observed that occasionally a small amount of a normally blocked protein may not be post-translationally modified. The NH$_2$ terminal assignment was confirmed by mass spectrometry of the protein after digestion with cyanogen bromide. The COOH-terminus of the isolated protein has not been definitely identified; however, by mixture sequencing of proteolytic digests, the mature sequence does not appear to extend past residue 241. Abbreviations for amino residues are: A, Ala; C, Cys; D, Asp; E, Glu; F, Phe; G, Gly; H, His; I, Ile; K, Lye; L, Leu; M, Met; N, Asn; P, Pro; Q, Gln; R, Arg; S, Ser; T, Thr; V, Val; W, Trp; and Y, Tyr. As a source of cDNA clones, an oligo(dT)-primed λgt10 (T. V. Huynn, R. A. Young, R. W. Davis, λgt10 and λgt11 DNA Cloning Techniques: A Practical Approach, D. Glover, Ed. (IRC Press, Oxford, (1984)) cDNA library was constructed (U. Gubler and B. J. Hoffman, Gene 25, 263 (1983)) with mRNA purified (J. M. Chirwin, A. E. Przbyla, R. J. MacDonald, W. J. Rutter, Biochemistry 18, 5294 (1979)) from MDA-MB-231 cells. The following eightfold degenerate antisense deoxyoligonucleotide encoding the 13-amino acid sequence AEKEKTFCVNGGE (SEQ ID No. 31) (13) was designed on the basis of human codon frequency optima (R. Lathe, J. Mol. Biol. 183, 1 (1985)) and chemically synthesized: 5'-CTCGCC (G OR T) CC (A OR G) TTCAC (A OR G) CAGAAGGTCTTCTCCTTCTCAGC-3' (SEQ ID No. 40). For the purpose of probe design a cysteine was assigned to an unknown residue in the amino acid sequence . The probe was labeled by phosphorylation and hybridized under low-stringency conditions to the cDNA library. The proHRG-α protein was identified in this library. HRB-β1 cDNA was identified by probing a second oligo(dT)-primed λgt10 library made from MDA-MB-231 cell mRNA with sequences derived from both the 5' and 3' ends of proHRG-α. Clone 13 (FIG. 2A) was a product of screening a primed (5'-CCTCGCTCCTTCTTCTTGCCCTTC-3' primer (SEQ ID No. 41); proHRG-α antisense nucleotides 33 to 56) MDA-MB-231 λgt10 library with 5' HRG-α sequence. A sequence corresponding to the 5' end of clone 13 as the probe was used to identify proHRGβ2 and proHRGβ3 in a third oligo(dT)-primed λgt10 library derived from MDA-MB-231 cell mRNA. Two cDNA clones encoding each of the four HRGs were sequenced (F. Sanger, S. Milken, A. R. Coulson, Proc. Natl. Acad. Sci. U.S.A. 74, 5463 1977]). Another cDNA designated clone 84 has an amino acid sequence identical to proHRGβ2 through amino acid 420. A stop codon at position 421 is followed by a different 3'-untranslated sequence.

EXAMPLE 9

Isolation of a Further Splicing Variant

The methods in Example 6 produced four closely related sequences (heregulin α, β1, β2, β3) which arise as a result of splicing variation. Peles et al. (Cell 69, 205 (1992)), and Wen et al. (Cell 69, 559 (1992)) have isolated another splicing variant (from rat) using a similar purification and cloning approach to that described in Examples 1–4 and 6 involving a protein which binds to p185$^{erbB2}$. The cDNA clone was obtained as follows (via the purification and sequencing of a p185$^{erbB2}$ binding protein from a transformed rat fibroblast cell line).

A p185$^{erbB2}$ binding protein was purified from conditioned medium as follows. Pooled conditioned medium from three harvests of 500 roller bottles (120 liters total) was cleared by filtration through 0.2μ filters and concentrated 31-fold with a Pelicon ultrafiltration system using membranes with a 20 kd molecular size cutoff. All the purification steps were performed by using a Pharmacia fast protein liquid chromatography system. The concentrated material was directly loaded on a column of heparin-Sepharose (150 ml, preequilibrated with phosphate-buffered saline (PBS)). The column was washed with PBS containing 0.2 M NaCl until no absorbance at 280 nm wavelength could be detected. Bound proteins were then eluted with a continuous gradient (250 ml) of NaCl (from 0.2 M to 1.0 M), and 5 ml fractions were collected. Samples (0.01 ml of the collected fractions were used for the quantitative assay of the kinase stimulatory activity. Active fractions from three column runs (total volume=360 ml) were pooled, concentrated to 25 ml by using a YM10 ultrafiltration membrane (Amicon, Danvers, Mass.), and ammonium sulfate was added to reach a concentration of 1.7 M. After clearance by centrifugation (10, 000×g, 15 min.), the pooled material was loaded on a phenyl-Superose column (HR10/10, Pharmacia) The column was developed with a 45 ml gradient of $(NH_4)_2SO_4$ (from 1.7 M to no salt) in 0.1 M $Na_2PO_4$ (pH 7.4), and 2 ml fractions were collected and assayed (0.002 ml per sample) for kinase stimulation (as described in Example 6). The major peak of activity was pooled and dialyzed against 50 mM sodium phosphate buffer (pH 7.3). A Mono-S cation-exchange column (HR5/5, Pharmacia) was preequilibrated with 50 mM sodium phosphate. After loading the active material (0.884 mg of protein; 35 ml), the column was washed with the starting buffer and then developed at a rate of 1 ml/min. with a gradient of NaCl. The kinase stipulatory activity was recovered at 0.45–0.55 M salt and was spread over four fractions of 2 ml each. These were pooled and loaded directly on a $Cu^{+2}$ chelating columns (1.6 ml, HR2/5 chelating Superose, Pharmacia). Most of the proteins adsorbed to the resin, but they gradually eluted with a 30 ml linear gradient of ammonium chloride (0–1 M). The activity eluted in a single peak of protein at the range of 0.05 to 0.2 M $NH_4Cl$. Samples from various steps of purification were analyzed by gel electrophoresis followed by silver staining using a kit from ICN (Costa Mesa, Calif.), and their protein contents were determined with a Coomassie blue dye binding assay using a kit from Bio-Rad (Richmond, Calif.).

The p44 protein (10 μg) was reconstituted in 200 μl of 0.1 M ammonium bicarbonate buffer (pH 7.8). Digestion was conducted with L-1-tosyl-amide 2-phenylethyl chloromethyl ketone-treated trypsin (Serva) at 37° C. for 18 hr. at an enzyme-to-substrate ratio of 1:10. The resulting peptide mixture was separated by reverse-phase HPLC and monitored at 215 nm using a Vydac C4 micro column (2.1 mm i.d.×15 cm, 300 Å) and an HP 1090 liquid chromatographic system equipped with a diode-array detector and a workstation. The column was equilibrated with 0.1% trifluoroacetic acid (mobile phase A), and elution was effected with a linear gradient from 0%–55% mobile phase B (90% acetonitrile in 0.1% trifluoroacetic acid) over 70 min. The flow rate was 0.2 ml/min. and the column temperature was controlled at 25° C. One-third aliquots of the peptide peaks collected manually from the HPLC system were characterized by N-terminal sequence analysis by Edman degradation. The fraction eluted after 27.7 min. (T27.7) contained mixed amino acid sequences and was further rechromatographed after reduction as follows: A 70% aliquot of the peptide fraction was dried in vacuo and reconstituted in 100 μl of 0.2 M ammonium bicarbonate buffer (pH 7.8). DTT (final concentration 2 mM) was added to the solution, which was then incubated at 37° C. for 30 min. The reduced peptide mixture was then separated by reverse-phase HPLC using a Vydac column (2.1 mm i.d.×15 cm). Elution conditions and flow rat were identical to those described above. Amino acid sequence analysis of the peptide was performed with a Model 477 protein sequencer (Applied Biosystems, Inc., Foster City, Calif.) equipped with an on-line phenylthiohy-dantoin (PTH) amino acid analyzer and a Model 900 data analysis system (Hunkapiller et al. (1986) In *Methods of Protein Microcharacterization*, J. E. Shively, ed. (Clifton, N.J.: Humana Press p. 223–247). The protein was loaded onto a trifluoroacetic acid-treated glass fiber disc precycled with polybrene and NaCl. The PTH-amino acid analysis was performed with a micro liquid chromatography system (Model 120) using dual syringe pumps and reverse-phase (C-18) narrow bore columns (Applied Biosystems, 2.1 mm×250 mm). RNA was isolated from Rat1-EJ cells by standard procedures (Maniatis et al., Molecular Cloning: A Laboratory Manual (Cold Spring Harbor, N.Y. (1982) and poly (A)+ was selected using an mRNA Separator kit (Clontech Lab, Inc., Palo Alto, Calif.). cDNA was synthesized with the Superscript kit (from BRL Life Technologies, Inc., Bethesda, Md.). Column-fractionated double-strand cDNA was ligated into an Sal1- and Not1-digested pJT-2 plasmid vector, a derivative of the pCD-X vector (Okayama and Berg, Mol. Cell Biol. 3: 280 (1983)) and transformed into DH10B E. coli cells by electroporation (Dower et al., Nucl. Acids Res. 16: 6127 (1988)). Approximately $5 \times 10^5$ primary transformants were screened with two oligonucleotide probes that were derived from the protein sequences of the N-terminus of NDF (residues 5–24) and the T40.4 tryptic peptide (residues 7–12). Their respective sequences were as follows (N indicates all 4 nt):

```
(1) 5'-ATA GGG AAG GGC GGG GGA AGG GTC NCC CTC NGC
         A   T
        AGG GCC GGG CTT GCC TCT GGA GCC TCT-3'

(2) 5'-TTT ACA CAT ATA TTC NCC-3'
       C   G       G   C
(1: SEQ ID No. 167; 2: SEQ ID No. 168)
```

The synthetic oligonucleotides were end-labeled with [γ-$^{32}$P]ATP with T4 polynucleotide kinase and used to screen replicate sets of nitrocellulose filters. The hybridization solution contained 6× SSC, 50 mM sodium phosphate (pH 6.8), 0.1% sodium pyrophosphate, 2× Denhardt's solution, 50 μg/ml salmon sperm DNA, and 20% formamide (for probe 1) or no formamide (for probe 2). The filters were washed at either 50° C. with 0.5× SSC, 0.2% SDS, 2 mM EDTA (for probe 1) or at 37° C. with 2× SSC, 0.2% SDS, 2 mM EDTA (for probe 2). Autoradiography of the filters gave ten clones that hybridized with both probes. These clones were purified by replating and probe hybridization as described above. The cDNA clones were sequenced using an Applied Biosystems 373A automated DNA sequencer and Applied Biosystems Taq DyeDeoxy™ Terminator cycle sequencing kits following the manufacture's instructions. In some instances, sequences were obtained using [$^{35}$S]dATP (Amersham) and Sequenase™ kits from U.S. Biochemicals following the manufacturer's instructions. Both strands of the cDNA clone 44 were sequenced by using synthetic oligonucleotides as primers. The sequence of the most 5' 350 nt was determined in seven independent cDNA clones. The resultant clone demonstrated the pattern shown in FIG. 30 (NDF).

EXAMPLE 10

Strategies for Detecting Other Possible Splicing Variants

Alignment of the deduced amino acid sequences of the cDNA clones and PCR products of the bovine, and the published human (FIG. 31) and rat sequences show a high level of similarity, indicating that these sequences are derived from homologous genes within the three species. The variable number of messenger RNA transcripts detectable at the cDNA/PCR product level is probably due to extensive tissue-specific splicing. The patterns obtained and shown in FIG. 30 suggests that other splicing variants exist. A list of probable splicing variants is indicated in FIG. 37. Many of these variants can be obtained by coding segment specific probing of cDNA libraries derived from different tissues and by PCR experiments using primer pairs specific to particular coding segments. Alternatively, the variants can be assembled from specific cDNA clones, PCR products or genomic DNA regions via cutting and splicing techniques known to one skilled in the art. For example, a rare restriction enzyme cutting site in a common coding segment (e.g., A), can be used to connect the FBA amino terminus of GGF2BPP5 to carboxy terminal sequences of GGF2BPP1, GGFBPP2, GGFBPP3, or GGFBPP4. If the presence or the absence of coding segment E and/or G provide benefit for contemplated and stated uses, then these coding segments can be included in expression constructs. These variant sequences can be expressed in recombinant systems and the recombinant products can be assayed to determine their level of Schwann cell mitogenic activity as well as their ability to bind and activate the p185$^{erbB2}$ receptor.

EXAMPLE 11

Identification of Functional Elements of GGF

The deduced structures of the family of GGF sequences indicate that the longest forms (as represented by GGF2BPP4) encode transmembrane proteins where the extracellular part contains a domain which resembles epidermal growth factor (see Carpenter and Wahl in Peptide Growth Factors and Their Receptors I pp. 69–133, Springer-Verlag, N.Y. 1991). The positions of the cysteine residues in coding segments C and C/D or C/D' peptide sequence are conserved with respect to the analogous residues in the epidermal growth factor (EGF) peptide sequence (see FIG. 35, SEQ ID Nos. 151–153). This suggests that the extracellular domain functions as receptor recognition and biological activation sites. Several of the variant forms lack the H, K, and L coding segments and thus may be expressed as secreted, diffusible biologically active proteins. GGF DNA sequences encoding polypeptides which encompass the EGF-like domain (EGFL) can have full biological activity for stimulating glial cell mitogenic activity.

Membrane bound versions of this protein may induce Schwann cell proliferation if expressed on the surface of neurons during embryogenesis or during nerve regeneration (where the surfaces of neurons are intimately associated with the surfaces of proliferating Schwann cells).

Secreted (non membrane bound) GGFs may act as classically diffusible factors which can interact with Schwann cells at some distance from their point of secretion. Other forms may be released from intracells by sources via tissue injury and cell disruption. An example of a secreted GGF is the protein encoded by GGF2HBS5 (see example 6); this is the only GGF known which has been found to be directed to the exterior of the cell (example 7). Secretion is probably mediated via an N-terminal hydrophobic sequence found only in region E, which is the N-terminal domain contained within recombinant GGF-II encoded by GGF2HBS5.

Other GGF's appear to be non-secreted (see example 6). These GGFs may be injury response forms which are released as a consequence of tissue damage.

Other regions of the predicted protein structure of GGF-II (encoded by GGF2HBS5) and other proteins containing regions B and A exhibit similarities to the human basement membrane heparin sulfate proteoglycan core protein (Kallunk, P. and Tryggvason, K., Cell Biology Vol. 116, p. 559–571 (1992)). The peptide ADSGEY, which is located next to the second cysteine of the C2 immunoglobulin fold in these GGF's, occurs in nine of twenty-two C-2 repeats found in that basal lamina protein. This evidence strongly suggests that these proteins may associate with matrix proteins such as those associated with neurons and glia, and may suggest a method for sequestration of glial growth factors at target sites.

EXAMPLE 12

Purification of GGFs from Recombinant Cells

In order to obtain full length or portions of GGFs to assay for biological activity, the proteins can be overproduced using cloned DNA. Several approaches can be used. A recombinant *E. coli* cell containing the sequences described above can be constructed. Expression systems such as pNH8a or pHH16a (Stratagene, Inc.) can be used for this purpose by following manufacturers procedures. Alternatively, these sequences can be inserted in a mammalian expression vector and an overproducing cell line can be constructed. As an example, for this purpose DNA encoding a GGF, clone GGF2BPP5 has been expressed in both COS cells and Chinese hamster ovary cells (see Example 7) (J. Biol. Chem. 263, 3521–3527, (1981)). This vector containing GGF DNA sequences can be transfected into host cells using established procedures.

Transient expression can be examined or G418-resistant clones can be grown in the presence of methotrexate to select for cells that amplify the dhfr gene (contained on the pMSXND vector) and, in the process, co-amplify the adjacent GGF protein encoding sequence. Because CHO cells can be maintained in a totally serum-free, protein-free medium (Hamilton and Ham, In Vitro 13, 537–547 (1977)), the desired protein can be purified from the medium. Western analysis using the antisera produced in Example 9 can be used to detect the presence of the desired protein in the conditioned medium of the overproducing cells.

Figure 50A:
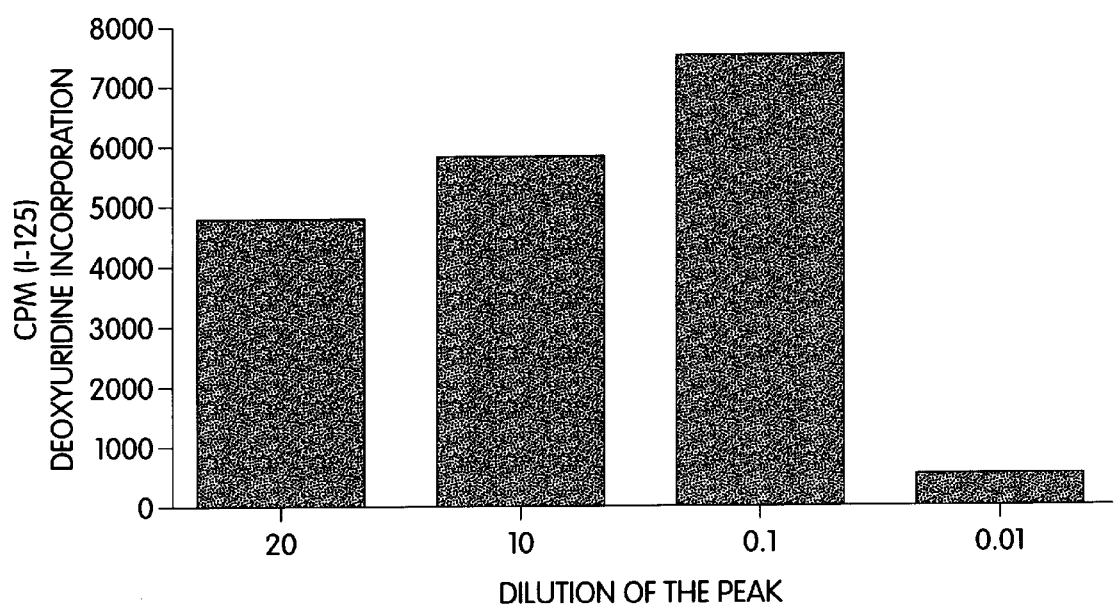
FIG. 50(A) is a graph of Schwann cell proliferation activity of recombinant (COS cell produced) human GGF-II (rhGGF-II) peak eluted from the cation exchange column; (B) is an immunoblot against recombinant GGFII peak using polyclonal antibody made against specific peptide of rhG-GFII.
Figure 50B:
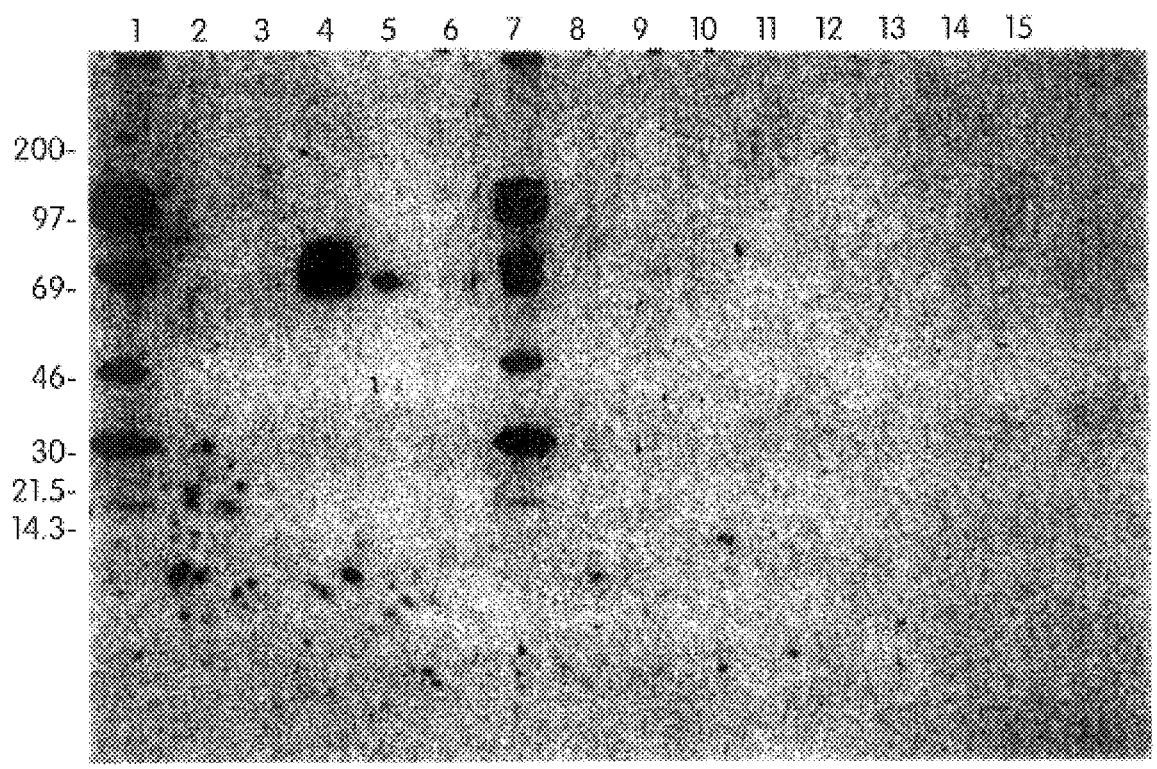

The desired protein (rGGF-II) was purified from the medium conditioned by transiently expressing COS cells as follows. rGGF-II was harvested from the conditioned medium and partially purified using Cation Exchange Chromatography (POROS-HS). The column was equilibrated with 33.3 mM MES at pH 6.0. Conditioned media was loaded at flow rate of 10 ml/min. The peak containing Schwann cell proliferation activity and immunoreactive (using the polyclonal antisera was against a GGFII peptide described above) was eluted with 50 mM Tris, 1M NaCl pH 8.0. (FIGS. 50A and 50B respectively).

rGGF-II is also expressed using a stable Chinese Hamster Ovary cell line. rGGF-II from the harvested conditioned media was partially purified using Cation Exchange Chromatograph (POROS-HS). The column was equilibrated with PBS pH 7.4. Conditioned media was loaded at 10 ml/min. The peak containing the Schwann Cell Proliferative activity and immunoreactivity (using GGFII polyclonal antisera) was eluted with 50 mM Hepes, 500 mM NaCl pH 8.0. An additional peak was observed at 50 mM Hepes, 1M NaCl pH 8.0 with both proliferation as well as immunoreactivity (FIG. 51).

rGGF-II can be further purified using Hydrophobic Interaction Chromatography as a high resolution step; Cation Exchange/Reverse phase Chromatography (if needed as second high resolution step); a viral inactivation step and a DNA removal step such as Anion Exchange chromatography.

Detailed description of procedures used are as follows:

Schwann Cell Proliferation Activity of the recombinant GGF-II peak eluted from the Cation Exchange column was determined as follows: Mitogenic responses of the cultured Schwann cells were measured in the presence of 5 μM forskolin using the peak eluted by 50 mM Tris 1 M NaCl pH 8.0. The peak was added at 20 1, 10 1 (1:10) 10 1 and (1:100) 10 1. Incorporation of $^{125}$I-Uridine was determined and expressed as (CPM) following an 18–24 hour exposure.

An immunoblot using polyclonal antibody raised against a peptide of GGF-II was carried out as follows: 10 μl of different fractions were run on 4–12% gradient gels. The gels were transferred on to Nitrocellulose paper, and the nitrocellulose blots were blocked with 5% BSA and probed with GGF-II-specific antibody (1:250 dilution). $^{125}$I protein A (1:500 dilution, Specific Activity=9.0/ci/g) was used as the secondary antibody. The immunoblots were exposed to Kodax X-Ray films for 6 hours. The peak fractions eluted with 1 M NaCl showed a broad immunoreactive band at 65–90 Kd which is the expected size range for GGFII and higher molecular weight glycoforms.

GGF-II purification on cation exchange columns was performed as follows: CHO cell conditioned media expressing rGGFII was loaded on the cation exchange column at 10 ml/min. The column was equilibrated with PBS pH 7.4. The elution was achieved with 50 mM Hepes 500 mM NaCl pH 8.0 and 50 mM Hepes 1M NaCl pH 8.0 respectively. All fractions were analyzed using the Schwann cell proliferation assay (CPM) described herein. The protein concentration (mg/ml) was determined by the Bradford assay using BSA as the standard.

Figure 51A:
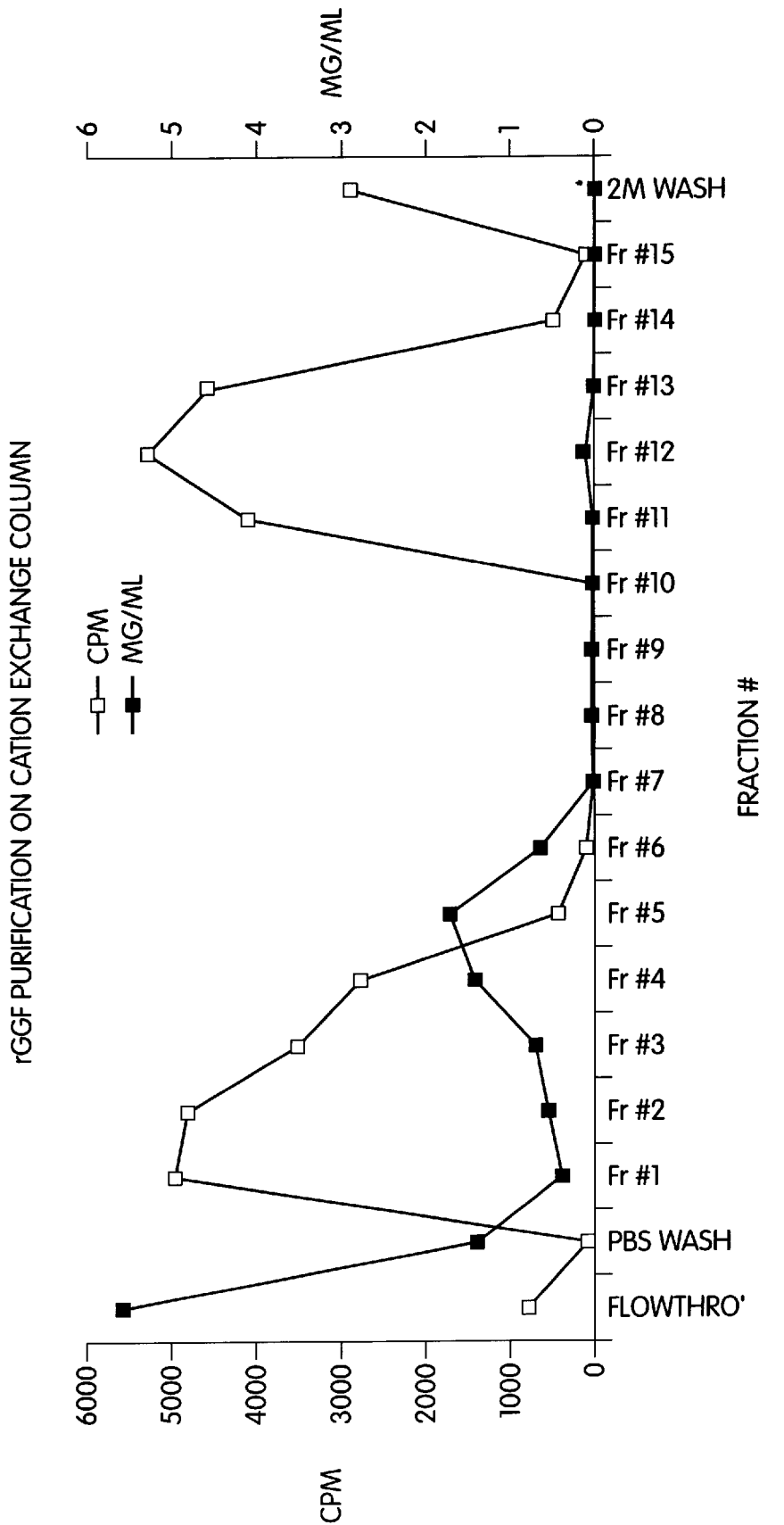
FIGS. 51(A–C) is a graph showing the purification of rhGGF-II (CHO cell produced) on cation exchange column by fraction; (B–C) is a photograph of a Western blot using fractions as depicted in (A) and a rhGGF-II specific antibody.
Figure 51B:
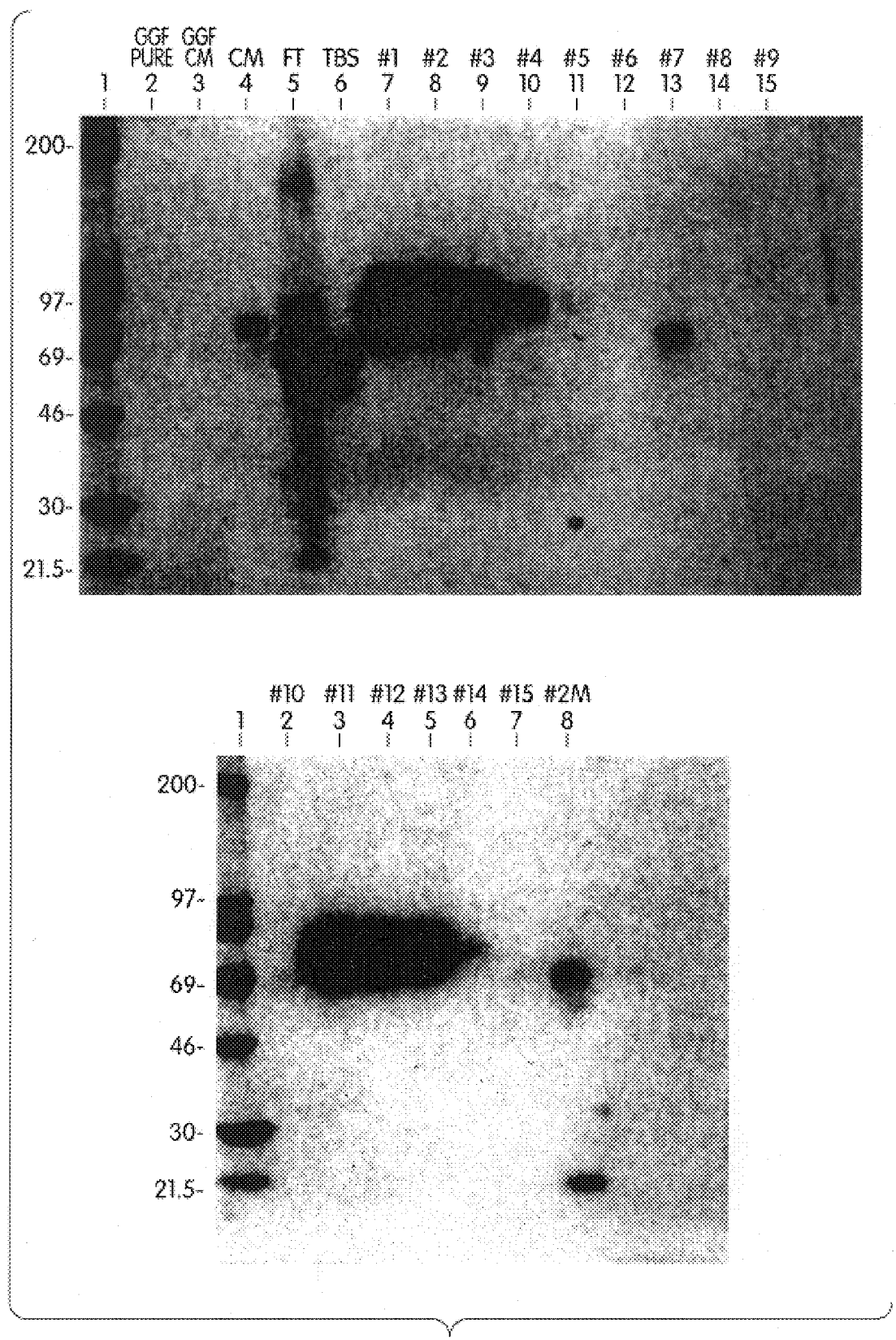

A Western blot using 10 μl of each fraction was performed. As indicated in FIGS. 51A and 51B, immunoreactivity and the Schwann cell activity co-migrates.

The Schwann cell mitogenic assay described herein may be used to assay the expressed product of the full length clone or any biologically active portions thereof. The full length clone GGF2BPP5 has been expressed transiently in COS cells. Intracellular extracts of transfected COS cells show biological activity when assayed in the Schwann cell proliferation assay described in Example 1. In addition, the full length close encoding GGF2HBS5 has been expressed stably in CHO and insect viral systems (Example 7) cells. In this case both cell extract and conditioned media show biological activity in the Schwann cell proliferation assay described in Example 1. Any member of the family of splicing variant complementary DNA's derived from the GGF gene (including the Heregulins) can be expressed in this manner and assayed in the Schwann cell proliferation assay by one skilled in the art.

Alternatively, recombinant material may be isolated from other variants according to Wen et al. (Cell 69, 559 (1992)) who expressed the splicing variant Neu differentiation factor (NDF) in COS-7 cells. cDNA clones inserted in the pJT-2 eukaryotic plasmid vector are under the control of the SV40 early promoter, and are 3'-flanked with the SV40 termination and polyadenylation signals. COS-7 cells were transfected with the pJT-2 plasmid DNA by electroporation as follows: $6 \times 10^6$ cells (in 0.8 ml of DMEM and 10% FEBS) were transferred to a 0.4 cm cuvette and mixed with 20 μg of plasmid DNA in 10 μl of TE solution (10 mM Tris-HCl (pH 8.0), 1 mM EDTA). Electroporation was performed at room temperature at 1600 V and 25 μF using a Bio-Rad Gene Pulser apparatus with the pulse controller unit set at 200 ohms. The cells were then diluted into 20 ml of DMEM, 10% FBS and transferred into a T75 flask (Falcon). After 14 hr. of incubation at 37° C., the medium was replaced with DMEM, 1% FBS, and the incubation continued for an additional 48 hr. Conditioned medium containing recombinant protein which was harvested from the cells demonstrated biological activity in a cell line expressing the receptor for this protein. This cell line (cultured human breast carcinoma cell line AU 565) was treated with recombinant material. The treated cells exhibited a morphology change which is characteristic of the activation of the erbB2 receptor. Conditioned medium of this type also can be tested in the Schwann cell proliferation assay.

EXAMPLE 13

Purification and Assay of Other Proteins which Bind $p185^{erbB2}$ Receptor

I. Purification of gp30 and p70

Lupu et al. (Science 249, 1552 (1990)) and Lippman and Lupu (patent application number PCT/US91/03443 (1990)), hereby incorporated by reference, have purified a protein from conditioned media of a human breast cancer cell line MDA-MB-231, as follows.

Conditioned media collections were carried using well-known procedures. The media was concentrated 100-fold in an Amicon ultra-filtration cell (YM5 membrane) (Anicon, Danvers, Mass.). Once clarified and concentrated, the media were stored at −20° C. while consecutive collections were made during the following days. The concentrated media were dialyzed using Spectra/por® 3 tubing (Spectrum Medical Industries, Los Angeles, Calif.) against 100 volumes of 0.1 M acetic acid over a two day period at 4° C. The material that precipitated during dialysis was removed by centrifugation at 4000 rpm for 30 min. at 4° C.; protease inhibitors were added. The clarified sample was then lyophilized.

Lyophilized conditioned medium was dissolved in 1 M acetic acid to a final concentration of about 25 mg/ml total protein. Insoluble material was removed by centrifugation at 10,000 rpm for 15 minutes. The sample was then loaded onto a Sephadex G-100 column (XK 16, Pharmacia, Piscataway, N.J.), was equilibrated and was subjected to elution with 1 M acetic acid at 4° C. with an upward flow of 30 ml/hr. 100 ng of protein was processed from 4 ml of 100-fold concentrated medium. Fractions containing 3 ml of eluate were lyophilized and resuspended in 300 μl PBS for assay and served as a source for further purification.

Sephadex G-100 purified material was run on reversed-phase high pressure liquid chromatography (HPLC). The first step involved a steep acetonitrile gradient. Steep acetonitrile gradient and all other HPLC steps were carried out at room temperature after equilibration of the C3-Reversed phase column with 0.05% TFA (Trifluoroacetic acid) in water (HPLC-grade). The samples were loaded and fractions were eluted with a linear gradient (0–45% acetonitrile in 0.05% TFA) at a flow rate of 1 ml/min. over a 30 minute period. Absorbance was monitored at 280 nm. One ml fractions were collected and lyophilized before analysis for EGF receptor-competing activity.

A second HPLC step involved a shallow acetonitrile gradient. The pool of active fractions from the previous HPLC step was rechromatographed over the same column. Elution was performed with a 0–18% acetonitrile gradient in 0.05% TFA over a 5 minute period followed by a linear 18–45% acetonitrile gradient in 0.05% TFA over a 30 minute period. The flow rate was 1.0 ml/min. and 1 ml fractions were collected. Human TGFα-like factor was eluted at a 30–32% acetonitrile concentration as a single peak detectable by RRA.

Lupu at al. (Proc. Natl. Acad. Sci. 89, 2287 (1992)) purified another protein which binds to the $p185^{erbB2}$ receptor. This particular protein, p75, was purified from conditioned medium used for the growth of SKBr-3 (a human breast cancer cell line) propagated in improved Eagle's medium (IMEM: GIBCO) supplemented with 10% fetal bovine serum (GIBCO). Protein p75 was purified from concentrated (100×) conditioned medium using a $p185^{erbB2}$ affinity column. The 94 Kilodalton extracellular domain of $p185^{erbB2}$ (which binds p75) was produced via recombinant expression and was coupled to a polyacrylamide hydrazido-Sepharose affinity chromatography matrix. Following coupling the matrix was washed extensively with ice cold 1.0 M HCl and the beads were activated with 0.5 M $NaNO_2$. The temperature was maintained at 0° C. for 20 minutes and this was followed by filtration and washing with ice cold 0.1 M HCl. 500 ml of concentrated conditioned medium was run through the beads by gravity. The column was washed and eluted stepwise with 1.0 M citric acid at pH values from 4.0 to 2.0 (to allow dissociation of the erbB2 and p75). All fractions were desalted on Pharmacia PD10 columns. Purification yielded a homogeneous polypeptide of 75 kDa at 3.0–3.5 elution pH (confirmed by analysis on SDS/PAGE by silver staining).

II. Binding of gp30 to $p185^{erb}B2$

The purified gp30 protein was tested in an assay to determine if it bound to $p185^{erbB2}$. A competition assay with a monoclonal antibody against $p185^{erbB2}$. The gp30 protein displaced antibody binding to $p185^{erbB2}$ in SK-BR-3 and MDA-MB-453 cells (human breast carcinoma cell lines expressing the $p185^{erbB2}$ receptor). Schwann cell proliferation activity of gp30 can also be demonstrated by treating Schwann cell cultures with purified gp30 using the assay procedure described in Examples 1–3.

III. Binding of p75 to $p185^{erbB2}$

To assess whether the 75-kDa polypeptide (p75) obtained from SKBr-3 conditioned medium was indeed a ligand for the erbB2 oncoprotein in SKBr-3 cells, a competition assay as described above for gp30 was used. It was found that the p75 exhibited binding activity, whereas material from other chromatography fractions did not show such activity (data not shown). The flow-through material showed osome binding activity. This might be due to the presence of shed erbB2 ECD.

IV. Other $p185^{erbB2}$ Ligands

Peles et al. (Cell 69, 205 (1992)) have also purified a $185^{erbB2}$ stimulating ligand from rat cells, (NDF, see Example 8 for method). Holmes et al. (Science 256, 1205 (1992)) have purified Heregulin α from human cells which binds and stimulates $185^{erbB2}$ (see example 6). Tarakovsky et al. Oncogene 6:218 (1991) have demonstrated bending of a 25 kD polypeptide isolated from activated macrophages to the Neu receptor, a $p185^{erbB2}$ homology, herein incorporated by reference.

VI. NDF Isolation

Yarden and Peles (Biochemistry 30, 3543 (1991)) have identified a 35 kilodalton glycoprotein which will stimulate the $185^{erbB2}$ receptor. The protein was identified in conditioned medium according to the following procedure. Rat I-EJ cells were grown to confluence in 175-$cm^2$ flasks (Falcon). Monolayers were washed with PBS and left in serum-free medium for 10–16 h. The medium was discarded and replaced by fresh serum-free medium that was collected after 3 days in culture. The conditioned medium was cleared by low-speed centrifugation and concentrated 100-fold in an Amicon ultrafiltration cell with a YM2 membrane (molecular weight cutoff of 2000). Biochemical analyses of the neu stimulatory activity in conditioned medium indicate that the ligand is a 35-kD glycoprotein that it is heat stable but sensitive to reduction. The factor is precipitable by either high salt concentrations or acidic alcohol. Partial purification of the molecule by selective precipitation, heparin-agarose chromatography, and gel filtration in dilute acid resulted in an active ligand, which is capable of stimulating the protooncogenic receptor but is ineffective on the oncogenic neu protein, which is constitutively active. The purified fraction, however, retained the ability to stimulate also the related receptor for EGF, suggesting that these two receptors are functionally coupled through a bidirectional mechanism. Alternatively, the presumed ligand interacts simultaneously with both receptors. The presented biochemical characteristic of the factor may be used to enable a completely purified factor with which to explore these possibilities.

In other publications, Davis et al. (Biochem. Biophys. Res. Commun. 179, 1536 (1991), Proc. Natl. Acad. Sci. 88, 8582 (1991) and Greene et al., PCT patent application PCT/US91/02331 (1990)) describe the purification of a protein from conditioned medium of a human T-cell (ATL-2) cell line.

ATL-2 cell line is an IL-2-independent HTLV-1 (+) T cell line. Mycoplasm-free ATL-2 cells were maintained in RPMI 1640 medium containing 10% FCB as the culture medium (10% FCS-RPMI 1640) at 37° C. in a humidified atmosphere with 5% $CO_2$.

For purification of the proteinaceous substance, ATL-2 cells were washed twice in 1× PBS and cultured at $3\times10^5$ ml in serum-free RPMI 1640 medium/2 mM L-glutamine for seventy-two hours followed by pelleting of the cells. The culture supernatant so produced is termed "conditioned medium" (C.M.).

C.M. was concentrated 100 fold, from 1 liter to 10 ml, using a YM-2 Diaflo membrane (Amicon, Boston, Mass.) with a 1000 d cutoff. For use in some assays, concentrated C.M. containing components greater than 1000 MW were rediluted to original volume with RPMI medium. Gel electrophoresis using a polyacrylamide gradient gel (Integrated Separation Systems, Hyde Park, Md. or Phorecast System by Amersham, Arlington Heights, Ill.) followed by silver staining of some of this two column purified material from the one liter preparation revealed at least four to five bands of which the 10 kD and 20 kD bands were unique to this material. Passed C.M. containing components less than 1000 NW were used without dilution.

Concentrated conditioned medium was filter sterilized with a 0.45$\mu$ uniflo filter (Schleicher and Schuell, Keene, N.H.) and then further purified by application to a DEAE-SW anion exchange column (Waters, Inc., Milford, Mass.) which had been preequilibrated with 10 mM Tris-Cl, pH 8.1 Concentrated C.M. proteins representing one liter of original ATL-2 conditioned medium per HPLC run were absorbed to the column and then eluted with a linear gradient of 0 mM to 40 mM NaCl at a flow rate of 4 ml/min. Fractions were assayed using an in vitro immune complex kinase assay with 10% of the appropriate DEAE fraction (1 column purified material) or 1% of the appropriate C18 fractions (two column purified material). The activity which increased the tyrosine kinase activity of p185c-neu in a dose-dependent manner using the in vitro immune complex kinase assay was eluted as one dominant peak across 4 to 5 fractions (36–40) around 220 to 240 mM of NaCl. After HPLC-DEAE purification, the proteins in the active fractions were concentrated and pooled, concentrated and subjected to C18 (million matrix) reverse phase chromatography (Waters, Inc., Milford, Mass.) (referred to as the C18+1 step or two column purified material). Elution was performed under a linear gradient of 2-propanol against 0.1% TFA. All the fractions were dialyzed against RPMI 1640 medium to remove the 2-propanol and assayed using the in vitro immune complex kinase assay, described below, and a 1% concentration of the appropriate fraction. The activity increasing the tyrosine kinase activity of p185c-neu was eluted in two peaks. One eluted in fraction 11–13, while a second, slightly less active peak of activity eluted in fractions 20–23. These two peaks correspond to around 5 to 7% of isopropanol and 11 to 14% isopropanol respectively. C18#1 generated fractions 11–13 were used in the characterization studies. Active fractions obtained from the second chromatographic step were pooled, and designated as the proteinaceous substance sample.

A twenty liter preparation employed the same purification strategy. The DEAE active fractions 35–41 were pooled and subjected to c18 chromatography as discussed above. C18#1 fractions 11–13 and 21–24 both had dose-dependent activity. The pool of fractions 11–13 was subjected to an additional C18 chromatographic step (referred to as C18#2 or three column purified material). Again, fractions 11–13 and 21–24 had activity. The dose response of fraction 23 as determined by in vitro immune complex kinase assay as described in Example 8 may be obtained upon addition of 0.005% by volume fraction 23 and 0.05% by volume fraction 23. This represents the greatest purity achieved.

Molecular weight ranges were determined based on gel filtration chromatography and ultrafiltration membrane analysis. Near equal amounts of tyrosine kinase activity were retained and passed by a 10,000 molecular weight cut off filter. Almost all activity was passed by a 30,000 molecular weight cut off filter. Molecular weight ranges for active chromatographic fractions were determined by comparing fractions containing dose-dependent neu-activating activity to the elution profiles of a set of protein molecular weight standards (Sigma Chemical Co., St. Louis, Mo.) generated using the same running conditions. A low molecular weight region of activity was identified between 7,000 and 14,000 daltons. A second range of activity ranged from about 14,000 to about 24,000 daltons.

After gel electrophoresis using a polyacrylamide gradient gel (Integrated Separation Systems, Hyde Park, Md. or Phorecase System by Amersham, Arlington Heights, Ill.), silver staining of the three-column purified material (c18#2) was done with a commercially available silver staining kit (BioRad, Rockville Centre, N.Y.). Fraction 21, 22, 23, and 24 from c18#2 purification of the twenty liter preparation were run with markers. Fractions 22 and 23 showed the most potent dose response in the $185^{erbB2}$ (neu) kinase assay (see below). The fact that selected molecular weight fractions interact with $185^{erbB2}$ was demonstrated with an immune complex kinase assay.

Huang et al. (1992, J. Biol. Chem. 257:11508–11512), hereby incorporated by reference, have isolated an additional neu/erb B2 ligand growth factor from bovine kidney. The 25 kD polypeptide factor was isolated as follows.

Fresh calf kidneys were obtained and homogenized in phosphate buffered saline at a ratio of 2 ml/g tissue. Kidney extracts were then subjected to ammonium sulfate fractionation (35–70% saturation), followed by sequential column chromatography on DEAE-cellulose (DE-52), and sulfadex (sulfated Sephadex G-50), as described by Huang et al., J. Biol. Chem. 265: 3340–3346 (1990), with some modification. In the Sulfadex column chromatography after extensive washing with 0.5 M NaCl in 10 mM Tris.HCl buffer, pH 7.4, NEL-GF was eluted with 2M NaCl in Tris.HCl buffer, pH 7.4. The NEL-GF containing fractions from Sulfadex column chromatography were then pooled, dialyzed, and applied onto a column of heparin-Sepharose 4B (60 ml volume), previously equilibrated with 10 mM Tris.HCl buffer, pH 7.4, 0.5 M NaCl. After extensive washing with 0.5 M NaCl in 10 mM Tris.HCl buffer, pH 7.4, NEL-GF was eluted with 1.1 M NaCl in Tris.HCl buffer. The 1.1 M NaCl eluents were then concentrated by ultrafiltration and applied onto Superdex 75 of FPLC at a flow rate of 0.4 ml/min (10 mM Tris.HCl buffer, pH 7.4 and 0.5 NaCl). NEL-GF appeared in fractions 16 and 15. NEL-GF stimulates tyrosine-specific autophosphorylation of the neu-erb β2 gene product.

VII. Immune Complex Assay NDF for Ligand Binding to p185$^{erb}$B2:

This assay reflects the differences in the autophosphorylation activity of immunoprecipitated p185 driven by pre-incubation of PN-NR6 cell lysate with varying amounts of ATL-2 conditioned medium (C.H.) or proteinaceous substance and is referred to hereinafter as neu-activating activity.

Cell lines used in the immune complex kinase assay were obtained, prepared and cultured according to the methods disclosed in Kokai et al., Cell 55, 287–292 (Jul. 28, 1989) the disclosures of which are hereby incorporated by reference as if fully set forth herein, and U.S. application Ser. No. 386,820 filed Jul. 27, 1989 in the name of Mark I. Green entitled "Methods of Treating Cancerous Cells with Anti-Receptor Antibodies", the disclosures of which are hereby incorporated by reference as if fully set forth herein.

Cell lines were all maintained in DMEM medium containing 5% FCS as the culture medium (5% FCS-DMEM) at 37° C. in a humidified atmosphere with 5% $CO_2$.

Dense cultures of cells in 150 mm dishes were washed twice with cold PBS, scraped into 10 ml of freeze-thaw buffer (150 mM NaCl, 1 mM $MgCl_2$, 20 mM Hepes, pH 7.2, 10% Glycerol, 1 mM EDTA, 1% Aprotinin), and centrifuged (600×6, 10 minutes). Cell pellets were resuspended in 1 ml Lysis buffer (50 mM Hepes, pH 7.5, 150 mM NaCl, 3% Brij 35, 1 mM EDTA, 1.5 mM $MgCl_2$, 1% Aprotinin, 1 mM EGTA, 20 μM $Na_3VO_4$, 10% Glycerol) and rotated for thirty minutes at 4° C. All chemicals were from Sigma Chemical Co., St. Louis, Mo., unless otherwise indicated. The insoluble materials were removed by centrifugation at 40,000×g for thirty minutes. The clear supernatant which was subsequently used in designated as cell lysate.

The cell lysates were incubated for fifteen minutes with 50 μl of 50% (volume/volume) Protein A-sepharose (Sigma Chemical Co., St. Louis, Mo.), and centrifugated for two minutes to preclear the lysates. 50 μl aliquots of precleared cell lysate were incubated on ice for fifteen minutes with conditioned medium, proteinaceous substance, or other factors as specified, in a final volume of 1 ml with lysis buffer. The sample was then incubated with 5 μg of 7.16.4 monoclonal antibody, which recognizes the extracellular domain of the p185neu and p185c-neu, or other appropriate antibodies, for twenty minutes on ice, followed by a twenty minute incubation with 50 μl of 50% (vol/vol) protein A-Sepharose with rotation at 4° C. Immune complexes were collected by centrifugation, washed four times with 500 μl of washing buffer (50 mM Hepes, pH 7.5, 0.1%, Brij 35, 150 mM NaCl, 2 mM EDTA, 1% Aprotinin, 30 μm $Na_3VO_4$), then twice with reaction buffer (20 mM Hepes (pH 7.4), 3 mM $MnCl_2$ and 0.1% Brij 35, 30 μm $Na_3VO_4$). Pellets were resuspended in 50 μl of reaction buffer and (Gamma-$^{32}$P]-ATP (Amersham, Arlington Heights, Ill.) was added giving a final concentration of 0.2 μm. The samples were incubated at 27° C. for twenty minutes or at 4° C. for 25 minutes with purer samples. The reactions were terminated by addition of 3× SDS sample buffer containing 2 mM ATP and 2 mM EDTA and then incubating them at 100° C. for five minutes. The samples were then subjected to SDS-PAGE analysis on 10% acrylamide gels. Gels were stained, dried, and exposed to Kodak XAR or XRP film with intensifying screens.

VIII. Purification of Acetylcholine Receptor Inducing Activity (ARIA)

ARIA, a 42 kD protein which stimulates acetylcholine receptor synthesis, has been isolated in the laboratory of Gerald Fischbach (Falls et al., Cell 72:801–815 (1993)). ARIA induces tyrosine phosphorylation of a 185 Kda muscle transmembrane protein which resembles p185$^{erbB2}$, and stimulates acetylcholine receptor synthesis in cultured embryonic myotubes. Sequence analysis of cDNA clones which encode ARIA shows that ARIA is a member of the GGF/erbB2 ligand group of proteins, and this is potentially useful in the glial cell mitogenesis stimulation and other applications of, e.g., GGF2 described herein.

EXAMPLE 14

Protein Tyrosine Phosphorylation Mediated by GGF in Schwann Cells

Figure 36:
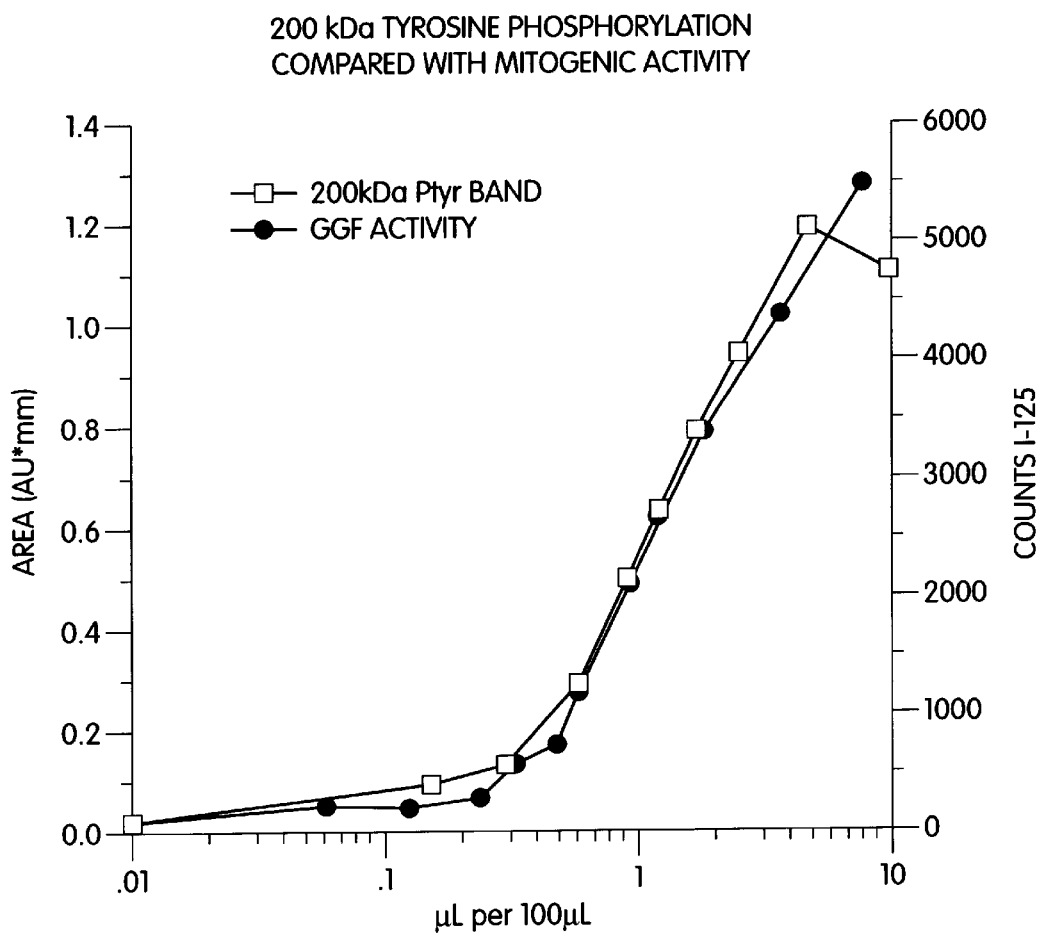
FIG. 36 depicts the level of GGF activity (Schwann cell mitogenic assay) and tyrosine phosphorylation of a ca. 200 kD protein (intensity of a 200 kD band on an autoradiogram of a Western blot developed with an antiphosphotyrosine polyclonal antibody) in response to increasing amounts of GGF.

Rat Schwann cells, following treatment with sufficient levels of Glial Growth Factor to induce proliferation, show stimulation of protein tyrosine phosphorylation (FIG. 36). Varying amounts of partially purified GGF were applied to a primary culture of rat Schwann cells according to the procedure outlined in Example 3. Schwann cells were grown in DMEM/10% fetal calf serum/5 μM forskolin/0.5 μg per mL GGF-CM (0.5 mL per well) in poly D-lysine coated 24 well plates. When confluent, the cells were fed with DMEM/10% fetal calf serum at 0.5 mL per well and left in the incubator overnight to quiesce. The following day, the cells were fed with 0.2 mL of DMEM/10% fetal calf serum and left in the incubator for 1 hour. Test samples were then added directly to the medium at different concentrations and for different lengths of time as required. The cells were then lysed in boiling lysis buffer (sodium phosphate, 5 mM, pH 6.8; SDS, 2%, β-mercapteothanol, 5%; dithiothreitol, 0.1M; glycerol, 10%; Bromophenol Blue, 0.4%; sodium vanadate, 10 mM), incubated in a boiling water bath for 10 minutes and then either analyzed directly or frozen at −70° C. Samples were analyzed by running on 7.5% SDS-PAGE gels and then electroblotting onto nitrocellulose using standard procedures as described by Towbin et al. (1979) Proc. Natl. Acad. Sci. USA 76:4350–4354. The blotted nitrocellulose was probed with antiphosphotyrosine antibodies using standard methods as described in Kamps and Selton (1988) Oncogene 2:305–315. The probed blots were exposed to autoradiography film overnight and developed using a standard laboratory processor. Densitometric measurements were carried out using an Ultrascan XL enhanced laser densitometer (LKB). Molecular weight assignments were made relative to prestained high molecular weight standards (Sigma). The dose responses of protein phosphorylation and Schwann cell proliferation are very similar (FIG. 36). The molecular weight of the phosphorylated band is very close to the molecular weight of p185$^{erbB2}$. Similar results were obtained when Schwann cells were treated with conditioned media prepared from COS cells translates with the GGF2HBS5 clone. These results correlate well with the expected interaction of the GGFs with and activation of 185$^{erbB2}$.

Figure 52:
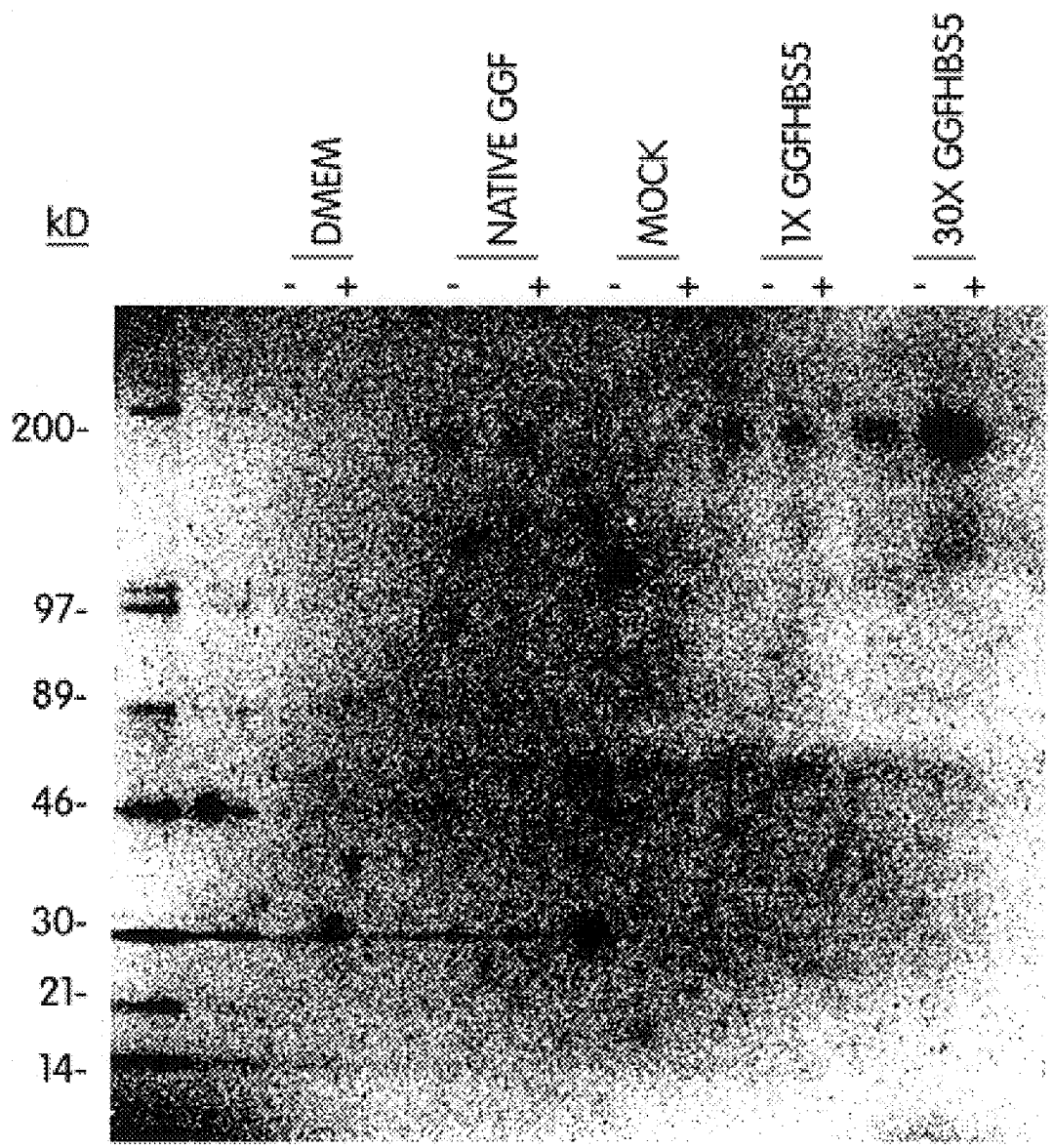
FIG. 52 is a photograph of a gel depicting tyrosine phosphorylation in Schwann cells treated with recombinant glial growth factors.

This experiment has been repeated with recombinant GGF-II. Conditioned medium derived from a CHO cell line stably transformed with the GGF-II clone (GGF2HBS5) stimulates protein tyrosine phosphorylation using the assay described above. Mock transfected CHO cells fail to stimulate this activity (FIG. 52).

EXAMPLE 15

Assay for Schwann Cell Proliferation by Protein Factor from the MDA-MB-321 Cell Line Schwann cell proliferation is mediated by conditioned medium derived from the human breast cancer cell line MDA-MB-231. On day 1 of the assay, 10$^4$ primary rat Schwann cells were plated in 100 μl of Dulbecco's Modified Eagle's medium supplemented with 5% fetal bovine plasma per well in a 96 well microtiter plate. On day 2 of the assay, 10 μl of conditioned medium (from the human breast cancer cell line MDA-MB-231, cultured as described in Example 6) was added to each well of the microtiter plate. One day 6, the number of Schwann cells per plate was determined using an acid phosphatase assay (according to the procedure of Connolly et al. Anal. Biochem. 152: 136 (1986)). The plate was washed with 100 μl of phosphate buffered saline (PBS) and 100 μl of reaction buffer (0.1M sodium acetate, (pH 5.5)), 0.1% Triton X-100, and 10 mM p-nitrophenyl phosphate) was added per well. The plate was incubated at 37° C. for two hours and the reaction was stopped by the addition of 10 μl of 1N NaOH. The optical density of each sample was read in a spectrophotometer at 410 nm. A 38% stimulation of cell number over Schwann cells treated with conditioned medium from a control cell line (HS-294T, a non-producer of erbB-2 ligand) was observed. This result shows that a protein secreted by the MDA-MB-231 cell line (which secretes a p185$^{erbB2}$ binding activity) stimulates Schwann cell proliferation.

EXAMPLE 16

N-glycosylation of GGF

The protein sequence predicted from the cDNA sequence of GGF-II candidate clones GGF2BPP1,2 and 3 contains a number of consensus N-glycosylation motifs. A gap in the GGFII02 peptide sequence coincides with the asparagine residue in one of these motifs, indicating that carbohydrate is probably bound at this site.

N-glycosylation of the GGFs was studied by observing mobility changes on SDS-PAGE after incubation with N-glycanase, an enzyme that cleaves the covalent linkages between carbohydrate and aspargine residues in proteins.

N-Glycanase treatment of GGF-II yielded a major band of MW 40–42 kDa and a minor band at 45–48 kDa. Activity elution experiments under non-reducing conditions showed a single active deglycosylated species at ca 45–50 kDa.

Activity elution experiments with GGF-I also demonstrate an increase in electrophoretic mobility when treated with N-Glycanase, giving an active species of MW 26–28 kDa. Silver staining confirmed that there is a mobility shift, although no N-deglycosylated band could be assigned because of background staining in the sample used.

Deposit

Nucleic acid encoding GGF-II (cDNA, GGF2HBS5) protein (Example 6) in a plasmid pBluescript 5k, under the control of the T7 promoter, was deposited in the American Type Culture Collection, Rockville, Md., on Sep. 2, 1992, and given ATCC Accession No. 75298. Applicant acknowledges its responsibility to replace this plasmid should it become non-viable before the end of the term of a patent issued hereon, and its responsibility to notify the ATCC of the issuance of such a patent, at which time the deposit will be made available to the public. Prior to that time the deposit will be made available to the Commissioner of Patents under the terms of 37 CFR §1.14 and 35 USC §112.

```

What is claimed is:

1. A method of stimulating mitogenic activity in a glial cell, said glial cell being an oligodendrocyte, a microglial cell, or a myelinating glial cell, said method comprising applying 35 kD polypeptide factor isolated from the rat I-EJ transformed fibroblast cell line to said glial cell.

2. A method of stimulating mitogenic activity in a glial cell, said glial cell being an oligodendrocyte, a microglial cell, or a myelinating glial cell, said method comprising applying 75 kD polypeptide factor isolated from the SKR\BR-3 human breast cell line to said glial cell.

3. A method of stimulating mitogenic activity in a glial cell, said glial cell being an oligodendrocyte, a microglial cell, or a myelinating glial cell, said method comprising applying 44 kD polypeptide factor isolated from the rat I-IJ transformed fibroblast cell line to said glial cell.

4. A method of stimulating mitogenic activity in a glial cell, said glial cell being an oligodendrocyte, a microglial cell, or a myelinating glial cell, said method comprising applying 45 kD polypeptide factor isolated from the MDA-MB 231 human breast cell line to said glial cell.

5. A method of stimulating mitogenic activity in a glial cell, said glial cell being an oligodendrocyte, a microglial cell, or a myelinating glial cell, said method comprising applying 7 to 14 kD polypeptide factor isolated from the ATL-2 human T-cell line to said glial cell.

6. A method of stimulating mitogenic activity in a glial cell, said glial cell being an oligodendrocyte, a microglial cell, or a myelinating glial cell, said method comprising applying 25 kD polypeptide factor isolated from activated mouse peritoneal macrophages to said glial cell.

7. A method of stimulating mitogenic activity in a glial cell, said glial cell being an oligodendrocyte, a microglial cell, or a myelinating glial cell, said method comprising applying a 25 kD polypeptide factor isolated from bovine kidney to said glial cell.

8. A method of stimulating mitogenic activity in a glial cell, said method comprising applying ARIA polypeptide to said glial cell.

* * * * *

                            SEQUENCE LISTING

<160> NUMBER OF SEQ ID NOS: 226

<210> SEQ ID NO 1
    <211> LENGTH: 8
    <212> TYPE: PRT
    <213> ORGANISM: Bos taurus

<400> SEQUENCE: 1

Phe Lys Gly Asp Ala His Thr Glu
    1               5

<210> SEQ ID NO 2
    <211> LENGTH: 13
    <212> TYPE: PRT
    <213> ORGANISM: Bos taurus
    <220> FEATURE:
    <221> NAME/KEY: VARIANT
    <222> LOCATION: (1)...(12)
    <223> OTHER INFORMATION: Xaa in position 1 is Lysine or Arginine; Xaa in
          position 12 is unknown

<400> SEQUENCE: 2

Xaa Ala Ser Leu Ala Asp Glu Tyr Glu Tyr Met Xaa Lys
    1               5                   10

<210> SEQ ID NO 3
    <211> LENGTH: 12
    <212> TYPE: PRT
    <213> ORGANISM: Bos taurus
    <220> FEATURE:
    <221> NAME/KEY: VARIANT
    <222> LOCATION: (1)...(10)
    <223> OTHER INFORMATION: Xaa in position 1 is Lysine or Arginine; Xaa in
          position 10 is unknown

<400> SEQUENCE: 3

Xaa Thr Glu Thr Ser Ser Ser Gly Leu Xaa Leu Lys
    1               5                   10
```

```
<210> SEQ ID NO 4
<211> LENGTH: 9
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine.

<400> SEQUENCE: 4

Xaa Lys Leu Gly Glu Met Trp Ala Glu
 1               5

<210> SEQ ID NO 5
<211> LENGTH: 7
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 5

Xaa Leu Gly Glu Lys Arg Ala
 1               5

<210> SEQ ID NO 6
<211> LENGTH: 16
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 6

Xaa Ile Lys Ser Glu His Ala Gly Leu Ser Ile Gly Asp Thr Ala Lys
 1               5                  10                  15

<210> SEQ ID NO 7
<211> LENGTH: 13
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 7

Xaa Ala Ser Leu Ala Asp Glu Tyr Glu Tyr Met Arg Lys
 1               5                  10

<210> SEQ ID NO 8
<211> LENGTH: 16
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 8

Xaa Ile Lys Gly Glu His Pro Gly Leu Ser Ile Gly Asp Val Ala Lys
 1               5                  10                  15

<210> SEQ ID NO 9
<211> LENGTH: 13
<212> TYPE: PRT
```

```
<213> ORGANISM: Bos taurus
<220> FEATURE:
<221> NAME/KEY: VARIANT
<222> LOCATION: (1)...(12)
<223> OTHER INFORMATION: Xaa in position 1 is Lysine or Arginine and
      Xaa in position 12 is unknown

<400> SEQUENCE: 9

Xaa Met Ser Glu Tyr Ala Phe Phe Val Gln Thr Xaa Arg
  1               5                  10

<210> SEQ ID NO 10
<211> LENGTH: 14
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 10

Xaa Ser Glu His Pro Gly Leu Ser Ile Gly Asp Thr Ala Lys
  1               5                  10

<210> SEQ ID NO 11
<211> LENGTH: 10
<212> TYPE: PRT
<213> ORGANISM: Bos taurus
<220> FEATURE:
<221> NAME/KEY: VARIANT
<222> LOCATION: (1)...(8)
<223> OTHER INFORMATION: Xaa in position 1 is Lysine or Arginine; Xaa in
      position 8 is unknown

<400> SEQUENCE: 11

Xaa Ala Gly Tyr Phe Ala Glu Xaa Ala Arg
  1               5                  10

<210> SEQ ID NO 12
<211> LENGTH: 9
<212> TYPE: PRT
<213> ORGANISM: Bos taurus
<220> FEATURE:
<221> NAME/KEY: VARIANT
<222> LOCATION: (1)...(7)
<223> OTHER INFORMATION: Xaa in position 1 is Lysine or Arginine; Xaa in
      position 7 is unknown

<400> SEQUENCE: 12

Xaa Lys Leu Glu Phe Leu Xaa Ala Lys
  1               5

<210> SEQ ID NO 13
<211> LENGTH: 11
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 13

Xaa Thr Thr Glu Met Ala Ser Glu Gln Gly Ala
  1               5                  10

<210> SEQ ID NO 14
<211> LENGTH: 10
<212> TYPE: PRT
<213> ORGANISM: Bos taurus
```

```
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 14

Xaa Ala Lys Glu Ala Leu Ala Ala Leu Lys
 1               5                  10

<210> SEQ ID NO 15
<211> LENGTH: 8
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 15

Xaa Phe Val Leu Gln Ala Lys Lys
 1               5

<210> SEQ ID NO 16
<211> LENGTH: 6
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 16

Xaa Leu Gly Glu Met Trp
 1               5

<210> SEQ ID NO 17
<211> LENGTH: 16
<212> TYPE: PRT
<213> ORGANISM: Bos taurus

<400> SEQUENCE: 17

Glu Tyr Lys Cys Leu Lys Phe Lys Trp Phe Lys Lys Ala Thr Val Met
 1               5                  10                  15

<210> SEQ ID NO 18
<211> LENGTH: 10
<212> TYPE: PRT
<213> ORGANISM: Bos taurus
<220> FEATURE:
<221> NAME/KEY: VARIANT
<222> LOCATION: (8)...(8)
<223> OTHER INFORMATION: Xaa in position 8 is unknown

<400> SEQUENCE: 18

Glu Ala Lys Tyr Phe Ser Lys Xaa Asp Ala
 1               5                  10

<210> SEQ ID NO 19
<211> LENGTH: 7
<212> TYPE: PRT
<213> ORGANISM: Bos taurus
<220> FEATURE:
<221> NAME/KEY: VARIANT
<222> LOCATION: (2)...(2)
<223> OTHER INFORMATION: Xaa in position 2 is unknown

<400> SEQUENCE: 19

Glu Xaa Lys Phe Tyr Val Pro
 1               5
```

-continued

<210> SEQ ID NO 20
<211> LENGTH: 26
<212> TYPE: PRT
<213> ORGANISM: Bos taurus

<400> SEQUENCE: 20

Glu Leu Ser Phe Ala Ser Val Arg Leu Pro Gly Cys Pro Pro Gly Val
 1               5                  10                  15

Asp Pro Met Val Ser Phe Pro Val Ala Leu
            20                  25

<210> SEQ ID NO 21
<211> LENGTH: 2003
<212> TYPE: DNA
<213> ORGANISM: Homo sapiens
<220> FEATURE:
<221> NAME/KEY: variation
<222> LOCATION: (31)...(32)
<223> OTHER INFORMATION: N in positions 31 and 32 could be either A or G.
<220> FEATURE:
<221> NAME/KEY: CDS
<222> LOCATION: (265)...(1530)

<400> SEQUENCE: 21

```
ggaattcctt tttttttttt tttttttctt nntttttttt tgcccttata cctcttcgcc    60
tttctgtggt tccatccact tcttcccct  cctcctccca taaacaactc tcctacccct   120
gcaccccaa  taaataaata aaaggaggag ggcaaggggg gaggaggagg agtggtgctg   180
cgagggaag  gaaaagggag gcagcgcgag aagagccggg cagagtccga accgacagcc   240
agaagcccgc acgcacctcg cacc atg aga tgg cga cgc gcc ccg cgc cgc       291
                          Met Arg Trp Arg Arg Ala Pro Arg Arg
                           1               5
tcc ggg cgt ccc ggc ccc cgg gcc cag cgc ccc ggc tcc gcc gcc cgc      339
Ser Gly Arg Pro Gly Pro Arg Ala Gln Arg Pro Gly Ser Ala Ala Arg
 10              15                  20                  25
tcg tcg ccg ccg ctg ccg ctg ctg cca cta ctg ctg ctg ggg acc          387
Ser Ser Pro Pro Leu Pro Leu Leu Pro Leu Leu Leu Leu Gly Thr
                 30                  35                  40
gcg gcc ctg gcg ccg ggg gcg gcg gcc aac gag gcg gct ccc gcg          435
Ala Ala Leu Ala Pro Gly Ala Ala Ala Gly Asn Glu Ala Ala Pro Ala
             45                  50                  55
ggg gcc tcg gtg tgc tac tcg tcc ccg ccc agc gtg gga tcg gtg cag      483
Gly Ala Ser Val Cys Tyr Ser Ser Pro Pro Ser Val Gly Ser Val Gln
         60                  65                  70
gag cta gct cag cgc gcc gcg gtg gtc atc gag gga aag gtg cac ccg      531
Glu Leu Ala Gln Arg Ala Ala Val Val Ile Glu Gly Lys Val His Pro
 75                  80                  85
cag cgg cgg cag cag ggg gca ctc gac agg aag gcg gcg gcg gcg gcg      579
Gln Arg Arg Gln Gln Gly Ala Leu Asp Arg Lys Ala Ala Ala Ala Ala
         90                  95                 100                 105
ggc gag gca ggg gcg tgg ggc ggc gat cgc gag ccg cca gcc gcg ggc      627
Gly Glu Ala Gly Ala Trp Gly Gly Asp Arg Glu Pro Pro Ala Ala Gly
                 110                 115                 120
cca cgg gcg ctg ggg ccg ccc gcc gag gag ccg ctc ctc gcc gcc aac      675
Pro Arg Ala Leu Gly Pro Pro Ala Glu Glu Pro Leu Leu Ala Ala Asn
             125                 130                 135
ggg acc gtg ccc tct tgg ccc acc gcc ccg gtg ccc agc gcc ggc gag      723
Gly Thr Val Pro Ser Trp Pro Thr Ala Pro Val Pro Ser Ala Gly Glu
         140                 145                 150
ccc ggg gag gag gcg ccc tat ctg gtg aag gtg cac cag gtg tgg gcg      771
Pro Gly Glu Glu Ala Pro Tyr Leu Val Lys Val His Gln Val Trp Ala
 155                 160                 165
gtg aaa gcc ggg ggc ttg aag aag gac tcg ctg ctc acc gtg cgc ctg      819
Val Lys Ala Gly Gly Leu Lys Lys Asp Ser Leu Leu Thr Val Arg Leu
170                  175                 180                 185
ggg acc tgg ggc cac ccc gcc ttc ccc tcc tgc ggg agg ctc aag gag      867
Gly Thr Trp Gly His Pro Ala Phe Pro Ser Cys Gly Arg Leu Lys Glu
                 190                 195                 200
gac agc agg tac atc ttc ttc atg gag ccc gac gcc aac agc acc agc      915
Asp Ser Arg Tyr Ile Phe Phe Met Glu Pro Asp Ala Asn Ser Thr Ser
             205                 210                 215
cgc gcg ccg gcc gcc ttc cga gcc tct ttc ccc cct ctg gag acg ggc      963
Arg Ala Pro Ala Ala Phe Arg Ala Ser Phe Pro Pro Leu Glu Thr Gly
```

```
                                220                   225                   230
cgg aac ctc aag aag gag gtc agc cgg gtg ctg tgc aag cgg tgc gcc          1011
Arg Asn Leu Lys Lys Glu Val Ser Arg Val Leu Cys Lys Arg Cys Ala
    235                   240                   245
ttg cct ccc caa ttg aaa gag atg aaa agc cag gaa tcg gct gca ggt          1059
Leu Pro Pro Gln Leu Lys Glu Met Lys Ser Gln Glu Ser Ala Ala Gly
250                   255                   260                   265
tcc aaa cta gtc ctt cgg tgt gaa acc agt tct gaa tac tcc tct ctc          1107
Ser Lys Leu Val Leu Arg Cys Glu Thr Ser Ser Glu Tyr Ser Ser Leu
                270                   275                   280
aga ttc aag tgg ttc aag aat ggg aat gaa ttg aat cga aaa aac aaa          1155
Arg Phe Lys Trp Phe Lys Asn Gly Asn Glu Leu Asn Arg Lys Asn Lys
            285                   290                   295
cca caa aat atc aag ata caa aaa aag cca ggg aag tca gaa ctt cgc          1203
Pro Gln Asn Ile Lys Ile Gln Lys Lys Pro Gly Lys Ser Glu Leu Arg
        300                   305                   310
att aac aaa gca tca ctg gct gat tct gga gag tat atg tgc aaa gtg          1251
Ile Asn Lys Ala Ser Leu Ala Asp Ser Gly Glu Tyr Met Cys Lys Val
    315                   320                   325
atc agc aaa tta gga aat gac agt gcc tct gcc aat atc acc atc gtg          1299
Ile Ser Lys Leu Gly Asn Asp Ser Ala Ser Ala Asn Ile Thr Ile Val
330                   335                   340                   345
gaa tca aac gct aca tct aca tcc acc act ggg aca agc cat ctt gta          1347
Glu Ser Asn Ala Thr Ser Thr Ser Thr Thr Gly Thr Ser His Leu Val
                350                   355                   360
aaa tgt gcg gag aag gag aaa act ttc tgt gtg aat gga ggg gag tgc          1395
Lys Cys Ala Glu Lys Glu Lys Thr Phe Cys Val Asn Gly Gly Glu Cys
            365                   370                   375
ttc atg gtg aaa gac ctt tca aac ccc tcg aga tac ttg tgc aag tgc          1443
Phe Met Val Lys Asp Leu Ser Asn Pro Ser Arg Tyr Leu Cys Lys Cys
        380                   385                   390
cca aat gag ttt act ggt gat cgc tgc caa aac tac gta atg gcc agc          1491
Pro Asn Glu Phe Thr Gly Asp Arg Cys Gln Asn Tyr Val Met Ala Ser
    395                   400                   405
ttc tac agt acg tcc act ccc ttt ctg tct ctg cct gaa taggagcatg           1540
Phe Tyr Ser Thr Ser Thr Pro Phe Leu Ser Leu Pro Glu
410                   415                   420
ctcagttggt gctgctttct tgttgctgca tctcccctca gattccacct agagctagat       1600
gtgtcttacc agatctaata ttgactgcct ctgcctgtcg catgagaaca ttaacaaaag       1660
caattgtatt acttcctctg ttcgcgacta gttggctctg agatactaat aggtgtgtga       1720
ggctccggat gtttctggaa ttgatattga atgatgtgat acaaattgat agtcaatatc       1780
aagcagtgaa atatgataat aaaggcattt caaagtctca cttttattga taaaataaaa       1840
atcattctac tgaacagtcc atcttcttta tacaatgacc acatcctgaa aagggtgttg       1900
ctaagctgta accgatatgc acttgaaatg atggtaagtt aattttgatt cagaatgtgt       1960
tatttgtcac aaataaacat aataaaagga aaaaaaaaa aaa                          2003

<210> SEQ ID NO 22
<211> LENGTH: 12
<212> TYPE: PRT
<213> ORGANISM: Bos taurus
<220> FEATURE:
<221> NAME/KEY: VARIANT
<222> LOCATION: (11)...(11)
<223> OTHER INFORMATION: Xaa in position 11 is unknown

<400> SEQUENCE: 22

Ala Ser Leu Ala Asp Glu Tyr Glu Tyr Met Xaa Lys
1               5                   10

<210> SEQ ID NO 23
<211> LENGTH: 11
<212> TYPE: PRT
<213> ORGANISM: Bos taurus
<220> FEATURE:
<221> NAME/KEY: VARIANT
<222> LOCATION: (9)...(9)
<223> OTHER INFORMATION: Xaa in position 9 is unknown

<400> SEQUENCE: 23

Thr Glu Thr Ser Ser Ser Gly Leu Xaa Leu Lys
1               5                   10

<210> SEQ ID NO 24
<211> LENGTH: 12
```

```
<212> TYPE: PRT
<213> ORGANISM: Bos taurus

<400> SEQUENCE: 24

Ala Ser Leu Ala Asp Glu Tyr Glu Tyr Met Arg Lys
 1               5                  10

<210> SEQ ID NO 25
<211> LENGTH: 9
<212> TYPE: PRT
<213> ORGANISM: Bos taurus
<220> FEATURE:
<221> NAME/KEY: VARIANT
<222> LOCATION: (7)...(7)
<223> OTHER INFORMATION: Xaa in position 7 is unknown

<400> SEQUENCE: 25

Ala Gly Tyr Phe Ala Glu Xaa Ala Arg
 1               5

<210> SEQ ID NO 26
<211> LENGTH: 10
<212> TYPE: PRT
<213> ORGANISM: Bos taurus

<400> SEQUENCE: 26

Thr Thr Glu Met Ala Ser Glu Gln Gly Ala
 1               5                  10

<210> SEQ ID NO 27
<211> LENGTH: 9
<212> TYPE: PRT
<213> ORGANISM: Bos taurus

<400> SEQUENCE: 27

Ala Lys Glu Ala Leu Ala Ala Leu Lys
 1               5

<210> SEQ ID NO 28
<211> LENGTH: 7
<212> TYPE: PRT
<213> ORGANISM: Bos taurus

<400> SEQUENCE: 28

Phe Val Leu Gln Ala Lys Lys
 1               5

<210> SEQ ID NO 29
<211> LENGTH: 21
<212> TYPE: PRT
<213> ORGANISM: Bos taurus

<400> SEQUENCE: 29

Glu Thr Gln Pro Asp Pro Gly Gln Ile Leu Lys Lys Val Pro Met Val
 1               5                  10                  15
Ile Gly Ala Tyr Thr
                20

<210> SEQ ID NO 30
<211> LENGTH: 21
<212> TYPE: PRT
<213> ORGANISM: Homo sapiens
<220> FEATURE:
<221> NAME/KEY: VARIANT
<222> LOCATION: (1)...(19)
<223> OTHER INFORMATION: Xaa in positions 1, 3, 17 and 19 is unknown
```

```
<400> SEQUENCE: 30

Xaa Glu Xaa Lys Glu Gly Arg Gly Lys Gly Lys Gly Lys Lys Lys Glu
1               5                  10                  15
Xaa Gly Xaa Gly Lys
            20

<210> SEQ ID NO 31
<211> LENGTH: 13
<212> TYPE: PRT
<213> ORGANISM: Homo sapiens

<400> SEQUENCE: 31

Ala Glu Lys Glu Lys Thr Phe Cys Val Asn Gly Gly Glu
1               5                  10

<210> SEQ ID NO 32
<211> LENGTH: 8
<212> TYPE: PRT
<213> ORGANISM: Bos taurus
<220> FEATURE:
<221> NAME/KEY: VARIANT
<222> LOCATION: (6)...(6)
<223> OTHER INFORMATION: Xaa in position 6 is unknown

<400> SEQUENCE: 32

Lys Leu Glu Phe Leu Xaa Ala Lys
1               5

<210> SEQ ID NO 33
<211> LENGTH: 9
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 33

Xaa Val His Gln Val Trp Ala Ala Lys
1               5

<210> SEQ ID NO 34
<211> LENGTH: 14
<212> TYPE: PRT
<213> ORGANISM: Bos taurus
<220> FEATURE:
<221> NAME/KEY: VARIANT
<222> LOCATION: (1)...(11)
<223> OTHER INFORMATION: Xaa in position 1 is Lysine or
      Arginine; Xaa in position 11 is unknown.

<400> SEQUENCE: 34

Xaa Tyr Ile Phe Phe Met Glu Pro Glu Ala Xaa Ser Ser Gly
1               5                  10

<210> SEQ ID NO 35
<211> LENGTH: 14
<212> TYPE: PRT
<213> ORGANISM: Bos taurus
<220> FEATURE:
<221> NAME/KEY: VARIANT
<222> LOCATION: (1)...(13)
<223> OTHER INFORMATION: Xaa in position 1 is Lysine or Arginine; Xaa in
      position 13 is unknown.

<400> SEQUENCE: 35

Xaa Leu Gly Ala Trp Gly Pro Pro Ala Phe Pro Val Xaa Tyr
1               5                  10
```

```
<210> SEQ ID NO 36
<211> LENGTH: 9
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine.

<400> SEQUENCE: 36

Xaa Trp Phe Val Val Ile Glu Gly Lys
 1               5

<210> SEQ ID NO 37
<211> LENGTH: 16
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 37

Xaa Ala Ser Pro Val Ser Val Gly Ser Val Gln Glu Leu Val Gln Arg
 1               5                  10                  15

<210> SEQ ID NO 38
<211> LENGTH: 13
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lysine or Arginine

<400> SEQUENCE: 38

Xaa Val Cys Leu Leu Thr Val Ala Ala Leu Pro Pro Thr
 1               5                  10

<210> SEQ ID NO 39
<211> LENGTH: 7
<212> TYPE: PRT
<213> ORGANISM: Bos taurus
<220> FEATURE:
<221> NAME/KEY: VARIANT
<222> LOCATION: (1)...(6)
<223> OTHER INFORMATION: Xaa in position 1 is Lysine or Arginine; Xaa in
      position 6 is unknown

<400> SEQUENCE: 39

Xaa Asp Leu Leu Leu Xaa Val
 1               5

<210> SEQ ID NO 40
<211> LENGTH: 23
<212> TYPE: DNA
<213> ORGANISM: Bos taurus

<400> SEQUENCE: 40
cagaaggtct tctccttctc agc                                              23

<210> SEQ ID NO 41
<211> LENGTH: 24
<212> TYPE: DNA
<213> ORGANISM: Bos taurus

<400> SEQUENCE: 41
```

```
cctcgctcct tcttcttgcc cttc                                         24
```

<210> SEQ ID NO 42
<211> LENGTH: 4
<212> TYPE: PRT
<213> ORGANISM: Bos taurus

<400> SEQUENCE: 42

Leu Val Leu Arg
 1

<210> SEQ ID NO 43
<211> LENGTH: 36
<212> TYPE: DNA
<213> ORGANISM: Bos taurus

<400> SEQUENCE: 43

```
agtacgtcca ctccctttct gtctctgcct gaatag                            36
```

<210> SEQ ID NO 44
<211> LENGTH: 569
<212> TYPE: DNA
<213> ORGANISM: Homo sapiens
<220> FEATURE:
<221> NAME/KEY: CDS
<222> LOCATION: (1)...(569)

<400> SEQUENCE: 44

```
aag gcg gag gag ctg tac cag aag aga gtg ctg acc ata acc ggc atc      48
Lys Ala Glu Glu Leu Tyr Gln Lys Arg Val Leu Thr Ile Thr Gly Ile
  1               5                  10                  15
tgc atc gcc ctc ctt gtg gtc ggc atc atg tgt gtg gtg gcc tac tgc      96
Cys Ile Ala Leu Leu Val Val Gly Ile Met Cys Val Val Ala Tyr Cys
             20                  25                  30
aaa acc aag aaa cag cgg aaa aag ctg cat gac cgt ctt cgg cag agc     144
Lys Thr Lys Lys Gln Arg Lys Lys Leu His Asp Arg Leu Arg Gln Ser
         35                  40                  45
ctt cgg tct gaa cga aac aat atg atg aac att gcc aat ggg cct cac     192
Leu Arg Ser Glu Arg Asn Asn Met Met Asn Ile Ala Asn Gly Pro His
     50                  55                  60
cat cct aac cca ccc ccc gag aat gtc cag ctg gtg aat caa tac gta     240
His Pro Asn Pro Pro Pro Glu Asn Val Gln Leu Val Asn Gln Tyr Val
 65                  70                  75                  80
tct aaa aac gtc atc tcc agt gag cat att gtt gag aga gaa gca gag     288
Ser Lys Asn Val Ile Ser Ser Glu His Ile Val Glu Arg Glu Ala Glu
                 85                  90                  95
aca tcc ttt tcc acc agt cac tat act tcc aca gcc cat cac tcc act     336
Thr Ser Phe Ser Thr Ser His Tyr Thr Ser Thr Ala His His Ser Thr
            100                 105                 110
act gtc acc cag act cct agc cac agc tgg agc aac ggc cac act gaa     384
Thr Val Thr Gln Thr Pro Ser His Ser Trp Ser Asn Gly His Thr Glu
        115                 120                 125
agc atc ctt tcc gaa agc cac tct gta atc gtg atg tca tcc gta gaa     432
Ser Ile Leu Ser Glu Ser His Ser Val Ile Val Met Ser Ser Val Glu
    130                 135                 140
aac agt agg cac agc agc cca act ggg ggc cca aga gga cgt ctt aat     480
Asn Ser Arg His Ser Ser Pro Thr Gly Gly Pro Arg Gly Arg Leu Asn
145                 150                 155                 160
ggc aca gga ggc cct cgt gaa tgt aac agc ttc ctc agg cat gcc aga     528
Gly Thr Gly Gly Pro Arg Glu Cys Asn Ser Phe Leu Arg His Ala Arg
                165                 170                 175
gaa acc cct gat tcc tac cga gac tct cct cat agt gaa ag              569
Glu Thr Pro Asp Ser Tyr Arg Asp Ser Pro His Ser Glu
            180                 185
```

<210> SEQ ID NO 45
<211> LENGTH: 8
<212> TYPE: PRT
<213> ORGANISM: Bos taurus

<400> SEQUENCE: 45

Val His Gln Val Trp Ala Ala Lys
1               5

<210> SEQ ID NO 46
<211> LENGTH: 13
<212> TYPE: PRT
<213> ORGANISM: Bos taurus
<220> FEATURE:
<221> NAME/KEY: VARIANT
<222> LOCATION: (10)...(10)
<223> OTHER INFORMATION: Xaa in position 10 is unknown

<400> SEQUENCE: 46

Tyr Ile Phe Phe Met Glu Pro Glu Ala Xaa Ser Ser Gly
1               5                   10

<210> SEQ ID NO 47
<211> LENGTH: 13
<212> TYPE: PRT
<213> ORGANISM: Bos taurus
<220> FEATURE:
<221> NAME/KEY: VARIANT
<222> LOCATION: (12)...(12)
<223> OTHER INFORMATION: Xaa in position 12 is unknown

<400> SEQUENCE: 47

Leu Gly Ala Trp Gly Pro Pro Ala Phe Pro Val Xaa Tyr
1               5                   10

<210> SEQ ID NO 48
<211> LENGTH: 8
<212> TYPE: PRT
<213> ORGANISM: Bos taurus

<400> SEQUENCE: 48

Trp Phe Val Val Ile Glu Gly Lys
1               5

<210> SEQ ID NO 49
<211> LENGTH: 15
<212> TYPE: PRT
<213> ORGANISM: Bos taurus

<400> SEQUENCE: 49

Ala Ser Pro Val Ser Val Gly Ser Val Gln Glu Leu Val Gln Arg
1               5                   10                  15

<210> SEQ ID NO 50
<211> LENGTH: 12
<212> TYPE: PRT
<213> ORGANISM: Bos taurus

<400> SEQUENCE: 50

Val Cys Leu Leu Thr Val Ala Ala Leu Pro Pro Thr
1               5                   10

<210> SEQ ID NO 51
<211> LENGTH: 9
<212> TYPE: PRT
<213> ORGANISM: Bos taurus

<400> SEQUENCE: 51

Lys Val His Gln Val Trp Ala Ala Lys
1               5

```
<210> SEQ ID NO 52
<211> LENGTH: 13
<212> TYPE: PRT
<213> ORGANISM: Bos taurus
<220> FEATURE:
<221> NAME/KEY: VARIANT
<222> LOCATION: (12)...(12)
<223> OTHER INFORMATION: Xaa in position 12 is unknown

<400> SEQUENCE: 52

Lys Ala Ser Leu Ala Asp Ser Gly Glu Tyr Met Xaa Lys
       1               5                  10

<210> SEQ ID NO 53
<211> LENGTH: 6
<212> TYPE: PRT
<213> ORGANISM: Bos taurus
<220> FEATURE:
<221> NAME/KEY: VARIANT
<222> LOCATION: (5)...(5)
<223> OTHER INFORMATION: Xaa in position 5 is unknown

<400> SEQUENCE: 53

Asp Leu Leu Leu Xaa Val
       1               5

<210> SEQ ID NO 54
<211> LENGTH: 20
<212> TYPE: DNA
<213> ORGANISM: Bos taurus
<220> FEATURE:
<221> NAME/KEY: variation
<222> LOCATION: (1)...(18)
<223> OTHER INFORMATION: N at positions 3, 12 and 18 is C or T; N at
      position 6 is A or G; N at positions 9 and 15 is
      A, T,  G or C.

<400> SEQUENCE: 54
ttnaanggng angcncanac                                          20

<210> SEQ ID NO 55
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at positions 7 and 13 is C or T; N at positions
      4, 10, and 16 is A or G; N at position 19 is A, T,
      G or C.

<400> SEQUENCE: 55
catntantcn tantcntcng c                                        21

<210> SEQ ID NO 56
<211> LENGTH: 20
<212> TYPE: DNA
<213> ORGANISM: Bos taurus
<220> FEATURE:
<221> NAME/KEY: variation
<222> LOCATION: (3)...(18)
<223> OTHER INFORMATION: N at positions 3 and 15 is C or T;  N at positions
      6, 9, and 18 is A, T, G or C

<400> SEQUENCE: 56
tgntcngang ccatntcngt                                          20

<210> SEQ ID NO 57
<211> LENGTH: 20
```

```
<212> TYPE: DNA
<213> ORGANISM: Bos taurus
<220> FEATURE:
<221> NAME/KEY: variation
<222> LOCATION: (3)...(17)
<223> OTHER INFORMATION: N at positions 3 and 15 is C or T; N at position 6
      is A or G; N at positions 9 and 18 is A, T, G or
      C.

<400> SEQUENCE: 57
tgntcnctng ccatntcngt                                              20

<210> SEQ ID NO 58
<211> LENGTH: 20
<212> TYPE: DNA
<213> ORGANISM: Bos taurus
<220> FEATURE:
<221> NAME/KEY: variation
<222> LOCATION: (3)...(18)
<223> OTHER INFORMATION: N at position 3 is A, G or T; N at position 18 is
      C or T; N at positions 6, 12, and 15 is A, T, G or
      C.

<400> SEQUENCE: 58
ccnatnacca tnggnacntt                                              20

<210> SEQ ID NO 59
<211> LENGTH: 20
<212> TYPE: DNA
<213> ORGANISM: Bos taurus
<220> FEATURE:
<221> NAME/KEY: variation
<222> LOCATION: (3)...(18)
<223> OTHER INFORMATION: N at position 12 is C or T; N at position 15 is A
      or G; N at positions 3, 9 and 18 is A, T, G or C.

<400> SEQUENCE: 59
gcngcccana cytgrtgnac                                              20

<210> SEQ ID NO 60
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 3 and 9 is C or T; N at positions 5
      and 8 is A or G; N at position 6 is A, T, G or C;
      N at positions 15 and 18 is A or G.

<400> SEQUENCE: 60
gcntcnggnt ccatnaanaa                                              20

<210> SEQ ID NO 61
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at position 6 is A, G or T;  N at position 3 is
      C or T; N at position 15 is A or G; N at positions
      9 and 12 is A, T, G or C.

<400> SEQUENCE: 61
ccntcnatna cnacnaacca                                              20

<210> SEQ ID NO 62
<211> LENGTH: 17
```

```
<212> TYPE: DNA
<213> ORGANISM: Bos taurus
<220> FEATURE:
<221> NAME/KEY: variation
<222> LOCATION: (1)...(17)
<223> OTHER INFORMATION: N at positions 6 and 9 is A or G; N at positions
      3, 12 and 15 is A, T, G or C.

<400> SEQUENCE: 62
tcngcnaant anccngc                                              17

<210> SEQ ID NO 63
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 12 and 15 is C or T;  N at
      positions 3, 6, 9 and 18 is A, T, G or C

<400> SEQUENCE: 63
gcngcnagng cntcnttngc                                           20

<210> SEQ ID NO 64
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 6, 12 and 15 is C or T; N at
      positions 3, 9, and 18 is A, T, G or C.

<400> SEQUENCE: 64
gcngcnaang cntcnttngc                                           20

<210> SEQ ID NO 65
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 3 and 9 is C or T; N at position 18
      is A or G; N at positions 6, 12 and 15 is A, T, G
      or C.

<400> SEQUENCE: 65
ttnttngcnt gnagnacnaa                                           20

<210> SEQ ID NO 66
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 3, 9 and 12 is C or T; N at
      position 18 is A or G; N at positions 6 and 15 is
      A, T, G or C.

<400> SEQUENCE: 66
ttnttngcnt gnaanacnaa                                           20

<210> SEQ ID NO 67
<211> LENGTH: 17
<212> TYPE: DNA
<213> ORGANISM: Bos taurus
```

```
<220> FEATURE:
<221> NAME/KEY: variation
<222> LOCATION: (1)...(17)
<223> OTHER INFORMATION: N at positions 9 and 12 is C or T; N at positions
      3, 6 and 15 is A, T, G or C.

<400> SEQUENCE: 67
tgnacnagnt cntgnac                                                    17

<210> SEQ ID NO 68
<211> LENGTH: 17
<212> TYPE: DNA
<213> ORGANISM: Bos taurus
<220> FEATURE:
<221> NAME/KEY: variation
<222> LOCATION: (1)...(17)
<223> OTHER INFORMATION: N at positions 6, 9, and 12 is C or T; N at
      positions 3 and 15 is A, T, G or C.

<400> SEQUENCE: 68
tgnacnaant cntgnac                                                    17

<210> SEQ ID NO 69
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at position 7 is C or T; N at positions 4 and 16
      is A or G; N at positions 10, 13 and 19 is A,
      T, G or C.

<400> SEQUENCE: 69
catntantcn ccngantcng c                                               21

<210> SEQ ID NO 70
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at position 7 is C or T; N at positions 4, 13
      and 16 is A or G; N at positions 10 and 19 is A,
      T, G or C.

<400> SEQUENCE: 70
catntantcn ccnctntcng c                                               21

<210> SEQ ID NO 71
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at positions 10 and 19 is C or T; N at position
      4 is A or G; N at positions 1, 7, 13 and 16 is A,
      T, G or C.

<400> SEQUENCE: 71
ngantcngcn aangangcnt t                                               21

<210> SEQ ID NO 72
<211> LENGTH: 21
<212> TYPE: DNA
<213> ORGANISM: Bos taurus
<220> FEATURE:
```

```
<221> NAME/KEY: variation
<222> LOCATION: (1)...(21)
<223> OTHER INFORMATION: N at position 19 is C or T; N at position 4 is A
      or G; N at positions 1, 7, 10, 13 and 16 is A, T,
      G or C.

<400> SEQUENCE: 72
ngantcngcn agngangcnt t                                            21

<210> SEQ ID NO 73
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at positions 10 and 19 is C or T; N at positions
      1 and 4 is A or G; N at positions 7, 13 and 16 is
      A, T, G or C.

<400> SEQUENCE: 73
nctntcngcn aangangcnt t                                            21

<210> SEQ ID NO 74
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at position 19 is C or T; N at positions 1 and 4
      is A or G; N at positions 7, 10, 13 and 16 is A,
      T, G or C.

<400> SEQUENCE: 74
nctntcngcn agngangcnt t                                            21

<210> SEQ ID NO 75
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at positions 10 and 19 is C or T; N at positions
      4 and 13 is A or G; N at positions 1, 7 and 16 is
      A, T, G or C.

<400> SEQUENCE: 75
ngantcngcn aanctngcnt t                                            21

<210> SEQ ID NO 76
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at position 19 is C or T; N at positions 4 and
      13 is A or G; N at positions 1, 7, 10 and 16 is A,
      T, G or C.

<400> SEQUENCE: 76
ngantcngcn agnctngcnt t                                            21

<210> SEQ ID NO 77
<211> LENGTH: 730
<212> TYPE: DNA
<213> ORGANISM: Homo sapiens
```

<400> SEQUENCE: 77

```
gtatgtgtca gccatgacca ccccggctcg tatgtcacct gtagatttcc acacgccaag    60
ctcccccaaa tcgccccctt cggaaatgtc tccacccgtg tccagcatga cggtgtccat   120
gccttccatg gcggtcagcc ccttcatgga agaagagaga cctctacttc tcgtgacacc   180
accaaggctg cgggagaaga agtttgacca tcaccctcag cagttcagct ccttccacca   240
caaccccgcg catgacagta acagcctccc tgctagcccc ttgaggatag tggaggatga   300
ggagtatgaa acgacccaag agtacgagcc agcccaagag cctgttaaga aactcgccaa   360
tagccggcgg gccaaaagaa ccaagcccaa tggccacatt gctaacagat tggaagtgga   420
cagcaacaca agctcccaga gcagtaactc agagagtgaa acagaagatg aaagagtagg   480
tgaagatacg cctttcctgg gcatacagaa cccctggca gccagtcttg aggcaacacc   540
tgccttccgc ctggctgaca gcaggactaa cccagcaggc cgcttctcga cacaggaaga   600
aatccaggcc aggctgtcta gtgtaattgc taaccaagac cctattgctg tataaaacct   660
aaataaacac atagattcac ctgtaaaact ttattttata taataaagta ttccaccttc   720
aattaaacaa                                                           730
```

<210> SEQ ID NO 78
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at positions 10 and 19 is C or T; N at positions
     1, 4 and 13 is A or G; N at positions 7 and 16 is
     A, T, G or C.

<400> SEQUENCE: 78

```
nctntcngcn aanctngcnt t                                               21
```

<210> SEQ ID NO 79
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at position 19 is C or T; N at positions 1, 4
     and 13 is A or G; N at positions 7, 10 and 16 is
     A, T, G or C.

<400> SEQUENCE: 79

```
nctnctngcn agnctngcnt t                                               21
```

<210> SEQ ID NO 80
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at position 9 is A or G; N at positions 3, 6, 17
     and 18 is A, T, G or C.

<400> SEQUENCE: 80

```
acnacngana tggctcnnga                                                 20
```

<210> SEQ ID NO 81
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at position 16 is C or T; N at position 9 is A
     or G; N at positions 3, 6, 17 and 18 is A, T, G or
     C.

<400> SEQUENCE: 81

```
acnacngana tggcagnnga                                                 20
```

<210> SEQ ID NO 82
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at position 3 is C or T; N at position 6 is A or
      G; N at positions 9, 15 and 18 is A, T, G or C.

<400> SEQUENCE: 82
cancangtnt gggcngcnaa                                              20

<210> SEQ ID NO 83
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at position 3 is C or T; N at position 15 is A
      or G; N at positions 5, 9 and 18 is A, T, G or C;
      N at position 12 is A, C or T.

<400> SEQUENCE: 83
ttngtngtna tnganggnaa                                              20

<210> SEQ ID NO 84
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 9 and 15 is C or T; N at position 3
      is A or G; N at positions 6, 12 and 18 is A, T, G
      or C.

<400> SEQUENCE: 84 aangngang cncanacnga                                               20

<210> SEQ ID NO 85
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 7 and 16 is C or T; N at position 3
      is A or G; N at positions 6, 9, 12, 15 and 18 is
      A, T, G or C.

<400> SEQUENCE: 85
gangcnntng cngcnntnaa                                              20

<210> SEQ ID NO 86
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at position 19 is C or T; N at positions 15 and
      18 is A or G; N at positions 3, 6, 9 and 12 is A,
      T, G or C.

<400> SEQUENCE: 86
gtnggntcng tncangannt                                              20

<210> SEQ ID NO 87
<211> LENGTH: 20
<212> TYPE: DNA
<213> ORGANISM: Bos taurus
<220> FEATURE:
<221> NAME/KEY: variation
<222> LOCATION: (1)...(20)
<223> OTHER INFORMATION: N at positions 9 and 19 is C or T; N at positions
    15 and 18 is A or G; N at positions 3, 6 and 12 is
    A, T, G or C.

<400> SEQUENCE: 87
gtnggnagng tncangannt                                           20

<210> SEQ ID NO 88
<211> LENGTH: 21
<212> TYPE: DNA
<213> ORGANISM: Bos taurus
<220> FEATURE:
<221> NAME/KEY: variation
<222> LOCATION: (1)...(21)
<223> OTHER INFORMATION: N at positions 4, 7 and 16 is C or T; N at
    position 12 is A or G; N at positions 1, 10 and 19
    is A, T, G or C; N at position 13 is A, C or T.

<400> SEQUENCE: 88
nacnttnttn annatntgnc c                                         21

<210> SEQ ID NO 89
<211> LENGTH: 417
<212> TYPE: DNA
<213> ORGANISM: Bos taurus

<400> SEQUENCE: 89
tctaaaacta cagagactgt attttcatga tcatcatagt tctgtgaaat atacttaaac    60
    cgctttggtc ctgatcttgt aggaagtcag aacttcgcat tagcaaagcg tcactggctg   120
    attctggaga atatatgtgc aaagtgatca gcaaactagg aaatgacagt gcctctgcca   180
    acatcaccat tgtggagtca aacggtaaga gatgcctact gcgtgctatt tctcagtctc   240
    taagaggagt gatcaaggta tgtggtcaca cttgaatcac gcaggtgtct gaaatctcat   300
    tgtgaacaaa taaaaatcat gaaaggaaaa ctctatgttt gaaatatctt atgggtcctc   360
    ctgtaaagct cttcactcca taaggtgaaa tagacctgaa atatatatag attattt      417

<210> SEQ ID NO 90
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 16 can be A or G; N in position 22
    can be A or G; N in position 28 can be C or T.

<400> SEQUENCE: 90
ccgaattctg cagganacuc anccugancc ugg                             33

<210> SEQ ID NO 91
<211> LENGTH: 37
<212> TYPE: DNA
<213> ORGANISM: Bos taurus
<220> FEATURE:
<221> NAME/KEY: variation
<222> LOCATION: (1)...(37)
<223> OTHER INFORMATION: N in position 17 can be A or G; N in position 26
    can be A, C or T.

<400> SEQUENCE: 91
aaggatcctg cagugtntau gcuccnatua ccatugg                         37

<210> SEQ ID NO 92
<211> LENGTH: 34
<212> TYPE: DNA
<213> ORGANISM: Bos taurus
<220> FEATURE:
<221> NAME/KEY: variation
<222> LOCATION: (1)...(34)
<223> OTHER INFORMATION: N in position 19 can be C or T; N in position 28
      can be A or G; N in position 31 can be C or T.

<400> SEQUENCE: 92
ccgaattctg caggcugant cugguganta natg                              34

<210> SEQ ID NO 93
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 19 can be C or T; N in position 22
      can be C or T; N in position 28 can be A or G; N
      in position 31 can be C or T.

<400> SEQUENCE: 93
ccgaattctg caggcugana gngguganta nat                               33

<210> SEQ ID NO 94
<211> LENGTH: 34
<212> TYPE: DNA
<213> ORGANISM: Bos taurus
<220> FEATURE:
<221> NAME/KEY: variation
<222> LOCATION: (1)...(34)
<223> OTHER INFORMATION: N in position 20 can be A or G; N in position 23
      can be C or T; N in position 32 can be A or G.

<400> SEQUENCE: 94
aaggatcctg caguuucatn tantcuccug antc                              34

<210> SEQ ID NO 95
<211> LENGTH: 34
<212> TYPE: DNA
<213> ORGANISM: Bos taurus
<220> FEATURE:
<221> NAME/KEY: variation
<222> LOCATION: (1)...(34)
<223> OTHER INFORMATION: N in position 20 can be A or G; N in position 23
      can be C or T; N in position 29 and 30 can be A or
      G; N in position 32 can be A or G.

<400> SEQUENCE: 95
aaggatcctg caguuucatn tantcuccnn tntc                              34

<210> SEQ ID NO 96
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 16 can be C or T; N in position 19
      can be A or G.

<400> SEQUENCE: 96
ccgaattctg cagcancang tutgggcugc taa                               33

<210> SEQ ID NO 97

```
<211> LENGTH: 35
<212> TYPE: DNA
<213> ORGANISM: Bos taurus
<220> FEATURE:
<221> NAME/KEY: variation
<222> LOCATION: (1)...(35)
<223> OTHER INFORMATION: N in position 16 can be A or G; N in position 19
      can be C or T; N in position 22 can be C or T; N
      in position 28 can be A or G; N in position 34 can
      be A or G.

<400> SEQUENCE: 97
ccgaattctg cagatnttnt tnatggancc ugang                          35

<210> SEQ ID NO 98
<211> LENGTH: 35
<212> TYPE: DNA
<213> ORGANISM: Bos taurus
<220> FEATURE:
<221> NAME/KEY: variation
<222> LOCATION: (30)...(30)
<223> OTHER INFORMATION: N in position 30 can be C or T.

<400> SEQUENCE: 98
ccgaattctg caggggguccc uccugcuttn ccugt                         35

<210> SEQ ID NO 99
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 19 can be C or T; N in position 28
      can be A or C or T; N in position 31 can be A or
      G.

<400> SEQUENCE: 99
ccgaattctg cagtggttng tugtuatnga ngg                            33

<210> SEQ ID NO 100
<211> LENGTH: 34
<212> TYPE: DNA
<213> ORGANISM: Bos taurus
<220> FEATURE:
<221> NAME/KEY: variation
<222> LOCATION: (1)...(34)
<223> OTHER INFORMATION: N at position 17, 20, and 26 is Inosinc. Y at 14
      and 29 can be cytidine or thymidine.

<400> SEQUENCE: 100
aaggatcctg cagyttngcn gcccanacyt grtg                           34

<210> SEQ ID NO 101
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 16 can be C or T; N in position 22
      can be C or T; N in position 28 can be A or G; N
      in position 31 can be A or G.

<400> SEQUENCE: 101
aaggatcctg caggcntcug gntccatnaa naa                            33

<210> SEQ ID NO 102
<211> LENGTH: 33
```

```
<212> TYPE: DNA
<213> ORGANISM: Bos taurus
<220> FEATURE:
<221> NAME/KEY: variation
<222> LOCATION: (1)...(33)
<223> OTHER INFORMATION: N in position 19 can be A or G.

<400> SEQUENCE: 102
aaggatcctg cagacuggna augcuggugg ucc                              33

<210> SEQ ID NO 103
<211> LENGTH: 35
<212> TYPE: DNA
<213> ORGANISM: Bos taurus
<220> FEATURE:
<221> NAME/KEY: variation
<222> LOCATION: (1)...(35)
<223> OTHER INFORMATION: N in position 14 can be C or T; N in position 20
      can be C or T; N in position 23 can be A or G or
      T; N in position 32 can be A or G.

<400> SEQUENCE: 103
aaggatcctg cagnttuccn tcnatuacua cnaac                            35

<210> SEQ ID NO 104
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 4 can be A or G; N in position 7 can
      be C or T; N in position 10 can be A or G; N in
      position 13 can be C or T.

<400> SEQUENCE: 104
catntantcn tantctcugc aaggatcctg cag                              33

<210> SEQ ID NO 105
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 16 can be A or G; N in position 22
      can be C or T; N in position 28 can be C or T.

<400> SEQUENCE: 105
ccgaattctg cagaanggug angcucanac uga                              33

<210> SEQ ID NO 106
<211> LENGTH: 33
<212> TYPE: DNA
<213> ORGANISM: Bos taurus
<220> FEATURE:
<221> NAME/KEY: variation
<222> LOCATION: (1)...(33)
<223> OTHER INFORMATION: N in position 6 can be C or T; N in position 12
      can be C or T; N in position 15 can be C or T.

<400> SEQUENCE: 106
gcugcnaaug cntcnttugc aaggatcctg cag                              33

<210> SEQ ID NO 107
<211> LENGTH: 33
<212> TYPE: DNA
<213> ORGANISM: Bos taurus
<220> FEATURE:
```

```
<221> NAME/KEY: variation
<222> LOCATION: (1)...(33)
<223> OTHER INFORMATION: N in position 12 can be C or T; N in position 15
      can be C or T.

<400> SEQUENCE: 107
gcugcuagug cntcntttgc aaggatcctg cag                              33

<210> SEQ ID NO 108
<211> LENGTH: 30
<212> TYPE: DNA
<213> ORGANISM: Bos taurus
<220> FEATURE:
<221> NAME/KEY: variation
<222> LOCATION: (1)...(30)
<223> OTHER INFORMATION: N in position 6 can be A or G; N in position 9 can
      be A or G.

<400> SEQUENCE: 108
tcugcnaant auccugcaag gatcctgcag                                  30

<210> SEQ ID NO 109
<211> LENGTH: 38
<212> TYPE: DNA
<213> ORGANISM: Bos taurus

<400> SEQUENCE: 109
catcgatctg caggctgatt ctggagaata tatgtgca                         38

<210> SEQ ID NO 110
<211> LENGTH: 37
<212> TYPE: DNA
<213> ORGANISM: Bos taurus

<400> SEQUENCE: 110
aaggatcctg cagccacatc tcgagtcgac atcgatt                          37

<210> SEQ ID NO 111
<211> LENGTH: 37
<212> TYPE: DNA
<213> ORGANISM: Bos taurus

<400> SEQUENCE: 111
ccgaattctg cagtgatcag caaactagga aatgaca                          37

<210> SEQ ID NO 112
<211> LENGTH: 37
<212> TYPE: DNA
<213> ORGANISM: Bos taurus

<400> SEQUENCE: 112
catcgatctg cagcctagtt tgctgatcac tttgcac                          37

<210> SEQ ID NO 113
<211> LENGTH: 37
<212> TYPE: DNA
<213> ORGANISM: Bos taurus

<400> SEQUENCE: 113
aaggatcctg cagtatattc tccagaatca gccagtg                          37

<210> SEQ ID NO 114
<211> LENGTH: 34
<212> TYPE: DNA
<213> ORGANISM: Bos taurus
```

<400> SEQUENCE: 114
aaggatcctg caggcacgca gtaggcatct ctta                                34

<210> SEQ ID NO 115
<211> LENGTH: 35
<212> TYPE: DNA
<213> ORGANISM: Bos taurus

<400> SEQUENCE: 115
ccgaattctg cagcagaact tcgcattagc aaagc                               35

<210> SEQ ID NO 116
<211> LENGTH: 33
<212> TYPE: DNA
<213> ORGANISM: Bos taurus

<400> SEQUENCE: 116
catcccggga tgaagagtca ggagtctgtg gca                                 33

<210> SEQ ID NO 117
<211> LENGTH: 39
<212> TYPE: DNA
<213> ORGANISM: Bos taurus

<400> SEQUENCE: 117
atacccgggc tgcagacaat gagatttcac acacctgcg                           39

<210> SEQ ID NO 118
<211> LENGTH: 36
<212> TYPE: DNA
<213> ORGANISM: Bos taurus

<400> SEQUENCE: 118
aaggatcctg cagtttggaa cctgccacag actcct                              36

<210> SEQ ID NO 119
<211> LENGTH: 39
<212> TYPE: DNA
<213> ORGANISM: Bos taurus

<400> SEQUENCE: 119
atacccgggc tgcagatgag atttcacaca cctgcgtga                           39

<210> SEQ ID NO 120
<211> LENGTH: 12
<212> TYPE: PRT
<213> ORGANISM: Bos taurus

<400> SEQUENCE: 120

His Gln Val Trp Ala Ala Lys Ala Ala Gly Leu Lys
      1               5                  10

<210> SEQ ID NO 121
<211> LENGTH: 16
<212> TYPE: PRT
<213> ORGANISM: Bos taurus

<400> SEQUENCE: 121

Gly Gly Leu Lys Lys Asp Ser Leu Leu Thr Val Arg Leu Gly Ala Asn
      1               5                  10                  15

<210> SEQ ID NO 122

```
<211> LENGTH: 13
<212> TYPE: PRT
<213> ORGANISM: Bos taurus
<220> FEATURE:
<221> NAME/KEY: VARIANT
<222> LOCATION: (1)...(12)
<223> OTHER INFORMATION: Xaa in position 12 is unknown

<400> SEQUENCE: 122

Leu Gly Ala Trp Gly Pro Pro Ala Phe Pro Val Xaa Tyr
    1               5                   10

<210> SEQ ID NO 123
<211> LENGTH: 23
<212> TYPE: PRT
<213> ORGANISM: Bos taurus

<400> SEQUENCE: 123

Leu Leu Thr Val Arg Leu Gly Ala Trp Gly His Pro Ala Phe Pro Ser
    1               5                   10                  15
    Cys Gly Arg Leu Lys Glu Asp
                20

<210> SEQ ID NO 124
<211> LENGTH: 13
<212> TYPE: PRT
<213> ORGANISM: Bos taurus
<220> FEATURE:
<221> NAME/KEY: VARIANT
<222> LOCATION: (10)...(10)
<223> OTHER INFORMATION: Xaa in position 10 is unknown.

<400> SEQUENCE: 124

Tyr Ile Phe Phe Met Glu Pro Glu Ala Xaa Ser Ser Gly
    1               5                   10

<210> SEQ ID NO 125
<211> LENGTH: 23
<212> TYPE: PRT
<213> ORGANISM: Bos taurus

<400> SEQUENCE: 125

Lys Glu Asp Ser Arg Tyr Ile Phe Phe Met Glu Pro Glu Ala Asn Ser
    1               5                   10                  15
    Ser Gly Gly Pro Gly Arg Leu
                20

<210> SEQ ID NO 126
<211> LENGTH: 14
<212> TYPE: PRT
<213> ORGANISM: Bos taurus

<400> SEQUENCE: 126

Val Ala Gly Ser Lys Leu Val Leu Arg Cys Glu Thr Ser Ser
    1               5                   10

<210> SEQ ID NO 127
<211> LENGTH: 16
<212> TYPE: PRT
<213> ORGANISM: Bos taurus

<400> SEQUENCE: 127

Glu Tyr Lys Cys Leu Lys Phe Lys Trp Phe Lys Lys Ala Thr Val Met
    1               5                   10                  15

<210> SEQ ID NO 128
<211> LENGTH: 26
```

```
<212> TYPE: PRT
<213> ORGANISM: Bos taurus

<400> SEQUENCE: 128

Cys Glu Thr Ser Ser Glu Tyr Ser Leu Lys Phe Lys Trp Phe Lys
      1               5                  10                  15
     Asn Gly Ser Glu Leu Ser Arg Lys Asn Lys
                  20                  25

<210> SEQ ID NO 129
<211> LENGTH: 11
<212> TYPE: PRT
<213> ORGANISM: Bos taurus

<400> SEQUENCE: 129

Lys Ala Ser Leu Ala Asp Ser Gly Glu Tyr Met
      1               5                  10

<210> SEQ ID NO 130
<211> LENGTH: 23
<212> TYPE: PRT
<213> ORGANISM: Bos taurus

<400> SEQUENCE: 130

Glu Leu Arg Ile Ser Lys Ala Ser Leu Ala Asp Ser Gly Glu Tyr Met
      1               5                  10                  15
     Cys Lys Val Ile Ser Lys Leu
                  20

<210> SEQ ID NO 131
<211> LENGTH: 12
<212> TYPE: PRT
<213> ORGANISM: Bos taurus

<400> SEQUENCE: 131

Ala Ser Leu Ala Asp Glu Tyr Glu Tyr Met Arg Lys
      1               5                  10

<210> SEQ ID NO 132
<211> LENGTH: 22
<212> TYPE: PRT
<213> ORGANISM: Bos taurus

<400> SEQUENCE: 132

Leu Arg Ile Ser Lys Ala Ser Leu Ala Asp Ser Gly Glu Tyr Met Cys
      1               5                  10                  15
     Lys Val Ile Ser Lys Leu
                  20

<210> SEQ ID NO 133
<211> LENGTH: 744
<212> TYPE: DNA
<213> ORGANISM: Bos taurus
<220> FEATURE:
<221> NAME/KEY: CDS
<222> LOCATION: (8)...(625)

<400> SEQUENCE: 133 cctgcag cat caa gtg tgg gcg gcg aaa gcc ggg ggc ttg aag aag gac      49
             His Gln Val Trp Ala Ala Lys Ala Gly Gly Leu Lys Lys Asp
              1               5                  10
     tcg ctg ctc acc gtg cgc ctg ggc gcc tgg ggc cac ccc gcc ttc ccc      97
     Ser Leu Leu Thr Val Arg Leu Gly Ala Trp Gly His Pro Ala Phe Pro
     15                  20                  25                  30
     tcc tgc ggg cgc ctc aag gag gac agc agg tac atc ttc ttc atg gag     145
     Ser Cys Gly Arg Leu Lys Glu Asp Ser Arg Tyr Ile Phe Phe Met Glu
                     35                  40                  45
     ccc gag gcc aac agc agc ggg ggg ccc ggc cgc ctt ccg agc ctc ctt     193
```

```
    Pro Glu Ala Asn Ser Ser Gly Gly Pro Gly Arg Leu Pro Ser Leu Leu
                 50                  55                  60
    ccc ccc tct cga gac ggg ccg gaa cct caa gaa gga ggt cag ccg ggt       241
    Pro Pro Ser Arg Asp Gly Pro Glu Pro Gln Glu Gly Gly Gln Pro Gly
             65                  70                  75
    gct gtg caa cgg tgc gcc ttg cct ccc cgc ttg aaa gag atg aag agt       289
    Ala Val Gln Arg Cys Ala Leu Pro Pro Arg Leu Lys Glu Met Lys Ser
     80                  85                  90
    cag gag tct gtg gca ggt tcc aaa cta gtg ctt cgg tgc gag acc agt       337
    Gln Glu Ser Val Ala Gly Ser Lys Leu Val Leu Arg Cys Glu Thr Ser
     95                 100                                 110
    tct gaa tac tcc tct ctc aag ttc aag tgg ttc aag aat ggg agt gaa       385
    Ser Glu Tyr Ser Ser Leu Lys Phe Lys Trp Phe Lys Asn Gly Ser Glu
                    115                 120                 125
    tta agc cga aag aac aaa cca gaa aac atc aag ata cag aag ccg           433
    Leu Ser Arg Lys Asn Lys Pro Glu Asn Ile Lys Ile Gln Lys Arg Pro
                130                 135                 140
    ggg aag tca gaa ctt cgc att agc aaa gcg tca ctg gct gat tct gga       481
    Gly Lys Ser Glu Leu Arg Ile Ser Lys Ala Ser Leu Ala Asp Ser Gly
                145                 150                 155
    gaa tat atg tgc aaa gtg atc agc aaa cta gga aat gac agt gcc tct       529
    Glu Tyr Met Cys Lys Val Ile Ser Lys Leu Gly Asn Asp Ser Ala Ser
    160                 165                 170
    gcc aac atc acc att gtg gag tca aac ggt aag tgc cta ctg cgt           577
    Ala Asn Ile Thr Ile Val Glu Ser Asn Gly Lys Arg Cys Leu Leu Arg
    175                 180                 185                 190
    gct att tct cag tct cta aga gga gtg atc aag gta tgt ggt cac act       625
    Ala Ile Ser Gln Ser Leu Arg Gly Val Ile Lys Val Cys Gly His Thr
                    195                 200                 205
    tgaatcacgc aggtgtgtga aatctcattg tcaacaaata aaaatcatga aaggaaaaaa     685
    aaaaaaaaaa aatcgatgtc gactcgagat gtggctgcag gtcgactcta gaggatccc     744
```

<210> SEQ ID NO 134
<211> LENGTH: 1193
<212> TYPE: DNA
<213> ORGANISM: Bos taurus

<400> SEQUENCE: 134

```
    cctgcagcat caagtgtggg cggcgaaagc cggggggcttg aagaaggact cgctgctcac    60
    cgtgcgcctg ggcgcctggg gccaccccgc cttcccctcc tgcgggcgcc tcaaggagga   120
    cagcaggtac atcttcttca tggagcccga ggccaacagc agcggcgggc ccggccgcct   180
    tccgagcctc cttcccccct ctcgagacgg gccggaacct caagaaggag gtcagccggg   240
    tgctgtgcaa cggtgcgcct tgcctcccg cttgaaagag atgaagagtc aggagtctgt    300
    ggcaggttcc aaactagtgc ttcggtgcga gaccagttct gaatactcct ctctcaagtt   360
    caagtggttc aagaatggga gtgaattaag ccgaaagaac aaaccagaaa acatcaagat   420
    acagaaaagg ccggggaagt caggacttcg cattagcaaa gcgtcactgg ctgattctgg   480
    agaatatatg tgcaaagtga tcagcaaact aggaaatgac agtgcctctg ccaacatcac   540
    cattgtggag tcaaacgcca catccacatc tacagctggg acaagccatc ttgtcaagtg   600
    tgcagagaag gagaaaactt ctgtgtgaa tggaggcgag tgcttcatgg tgaaagacct   660
    ttcaaatccc tcaagatact tgtgcaagtg ccaacctgga ttcactggag cgagatgtac   720
    tgagaatgtg cccatgaaag tccaaaccca agaaagtgcc caaatgagtt tactggtgat   780
    cgctgccaaa actacgtaat ggccagcttc tacagtacgt ccactccctt tctgtctctg   840
    cctgaatagc gcatctcagt cggtgccgct ttcttgttgc cgcatctccc ctcagattcc   900
    tcctagagct agatgcgttt taccaggtct aacattgact gcctctgcct gtcgcatgag   960
    aacattaaca caagcgattg tatgacttcc tctgtccgtg actagtgggc tctgagctac  1020
    tcgtaggtgc gtaaggctcc agtgtttctg aaattgatct tgaattactg tgatacgaca  1080
    tgatagtccc tctcacccag tgcaatgaca ataaaggcct tgaaaagtca aaaaaaaaa   1140
    aaaaaaaaaa aatcgatgtc gactcgagat gtggctgcag gtcgactcta gag         1193
```

<210> SEQ ID NO 135
<211> LENGTH: 1108
<212> TYPE: DNA
<213> ORGANISM: Bos taurus
<220> FEATURE:
<221> NAME/KEY: CDS
<222> LOCATION: (8)...(778)

<400> SEQUENCE: 135

```
    cctgcag cat caa gtg tgg gcg gcg aaa gcc ggg ggc ttg aag aag gac        49
            His Gln Val Trp Ala Ala Lys Ala Gly Gly Leu Lys Lys Asp
              1               5                  10
    tcg ctg ctc acc gtg cgc ctg ggc gcc tgg ggc cac ccc gcc ttc ccc        97
    Ser Leu Leu Thr Val Arg Leu Gly Ala Trp Gly His Pro Ala Phe Pro
     15                  20                  25                  30
    tcc tgc ggg cgc ctc aag gag gac agc agg tac atc ttc ttc atg gag       145
```

```
                Ser Cys Gly Arg Leu Lys Glu Asp Ser Arg Tyr Ile Phe Met Glu
                                 35                  40                  45
ccc gag gcc aac agc agc ggc ggg ccc ggc cgc ctt ccg agc ctc ctt            193
Pro Glu Ala Asn Ser Ser Gly Gly Pro Gly Arg Leu Pro Ser Leu Leu
             50                  55                  60
ccc ccc tct cga gac ggg ccg gaa cct caa gaa gga gtt cag ccg ggt            241
Pro Pro Ser Arg Asp Gly Pro Glu Pro Gln Glu Gly Gln Pro Gly
         65                  70                  75
gct gtg caa cgg tgc gcc ttg cct ccc cgc ttg aaa gag atg aag agt            289
Ala Val Gln Arg Cys Ala Leu Pro Pro Arg Leu Lys Glu Met Lys Ser
 80                  85                  90
cag gag tct gtg gca ggt tcc aaa cta gtg ctt cgg tgc gag acc agt            337
Gln Glu Ser Val Ala Gly Ser Lys Leu Val Leu Arg Cys Glu Thr Ser
 95                  100                 105                 110
tct gaa tac tcc tct ctc aag ttc aag tgg ttc aag aat ggg agt gaa            385
Ser Glu Tyr Ser Ser Leu Lys Phe Lys Trp Phe Lys Asn Gly Ser Glu
                 115                 120                 125
tta agc cga aag aac aaa cca gaa aac atc aag ata cag aaa agg ccg            433
Leu Ser Arg Lys Asn Lys Pro Glu Asn Ile Lys Ile Gln Lys Arg Pro
             130                 135                 140
ggg aag tca gaa ctt cgc att agc aaa gcg tca ctg gct gat tct gga            481
Gly Lys Ser Glu Leu Arg Ile Ser Lys Ala Ser Leu Ala Asp Ser Gly
         145                 150                 155
gaa tat atg tgc aaa gtg atc agc aaa cta gga aat gac agt gcc tct            529
Glu Tyr Met Cys Lys Val Ile Ser Lys Leu Gly Asn Asp Ser Ala Ser
     160                 165                 170
gcc aac atc acc att gtg gag tca aac gcc aca tcc aca tct aca gct            577
Ala Asn Ile Thr Ile Val Glu Ser Asn Ala Thr Ser Thr Ser Thr Ala
175                 180                 185                 190
ggg aca agc cat ctt gtc aag tgt gca gag aag gag aaa act ttc tgt            625
Gly Thr Ser His Leu Val Lys Cys Ala Glu Lys Glu Lys Thr Phe Cys
                 195                 200                 205
gtg aat gga ggc gag tgc ttc atg gtg aaa gac ctt tca aat ccc tca            673
Val Asn Gly Gly Glu Cys Phe Met Val Lys Asp Leu Ser Asn Pro Ser
             210                 215                 220
aga tac ttg tgc aag tgc cca aat gag ttt act ggt gat cgc tgc caa            721
Arg Tyr Leu Cys Lys Cys Pro Asn Glu Phe Thr Gly Asp Arg Cys Gln
         225                 230                 235
aac tac gta atg gcc agc ttc tac agt acg tcc act ccc ttt ctg tct            769
Asn Tyr Val Met Ala Ser Phe Tyr Ser Thr Ser Thr Pro Phe Leu Ser
     240                 245                 250
ctg cct gaa tagcgcatct cagtcggtgc cgctttcttg ttgccgcatc                    818
Leu Pro Glu
255
tcccctcaga ttccgcctag agctagatgc gttttaccag gtctaacatt gactgcctct          878
gcctgtcgca tgagaacatt aacacaagcg attgtatgac ttcctctgtc cgtgactagt          938
gggctctgag ctactcgtag gtgcgtaagg ctccagtgtt tctgaaattg atcttgaatt          998
actgtgatac gacatgatag tccctctcac ccagtgcaat gacaataaag gccttgaaaa         1058
gtcaaaaaaa aaaaaaaaaa aaaaatcgat gtcgactcga gatgtggctg                    1108

<210> SEQ ID NO 136
<211> LENGTH: 559
<212> TYPE: DNA
<213> ORGANISM: Bos taurus
<220> FEATURE:
<221> NAME/KEY: variation
<222> LOCATION: (214)...(214)
<223> OTHER INFORMATION: N is unknown

<400> SEQUENCE: 136
agtttccccc cccaacttgt cggaactctg ggctcgcgcg cagggcagga gcggagcggc           60
ggcggctgcc caggcgatgc gagcgcgggc cggacggtaa tcgcctctcc ctcctcgggc          120
tgcgagcgcg ccggaccgag gcagcgacag gagcggaccg cggcgggaac cgaggactcc          180
ccagcggcgc gccagcagga gccacccgcg gagncgtgcg accgggacgg agcgcccgcc          240
agtcccaggt ggcccggacc gcacgttgcg tccccgcgct ccccgccggc gacaggagac          300
gctcccccc acgccgcgcg cgcctcggcc cggtcgctgg cccgcctcca ctccgggac           360
aaacttttcc cgaagccgat cccagccctc ggacccaaac ttgtcgcgcg tcgccttcgc          420
cgggagccgt ccgcgcagag cgtgcacttc tcgggcgaga tgtcggagcg cagagaaggc          480
aaaggcaagg ggaagggcgg caagaaggac cgaggctccg ggaagaagcc cgtgcccgcg          540
gctggcggcc cgagcccag                                                      559

<210> SEQ ID NO 137
<211> LENGTH: 252
<212> TYPE: DNA
<213> ORGANISM: Bos taurus
<220> FEATURE:
```

-continued

```
<221> NAME/KEY: CDS
<222> LOCATION: (3)...(251)
<221> NAME/KEY: variation
<222> LOCATION: (8)...(8)
<223> OTHER INFORMATION: N in position 8 could be either A or G.
<220> FEATURE:
<221> NAME/KEY: variation
<222> LOCATION: (2)...(2)
<223> OTHER INFORMATION: Xaa is unknown.

<400> SEQUENCE: 137 cc cat can gtg tgg gcg gcg aaa gcc ggg ggc ttg aag aag gac tcg      47
         His Xaa Val Trp Ala Ala Lys Ala Gly Gly Leu Lys Lys Asp Ser
          1               5                  10                  15
      ctg ctc acc gtg cgc ctg ggc gcc tgg ggc cac ccc gcc ttc ccc tcc     95
      Leu Leu Thr Val Arg Leu Gly Ala Trp Gly His Pro Ala Phe Pro Ser
                       20                  25                  30
      tgc ggg cgc ctc aag gag gac agc agg tac atc ttc ttc atg gag ccc    143
      Cys Gly Arg Leu Lys Glu Asp Ser Arg Tyr Ile Phe Phe Met Glu Pro
                   35                  40                  45
      gag gcc aac agc agc ggc ggg ccc ggc cgc ctt ccg agc ctc ctt ccc    191
      Glu Ala Asn Ser Ser Gly Gly Pro Gly Arg Leu Pro Ser Leu Leu Pro
               50                  55                  60
      ccc tct cga gac ggg ccg gaa cct caa gaa gga ggt cag ccg ggt gct    239
      Pro Ser Arg Asp Gly Pro Glu Pro Gln Glu Gly Gly Gln Pro Gly Ala
           65                  70                  75
      gtg caa cgg tgc g                                                  252
      Val Gln Arg Cys
       80

<210> SEQ ID NO 138
<211> LENGTH: 178
<212> TYPE: DNA
<213> ORGANISM: Bos taurus

<400> SEQUENCE: 138
ccttgcctcc ccgcttgaaa gagatgaaga gtcaggagtc tgtggcaggt tccaaactag    60
      tgcttcggtg cgagaccagt tctgaatact cctctctcaa gttcaagtgg ttcaagaatg   120
      ggagtgaatt aagccgaaag aacaaaccac aaaacatcaa gatacagaaa aggccggg    178

<210> SEQ ID NO 139
<211> LENGTH: 122
<212> TYPE: DNA
<213> ORGANISM: Bos taurus
<220> FEATURE:
<221> NAME/KEY: CDS
<222> LOCATION: (2)...(121)

<400> SEQUENCE: 139 g aag tca gaa ctt cgc att agc aaa gcg tca ctg gct gat tct gga gaa    49
        Lys Ser Glu Leu Arg Ile Ser Lys Ala Ser Leu Ala Asp Ser Gly Glu
         1               5                  10                  15
      tat atg tgc aaa gtg atc agc aaa cta gga aat gac agt gcc tct gcc     97
      Tyr Met Cys Lys Val Ile Ser Lys Leu Gly Asn Asp Ser Ala Ser Ala
                   20                  25                  30
      aac atc acc att gtg gag tca aac g                                  122
      Asn Ile Thr Ile Val Glu Ser Asn
                   35                  40

<210> SEQ ID NO 140
<211> LENGTH: 417
<212> TYPE: DNA
<213> ORGANISM: Bos taurus
<220> FEATURE:
<221> NAME/KEY: CDS
<222> LOCATION: (84)...(272)

<400> SEQUENCE: 140
tctaaaacta cagagactgt attttcatga tcatcatagt tctgtgaaat atacttaaac    60
      cgctttggtc ctgatcttgt agg aag tca gaa ctt cgc att agc aaa gcg tca   113
                             Lys Ser Glu Leu Arg Ile Ser Lys Ala Ser
                              1               5                  10
```

```
        ctg gct gat tct gga gaa tat atg tgc aaa gtg atc agc aaa cta gga      161
        Leu Ala Asp Ser Gly Glu Tyr Met Cys Lys Val Ile Ser Lys Leu Gly
                        15                  20                  25
        aat gac agt gcc tct gcc aac atc acc att gtg gag tca aac ggt aag      209
        Asn Asp Ser Ala Ser Ala Asn Ile Thr Ile Val Glu Ser Asn Gly Lys
                30                      35                      40
        aga tgc cta ctg cgt gct att tct cag tct cta aga gga gtg atc aag      257
        Arg Cys Leu Leu Arg Ala Ile Ser Gln Ser Leu Arg Gly Val Ile Lys
                    45                  50                  55
        gta tgt ggt cac act tgaatcacgc aggtgtgtga aatctcattg tgaacaaata      312
        Val Cys Gly His Thr
                60
        aaaatcatga aaggaaaact ctatgtttga aatatcttat gggtcctcct gtaaagctct    372
        tcactccata aggtgaaata gacctgaaat atatatagat tattt                    417

<210> SEQ ID NO 141
<211> LENGTH: 102
<212> TYPE: DNA
<213> ORGANISM: Bos taurus
<220> FEATURE:
<221> NAME/KEY: CDS
<222> LOCATION: (3)...(101)

<400> SEQUENCE: 141 ag atc acc act ggc atg cca gcc tca act gag aca gcg tat gtg tct       47
           Ile Thr Thr Gly Met Pro Ala Ser Thr Glu Thr Ala Tyr Val Ser
             1               5                  10                  15
        tca gag tct ccc att aga ata tca gta tca aca gaa gga aca aat act      95
        Ser Glu Ser Pro Ile Arg Ile Ser Val Ser Thr Glu Gly Thr Asn Thr
                        20                  25                  30
        tct tca t                                                           102
        Ser Ser <210> SEQ ID NO 142
<211> LENGTH: 69
<212> TYPE: DNA
<213> ORGANISM: Bos taurus
<220> FEATURE:
<221> NAME/KEY: CDS
<222> LOCATION: (1)...(69)

<400> SEQUENCE: 142 aag tgc caa cct gga ttc act gga gcg aga tgt act gag aat gtg ccc      48
        Lys Cys Gln Pro Gly Phe Thr Gly Ala Arg Cys Thr Glu Asn Val Pro
         1               5                  10                  15
        atg aaa gtc caa acc caa gaa                                         69
        Met Lys Val Gln Thr Gln Glu
                    20

<210> SEQ ID NO 143
<211> LENGTH: 60
<212> TYPE: DNA
<213> ORGANISM: Bos taurus, Homo sapiens
<220> FEATURE:
<221> NAME/KEY: CDS
<222> LOCATION: (1)...(60)

<400> SEQUENCE: 143 aag tgc cca aat gag ttt act ggt gat cgc tgc caa aac tac gta atg      48
        Lys Cys Pro Asn Glu Phe Thr Gly Asp Arg Cys Gln Asn Tyr Val Met
         1               5                  10                  15
        gcc agc ttc tac                                                     60
        Ala Ser Phe Tyr
                    20

<210> SEQ ID NO 144
<211> LENGTH: 36
<212> TYPE: DNA
<213> ORGANISM: Bos taurus, Homo sapiens

<400> SEQUENCE: 144
```

```
                        agtacgtcca ctccctttct gtctctgcct gaatag                                       36

<210> SEQ ID NO 145
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 145 aag cat ctt ggg att gaa ttt atg gag                                                          27
         Lys His Leu Gly Ile Glu Phe Met Glu
         1               5

<210> SEQ ID NO 146
<211> LENGTH: 569
<212> TYPE: DNA
<213> ORGANISM: Bos taurus
<220> FEATURE:
<221> NAME/KEY: CDS
<222> LOCATION: (1)...(565)

<400> SEQUENCE: 146 aaa gcg gag gag ctc tac cag aag aga gtg ctc acc att acc ggc att      48
         Lys Ala Glu Glu Leu Tyr Gln Lys Arg Val Leu Thr Ile Thr Gly Ile
         1               5                   10                  15
         tgc atc gcg ctg ctc gtg gtt ggc atc atg tgt gtg gtc tac tgc          96
         Cys Ile Ala Leu Leu Val Val Gly Ile Met Cys Val Val Val Tyr Cys
                         20                  25                  30
         aaa acc aag aaa caa cgg aaa aag ctt cat gac cgg ctt cgg cag agc     144
         Lys Thr Lys Lys Gln Arg Lys Lys Leu His Asp Arg Leu Arg Gln Ser
                     35                  40                  45
         ctt cgg tct gaa aga aac acc atg atg aac gta gcc aac ggg ccc cac     192
         Leu Arg Ser Glu Arg Asn Thr Met Met Asn Val Ala Asn Gly Pro His
                 50                  55                  60
         cac ccc aat ccg ccc ccc gag aac gtg cag ctg gtg aat caa tac gta     240
         His Pro Asn Pro Pro Pro Glu Asn Val Gln Leu Val Asn Gln Tyr Val
         65                  70                  75                  80
         tct aaa aat gtc atc tct agc gag cat att gtt gag aga gag gcg gag     288
         Ser Lys Asn Val Ile Ser Ser Glu His Ile Val Glu Arg Glu Ala Glu
                         85                  90                  95
         agc tct ttt tcc acc agt cac tac act tcg aca gct cat cat tcc act     336
         Ser Ser Phe Ser Thr Ser His Tyr Thr Ser Thr Ala His His Ser Thr
                         100                 105                 110
         act gtc act cag act ccc agt cac agc tgg agc aat gga cac act gaa     384
         Thr Val Thr Gln Thr Pro Ser His Ser Trp Ser Asn Gly His Thr Glu
                     115                 120                 125
         agc atc att tcg gaa agc cac tct gtc atc gtg atg tca tcc gta gaa     432
         Ser Ile Ile Ser Glu Ser His Ser Val Ile Val Met Ser Ser Val Glu
                 130                 135                 140
         aac agt agg cac agc agc ccg act ggg ggc ccg aga gga cgt ctc aat     480
         Asn Ser Arg His Ser Ser Pro Thr Gly Gly Pro Arg Gly Arg Leu Asn
         145                 150                 155                 160
         ggc ttg gga ggc cct cgt gaa tgt aac agc ttc ctc agg cat gcc aga     528
         Gly Leu Gly Gly Pro Arg Glu Cys Asn Ser Phe Leu Arg His Ala Arg
                         165                 170                 175
         gaa acc cct gac tcc tac cga gac tct cct cat agt g aaag             569
         Glu Thr Pro Asp Ser Tyr Arg Asp Ser Pro His Ser
                     180                 185

<210> SEQ ID NO 147
<211> LENGTH: 730
<212> TYPE: DNA
<213> ORGANISM: Bos taurus
<220> FEATURE:
<221> NAME/KEY: CDS
<222> LOCATION: (2)...(652)

<400> SEQUENCE: 147 g tat gta tca gca atg acc acc ccg gct cgt atg tca cct gta gat ttc    49
           Tyr Val Ser Ala Met Thr Thr Pro Ala Arg Met Ser Pro Val Asp Phe
           1               5                   10                  15
```

```
cac acg cca agc tcc ccc aag tca ccc cct tcg gaa atg tcc ccg ccc      97
His Thr Pro Ser Ser Pro Lys Ser Pro Pro Ser Glu Met Ser Pro Pro
             20                  25                  30
gtg tcc agc acg acg gtc tcc atg ccc tcc atg gcg gtc agt ccc ttc     145
Val Ser Ser Thr Thr Val Ser Met Pro Ser Met Ala Val Ser Pro Phe
         35                  40                  45
gtg gaa gag gag aga ccc ctg ctc ctt gtg acg cca cca cgg ctg cgg     193
Val Glu Glu Glu Arg Pro Leu Leu Leu Val Thr Pro Pro Arg Leu Arg
     50                  55                  60
gag aag tat gac cac cac gcc cag caa ttc aac tcg ttc cac tgc aac     241
Glu Lys Tyr Asp His His Ala Gln Gln Phe Asn Ser Phe His Cys Asn
 65                  70                  75                  80
ccc gcg cat gag agc aac agc ctg ccc ccc agc ccc ttg agg ata gtg     289
Pro Ala His Glu Ser Asn Ser Leu Pro Pro Ser Pro Leu Arg Ile Val
                 85                  90                  95
gag gat gag gaa tat gaa acg acc cag gag tac gaa cca gct caa gag     337
Glu Asp Glu Glu Tyr Glu Thr Thr Gln Glu Tyr Glu Pro Ala Gln Glu
             100                 105                 110
ccg gtt aag aaa ctc acc aac agc agc cgg cgg gcc aaa aga acc aag     385
Pro Val Lys Lys Leu Thr Asn Ser Ser Arg Arg Ala Lys Arg Thr Lys
         115                 120                 125
ccc aat ggt cac att gcc cac agg ttg gaa atg gac aac aac aca ggc     433
Pro Asn Gly His Ile Ala His Arg Leu Glu Met Asp Asn Asn Thr Gly
     130                 135                 140
gct gac agc agt aac tca gag agc gaa aca gag gat gaa aga gta gga     481
Ala Asp Ser Ser Asn Ser Glu Ser Glu Thr Glu Asp Glu Arg Val Gly
145                 150                 155                 160
gaa gat acg cct ttc ctg gcc ata cag aac ccc ctg gca gcc agt ctc     529
Glu Asp Thr Pro Phe Leu Ala Ile Gln Asn Pro Leu Ala Ala Ser Leu
                 165                 170                 175
gag gcg gcc cct gcc ttc cgc ctg gtc gac agc agg act aac cca aca     577
Glu Ala Ala Pro Ala Phe Arg Leu Val Asp Ser Arg Thr Asn Pro Thr
             180                 185                 190
ggc ggc ttc tct ccg cag gaa gaa ttg cag gcc agg ctc tcc ggt gta     625
Gly Gly Phe Ser Pro Gln Glu Glu Leu Gln Ala Arg Leu Ser Gly Val
         195                 200                 205
atc gct aac caa gac cct atc gct gtc taaaaccgaa atacacccat           672
Ile Ala Asn Gln Asp Pro Ile Ala Val
     210                 215
agattcacct gtaaaacttt attttatata ataaagtatt ccaccttaaa ttaaacaa     730
```

<210> SEQ ID NO 148
<211> LENGTH: 1652
<212> TYPE: DNA
<213> ORGANISM: Bos taurus
<220> FEATURE:
<221> NAME/KEY: CDS
<222> LOCATION: (459)...(1181)

<400> SEQUENCE: 148

```
agtttccccc cccaacttgt cggaactctg ggctcgcgcg cagggcagga gcggagcggc      60
ggcggctgcc caggcgatgc gagcgcgggc cggacggtaa tcgcctctcc ctcctcgggc     120
tgcgagcgcg ccggaccgag gcagcgacag gagcggaccg cggcgggaac cgaggactcc     180
ccagcggcgc gccagcagga gccaccccgc gagcgtgcga ccgggacgga gcgcccgcca     240
gtcccaggtg gcccggaccg cacgttgcgt ccccgccgtg acaggagacg                300
ctcccccca cgccgcgcgc gcctcggccc ggtcgctggc ccgcctccac tccggggaca     360
aacttttccc gaagccgatc ccagccctcg gacccaaact tgtcgcgcgt cgccttcgcc     420
gggagccgtc cgcgcagagc gtgcacttct cgggcgag atg tcg gag cgc aga gaa    476
                                        Met Ser Glu Arg Arg Glu
                                         1               5
ggc aaa ggc aag ggg aag ggc ggc aag aag gac cga ggc tcc ggg aag      524
Gly Lys Gly Lys Gly Lys Gly Gly Lys Lys Asp Arg Gly Ser Gly Lys
         10                  15                  20
aag ccc gtg ccc gcg gct ggc ggc ccg agc cca gcc ttg cct ccc cgc      572
Lys Pro Val Pro Ala Ala Gly Gly Pro Ser Pro Ala Leu Pro Pro Arg
     25                  30                  35
ttg aaa gag atg aag atg cag gag tct gtg gca ggt tcc aaa cta gtg      620
Leu Lys Glu Met Lys Met Gln Glu Ser Val Ala Gly Ser Lys Leu Val
 40                  45                  50
ctt cgg tgc gag acc agt tct gaa tac tcc tct ctc aag ttc aag tgg      668
Leu Arg Cys Glu Thr Ser Ser Glu Tyr Ser Ser Leu Lys Phe Lys Trp
 55                  60                  65                  70
ttc aag aat ggg agt gaa tta agc cga aag aac aaa cca caa aac atc      716
Phe Lys Asn Gly Ser Glu Leu Ser Arg Lys Asn Lys Pro Gln Asn Ile
             75                  80                  85
aag ata cag aaa agg ccg ggg aag tca gaa ctt cgc att agc aaa gcg      764
Lys Ile Gln Lys Arg Pro Gly Lys Ser Glu Leu Arg Ile Ser Lys Ala
```

-continued

```
            90                  95                 100
tca ctg gct gat tct gga gaa tat atg tgc aaa gtg atc agc aaa cta    812
Ser Leu Ala Asp Ser Gly Glu Tyr Met Cys Lys Val Ile Ser Lys Leu
        105                 110                 115
gga aat gac agt gcc tct gcc aac atc acc att gtg gag tca aac gag    860
Gly Asn Asp Ser Ala Ser Ala Asn Ile Thr Ile Val Glu Ser Asn Glu
120                 125                 130
atc acc act ggc atg cca gcc tca act gag aca gcg tat gtg tct tca    908
Ile Thr Thr Gly Met Pro Ala Ser Thr Glu Thr Ala Tyr Val Ser Ser
135                 140                 145                 150
gag tct ccc att aga ata tca gta tca aca gaa gga aca aat act tct    956
Glu Ser Pro Ile Arg Ile Ser Val Ser Thr Glu Gly Thr Asn Thr Ser
                155                 160                 165
tca tcc aca tcc aca tct aca gct ggg aca agc cat ctt gtc aag tgt   1004
Ser Ser Thr Ser Thr Ser Thr Ala Gly Thr Ser His Leu Val Lys Cys
            170                 175                 180
gca gag aag gag aaa act ttc tgt gtg aat gga ggc gag tgc ttc atg   1052
Ala Glu Lys Glu Lys Thr Phe Cys Val Asn Gly Gly Glu Cys Phe Met
        185                 190                 195
gtg aaa gac ctt tca aat ccc tca aga tac ttg tgc aag tgc cca aat   1100
Val Lys Asp Leu Ser Asn Pro Ser Arg Tyr Leu Cys Lys Cys Pro Asn
200                 205                 210
gag ttt act ggt gat cgc tgc caa aac tac gta atg gcc agc ttc tac   1148
Glu Phe Thr Gly Asp Arg Cys Gln Asn Tyr Val Met Ala Ser Phe Tyr
215                 220                 225                 230
agt acg tcc act ccc ttt ctg tct ctg cct gaa taggcgcatg ctcagtcggt 1201
Ser Thr Ser Thr Pro Phe Leu Ser Leu Pro Glu
                235                 240
gccgctttct tgttgccgca tctcccctca gattcaacct agagctagat gcgttttacc 1261
aggtctaaca ttgactgcct ctgcctgtcg catgagaaca ttaacacaag cgattgtatg 1321
acttcctctg tccgtgacta gtgggtctg agctactcgt aggtgcgtaa ggctccagtg  1381
tttctgaaat tgatcttgaa ttactgtgat acgacatgat agtccctctc acccagtgca 1441
atgacaataa aggccttgaa aagtctcact tttattgaga aaataaaaat cgttccacgg 1501
gacagtccct cttctttata aaatgaccct atccttgaaa aggaggtgtg ttaagttgta 1561
accagtacac acttgaaatg atggtaagtt cgcttcggtt cagaatgtgt tctttctgac 1621
aaataaacag aataaaaaaa aaaaaaaaaa a                                1652
```

<210> SEQ ID NO 149
<211> LENGTH: 1140
<212> TYPE: DNA
<213> ORGANISM: Bos taurus
<220> FEATURE:
<221> NAME/KEY: CDS
<222> LOCATION: (1)...(840)
<221> NAME/KEY: variation
<222> LOCATION: (6)...(6)
<223> OTHER INFORMATION: N is unknown.
<220> FEATURE:
<221> NAME/KEY: variation
<222> LOCATION: (2)...(2)
<223> OTHER INFORMATION: Xaa is unknown.

<400> SEQUENCE: 149

```
cat can gtg tgg gcg gcg aaa gcc ggg ggc ttg aag aag gac tcg ctg     48
His Xaa Val Trp Ala Ala Lys Ala Gly Gly Leu Lys Lys Asp Ser Leu
1               5                   10                  15
ctc acc gtg cgc ctg ggc gcc tgg ggc cac ccc gcc ttc ccc tcc tgc     96
Leu Thr Val Arg Leu Gly Ala Trp Gly His Pro Ala Phe Pro Ser Cys
            20                  25                  30
ggg cgc ctc aag gag gac agc agg tac atc ttc ttc atg gag ccc gag    144
Gly Arg Leu Lys Glu Asp Ser Arg Tyr Ile Phe Phe Met Glu Pro Glu
        35                  40                  45
gcc aac agc agc ggc ggg ccc ggc cgc ctt ccg agc ctc ctt ccc ccc    192
Ala Asn Ser Ser Gly Gly Pro Gly Arg Leu Pro Ser Leu Leu Pro Pro
50                  55                  60
tct cga gac ggg ccg gaa cct caa gaa gga ggt cag ccg ggt gct gtg    240
Ser Arg Asp Gly Pro Glu Pro Gln Glu Gly Gly Gln Pro Gly Ala Val
65                  70                  75                  80
caa cgg tgc gcc ttg cct ccc cgc ttg aaa gag atg aag agt cag gag    288
Gln Arg Cys Ala Leu Pro Pro Arg Leu Lys Glu Met Lys Ser Gln Glu
                85                  90                  95
tct gtg gca ggt tcc aaa cta gtg ctt cgg tgc gag acc tct tct gaa    336
Ser Val Ala Gly Ser Lys Leu Val Leu Arg Cys Glu Thr Ser Ser Glu
            100                 105                 110
tac tcc tct ctc aag ttc aag tgg ttc aag aat ggg agt gaa tta agc    384
Tyr Ser Ser Leu Lys Phe Lys Trp Phe Lys Asn Gly Ser Glu Leu Ser
        115                 120                 125
```

```
    cga aag aac aaa cca gaa aac atc aag ata cag aaa agg ccg ggg aag        432
    Arg Lys Asn Lys Pro Glu Asn Ile Lys Ile Gln Lys Arg Pro Gly Lys
            130                 135                 140
    tca gaa ctt cgc att agc aaa gcg tca ctg gct gat tct gga gaa tat        480
    Ser Glu Leu Arg Ile Ser Lys Ala Ser Leu Ala Asp Ser Gly Glu Tyr
    145                 150                 155                 160
    atg tgc aaa gtg atc agc aaa cta gga aat gac agt gcc tct gcc aac        528
    Met Cys Lys Val Ile Ser Lys Leu Gly Asn Asp Ser Ala Ser Ala Asn
                    165                 170                 175
    atc acc att gtg gag tca aac gcc aca tcc aca tct aca gct ggg aca        576
    Ile Thr Ile Val Glu Ser Asn Ala Thr Ser Thr Ser Thr Ala Gly Thr
                180                 185                 190
    agc cat ctt gtc aag tgt gca gag aag gag aaa act ttc tgt gtg aat        624
    Ser His Leu Val Lys Cys Ala Glu Lys Glu Lys Thr Phe Cys Val Asn
            195                 200                 205
    gga ggc gag tgc ttc atg gtg aaa gac ctt tca aat ccc tca aga tac        672
    Gly Gly Glu Cys Phe Met Val Lys Asp Leu Ser Asn Pro Ser Arg Tyr
        210                 215                 220
    ttg tgc aag tgc caa cct gga ttc act gga gcg aga tgt act gag aat        720
    Leu Cys Lys Cys Gln Pro Gly Phe Thr Gly Ala Arg Cys Thr Glu Asn
    225                 230                 235                 240
    gtg ccc atg aaa gtc caa acc caa gaa aag tgc cca aat gag ttt act        768
    Val Pro Met Lys Val Gln Thr Gln Glu Lys Cys Pro Asn Glu Phe Thr
                    245                 250                 255
    ggt gat cgc tgc caa aac tac gta atg gcc agc ttc tac agt acg tcc        816
    Gly Asp Arg Cys Gln Asn Tyr Val Met Ala Ser Phe Tyr Ser Thr Ser
                260                 265                 270
    act ccc ttt ctg tct ctg cct gaa tagcgcatct cagtcggtgc cgctttcttg       870
    Thr Pro Phe Leu Ser Leu Pro Glu
            275                 280
    ttgccgcatc tcccctcaga ttccncctag agctagatgc gttttaccag gtctaacatt       930
    gactgcctct gcctgtcgca tgagaacatt aacacaagcg attgtatgac ttcctctgtc       990
    cgtgactagt gggctctgag ctactcgtag gtgcgtaagg ctccagtgtt tctgaaattg      1050
    atcttgaatt actgtgtatac gacatgatag tccctctcac ccagtgcaat gacaataaag     1110
    gccttgaaaa gtcaaaaaaa aaaaaaaaaa                                        1140

<210> SEQ ID NO 150
<211> LENGTH: 1764
<212> TYPE: DNA
<213> ORGANISM: Bos taurus
<220> FEATURE:
<221> NAME/KEY: CDS
<222> LOCATION: (2)...(1681)

<400> SEQUENCE: 150 g aag tca gaa ctt cgc att agc aaa gcg tca ctg gct gat tct gga gaa       49
      Lys Ser Glu Leu Arg Ile Ser Lys Ala Ser Leu Ala Asp Ser Gly Glu
      1               5                  10                  15
    tat atg tgc aaa gtg atc agc aaa cta gga aat gac agt gcc tct gcc        97
    Tyr Met Cys Lys Val Ile Ser Lys Leu Gly Asn Asp Ser Ala Ser Ala
                    20                  25                  30
    aac atc acc att gtg gag tca aac gcc aca tcc aca tct aca gct ggg       145
    Asn Ile Thr Ile Val Glu Ser Asn Ala Thr Ser Thr Ser Thr Ala Gly
                35                  40                  45
    aca agc cat ctt gtc aag tgt gca gag aag gag aaa act ttc tgt gtg       193
    Thr Ser His Leu Val Lys Cys Ala Glu Lys Glu Lys Thr Phe Cys Val
        50                  55                  60
    aat gga ggc gac tgc ttc atg gtg aaa gac ctt tca aat ccc tca aga       241
    Asn Gly Gly Asp Cys Phe Met Val Lys Asp Leu Ser Asn Pro Ser Arg
    65                  70                  75                  80
    tac ttg tgc aag tgc caa cct gga ttc act gga gcg aga tgt act gag       289
    Tyr Leu Cys Lys Cys Gln Pro Gly Phe Thr Gly Ala Arg Cys Thr Glu
                    85                  90                  95
    aat gtg ccc atg aaa gtc caa acc caa gaa aaa gcg gag gag ctc tac       337
    Asn Val Pro Met Lys Val Gln Thr Gln Glu Lys Ala Glu Glu Leu Tyr
                100                 105                 110
    cag aag aga gtg ctc acc att acc ggc att tgc atc gcg ctg ctc gtg       385
    Gln Lys Arg Val Leu Thr Ile Thr Gly Ile Cys Ile Ala Leu Leu Val
        115                 120                 125
    gtt ggc atc atg tgt gtg gtg tac tgc aaa acc aag aaa caa cgg            433
    Val Gly Ile Met Cys Val Val Tyr Cys Lys Thr Lys Lys Gln Arg
    130                 135                 140
    aaa aag ctt cat gac cgg ctt cgg cag agc ctt cgg tct gaa aga aac       481
    Lys Lys Leu His Asp Arg Leu Arg Gln Ser Leu Arg Ser Glu Arg Asn
    145                 150                 155                 160
    acc atg atg aac gta gcc aac ggg ccc cac cac ccc aat ccg ccc ccc       529
    Thr Met Met Asn Val Ala Asn Gly Pro His His Pro Asn Pro Pro Pro
```

-continued

```
                     165                 170                 175
        gag aac gtg cag ctg gtg aat caa tac gta tct aaa aat gtc atc tct     577
        Glu Asn Val Gln Leu Val Asn Gln Tyr Val Ser Lys Asn Val Ile Ser
                    180                 185                 190
        agc gag cat att gtt gag aga gag gcg gag agc tct ttt tcc acc agt     625
        Ser Glu His Ile Val Glu Arg Glu Ala Glu Ser Ser Phe Ser Thr Ser
                    195                 200                 205
        cac tac act tcg aca gct cat cat tcc act act gtc act cag act ccc     673
        His Tyr Thr Ser Thr Ala His His Ser Thr Thr Val Thr Gln Thr Pro
                    210                 215                 220
        agt cac agc tgg agc aat gga cac act gaa agc atc att tcg gaa agc     721
        Ser His Ser Trp Ser Asn Gly His Thr Glu Ser Ile Ile Ser Glu Ser
        225                 230                 235                 240
        cac tct gtc atc gtg atg tca tcc gta gaa aac agt agg cac agc agc     769
        His Ser Val Ile Val Met Ser Ser Val Glu Asn Ser Arg His Ser Ser
                    245                 250                 255
        ccg act ggg ggc ccg aga gga cgt ctc aat ggc ttg gga ggc cct cgt     817
        Pro Thr Gly Gly Pro Arg Gly Arg Leu Asn Gly Leu Gly Gly Pro Arg
                    260                 265                 270
        gaa tgt aac agc ttc ctc agg cat gcc aga gaa acc cct gac tcc tac     865
        Glu Cys Asn Ser Phe Leu Arg His Ala Arg Glu Thr Pro Asp Ser Tyr
                    275                 280                 285
        cga gac tct cct cat agt gaa aga cat aac ctt ata gct gag cta agg     913
        Arg Asp Ser Pro His Ser Glu Arg His Asn Leu Ile Ala Glu Leu Arg
                    290                 295                 300
        aga aac aag gcc cac aga tcc aaa tgc atg cag atc cag ctt tcc gca     961
        Arg Asn Lys Ala His Arg Ser Lys Cys Met Gln Ile Gln Leu Ser Ala
        305                 310                 315                 320
        act cat ctt aga gct tct tcc att ccc cat tgg gct tca ttc tct aag    1009
        Thr His Leu Arg Ala Ser Ser Ile Pro His Trp Ala Ser Phe Ser Lys
                    325                 330                 335
        acc cct tgg cct tta gga agg tat gta tca gca atg acc acc ccg gct    1057
        Thr Pro Trp Pro Leu Gly Arg Tyr Val Ser Ala Met Thr Thr Pro Ala
                    340                 345                 350
        cgt atg tca cct gta gat ttc cac acg cca agc tcc ccc aag tca ccc    1105
        Arg Met Ser Pro Val Asp Phe His Thr Pro Ser Ser Pro Lys Ser Pro
                    355                 360                 365
        cct tcg gaa atg tcc ccg ccc gtg tcc agc acg acg gtc tcc atg ccc    1153
        Pro Ser Glu Met Ser Pro Pro Val Ser Ser Thr Thr Val Ser Met Pro
                    370                 375                 380
        tcc atg gcg gtc agt ccc ttc gtg gaa gag gag aga ccc ctg ctc ctt    1201
        Ser Met Ala Val Ser Pro Phe Val Glu Glu Glu Arg Pro Leu Leu Leu
        385                 390                 395                 400
        gtg acg cca cca cgg ctg cgg gag aag tat gac cac cac gcc cag caa    1249
        Val Thr Pro Pro Arg Leu Arg Glu Lys Tyr Asp His His Ala Gln Gln
                    405                 410                 415
        ttc aac tcg ttc cac tgc aac ccc gcg cat gag agc aac agc ctg ccc    1297
        Phe Asn Ser Phe His Cys Asn Pro Ala His Glu Ser Asn Ser Leu Pro
                    420                 425                 430
        ccc agc ccc ttg agg ata gtg gag gat gag gaa tat gaa acg acc cag    1345
        Pro Ser Pro Leu Arg Ile Val Glu Asp Glu Glu Tyr Glu Thr Thr Gln
                    435                 440                 445
        gag tac gaa cca gct caa gag ccg gtt aag aaa ctc acc aac agc agc    1393
        Glu Tyr Glu Pro Ala Gln Glu Pro Val Lys Lys Leu Thr Asn Ser Ser
                    450                 455                 460
        cgg cgg gcc aaa aga acc aag ccc aat ggt cac att gcc cac agg ttg    1441
        Arg Arg Ala Lys Arg Thr Lys Pro Asn Gly His Ile Ala His Arg Leu
        465                 470                 475                 480
        gaa atg gac aac aac aca ggc gct gac agc agt aac tca gag agc gaa    1489
        Glu Met Asp Asn Asn Thr Gly Ala Asp Ser Ser Asn Ser Glu Ser Glu
                    485                 490                 495
        aca gag gat gaa aga gta gga gaa gat acg cct ttc ctg gcc ata cag    1537
        Thr Glu Asp Glu Arg Val Gly Glu Asp Thr Pro Phe Leu Ala Ile Gln
                    500                 505                 510
        aac ccc ctg gca gcc agt ctc gag gcg gcc cct gcc ttc cgc ctg gtc    1585
        Asn Pro Leu Ala Ala Ser Leu Glu Ala Ala Pro Ala Phe Arg Leu Val
                    515                 520                 525
        gac agc agg act aac cca aca ggc ggc ttc tct ccg cag gaa gaa ttg    1633
        Asp Ser Arg Thr Asn Pro Thr Gly Gly Phe Ser Pro Gln Glu Glu Leu
                    530                 535                 540
        cag gcc agg ctc tcc ggt gta atc gct aac caa gac cct atc gct gtc    1681
        Gln Ala Arg Leu Ser Gly Val Ile Ala Asn Gln Asp Pro Ile Ala Val
        545                 550                 555                 560
        taaaaccgaa atacacccat agattcacct gtaaaacttt attttatata ataaagtatt   1741
        ccaccttaaa ttaaacaaaa aaa                                            1764
```

<210> SEQ ID NO 151
<211> LENGTH: 50

```
<212> TYPE: PRT
<213> ORGANISM: Bos taurus

<400> SEQUENCE: 151

Lys Cys Ala Glu Lys Glu Lys Thr Phe Cys Val Asn Gly Gly Glu Cys
       1               5                  10                  15
     Phe Met Val Lys Asp Leu Ser Asn Pro Ser Arg Tyr Leu Cys Lys Cys
                  20                  25                  30
     Pro Asn Glu Phe Thr Gly Asp Arg Cys Gln Asn Tyr Val Met Ala Ser
              35                  40                  45
     Phe Tyr
         50

<210> SEQ ID NO 152
<211> LENGTH: 50
<212> TYPE: PRT
<213> ORGANISM: Bos taurus

<400> SEQUENCE: 152

Lys Cys Ala Glu Lys Glu Lys Thr Phe Cys Val Asn Gly Gly Glu Cys
       1               5                  10                  15
     Phe Met Val Lys Asp Leu Ser Asn Pro Ser Arg Tyr Leu Cys Lys Cys
                  20                  25                  30
     Gln Pro Gly Phe Thr Gly Ala Arg Cys Thr Glu Asn Val Pro Met Lys
              35                  40                  45
     Val Gln
         50

<210> SEQ ID NO 153
<211> LENGTH: 46
<212> TYPE: PRT
<213> ORGANISM: Homo sapiens

<400> SEQUENCE: 153

Glu Cys Leu Arg Lys Tyr Lys Asp Phe Cys Ile His Gly Glu Cys Lys
       1               5                  10                  15
     Tyr Val Lys Glu Leu Arg Ala Pro Ser Cys Lys Cys Gln Gln Glu Tyr
                  20                  25                  30
     Phe Gly Glu Arg Cys Gly Glu Lys Ser Asn Lys Thr His Ser
              35                  40                  45

<210> SEQ ID NO 154
<211> LENGTH: 198
<212> TYPE: DNA
<213> ORGANISM: Homo sapiens

<400> SEQUENCE: 154
agccatcttg tcaagtgtgc agagaaggag aaaactttct gtgtgaatgg aggcgagtgc      60
     ttcatggtga agacctttc aaatccctca agatacttgt gcaagtgccc aaatgagttt     120
     actggtgatc gctgccaaaa ctacgtaatg gccagcttct acagtacgtc cactcccttt     180
     ctgtctctgc ctgaatag                                                  198

<210> SEQ ID NO 155
<211> LENGTH: 192
<212> TYPE: DNA
<213> ORGANISM: Homo sapiens

<400> SEQUENCE: 155
agccatcttg tcaagtgtgc agagaaggag aaaactttct gtgtgaatgg aggcgagtgc      60
     ttcatggtga agacctttc aaatccctca agatacttgt gcaagtgcca acctggattc     120
     actggagcga gatgtactga gaatgtgccc atgaaagtcc aaacccaaga aaaagcggag     180
     gagctctact aa                                                        192

<210> SEQ ID NO 156
<211> LENGTH: 183
<212> TYPE: DNA
<213> ORGANISM: Homo sapiens

<400> SEQUENCE: 156
```

```
                agccatcttg tcaagtgtgc agagaaggag aaaactttct gtgtgaatgg aggcgagtgc        60
                ttcatggtga agacctttc aaatccctca agatacttgt gcaagtgccc aaatgagttt       120
                actggtgatc gctgccaaaa ctacgtaatg gccagcttct acaaagcgga ggagctctac       180
                taa                                                                     183

<210> SEQ ID NO 157
<211> LENGTH: 210
<212> TYPE: DNA
<213> ORGANISM: Homo sapiens

<400> SEQUENCE: 157
agccatcttg tcaagtgtgc agagaaggag aaaactttct gtgtgaatgg aggcgagtgc        60
                ttcatggtga agacctttc aaatccctca agatacttgt gcaagtgccc aaatgagttt       120
                actggtgatc gctgccaaaa ctacgtaatg gccagcttct acaagcatct tgggattgaa       180
                tttatggaga aagcggagga gctctactaa                                         210

<210> SEQ ID NO 158
<211> LENGTH: 267
<212> TYPE: DNA
<213> ORGANISM: Homo sapiens

<400> SEQUENCE: 158
agccatcttg tcaagtgtgc agagaaggag aaaactttct gtgtgaatgg aggcgagtgc        60
                ttcatggtga agacctttc aaatccctca agatacttgt gcaagtgcca acctggattc       120
                actggagcga gatgtactga gaatgtgccc atgaaagtcc aaacccaaga aaagtgccca       180
                aatgagttta ctggtgatcg ctgccaaaac tacgtaatgg ccagcttcta cagtacgtcc       240
                actccctttc tgtctctgcc tgaatag                                            267

<210> SEQ ID NO 159
<211> LENGTH: 252
<212> TYPE: DNA
<213> ORGANISM: Homo sapiens

<400> SEQUENCE: 159
agccatcttg tcaagtgtgc agagaaggag aaaactttct gtgtgaatgg aggcgagtgc        60
                ttcatggtga agacctttc aaatccctca agatacttgt gcaagtgcca acctggattc       120
                actggagcga gatgtactga gaatgtgccc atgaaagtcc aaacccaaga aaagtgccca       180
                aatgagttta ctggtgatcg ctgccaaaac tacgtaatgg ccagcttcta caaagcggag       240
                gagctctact aa                                                            252

<210> SEQ ID NO 160
<211> LENGTH: 128
<212> TYPE: DNA
<213> ORGANISM: Bos taurus
<220> FEATURE:
<221> NAME/KEY: CDS
<222> LOCATION: (3)...(125)

<400> SEQUENCE: 160 cc aca tcc aca tct aca gct ggg aca agc cat ctt gtc aag tgt gca        47
               Thr Ser Thr Ser Thr Ala Gly Thr Ser His Leu Val Lys Cys Ala
                1               5                  10                  15
            gag aag gag aaa act ttc tgt gtg aat gga ggc gag tgc ttc atg gtg        95
            Glu Lys Glu Lys Thr Phe Cys Val Asn Gly Gly Glu Cys Phe Met Val
                            20                  25                  30
            aaa gac ctt tca aat ccc tca aga tac ttg tgc                            128
            Lys Asp Leu Ser Asn Pro Ser Arg Tyr Leu
                        35                  40

<210> SEQ ID NO 161
<211> LENGTH: 141
<212> TYPE: DNA
<213> ORGANISM: Bos taurus
<220> FEATURE:
<221> NAME/KEY: CDS
<222> LOCATION: (2)...(139)

<400> SEQUENCE: 161
```

```
      a cat aac ctt ata gct gag cta agg aga aac aag gcc cac aga tcc aaa      49
        His Asn Leu Ile Ala Glu Leu Arg Arg Asn Lys Ala His Arg Ser Lys
          1               5                  10                  15
      tgc atg cag atc cag ctt tcc gca act cat ctt aga gct tct tcc att         97
      Cys Met Gln Ile Gln Leu Ser Ala Thr His Leu Arg Ala Ser Ser Ile
                       20                  25                  30
      ccc cat tgg gct tca ttc tct aag acc cct tgg cct tta gga                139
      Pro His Trp Ala Ser Phe Ser Lys Thr Pro Trp Pro Leu Gly
                   35                  40                  45
      ag                                                                     141
```

<210> SEQ ID NO 162
<211> LENGTH: 24
<212> TYPE: PRT
<213> ORGANISM: Homo sapiens
<220> FEATURE:
<221> NAME/KEY: VARIANT
<222> LOCATION: (15)...(22)
<223> OTHER INFORMATION: Xaa in positions 15 and 22 is unknown.

<400> SEQUENCE: 162

```
    Ala Ala Glu Lys Glu Lys Thr Phe Cys Val Asn Gly Gly Glu Xaa Phe
     1               5                  10                  15
    Met Val Lys Asp Leu Xaa Asn Pro
                    20
```

<210> SEQ ID NO 163
<211> LENGTH: 745
<212> TYPE: DNA
<213> ORGANISM: Homo sapiens
<220> FEATURE:
<221> NAME/KEY: CDS
<222> LOCATION: (1)...(744)

<400> SEQUENCE: 163

```
      atg aga tgg cga cgc gcc ccg cgc cgc tcc ggg cgt ccc ggc ccc cgg         48
      Met Arg Trp Arg Arg Ala Pro Arg Arg Ser Gly Arg Pro Gly Pro Arg
        1               5                  10                  15
      gcc cag cgc ccc ggt tcc gcc gcc cgc tcg tcg ccg ccg ctg ccg ctg         96
      Ala Gln Arg Pro Gly Ser Ala Ala Arg Ser Ser Pro Pro Leu Pro Leu
                       20                  25                  30
      ctg cca cta ctg ctg ctg ctg ggg acc gcg gcc ctg gcg ccg ggg gcg        144
      Leu Pro Leu Leu Leu Leu Leu Gly Thr Ala Ala Leu Ala Pro Gly Ala
                   35                  40                  45
      gcg gcc ggc aac gag gcg gct ccc gcg ggg gcc tcg gtg tgc tac tcg        192
      Ala Ala Gly Asn Glu Ala Ala Pro Ala Gly Ala Ser Val Cys Tyr Ser
           50                  55                  60
      tcc ccg ccc agc gtg gga tcg gtg cag gag cta gct cag cgc gcc gcg        240
      Ser Pro Pro Ser Val Gly Ser Val Gln Glu Leu Ala Gln Arg Ala Ala
       65                  70                  75                  80
      gtg gtg atc gag gga aag gtg cac ccg cag cgg cgg cag cag ggg gca        288
      Val Val Ile Glu Gly Lys Val His Pro Gln Arg Arg Gln Gln Gly Ala
                       85                  90                  95
      ctc gac agg aag gcg gcg gcg gcg ggc gag gca ggg gcg tgg ggc            336
      Leu Asp Arg Lys Ala Ala Ala Ala Gly Glu Ala Gly Ala Trp Gly
                      100                 105                 110
      ggc gat cgc gag ccg cca gcc gcg ggc cca cgg gcg ctg ggg ccg ccc        384
      Gly Asp Arg Glu Pro Pro Ala Ala Gly Pro Arg Ala Leu Gly Pro Pro
                  115                 120                 125
      gcc gag gag ccg ctg ctc gcc gcc aac ggg acc gtg ccc tct tgg ccc        432
      Ala Glu Glu Pro Leu Leu Ala Ala Asn Gly Thr Val Pro Ser Trp Pro
              130                 135                 140
      acc gcc ccg gtg ccc agc gcc ggc gag ccc ggg gag gag gcg ccc tat        480
      Thr Ala Pro Val Pro Ser Ala Gly Glu Pro Gly Glu Glu Ala Pro Tyr
      145                 150                 155                 160
      ctg gtg aag gtg cac cag gtg tgg gcg gtg aaa gcc ggg ggc ttg aag        528
      Leu Val Lys Val His Gln Val Trp Ala Val Lys Ala Gly Gly Leu Lys
                      165                 170                 175
      aag gac tcg ctg ctc acc gtg cgc ctg ggg acc tgg ggc cac ccc gcc        576
      Lys Asp Ser Leu Leu Thr Val Arg Leu Gly Thr Trp Gly His Pro Ala
                  180                 185                 190
      ttc ccc tcc tgc ggg agg ctc aag gag gac agc agg tac atc ttc ttc        624
      Phe Pro Ser Cys Gly Arg Leu Lys Glu Asp Ser Arg Tyr Ile Phe Phe
              195                 200                 205
      atg gag ccc gac gcc aac agc acc agc cgc gcg ccg gcc gcc ttc cga        672
```

```
        Met Glu Pro Asp Ala Asn Ser Thr Ser Arg Ala Pro Ala Ala Phe Arg
            210                 215                 220
        gcc tct ttc ccc cct ctg gag acg ggc cgg aac ctc aag aag gag gtc    720
        Ala Ser Phe Pro Pro Leu Glu Thr Gly Arg Asn Leu Lys Lys Glu Val
        225                 230                 235                 240
        agc cgg gtg ctg tgc aag cgg tgc g                                  745
        Ser Arg Val Leu Cys Lys Arg Cys
                        245
```

<210> SEQ ID NO 164
<211> LENGTH: 12
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lys or Arg.

<400> SEQUENCE: 164

```
        Xaa Ala Leu Ala Ala Ala Gly Tyr Asp Val Glu Lys
        1               5                   10
```

<210> SEQ ID NO 165
<211> LENGTH: 5
<212> TYPE: PRT
<213> ORGANISM: Bos taurus
<220> FEATURE:
<221> NAME/KEY: VARIANT
<222> LOCATION: (1)...(1)
<223> OTHER INFORMATION: Xaa in position 1 is Lys or Arg.

<400> SEQUENCE: 165

```
        Xaa Leu Val Leu Arg
        1               5
```

<210> SEQ ID NO 166
<211> LENGTH: 11
<212> TYPE: PRT
<213> ORGANISM: Bos taurus
<220> FEATURE:
<221> NAME/KEY: VARIANT
<222> LOCATION: (1)...(3)
<223> OTHER INFORMATION: Xaa in position 1 is Lys or Arg; Xaa in positions
      2 and 3 is unknown.

<400> SEQUENCE: 166

```
        Xaa Xaa Xaa Tyr Pro Gly Gln Ile Thr Ser Asn
        1               5                   10
```

<210> SEQ ID NO 167
<211> LENGTH: 60
<212> TYPE: DNA
<213> ORGANISM: Homo sapiens
<220> FEATURE:
<221> NAME/KEY: variation
<222> LOCATION: (25)...(36)
<223> OTHER INFORMATION: N in positions 25 and 31 is unknown.

<400> SEQUENCE: 167

```
        atagggaagg gcgggggaag ggtcnccctc ngcagggccg ggcttgcctc tggagcctct    60
```

<210> SEQ ID NO 168
<211> LENGTH: 18
<212> TYPE: DNA
<213> ORGANISM: Homo sapiens
<220> FEATURE:
<221> NAME/KEY: variation
<222> LOCATION: (16)...(16)
<223> OTHER INFORMATION: N in position 16 is unknown.

-continued

<400> SEQUENCE: 168
tttacacata tattcncc                                                        18

<210> SEQ ID NO 169
<211> LENGTH: 21
<212> TYPE: PRT
<213> ORGANISM: Bos taurus

<400> SEQUENCE: 169

Glu Thr Gln Pro Asp Pro Gly Gln Ile Leu Lys Lys Val Pro Met Val
  1               5                  10                  15
Ile Gly Ala Tyr Thr
             20

<210> SEQ ID NO 170
<211> LENGTH: 422
<212> TYPE: PRT
<213> ORGANISM: Homo sapiens

<400> SEQUENCE: 170

Met Arg Trp Arg Arg Ala Pro Arg Ser Gly Arg Pro Gly Pro Arg
  1               5                  10                  15
Ala Gln Arg Pro Gly Ser Ala Ala Arg Ser Ser Pro Pro Leu Pro Leu
                 20                  25                  30
Leu Pro Leu Leu Leu Leu Leu Gly Thr Ala Ala Leu Ala Pro Gly Ala
             35                  40                  45
Ala Ala Gly Asn Glu Ala Ala Pro Ala Gly Ala Ser Val Cys Tyr Ser
         50                  55                  60
Ser Pro Pro Ser Val Gly Ser Val Gln Glu Leu Ala Gln Arg Ala Ala
 65                  70                  75                  80
Val Val Ile Glu Gly Lys Val His Pro Gln Arg Arg Gln Gln Gly Ala
                 85                  90                  95
Leu Asp Arg Lys Ala Ala Ala Ala Gly Glu Ala Gly Ala Trp Gly
            100                 105                 110
Gly Asp Arg Glu Pro Pro Ala Ala Gly Pro Arg Ala Leu Gly Pro Pro
            115                 120                 125
Ala Glu Glu Pro Leu Leu Ala Ala Asn Gly Thr Val Pro Ser Trp Pro
        130                 135                 140
Thr Ala Pro Val Pro Ser Ala Gly Glu Pro Gly Glu Ala Pro Tyr
145                 150                 155                 160
Leu Val Lys Val His Gln Val Trp Ala Val Lys Ala Gly Gly Leu Lys
                165                 170                 175
Lys Asp Ser Leu Leu Thr Val Arg Leu Gly Thr Trp Gly His Pro Ala
            180                 185                 190
Phe Pro Ser Cys Gly Arg Leu Lys Glu Asp Ser Arg Tyr Ile Phe Phe
        195                 200                 205
Met Glu Pro Asp Ala Asn Ser Thr Ser Arg Ala Pro Ala Ala Phe Arg
    210                 215                 220
Ala Ser Phe Pro Pro Leu Glu Thr Gly Arg Asn Leu Lys Lys Glu Val
225                 230                 235                 240
Ser Arg Val Leu Cys Lys Arg Cys Ala Leu Pro Pro Gln Leu Lys Glu
                245                 250                 255
Met Lys Ser Gln Glu Ser Ala Ala Gly Ser Lys Leu Val Leu Arg Cys
            260                 265                 270
Glu Thr Ser Ser Glu Tyr Ser Ser Leu Arg Phe Lys Trp Phe Lys Asn
        275                 280                 285
Gly Asn Glu Leu Asn Arg Lys Asn Lys Pro Gln Asn Ile Lys Ile Gln
    290                 295                 300
Lys Lys Pro Gly Lys Ser Glu Leu Arg Ile Asn Lys Ala Ser Leu Ala
305                 310                 315                 320
Asp Ser Gly Glu Tyr Met Cys Lys Val Ile Ser Lys Leu Gly Asn Asp
                325                 330                 335
Ser Ala Ser Ala Asn Ile Thr Ile Val Glu Ser Asn Ala Thr Ser Thr
            340                 345                 350
Ser Thr Thr Gly Thr Ser His Leu Val Lys Cys Ala Glu Lys Glu Lys
        355                 360                 365
Thr Phe Cys Val Asn Gly Gly Glu Cys Phe Met Val Lys Asp Leu Ser
    370                 375                 380
Asn Pro Ser Arg Tyr Leu Cys Lys Cys Pro Asn Glu Phe Thr Gly Asp
385                 390                 395                 400
Arg Cys Gln Asn Tyr Val Met Ala Ser Phe Tyr Ser Thr Ser Thr Pro
                405                 410                 415
Phe Leu Ser Leu Pro Glu
            420

<210> SEQ ID NO 171
<211> LENGTH: 69
<212> TYPE: PRT
<213> ORGANISM: Homo sapiens

<400> SEQUENCE: 171

```
Met Ser Glu Arg Lys Glu Gly Arg Gly Lys Gly Lys Lys
  1               5                  10              15
Glu Arg Gly Ser Gly Lys Lys Pro Glu Ser Ala Ala Gly Ser Gln Ser
              20                  25                  30
Pro Arg Glu Ile Ile Thr Gly Met Pro Ala Ser Thr Glu Gly Ala Tyr
          35                  40                  45
Val Ser Ser Glu Ser Pro Ile Arg Ile Ser Val Ser Thr Glu Gly Ala
      50                  55                  60
Asn Thr Ser Ser Ser
 65
```

<210> SEQ ID NO 172
<211> LENGTH: 19
<212> TYPE: PRT
<213> ORGANISM: Bos taurus

<400> SEQUENCE: 172

```
Arg Lys Gly Asp Val Pro Gly Pro Arg Val Lys Ser Ser Arg Ser Thr
  1               5                  10                  15
Thr Thr Ala
```

<210> SEQ ID NO 173
<211> LENGTH: 231
<212> TYPE: DNA
<213> ORGANISM: Homo sapiens
<220> FEATURE:
<221> NAME/KEY: CDS
<222> LOCATION: (132)...(231)

<400> SEQUENCE: 173

```
cgcgagcgcc tcagcgcggc cgctcgctct cccctcgag ggacaaactt ttcccaaacc      60
cgatccgagc ccttggacca aactcgcctg cgccgagagc cgtccgcgta gagcgctccg     120
tctccggcga g atg tcc gag cgc aaa gaa ggc aga ggc aaa ggg aag ggc     170
            Met Ser Glu Arg Lys Glu Gly Arg Gly Lys Gly Lys Gly
              1               5                  10
aag aag aag gag cga ggc tcc ggc aag aag ccg gag tcc gcg gcg ggc       218
Lys Lys Lys Glu Arg Gly Ser Gly Lys Lys Pro Glu Ser Ala Ala Gly
         15                  20                  25
agc cag agc cca g                                                    231
Ser Gln Ser Pro
         30
```

<210> SEQ ID NO 174
<211> LENGTH: 178
<212> TYPE: DNA
<213> ORGANISM: Homo sapiens
<220> FEATURE:
<221> NAME/KEY: CDS
<222> LOCATION: (3)...(178)

<400> SEQUENCE: 174

```
cc ttg cct ccc cga ttg aaa gag atg aaa agc cag gaa tcg gct gca        47
   Leu Pro Pro Arg Leu Lys Glu Met Lys Ser Gln Glu Ser Ala Ala
     1               5                  10                  15
ggt tcc aaa cta gtc ctt cgg tgt gaa acc agt tct gaa tac tcc tct       95
Gly Ser Lys Leu Val Leu Arg Cys Glu Thr Ser Ser Glu Tyr Ser Ser
              20                  25                  30
ctc aga ttc aag tgg ttc aag aat ggg aat gaa ttg aat cga aaa aac      143
Leu Arg Phe Lys Trp Phe Lys Asn Gly Asn Glu Leu Asn Arg Lys Asn
          35                  40                  45
aaa cca caa aat atc aag ata caa aaa aag cca gg                       178
Lys Pro Gln Asn Ile Lys Ile Gln Lys Lys Pro
         50                  55
```

```
<210> SEQ ID NO 175
<211> LENGTH: 122
<212> TYPE: DNA
<213> ORGANISM: Homo sapiens
<220> FEATURE:
<221> NAME/KEY: CDS
<222> LOCATION: (2)...(122)

<400> SEQUENCE: 175 g aag tca gaa ctt cgc att aac aaa gca tca ctg gct gat tct gga gag        49
      Lys Ser Glu Leu Arg Ile Asn Lys Ala Ser Leu Ala Asp Ser Gly Glu
       1               5                  10                  15
    tat atg tgc aaa gtg atc agc aaa tta gga aat gac agt gcc tct gcc          97
    Tyr Met Cys Lys Val Ile Ser Lys Leu Gly Asn Asp Ser Ala Ser Ala
                 20                  25                  30
    aat atc acc atc gtg gaa tca aac g                                        122
    Asn Ile Thr Ile Val Glu Ser Asn
             35                  40

<210> SEQ ID NO 176
<211> LENGTH: 102
<212> TYPE: DNA
<213> ORGANISM: Homo sapiens

<400> SEQUENCE: 176
agatcatcac tggtatgcca gcctcaactg aaggagcata tgtgtcttca gagtctccca         60
    ttagaatatc agtatccaca gaaggagcaa atacttcttc at                           102

<210> SEQ ID NO 177
<211> LENGTH: 128
<212> TYPE: DNA
<213> ORGANISM: Homo sapiens
<220> FEATURE:
<221> NAME/KEY: CDS
<222> LOCATION: (3)...(128)

<400> SEQUENCE: 177 ct aca tct aca tcc acc act ggg aca agc cat ctt gta aaa tgt gcg           47
       Thr Ser Thr Ser Thr Thr Gly Thr Ser His Leu Val Lys Cys Ala
        1               5                  10                  15
    gag aag gag aaa act ttc tgt gtg aat gga ggg gag tgc ttc atg gtg          95
    Glu Lys Glu Lys Thr Phe Cys Val Asn Gly Gly Glu Cys Phe Met Val
                 20                  25                  30
    aaa gac ctt tca aac ccc tcg aga tac ttg tgc                              128
    Lys Asp Leu Ser Asn Pro Ser Arg Tyr Leu Cys
                 35                  40

<210> SEQ ID NO 178
<211> LENGTH: 69
<212> TYPE: DNA
<213> ORGANISM: Homo sapiens
<220> FEATURE:
<221> NAME/KEY: CDS
<222> LOCATION: (1)...(69)

<400> SEQUENCE: 178 aag tgc caa cct gga ttc act gga gca aga tgt act gag aat gtg ccc          48
    Lys Cys Gln Pro Gly Phe Thr Gly Ala Arg Cys Thr Glu Asn Val Pro
     1               5                  10                  15
    atg aaa gtc caa aac caa gaa                                              69
    Met Lys Val Gln Asn Gln Glu
                 20

<210> SEQ ID NO 179
<211> LENGTH: 23
<212> TYPE: DNA
<213> ORGANISM: Bos taurus

<400> SEQUENCE: 179
```

```
       tcgggctcca tgaagaagat gta                                          23

<210> SEQ ID NO 180
<211> LENGTH: 23
<212> TYPE: DNA
<213> ORGANISM: Bos taurus

<400> SEQUENCE: 180
tccatgaaga agatgtacct gct                                          23

<210> SEQ ID NO 181
<211> LENGTH: 22
<212> TYPE: DNA
<213> ORGANISM: Bos taurus

<400> SEQUENCE: 181
atgtacctgc tgtcctcctt ga                                           22

<210> SEQ ID NO 182
<211> LENGTH: 22
<212> TYPE: DNA
<213> ORGANISM: Bos taurus

<400> SEQUENCE: 182
atgtacctgc tgtcctcctt ga                                           22

<210> SEQ ID NO 183
<211> LENGTH: 22
<212> TYPE: DNA
<213> ORGANISM: Bos taurus

<400> SEQUENCE: 183
atgtacctgc tgtcctcctt ga                                           22

<210> SEQ ID NO 184
<211> LENGTH: 20
<212> TYPE: DNA
<213> ORGANISM: Bos taurus

<400> SEQUENCE: 184
atgargtgtg ggcggcgaaa                                              20

<210> SEQ ID NO 185
<211> LENGTH: 15
<212> TYPE: PRT
<213> ORGANISM: Bos taurus

<400> SEQUENCE: 185

Glu Gly Lys Val His Pro Gln Arg Arg Gly Ala Leu Asp Arg Lys
        1               5                  10                  15

<210> SEQ ID NO 186
<211> LENGTH: 17
<212> TYPE: PRT
<213> ORGANISM: Bos taurus

<400> SEQUENCE: 186

Pro Ser Cys Gly Arg Leu Lys Glu Asp Ser Arg Tyr Ile Phe Phe Met
        1               5                  10                  15
       Glu

<210> SEQ ID NO 187
<211> LENGTH: 16
<212> TYPE: PRT
```

<213> ORGANISM: Bos taurus

<400> SEQUENCE: 187

```
Glu Leu Asn Arg Lys Asn Lys Pro Gln Asn Ile Lys Ile Gln Lys Lys
1               5                   10                  15
```

<210> SEQ ID NO 188
<211> LENGTH: 414
<212> TYPE: PRT
<213> ORGANISM: Homo sapiens

<400> SEQUENCE: 188

```
Met Arg Trp Arg Arg Ala Pro Arg Ser Gly Arg Pro Gly Arg
1               5                   10                  15
Ala Gln Arg Pro Gly Ser Ala Ala Arg Ser Ser Pro Pro Leu Pro Leu
                20                  25                  30
Leu Pro Leu Leu Leu Leu Leu Gly Thr Ala Ala Leu Ala Pro Gly Ala
            35                  40                  45
Ala Ala Gly Asn Glu Ala Ala Pro Ala Gly Ala Ser Val Cys Tyr Ser
        50                  55                  60
Ser Pro Pro Ser Val Gly Ser Val Gln Glu Leu Ala Gln Arg Ala Ala
65                  70                  75                  80
Val Val Ile Glu Gly Lys Val His Pro Gln Arg Arg Gln Gln Gly Ala
                85                  90                  95
Leu Asp Arg Lys Ala Ala Ala Ala Gly Glu Ala Gly Ala Trp Gly
                100                 105                 110
Gly Asp Arg Glu Pro Pro Ala Ala Gly Pro Arg Ala Leu Gly Pro Pro
            115                 120                 125
Ala Glu Glu Pro Leu Leu Ala Ala Asn Gly Thr Val Pro Ser Trp Pro
        130                 135                 140
Thr Ala Pro Val Pro Ser Ala Gly Glu Pro Gly Glu Glu Ala Pro Tyr
145                 150                 155                 160
Leu Val Lys Val His Gln Val Trp Ala Val Lys Ala Gly Gly Leu Lys
                165                 170                 175
Lys Asp Ser Leu Leu Thr Val Arg Leu Gly Thr Trp Gly His Pro Ala
            180                 185                 190
Phe Pro Ser Cys Gly Arg Leu Lys Glu Asp Ser Arg Tyr Ile Phe Phe
        195                 200                 205
Met Glu Pro Asp Ala Asn Ser Thr Ser Arg Ala Pro Ala Ala Phe Arg
    210                 215                 220
Ala Ser Phe Pro Pro Leu Glu Thr Gly Arg Asn Leu Lys Lys Glu Val
225                 230                 235                 240
Ser Arg Val Leu Cys Lys Arg Cys Ala Leu Pro Pro Arg Leu Lys Glu
                245                 250                 255
Met Lys Ser Gln Glu Ser Ala Ala Gly Ser Lys Leu Val Leu Arg Cys
            260                 265                 270
Glu Thr Ser Ser Glu Tyr Ser Ser Leu Arg Phe Lys Trp Phe Lys Asn
        275                 280                 285
Gly Asn Glu Leu Asn Arg Lys Asn Lys Pro Gln Asn Ile Lys Ile Gln
    290                 295                 300
Lys Lys Pro Gly Lys Ser Glu Leu Arg Ile Asn Lys Ala Ser Leu Ala
305                 310                 315                 320
Asp Ser Gly Glu Tyr Met Cys Lys Val Ile Ser Lys Leu Gly Asn Asp
                325                 330                 335
Ser Ala Ser Ala Asn Ile Thr Ile Val Glu Ser Asn Ala Thr Ser Thr
            340                 345                 350
Ser Thr Thr Gly Thr Ser His Leu Val Lys Cys Ala Glu Lys Glu Lys
        355                 360                 365
Thr Phe Cys Val Asn Gly Gly Glu Cys Phe Met Val Lys Asp Leu Ser
    370                 375                 380
Asn Pro Ser Arg Tyr Leu Cys Lys Cys Gln Pro Gly Phe Thr Gly Ala
385                 390                 395                 400
Arg Cys Thr Glu Asn Val Pro Met Lys Val Gln Asn Gln Glu
                405                 410
```

<210> SEQ ID NO 189
<211> LENGTH: 411
<212> TYPE: PRT
<213> ORGANISM: Homo sapiens

<400> SEQUENCE: 189

```
Met Arg Trp Arg Arg Ala Pro Arg Ser Gly Arg Pro Gly Arg
1               5                   10                  15
Ala Gln Arg Pro Gly Ser Ala Ala Arg Ser Ser Pro Pro Leu Pro Leu
```

-continued

```
                    20                  25                  30
        Leu Pro Leu Leu Leu Leu Gly Thr Ala Ala Leu Ala Pro Gly Ala
                35                  40                  45
        Ala Ala Gly Asn Glu Ala Ala Pro Ala Gly Ala Ser Val Cys Tyr Ser
         50                  55                  60
        Ser Pro Pro Ser Val Gly Ser Val Gln Glu Leu Ala Gln Arg Ala Ala
         65                  70                  75                  80
        Val Val Ile Glu Gly Lys Val His Pro Gln Arg Gln Gln Gly Ala
                        85                  90                  95
        Leu Asp Arg Lys Ala Ala Ala Ala Gly Glu Ala Gly Ala Trp Gly
                    100                 105                 110
        Gly Asp Arg Glu Pro Pro Ala Ala Gly Pro Arg Ala Leu Gly Pro Pro
                    115                 120                 125
        Ala Glu Glu Pro Leu Leu Ala Ala Asn Gly Thr Val Pro Ser Trp Pro
                    130                 135                 140
        Thr Ala Pro Val Pro Ser Ala Gly Glu Pro Gly Glu Glu Ala Pro Tyr
         145                 150                 155                 160
        Leu Val Lys Val His Gln Val Trp Ala Val Lys Ala Gly Gly Leu Lys
                        165                 170                 175
        Lys Asp Ser Leu Leu Thr Val Arg Leu Gly Thr Trp Gly His Pro Ala
                    180                 185                 190
        Phe Pro Ser Cys Gly Arg Leu Lys Glu Asp Ser Arg Tyr Ile Phe Phe
                    195                 200                 205
        Met Glu Pro Asp Ala Asn Ser Thr Ser Arg Ala Pro Ala Ala Phe Arg
                    210                 215                 220
        Ala Ser Phe Pro Pro Leu Glu Thr Gly Arg Asn Leu Lys Lys Glu Val
         225                 230                 235                 240
        Ser Arg Val Leu Cys Lys Arg Cys Ala Leu Pro Pro Arg Leu Lys Glu
                        245                 250                 255
        Met Lys Ser Gln Glu Ser Ala Ala Gly Ser Lys Leu Val Leu Arg Cys
                    260                 265                 270
        Glu Thr Ser Ser Glu Tyr Ser Ser Leu Arg Phe Lys Trp Phe Lys Asn
                    275                 280                 285
        Gly Asn Glu Leu Asn Arg Lys Asn Lys Pro Gln Asn Ile Lys Ile Gln
                    290                 295                 300
        Lys Lys Pro Gly Lys Ser Glu Leu Arg Ile Asn Lys Ala Ser Leu Ala
         305                 310                 315                 320
        Asp Ser Gly Glu Tyr Met Cys Lys Val Ile Ser Lys Leu Gly Asn Asp
                        325                 330                 335
        Ser Ala Ser Ala Asn Ile Thr Ile Val Glu Ser Asn Ala Thr Ser Thr
                    340                 345                 350
        Ser Thr Thr Gly Thr Ser His Leu Val Lys Cys Ala Glu Lys Glu Lys
                    355                 360                 365
        Thr Phe Cys Val Asn Gly Gly Glu Cys Phe Met Val Lys Asp Leu Ser
                    370                 375                 380
        Asn Pro Ser Arg Tyr Leu Cys Lys Cys Pro Asn Glu Phe Thr Gly Asp
         385                 390                 395                 400
        Arg Cys Gln Asn Tyr Val Met Ala Ser Phe Tyr
                        405                 410
```

<210> SEQ ID NO 190
<211> LENGTH: 206
<212> TYPE: PRT
<213> ORGANISM: Bos taurus

<400> SEQUENCE: 190

```
        His Gln Val Trp Ala Ala Lys Ala Gly Gly Leu Lys Lys Asp Ser Leu
         1                   5                  10                  15
        Leu Thr Val Arg Leu Gly Ala Trp Gly His Pro Ala Phe Pro Ser Cys
                        20                  25                  30
        Gly Arg Leu Lys Glu Asp Ser Arg Tyr Ile Phe Phe Met Glu Pro Glu
                    35                  40                  45
        Ala Asn Ser Ser Gly Gly Pro Gly Arg Leu Pro Ser Leu Leu Pro Pro
         50                  55                  60
        Ser Arg Asp Gly Pro Glu Pro Gln Glu Gly Gln Pro Gly Ala Val
         65                  70                  75                  80
        Gln Arg Cys Ala Leu Pro Pro Arg Leu Lys Glu Met Lys Ser Gln Glu
                        85                  90                  95
        Ser Val Ala Gly Ser Lys Leu Val Leu Arg Cys Glu Thr Ser Ser Glu
                    100                 105                 110
        Tyr Ser Ser Leu Lys Phe Lys Trp Phe Lys Asn Gly Ser Glu Leu Ser
                    115                 120                 125
        Arg Lys Asn Lys Pro Glu Asn Ile Lys Ile Gln Lys Arg Pro Gly Lys
                    130                 135                 140
        Ser Glu Leu Arg Ile Ser Lys Ala Ser Leu Ala Asp Ser Gly Glu Tyr
         145                 150                 155                 160
        Met Cys Lys Val Ile Ser Lys Leu Gly Asn Asp Ser Ala Ser Ala Asn
```

-continued

```
                        165                 170                 175
        Ile Thr Ile Val Glu Ser Asn Gly Lys Arg Cys Leu Leu Arg Ala Ile
                    180                 185                 190
        Ser Gln Ser Leu Arg Gly Val Ile Lys Val Cys Gly His Thr
                195                 200                 205
```

<210> SEQ ID NO 191
<211> LENGTH: 263
<212> TYPE: PRT
<213> ORGANISM: Bos taurus

<400> SEQUENCE: 191

```
        His Gln Val Trp Ala Ala Lys Ala Gly Gly Leu Lys Lys Asp Ser Leu
        1               5                   10                  15
        Leu Thr Val Arg Leu Gly Ala Trp Gly His Pro Ala Phe Pro Ser Cys
                    20                  25                  30
        Gly Arg Leu Lys Glu Asp Ser Arg Tyr Ile Phe Phe Met Glu Pro Glu
                    35                  40                  45
        Ala Lys Ser Ser Gly Gly Pro Gly Arg Leu Pro Ser Leu Leu Pro Pro
                50                  55                  60
        Ser Arg Asp Gly Pro Glu Pro Gln Glu Gly Gly Gln Pro Gly Ala Val
        65                  70                  75                  80
        Gln Arg Cys Ala Leu Pro Pro Arg Leu Lys Glu Met Lys Ser Gln Glu
                        85                  90                  95
        Ser Val Ala Gly Ser Lys Leu Val Leu Arg Cys Glu Thr Ser Ser Glu
                    100                 105                 110
        Tyr Ser Ser Leu Lys Phe Lys Trp Phe Lys Asn Gly Ser Glu Leu Ser
                    115                 120                 125
        Arg Lys Asn Lys Gly Gly Asn Ile Lys Ile Gln Lys Arg Pro Gly Lys
                130                 135                 140
        Ser Gly Leu Arg Ile Ser Lys Ala Ser Leu Ala Asp Ser Gly Glu Tyr
        145                 150                 155                 160
        Met Cys Lys Val Ile Ser Lys Leu Gly Asn Asp Ser Ala Ser Ala Asn
                        165                 170                 175
        Ile Thr Ile Val Glu Ser Asn Ala Thr Ser Thr Ser Thr Ala Gly Thr
                    180                 185                 190
        Ser His Leu Val Lys Ser Ala Glu Lys Glu Lys Thr Phe Cys Val Asn
                    195                 200                 205
        Gly Gly Glu Cys Phe Met Val Lys Asp Leu Ser Asn Pro Ser Arg Tyr
                    210                 215                 220
        Leu Cys Lys Cys Gln Pro Gly Phe Thr Gly Ala Arg Cys Thr Glu Asn
        225                 230                 235                 240
        Val Pro Met Lys Val Gln Thr Gln Glu Ser Ala Gln Met Ser Leu Leu
                        245                 250                 255
        Val Ile Ala Ala Lys Thr Thr
                    260
```

<210> SEQ ID NO 192
<211> LENGTH: 280
<212> TYPE: PRT
<213> ORGANISM: Bos taurus

<400> SEQUENCE: 192

```
        His Gln Val Trp Ala Ala Lys Ala Gly Gly Leu Lys Lys Asp Ser Leu
        1               5                   10                  15
        Leu Thr Val Arg Leu Gly Ala Trp Gly His Pro Ala Phe Pro Ser Cys
                    20                  25                  30
        Gly Arg Leu Lys Glu Asp Ser Arg Tyr Ile Phe Phe Met Glu Pro Glu
                    35                  40                  45
        Ala Asn Ser Ser Gly Gly Pro Gly Arg Leu Pro Ser Leu Leu Pro Pro
                50                  55                  60
        Ser Arg Asp Gly Pro Glu Pro Gln Glu Gly Gly Gln Pro Gly Ala Val
        65                  70                  75                  80
        Gln Arg Cys Ala Leu Pro Pro Arg Leu Lys Glu Met Lys Ser Gln Glu
                        85                  90                  95
        Ser Val Ala Gly Ser Lys Leu Val Leu Arg Cys Glu Thr Ser Ser Glu
                    100                 105                 110
        Tyr Ser Ser Leu Lys Phe Lys Trp Phe Lys Asn Gly Ser Glu Leu Ser
                    115                 120                 125
        Arg Lys Asn Lys Pro Glu Asn Ile Lys Ile Gln Lys Arg Pro Gly Lys
                130                 135                 140
        Ser Glu Leu Arg Ile Ser Lys Ala Ser Leu Ala Asp Ser Gly Glu Tyr
        145                 150                 155                 160
        Met Cys Lys Val Ile Ser Lys Leu Gly Asn Asp Ser Ala Ser Ala Asn
                        165                 170                 175
```

-continued

```
            Ile Thr Ile Val Glu Ser Asn Ala Thr Ser Thr Ser Thr Ala Gly Thr
                        180                 185                 190
            Ser His Leu Val Lys Cys Ala Glu Lys Glu Lys Thr Phe Cys Val Asn
                        195                 200                 205
            Gly Gly Glu Cys Phe Met Val Lys Asp Leu Ser Asn Pro Ser Arg Tyr
                        210                 215                 220
            Leu Cys Lys Cys Gln Pro Gly Phe Thr Gly Ala Arg Cys Thr Glu Asn
            225                 230                 235                 240
            Val Pro Met Lys Val Gln Thr Gln Glu Lys Cys Pro Asn Glu Phe Thr
                                245                 250                 255
            Gly Asp Arg Cys Gln Asn Tyr Val Met Ala Ser Phe Tyr Ser Thr Ser
                        260                 265                 270
            Thr Pro Phe Leu Ser Leu Pro Glu
                        275                 280

<210> SEQ ID NO 193
<211> LENGTH: 257
<212> TYPE: PRT
<213> ORGANISM: Bos taurus

<400> SEQUENCE: 193

His Gln Val Trp Ala Ala Lys Ala Gly Gly Leu Lys Lys Asp Ser Leu
            1               5                   10                  15
            Leu Thr Val Arg Leu Gly Ala Trp Gly His Pro Ala Phe Pro Ser Cys
                        20                  25                  30
            Gly Arg Leu Lys Glu Asp Ser Arg Tyr Ile Phe Phe Met Glu Pro Glu
                        35                  40                  45
            Ala Asn Ser Ser Gly Gly Pro Gly Arg Leu Pro Ser Leu Pro Pro
                        50                  55                  60
            Ser Arg Asp Gly Pro Glu Pro Gln Glu Gly Gln Pro Gly Ala Val
            65                  70                  75                  80
            Gln Arg Cys Ala Leu Pro Pro Arg Leu Lys Glu Met Lys Ser Gln Glu
                        85                  90                  95
            Ser Val Ala Gly Ser Lys Leu Val Leu Arg Cys Glu Thr Ser Ser Glu
                        100                 105                 110
            Tyr Ser Ser Leu Lys Phe Lys Trp Phe Lys Asn Gly Ser Glu Leu Ser
                        115                 120                 125
            Arg Lys Asn Lys Pro Glu Asn Ile Lys Ile Gln Lys Lys Arg Pro Gly Lys
                        130                 135                 140
            Ser Glu Leu Arg Ile Ser Lys Ala Ser Leu Ala Asp Ser Gly Glu Tyr
            145                 150                 155                 160
            Met Cys Lys Val Ile Ser Lys Leu Gly Asn Asp Ser Ala Ser Ala Asn
                        165                 170                 175
            Ile Thr Ile Val Glu Ser Asn Ala Thr Ser Thr Ser Thr Ala Gly Thr
                        180                 185                 190
            Ser His Leu Val Lys Cys Ala Glu Lys Glu Lys Thr Phe Cys Val Asn
                        195                 200                 205
            Gly Gly Glu Cys Phe Met Val Lys Asp Leu Ser Asn Pro Ser Arg Tyr
                        210                 215                 220
            Leu Cys Lys Cys Pro Asn Glu Phe Thr Gly Asp Arg Cys Gln Asn Tyr
            225                 230                 235                 240
            Val Met Ala Ser Phe Tyr Ser Thr Ser Thr Pro Phe Leu Ser Leu Pro
                                245                 250                 255
            Glu

<210> SEQ ID NO 194
<211> LENGTH: 560
<212> TYPE: PRT
<213> ORGANISM: Bos taurus

<400> SEQUENCE: 194

Lys Ser Glu Leu Arg Ile Ser Lys Ala Ser Leu Ala Asp Ser Gly Glu
            1               5                   10                  15
            Tyr Met Cys Lys Val Ile Ser Lys Leu Gly Asn Asp Ser Ala Ser Ala
                        20                  25                  30
            Asn Ile Thr Ile Val Glu Ser Asn Ala Thr Ser Thr Ser Thr Ala Gly
                        35                  40                  45
            Thr Ser His Leu Val Lys Cys Ala Glu Lys Glu Lys Thr Phe Cys Val
                        50                  55                  60
            Asn Gly Gly Asp Cys Phe Met Val Lys Asp Leu Ser Asn Pro Ser Arg
            65                  70                  75                  80
            Tyr Leu Cys Lys Cys Gln Pro Gly Phe Thr Gly Ala Arg Cys Thr Glu
                        85                  90                  95
            Asn Val Pro Met Lys Val Gln Thr Gln Glu Lys Ala Glu Glu Leu Tyr
                        100                 105                 110
```

```
        Gln Lys Arg Val Leu Thr Ile Thr Gly Ile Cys Ile Ala Leu Leu Val
                    115                 120                 125
        Val Gly Ile Met Cys Val Val Val Tyr Cys Lys Thr Lys Lys Gln Arg
                130                 135                 140
        Lys Lys Leu His Asp Arg Leu Arg Gln Ser Leu Arg Ser Glu Arg Asn
        145                 150                 155                 160
        Thr Met Met Asn Val Ala Asn Gly Pro His His Pro Asn Pro Pro Pro
                        165                 170                 175
        Glu Asn Val Gln Leu Val Asn Gln Tyr Val Ser Lys Asn Val Ile Ser
                    180                 185                 190
        Ser Glu His Ile Val Glu Arg Glu Ala Glu Ser Ser Phe Ser Thr Ser
                195                 200                 205
        His Tyr Thr Ser Thr Ala His His Ser Thr Val Thr Gln Thr Pro
            210                 215                 220
        Ser His Ser Trp Ser Asn Gly His Thr Glu Ser Ile Ile Ser Glu Ser
        225                 230                 235                 240
        His Ser Val Ile Val Met Ser Ser Val Glu Asn Ser Arg His Ser Ser
                        245                 250                 255
        Pro Thr Gly Gly Pro Arg Gly Arg Leu Asn Gly Leu Gly Ser Pro Arg
                    260                 265                 270
        Glu Cys Asn Ser Phe Leu Arg His Ala Arg Glu Thr Pro Asp Ser Tyr
                275                 280                 285
        Arg Asp Ser Pro His Ser Glu Arg His Asn Leu Ile Ala Glu Leu Arg
            290                 295                 300
        Arg Asn Lys Ala His Arg Ser Lys Cys Met Gln Ile Gln Leu Ser Ala
        305                 310                 315                 320
        Thr His Leu Arg Ala Ser Ser Ile Pro His Trp Ala Ser Phe Ser Lys
                        325                 330                 335
        Thr Pro Trp Pro Leu Gly Arg Tyr Val Ser Ala Met Thr Thr Pro Ala
                    340                 345                 350
        Arg Met Ser Pro Val Asp Phe His Thr Pro Ser Ser Pro Lys Ser Pro
                355                 360                 365
        Pro Ser Glu Met Ser Pro Pro Val Ser Ser Thr Thr Val Ser Met Pro
            370                 375                 380
        Ser Met Ala Val Ser Pro Phe Val Glu Glu Glu Arg Pro Leu Leu Leu
        385                 390                 395                 400
        Val Thr Pro Pro Arg Leu Arg Glu Lys Tyr Asp His His Ala Gln Gln
                        405                 410                 415
        Phe Asn Ser Phe His Cys Asn Pro Ala His Glu Ser Asn Ser Leu Pro
                    420                 425                 430
        Pro Ser Pro Leu Arg Ile Val Glu Asp Glu Glu Tyr Glu Thr Thr Gln
                435                 440                 445
        Glu Tyr Glu Pro Ala Gln Glu Pro Val Lys Lys Leu Thr Asn Ser Ser
            450                 455                 460
        Arg Arg Ala Lys Arg Thr Lys Pro Asn Gly His Ile Ala His Arg Leu
        465                 470                 475                 480
        Glu Met Asp Asn Asn Thr Gly Ala Asp Ser Ser Asn Ser Glu Ser Glu
                        485                 490                 495
        Thr Glu Asp Glu Arg Val Gly Glu Asp Thr Pro Phe Leu Ala Ile Gln
                    500                 505                 510
        Asn Pro Leu Ala Ala Ser Leu Glu Ala Ala Pro Ala Phe Arg Leu Val
                515                 520                 525
        Asp Ser Arg Thr Asn Pro Thr Gly Gly Phe Ser Pro Gln Glu Glu Leu
            530                 535                 540
        Gln Ala Arg Leu Ser Gly Val Ile Ala Asn Gln Asp Pro Ile Ala Val
        545                 550                 555                 560

<210> SEQ ID NO 195
<211> LENGTH: 241
<212> TYPE: PRT
<213> ORGANISM: Bos taurus

<400> SEQUENCE: 195

Met Ser Glu Arg Arg Glu Gly Lys Gly Lys Gly Lys Gly Lys Lys
        1               5                   10                  15
        Asp Arg Gly Ser Gly Lys Lys Pro Val Pro Ala Ala Gly Gly Pro Ser
                    20                  25                  30
        Pro Ala Leu Pro Pro Arg Leu Lys Glu Met Lys Met Gln Glu Ser Val
                35                  40                  45
        Ala Gly Ser Lys Leu Val Leu Arg Cys Glu Thr Ser Ser Glu Tyr Ser
            50                  55                  60
        Ser Leu Lys Phe Lys Trp Phe Lys Asn Gly Asn Glu Leu Ser Arg Lys
        65                  70                  75                  80
        Asn Lys Pro Gln Asn Ile Lys Ile Gln Lys Arg Pro Gly Lys Ser Glu
                        85                  90                  95
        Leu Arg Ile Ser Lys Ala Ser Leu Ala Asp Ser Gly Glu Tyr Met Cys
                    100                 105                 110
```

-continued

```
      Lys Val Ile Ser Lys Leu Gly Asn Asp Ser Ala Ser Ala Asn Ile Thr
                      115                 120                 125
      Ile Val Glu Ser Asn Glu Ile Thr Thr Gly Met Pro Ala Ser Thr Glu
              130                 135                 140
      Thr Ala Tyr Val Ser Ser Glu Ser Pro Ile Arg Ile Ser Val Ser Thr
      145                 150                 155                 160
      Glu Gly Thr Asn Thr Ser Ser Ser Thr Thr Ser Thr Ala Gly Thr
                      165                 170                 175
      Ser His Leu Val Lys Cys Ala Glu Lys Glu Lys Thr Phe Cys Val Asn
                  180                 185                 190
      Gly Gly Glu Cys Phe Met Val Lys Asp Leu Ser Asn Pro Ser Arg Tyr
                      195                 200                 205
      Leu Cys Lys Cys Pro Asn Glu Phe Thr Gly Asp Arg Cys Gln Asn Tyr
                  210                 215                 220
      Val Met Ala Ser Phe Tyr Ser Thr Ser Thr Pro Phe Leu Ser Leu Pro
      225                 230                 235                 240
      Glu
```

```
<210> SEQ ID NO 196
<211> LENGTH: 137
<212> TYPE: PRT
<213> ORGANISM: Bos taurus
<220> FEATURE:
<221> NAME/KEY: VARIANT
<222> LOCATION: (14)...(135)
<223> OTHER INFORMATION: Xaa in positions 14, 23, 90, 100, 126, and 135 is
      unknown.

<400> SEQUENCE: 196

Asn Tyr Arg Asp Cys Ile Phe Met Ile Ile Ile Val Leu Xaa Asn Ile
      1               5                   10                  15
      Leu Lys Pro Leu Trp Ser Xaa Ser Cys Arg Lys Ser Glu Leu Arg Ile
                      20                  25                  30
      Ser Lys Ala Ser Leu Ala Asp Ser Gly Glu Ser Met Cys Lys Val Ile
                  35                  40                  45
      Ser Lys Leu Gly Asn Asp Ser Ala Ser Ala Asn Ile Arg Ile Val Glu
              50                  55                  60
      Ser Asn Gly Lys Arg Cys Leu Leu Arg Ala Ile Ser Gln Ser Leu Arg
      65                  70                  75                  80
      Gly Val Ile Lys Val Cys Gly His Thr Xaa Ile Thr Gln Val Ser Glu
                      85                  90                  95
      Ile Ser Cys Xaa Thr Asn Lys Asn His Glu Arg Lys Thr Leu Cys Leu
                  100                 105                 110
      Lys Tyr Leu Met Gly Pro Pro Val Lys Leu Phe Thr Pro Xaa Gly Glu
              115                 120                 125
      Ile Asp Leu Lys Tyr Ile Xaa Ile Ile
              130                 135
```

```
<210> SEQ ID NO 197
<211> LENGTH: 34
<212> TYPE: PRT
<213> ORGANISM: Bos taurus

<400> SEQUENCE: 197

Met Ser Glu Arg Arg Glu Gly Lys Gly Lys Gly Lys Gly Lys Lys
      1               5                   10                  15
      Asp Arg Gly Ser Gly Lys Lys Pro Val Pro Ala Ala Gly Gly Pro Ser
                      20                  25                  30
      Pro Ala
```

```
<210> SEQ ID NO 198
<211> LENGTH: 83
<212> TYPE: PRT
<213> ORGANISM: Bos taurus

<400> SEQUENCE: 198

His Gln Val Trp Ala Ala Lys Ala Gly Gly Leu Lys Lys Asp Ser Leu
      1               5                   10                  15
      Leu Thr Val Arg Leu Gly Ala Trp Gly His Pro Ala Phe Pro Ser Cys
                      20                  25                  30
      Gly Arg Leu Lys Glu Asp Ser Arg Tyr Ile Phe Phe Met Glu Pro Glu
                  35                  40                  45
      Ala Asn Ser Ser Gly Gly Pro Gly Arg Leu Pro Ser Leu Leu Pro Pro
```

```
            50                  55                  60
        Ser Arg Asp Gly Pro Glu Pro Gln Glu Gly Gly Gln Pro Gly Ala Val
        65                  70                  75                  80
        Gln Arg Cys

<210> SEQ ID NO 199
<211> LENGTH: 59
<212> TYPE: PRT
<213> ORGANISM: Bos taurus

<400> SEQUENCE: 199

Leu Pro Pro Arg Leu Lys Glu His Lys Ser Gln Glu Ser Val Ala Gly
        1               5                   10                  15
        Ser Lys Leu Val Leu Arg Cys Glu Thr Ser Ser Glu Tyr Ser Ser Leu
                    20                  25                  30
        Lys Phe Lys Trp Phe Lys Asn Gly Ser Glu Leu Ser Arg Lys Asn Lys
                35                  40                  45
        Pro Gly Asn Ile Lys Ile Gln Lys Arg Pro Gly
            50                  55

<210> SEQ ID NO 200
<211> LENGTH: 41
<212> TYPE: PRT
<213> ORGANISM: Bos taurus

<400> SEQUENCE: 200

Lys Ser Glu Leu Arg Ile Ser Lys Ala Ser Leu Ala Asp Ser Gly Glu
        1               5                   10                  15
        Tyr Met Cys Lys Val Ile Ser Lys Leu Gly Asn Asp Ser Ala Ser Ala
                    20                  25                  30
        Asn Ile Thr Ile Val Glu Ser Asn Ala
                35                  40

<210> SEQ ID NO 201
<211> LENGTH: 35
<212> TYPE: PRT
<213> ORGANISM: Bos taurus

<400> SEQUENCE: 201

Glu Ile Thr Thr Gly Met Pro Ala Ser Thr Glu Thr Ala Tyr Val Ser
        1               5                   10                  15
        Ser Glu Ser Pro Ile Arg Ile Ser Val Ser Thr Glu Gly Thr Asn Thr
                    20                  25                  30
        Ser Ser Ser
                35

<210> SEQ ID NO 202
<211> LENGTH: 42
<212> TYPE: PRT
<213> ORGANISM: Bos taurus

<400> SEQUENCE: 202

Thr Ser Thr Ser Thr Ala Gly Thr Ser His Leu Val Lys Cys Ala Glu
        1               5                   10                  15
        Lys Glu Lys Thr Phe Cys Val Asn Gly Gly Glu Cys Phe Met Val Lys
                    20                  25                  30
        Asp Leu Ser Asn Pro Ser Arg Tyr Leu Cys
                35                  40

<210> SEQ ID NO 203
<211> LENGTH: 23
<212> TYPE: PRT
<213> ORGANISM: Bos taurus

<400> SEQUENCE: 203

Lys Cys Gln Pro Gly Phe Thr Gly Ala Arg Cys Thr Glu Asn Val Pro
        1               5                   10                  15
        Met Lys Val Gln Thr Gln Glu
                    20
```

```
<210> SEQ ID NO 204
<211> LENGTH: 190
<212> TYPE: PRT
<213> ORGANISM: Bos taurus

<400> SEQUENCE: 204

Lys Ala Glu Glu Leu Tyr Gln Lys Arg Val Leu Thr Ile Thr Gly Ile
    1               5                   10                  15
    Cys Ile Ala Leu Leu Val Val Gly Ile Met Cys Val Val Tyr Cys
                20                  25                  30
    Lys Thr Lys Lys Gln Arg Lys Lys Leu His Asp Arg Leu Arg Gln Ser
                35                  40                  45
    Leu Arg Ser Glu Arg Asn Thr Met Met Asn Val Ala Asn Gly Pro His
                50                  55                  60
    His Pro Asn Pro Pro Glu Asn Val Gln Leu Val Asn Gln Tyr Val
    65                  70                  75                  80
    Ser Lys Asn Val Ile Ser Ser Glu His Ile Val Glu Arg Glu Ala Glu
                        85                  90                  95
    Ser Ser Phe Ser Thr Ser His Tyr Thr Ser Thr Ala His Ser Ser Thr
                    100                 105                 110
    Thr Val Thr Gln Thr Pro Ser His Ser Trp Ser Asn Gly His Thr Glu
                    115                 120                 125
    Ser Ile Ile Ser Glu Ser His Ser Val Ile Val Met Ser Ser Val Glu
                130                 135                 140
    Asn Ser Arg His Ser Ser Pro Thr Gly Gly Pro Arg Gly Arg Leu Asn
    145                 150                 155                 160
    Gly Leu Gly Gly Pro Arg Glu Cys Asn Ser Phe Leu Arg His Ala Arg
                    165                 170                 175
    Glu Thr Pro Asp Ser Tyr Arg Asp Ser Pro His Ser Glu Arg
                    180                 185                 190

<210> SEQ ID NO 205
<211> LENGTH: 217
<212> TYPE: PRT
<213> ORGANISM: Bos taurus

<400> SEQUENCE: 205

Tyr Val Ser Ala Met Thr Thr Pro Ala Arg Met Ser Pro Val Asp Phe
    1               5                   10                  15
    His Thr Pro Ser Ser Pro Lys Ser Pro Ser Glu Met Ser Pro Pro
                20                  25                  30
    Val Ser Ser Thr Thr Val Ser Met Pro Ser Met Ala Val Ser Pro Phe
                35                  40                  45
    Val Glu Glu Arg Pro Leu Leu Val Thr Pro Pro Arg Leu Arg
        50                  55                  60
    Glu Lys Tyr Asp His His Ala Gln Gln Phe Asn Ser Phe His Cys Asn
    65                  70                  75                  80
    Pro Ala His Glu Ser Asn Ser Leu Pro Pro Ser Pro Leu Arg Ile Val
                    85                  90                  95
    Glu Asp Glu Glu Tyr Glu Thr Thr Gln Glu Tyr Glu Pro Ala Gln Glu
                    100                 105                 110
    Pro Val Lys Lys Leu Thr Asn Ser Ser Arg Arg Ala Lys Arg Thr Lys
                    115                 120                 125
    Pro Asn Gly His Ile Ala His Arg Leu Glu Met Asp Asn Asn Thr Gly
                    130                 135                 140
    Ala Asp Ser Ser Asn Ser Glu Ser Glu Thr Glu Asp Glu Arg Val Gly
    145                 150                 155                 160
    Glu Asp Thr Pro Phe Leu Ala Ile Gln Asn Pro Leu Ala Ala Ser Leu
                    165                 170                 175
    Glu Ala Ala Pro Ala Phe Arg Leu Val Asp Ser Arg Thr Asn Pro Thr
                    180                 185                 190
    Gly Gly Phe Ser Pro Gln Glu Glu Leu Gln Ala Arg Leu Ser Gly Val
                    195                 200                 205
    Ile Ala Asn Gln Asp Pro Ile Ala Val
                    210                 215

<210> SEQ ID NO 206
<211> LENGTH: 63
<212> TYPE: PRT
<213> ORGANISM: Bos taurus & Homo sapiens

<400> SEQUENCE: 206
```

```
        Lys Ser Glu Leu Arg Ile Ser Lys Ala Ser Leu Ala Asp Ser Gly Glu
        1               5                   10                  15
        Tyr Met Cys Lys Val Ile Ser Lys Leu Gly Asn Asp Ser Ala Ser Ala
                        20                  25                  30
        Asn Ile Thr Ile Val Glu Ser Asn Gly Lys Arg Cys Leu Leu Arg Ala
                    35                  40                  45
        Ile Ser Gln Ser Leu Arg Gly Val Ile Lys Val Cys Gly His Thr
            50                  55                  60
```

```
<210> SEQ ID NO 207
<211> LENGTH: 20
<212> TYPE: PRT
<213> ORGANISM: Bos taurus & Homo sapiens

<400> SEQUENCE: 207

Lys Cys Pro Asn Glu Phe Thr Gly Asp Arg Cys Gln Asn Tyr Val Met
        1               5                   10                  15
        Ala Ser Phe Tyr
                    20
```

```
<210> SEQ ID NO 208
<211> LENGTH: 11
<212> TYPE: PRT
<213> ORGANISM: Bos taurus & Homo sapiens

<400> SEQUENCE: 208

Ser Thr Ser Thr Pro Phe Leu Ser Leu Pro Glu
        1               5                   10
```

```
<210> SEQ ID NO 209
<211> LENGTH: 33
<212> TYPE: PRT
<213> ORGANISM: Homo sapiens

<400> SEQUENCE: 209

Met Ser Glu Arg Lys Glu Gly Arg Gly Lys Gly Lys Gly Lys Lys Lys
        1               5                   10                  15
        Glu Arg Gly Ser Gly Lys Lys Pro Glu Ser Ala Ala Gly Ser Gln Ser
                        20                  25                  30
        Pro
```

```
<210> SEQ ID NO 210
<211> LENGTH: 248
<212> TYPE: PRT
<213> ORGANISM: Homo sapiens

<400> SEQUENCE: 210

Met Arg Trp Arg Arg Ala Pro Arg Arg Ser Gly Arg Pro Gly Pro Arg
        1               5                   10                  15
        Ala Gln Arg Pro Gly Ser Ala Ala Arg Ser Ser Pro Pro Leu Pro Leu
                        20                  25                  30
        Leu Pro Leu Leu Leu Leu Leu Gly Thr Ala Ala Leu Ala Pro Gly Ala
                    35                  40                  45
        Ala Ala Gly Asn Glu Ala Ala Pro Ala Gly Ala Ser Val Cys Tyr Ser
            50                  55                  60
        Ser Pro Pro Ser Val Gly Ser Val Gln Glu Leu Ala Gln Arg Ala Ala
        65                  70                  75                  80
        Val Val Ile Glu Gly Lys Val His Pro Gln Arg Arg Gln Gln Gly Ala
                        85                  90                  95
        Leu Asp Arg Lys Ala Ala Ala Ala Gly Glu Ala Gly Ala Trp Gly
                    100                 105                 110
        Gly Asp Arg Glu Pro Pro Ala Ala Gly Pro Arg Ala Leu Gly Pro Pro
                    115                 120                 125
        Ala Glu Glu Pro Leu Leu Ala Ala Asn Gly Thr Val Pro Ser Trp Pro
                130                 135                 140
        Thr Ala Pro Val Pro Ser Ala Gly Glu Pro Gly Glu Ala Pro Tyr
        145                 150                 155                 160
        Leu Val Lys Val His Gln Val Trp Ala Val Lys Ala Gly Leu Lys
                        165                 170                 175
        Lys Asp Ser Leu Leu Thr Val Arg Leu Gly Thr Trp Gly His Pro Ala
                    180                 185                 190
```

```
              Phe Pro Ser Cys Gly Arg Leu Lys Glu Asp Ser Arg Tyr Ile Phe Phe
                      195                 200                 205
              Met Glu Pro Asp Ala Asn Ser Thr Ser Arg Ala Pro Ala Ala Phe Arg
                  210                 215                 220
              Ala Ser Phe Pro Pro Leu Glu Thr Gly Arg Asn Leu Lys Lys Glu Val
              225                 230                 235                 240
              Ser Arg Val Leu Cys Lys Arg Cys
                              245

<210> SEQ ID NO 211
<211> LENGTH: 58
<212> TYPE: PRT
<213> ORGANISM: Homo sapiens

<400> SEQUENCE: 211

Leu Pro Pro Arg Leu Lys Glu Met Lys Ser Gln Glu Ser Ala Ala Gly
              1               5                   10                  15
              Ser Lys Leu Val Leu Arg Cys Glu Thr Ser Ser Glu Tyr Ser Ser Leu
                          20                  25                  30
              Arg Phe Lys Trp Phe Lys Asn Gly Asn Glu Leu Asn Arg Lys Asn Lys
                      35                  40                  45
              Pro Gln Asn Ile Lys Ile Gln Lys Lys Pro
                  50                  55

<210> SEQ ID NO 212
<211> LENGTH: 41
<212> TYPE: PRT
<213> ORGANISM: Homo sapiens

<400> SEQUENCE: 212

Lys Ser Glu Leu Arg Ile Asn Lys Ala Ser Leu Ala Asp Ser Gly Glu
              1               5                   10                  15
              Tyr Met Cys Lys Val Ile Ser Lys Leu Gly Asn Asp Ser Ala Ser Ala
                          20                  25                  30
              Asn Ile Thr Ile Val Glu Ser Asn Ala
                      35                  40

<210> SEQ ID NO 213
<211> LENGTH: 34
<212> TYPE: PRT
<213> ORGANISM: Homo sapiens

<400> SEQUENCE: 213

Glu Ile Ile Thr Gly Met Pro Ala Ser Thr Glu Gly Ala Tyr Val Ser
              1               5                   10                  15
              Ser Glu Ser Pro Ile Arg Ile Ser Val Ser Thr Glu Gly Ala Asn Thr
                          20                  25                  30
              Ser Ser

<210> SEQ ID NO 214
<211> LENGTH: 42
<212> TYPE: PRT
<213> ORGANISM: Homo sapiens

<400> SEQUENCE: 214

Thr Ser Thr Ser Thr Thr Gly Thr Ser His Leu Val Lys Cys Ala Glu
              1               5                   10                  15
              Lys Glu Lys Thr Phe Cys Val Asn Gly Gly Glu Cys Phe Met Val Lys
                          20                  25                  30
              Asp Leu Ser Asn Pro Ser Arg Tyr Leu Cys
                      35                  40

<210> SEQ ID NO 215
<211> LENGTH: 23
<212> TYPE: PRT
<213> ORGANISM: Homo sapiens

<400> SEQUENCE: 215

Lys Cys Gln Pro Gly Phe Thr Gly Ala Arg Cys Thr Glu Asn Val Pro
```

```
            1               5                  10                  15
        Met Lys Val Gln Asn Gln Glu
                        20
```

<210> SEQ ID NO 216
<211> LENGTH: 9
<212> TYPE: PRT
<213> ORGANISM: Homo sapiens

<400> SEQUENCE: 216

```
        Lys His Leu Gly Ile Glu Phe Met Glu
         1               5
```

<210> SEQ ID NO 217
<211> LENGTH: 190
<212> TYPE: PRT
<213> ORGANISM: Homo sapiens

<400> SEQUENCE: 217

```
        Lys Ala Glu Glu Leu Tyr Gln Lys Arg Val Leu Thr Ile Thr Gly Ile
         1               5                  10                  15
        Cys Ile Ala Leu Leu Val Val Gly Ile Met Cys Val Val Ala Tyr Cys
                        20                  25                  30
        Lys Thr Lys Lys Gln Arg Lys Lys Leu His Asp Arg Leu Arg Gln Ser
                    35                  40                  45
        Leu Arg Ser Glu Arg Asn Asn Met Met Asn Ile Ala Asn Gly Pro His
                50                  55                  60
        His Pro Asn Pro Pro Glu Asn Val Gln Leu Val Asn Gln Tyr Val
         65                  70                  75                  80
        Ser Lys Asn Val Ile Ser Glu His Ile Val Glu Arg Glu Ala Glu
                        85                  90                  95
        Thr Ser Phe Ser Thr Ser His Tyr Thr Ser Thr Ala His His Ser Thr
                    100                 105                 110
        Thr Val Thr Gln Thr Pro Ser His Ser Trp Ser Asn Gly His Thr Glu
                    115                 120                 125
        Ser Ile Leu Ser Glu Ser His Ser Val Ile Val Met Ser Ser Val Glu
                130                 135                 140
        Asn Ser Arg His Ser Ser Pro Thr Gly Gly Pro Arg Gly Arg Leu Asn
        145                 150                 155                 160
        Gly Thr Gly Gly Pro Arg Glu Cys Asn Ser Phe Leu Arg His Ala Arg
                        165                 170                 175
        Glu Thr Pro Asp Ser Tyr Arg Asp Ser Pro His Ser Glu Arg
                    180                 185                 190
```

<210> SEQ ID NO 218
<211> LENGTH: 47
<212> TYPE: PRT
<213> ORGANISM: Homo sapiens

<400> SEQUENCE: 218

```
        His Asn Leu Ile Ala Glu Leu Arg Arg Asn Lys Ala His Arg Ser Lys
         1               5                  10                  15
        Cys Met Gln Ile Gln Leu Ser Ala Thr His Leu Arg Ala Ser Ser Ile
                        20                  25                  30
        Pro His Trp Ala Ser Phe Ser Lys Thr Pro Trp Pro Leu Gly Arg
                    35                  40                  45
```

<210> SEQ ID NO 219
<211> LENGTH: 239
<212> TYPE: PRT
<213> ORGANISM: Homo sapiens

<400> SEQUENCE: 219

```
        Tyr Val Ser Ala Met Thr Thr Pro Ala Arg Met Ser Pro Asp Phe
         1               5                  10                  15
        His Thr Pro Ser Ser Pro Lys Ser Pro Ser Glu Met Ser Pro Pro
                        20                  25                  30
        Val Ser Ser Met Thr Val Ser Met Pro Ser Met Ala Val Ser Pro Phe
                    35                  40                  45
        Met Glu Glu Glu Arg Pro Leu Leu Leu Val Thr Pro Pro Arg Leu Arg
                50                  55                  60
```

```
        Glu Lys Lys Phe Asp His His Pro Gln Gln Phe Ser Ser Phe His His
        65                  70                  75                  80
        Asn Pro Ala His Asp Ser Asn Ser Leu Pro Ala Ser Pro Leu Arg Ile
                        85                  90                  95
        Val Glu Asp Glu Glu Tyr Glu Thr Thr Gln Glu Tyr Glu Pro Ala Gln
                       100                 105                 110
        Glu Pro Val Lys Lys Leu Ala Asn Ser Arg Arg Ala Lys Arg Thr Lys
                   115                 120                 125
        Pro Asn Gly His Ile Ala Asn Arg Leu Glu Val Asp Ser Asn Thr Ser
                   130                 135                 140
        Ser Gln Ser Ser Asn Gly Ser Glu Thr Glu Asp Glu Arg Val Gly
        145                 150                 155                 160
        Glu Asp Thr Pro Phe Leu Gly Ile Gln Asn Pro Leu Ala Ala Ser Leu
                       165                 170                 175
        Glu Ala Thr Pro Ala Phe Arg Leu Ala Asp Ser Arg Thr Asn Pro Ala
                   180                 185                 190
        Gly Arg Phe Ser Thr Gln Glu Glu Ile Gln Ala Arg Leu Ser Ser Val
                   195                 200                 205
        Ile Ala Asn Gln Asp Pro Ile Ala Val Asn Leu Asn Lys His Ile Asp
        210                 215                 220
        Ser Pro Val Lys Leu Tyr Phe Ile Ser Ile Pro Pro Ile Lys Gln
        225                 230                 235

<210> SEQ ID NO 220
<211> LENGTH: 65
<212> TYPE: PRT
<213> ORGANISM: Homo sapiens

<400> SEQUENCE: 220

Ser His Leu Val Lys Cys Ala Glu Lys Glu Lys Thr Phe Cys Val Asn
        1               5                   10                  15
        Gly Gly Glu Cys Phe Met Val Lys Asp Leu Ser Asn Pro Ser Arg Tyr
                    20                  25                  30
        Leu Cys Lys Cys Pro Asn Glu Phe Thr Gly Asp Arg Cys Gln Asn Tyr
                    35                  40                  45
        Val Met Ala Ser Phe Tyr Ser Thr Ser Thr Pro Phe Leu Ser Leu Pro
                50                  55                  60
        Glu
        65

<210> SEQ ID NO 221
<211> LENGTH: 63
<212> TYPE: PRT
<213> ORGANISM: Homo sapiens

<400> SEQUENCE: 221

Ser His Leu Val Lys Cys Ala Glu Lys Glu Lys Thr Phe Cys Val Asn
        1               5                   10                  15
        Gly Gly Glu Cys Phe Met Val Lys Asp Leu Ser Asn Pro Ser Arg Tyr
                    20                  25                  30
        Leu Cys Lys Cys Gln Pro Gly Phe Thr Gly Ala Arg Cys Thr Glu Asn
                    35                  40                  45
        Val Pro Met Lys Val Gln Thr Gln Glu Lys Ala Glu Glu Leu Tyr
                50                  55                  60

<210> SEQ ID NO 222
<211> LENGTH: 60
<212> TYPE: PRT
<213> ORGANISM: Homo sapiens

<400> SEQUENCE: 222

Ser His Leu Val Lys Cys Ala Glu Lys Glu Lys Thr Phe Cys Val Asn
        1               5                   10                  15
        Gly Gly Glu Cys Phe Met Val Lys Asp Leu Ser Asn Pro Ser Arg Tyr
                    20                  25                  30
        Leu Cys Lys Cys Pro Asn Glu Phe Thr Gly Asp Arg Cys Gln Asn Tyr
                    35                  40                  45
        Val Met Ala Ser Phe Tyr Lys Ala Glu Glu Leu Tyr
                50                  55                  60

<210> SEQ ID NO 223
<211> LENGTH: 69
```

```
<212> TYPE: PRT
<213> ORGANISM: Homo sapiens

<400> SEQUENCE: 223

Ser His Leu Val Lys Cys Ala Glu Lys Glu Lys Thr Phe Cys Val Asn
    1               5                   10                  15
    Gly Gly Glu Cys Phe Met Val Lys Asp Leu Ser Asn Pro Ser Arg Tyr
                20                  25                  30
    Leu Cys Lys Cys Pro Asn Glu Phe Thr Gly Asp Arg Cys Gln Asn Tyr
                35                  40                  45
    Val Met Ala Ser Phe Tyr Lys His Leu Gly Ile Glu Phe Met Glu Lys
            50                  55                  60
    Ala Glu Glu Leu Tyr
    65

<210> SEQ ID NO 224
<211> LENGTH: 88
<212> TYPE: PRT
<213> ORGANISM: Homo sapiens

<400> SEQUENCE: 224

Ser His Leu Val Lys Cys Ala Glu Lys Glu Lys Thr Phe Cys Val Asn
    1               5                   10                  15
    Gly Gly Glu Cys Phe Met Val Lys Asp Leu Ser Asn Pro Ser Arg Tyr
                20                  25                  30
    Leu Cys Lys Cys Gln Pro Gly Phe Thr Gly Ala Arg Cys Thr Glu Asn
                35                  40                  45
    Val Pro Met Lys Val Gln Thr Gln Glu Lys Cys Pro Asn Glu Phe Thr
            50                  55                  60
    Gly Asp Arg Cys Gln Asn Tyr Val Met Ala Ser Phe Tyr Ser Thr Ser
    65                  70                  75                  80
    Thr Pro Phe Leu Ser Leu Pro Glu
                    85

<210> SEQ ID NO 225
<211> LENGTH: 83
<212> TYPE: PRT
<213> ORGANISM: Homo sapiens

<400> SEQUENCE: 225

Ser His Leu Val Lys Cys Ala Glu Lys Glu Lys Thr Phe Cys Val Asn
    1               5                   10                  15
    Gly Gly Glu Cys Phe Met Val Lys Asp Leu Ser Asn Pro Ser Arg Tyr
                20                  25                  30
    Leu Cys Lys Cys Gln Pro Gly Phe Thr Gly Ala Arg Cys Thr Glu Asn
                35                  40                  45
    Val Pro Met Lys Val Gln Thr Gln Glu Lys Cys Pro Asn Glu Phe Thr
            50                  55                  60
    Gly Asp Arg Cys Gln Asn Tyr Val Met Ala Ser Phe Tyr Lys Ala Glu
    65                  70                  75                  80
    Glu Leu Tyr

<210> SEQ ID NO 226
<211> LENGTH: 6
<212> TYPE: DNA
<213> ORGANISM: Bos taurus & Homo sapiens

<400> SEQUENCE: 226 aataaa                                                         6
```